(12) United States Patent
Reed et al.

(10) Patent No.: US 12,234,578 B2
(45) Date of Patent: Feb. 25, 2025

(54) TANNIN COMPOSITE FIBERS

(71) Applicant: Wisconsin Alumni Research Foundation, Madison, WI (US)

(72) Inventors: Jess Dreher Reed, Verona, WI (US); Christian Gerald Krueger, Cambridge, WI (US); Emilia Alfaro-Viquez, Madison, WI (US); Sergio Madrigal-Carballo, Madison, WI (US); Hilary Urena Saborio, Madison, WI (US); Sundaram Gunasekaran, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 711 days.

(21) Appl. No.: 16/898,633

(22) Filed: Jun. 11, 2020

(65) Prior Publication Data

US 2021/0230777 A1  Jul. 29, 2021

Related U.S. Application Data

(60) Provisional application No. 62/967,412, filed on Jan. 29, 2020.

(51) Int. Cl.
*D01F 8/18* (2006.01)
*C08G 73/02* (2006.01)
(Continued)

(52) U.S. Cl.
CPC .......... *D01F 8/18* (2013.01); *C08G 73/0266* (2013.01); *C08K 11/00* (2013.01); *D01F 8/14* (2013.01);
(Continued)

(58) Field of Classification Search
CPC .. D01F 8/04–18; D01F 1/02; D01F 1/10–103; D06M 13/238; D04H 1/728; D01D 5/0007–0046
(Continued)

(56) References Cited

U.S. PATENT DOCUMENTS 4,090,919 A   5/1978 Chibata
4,559,157 A   12/1985 Smith
(Continued)

FOREIGN PATENT DOCUMENTS

CN   103709115 A      4/2014
CN   109395170 A  *  3/2019   ............. A61L 15/20
(Continued)

OTHER PUBLICATIONS

English translation of WO 2011129230 A1 obtained by Global Dossier (Year: 2011).*
(Continued)

*Primary Examiner* — Matthew D Matzek
*Assistant Examiner* — Braelyn R Watson
(74) *Attorney, Agent, or Firm* — Daniel A. Blasiole; DeWitt LLP

(57) ABSTRACT

Composite nanofibers comprising polymers and tannins, methods of making same, and methods of use. The nanofibers include a polymer, such as a synthetic polymer, and a tannin. The tannin can include condensed tannins (proanthocyanidins) and/or hydrolyzable tannins. The nanofibers exhibit a number of structural and functional characteristics, such as enhanced swelling in aqueous liquid, enhanced antibacterial activity, enhanced bacterial adsorption, enhanced fibroblast adhesion, enhanced fibroblast proliferation, and enhanced surface coating of silver nanoparticles, among others. The nanofibers can be made by electrospinning a solvent mixture comprising the synthetic polymer and
(Continued)

the tannin in a solvent. The nanofibers can be used in methods of isolating cells, methods of filtration, and methods of detecting cells, among others.

24 Claims, 47 Drawing Sheets
(45 of 47 Drawing Sheet(s) Filed in Color)

(51) Int. Cl.
| | | |
|---|---|---|
| C08K 11/00 | (2006.01) | |
| D01F 8/14 | (2006.01) | |
| D04H 13/00 | (2006.01) | |
| C12Q 1/18 | (2006.01) | |

(52) U.S. Cl.
CPC ............... *D04H 13/00* (2013.01); *C12Q 1/18* (2013.01); *D10B 2505/04* (2013.01); *D10B 2509/00* (2013.01)

(58) Field of Classification Search
USPC .......... 428/373–374, 357–407; 442/340–351
See application file for complete search history.

(56) References Cited

U.S. PATENT DOCUMENTS

| | | | |
|---|---|---|---|
| 4,608,392 A | 8/1986 | Jacquet | |
| 4,820,508 A | 4/1989 | Wortzman | |
| 4,938,949 A | 7/1990 | Borch | |
| 4,983,584 A | 1/1991 | Fukaya et al. | |
| 4,992,478 A | 2/1991 | Geria | |
| 5,153,281 A | 10/1992 | Shimizu | |
| 5,633,388 A | 5/1997 | Diana et al. | |
| 5,856,326 A | 1/1999 | Anthony et al. | |
| 6,020,422 A | 2/2000 | Connors | |
| 6,780,504 B2 | 8/2004 | Rupprecht | |
| 6,960,617 B2 | 11/2005 | Omidian | |
| 7,122,574 B2 | 10/2006 | Romanczyk, Jr. et al. | |
| 7,288,532 B1 | 10/2007 | Payne | |
| 7,427,631 B2 | 9/2008 | Eriksson et al. | |
| 7,482,503 B2 | 1/2009 | Gregory | |
| 7,741,367 B2 | 6/2010 | Bassaganya-Riera et al. | |
| 7,754,724 B2 | 7/2010 | Lorsbach et al. | |
| 7,767,235 B2 | 8/2010 | Shrikhande | |
| 7,842,692 B2 | 11/2010 | Kugimiya et al. | |
| 7,956,082 B2 | 6/2011 | Kugimiya et al. | |
| 8,143,285 B2 | 3/2012 | Kugimiya et al. | |
| 8,354,401 B2 | 1/2013 | Ishibuchi et al. | |
| 8,642,088 B2 | 2/2014 | Reed | |
| 8,993,763 B2 | 3/2015 | Kugimiya et al. | |
| 9,545,423 B2 | 1/2017 | Reed | |
| 9,556,146 B2 | 1/2017 | Bassaganya-Riera | |
| 9,839,635 B2 | 12/2017 | Bassaganya-Riera | |
| 10,028,950 B2 | 7/2018 | Bassaganya-Riera | |
| 10,104,888 B2 | 10/2018 | Reed | |
| 10,201,537 B2 | 2/2019 | Bassaganya-Riera | |
| 10,493,072 B2 | 12/2019 | Bassaganya-Riera | |
| 2001/0051189 A1 | 12/2001 | Alonso Fernandez et al. | |
| 2003/0232895 A1 | 12/2003 | Omidian et al. | |
| 2004/0151778 A1 | 8/2004 | Richard et al. | |
| 2005/0049472 A1* | 3/2005 | Manda ............... A61B 5/14865 | |
| | | | 607/6 |
| 2005/0147656 A1 | 7/2005 | Dunfield et al. | |
| 2005/0150489 A1 | 7/2005 | Dunfield et al. | |
| 2005/0281886 A1 | 12/2005 | Cattaneo | |
| 2006/0046977 A1 | 3/2006 | Nunes et al. | |
| 2006/0093580 A1 | 5/2006 | Iwashima et al. | |
| 2007/0004750 A1 | 1/2007 | Lorsbach et al. | |
| 2007/0066924 A1 | 3/2007 | Hopman et al. | |
| 2007/0071871 A1 | 3/2007 | Shrikhande et al. | |
| 2007/0196401 A1* | 8/2007 | Naruse .................. D21H 15/02 | |
| | | | 424/443 |
| 2007/0203236 A1 | 8/2007 | Smith et al. | |
| 2007/0292539 A1 | 12/2007 | Vorsa et al. | |
| 2008/0069779 A1 | 3/2008 | Tamarkin et al. | |
| 2008/0095810 A1 | 4/2008 | Alonso Fernandez et al. | |
| 2008/0286254 A1 | 11/2008 | Sakamoto et al. | |
| 2009/0035440 A1 | 2/2009 | Velikov | |
| 2009/0143331 A1 | 6/2009 | Stroumpoulis et al. | |
| 2010/0160166 A1 | 6/2010 | Abrams et al. | |
| 2010/0160355 A1 | 6/2010 | Degoey et al. | |
| 2010/0216883 A1 | 8/2010 | Bassaganya-Riera et al. | |
| 2011/0059162 A1 | 3/2011 | Reed et al. | |
| 2011/0250812 A1* | 10/2011 | Pourdeyhimi ........... D04H 1/49 | |
| | | | 442/337 |
| 2011/0274726 A1 | 11/2011 | Guo et al. | |
| 2011/0275558 A1 | 11/2011 | Bassaganya-Riera | |
| 2012/0286254 A1 | 11/2012 | Stoessel et al. | |
| 2013/0142825 A1 | 6/2013 | Bassaganya-Riera et al. | |
| 2013/0291878 A1* | 11/2013 | Takayama .............. D04H 1/728 | |
| | | | 264/465 |
| 2015/0087673 A1 | 3/2015 | Hitoshi et al. | |
| 2015/0093694 A1 | 4/2015 | Watariguchi et al. | |
| 2015/0335593 A1 | 11/2015 | Zolotarsky et al. | |
| 2017/0119762 A1 | 5/2017 | Bassaganya-Riera | |
| 2019/0046688 A1* | 2/2019 | Miller ...................... A61L 27/46 | |
| 2020/0056057 A1* | 2/2020 | Nagarajan ........... D06M 13/292 | |

FOREIGN PATENT DOCUMENTS

| | | | |
|---|---|---|---|
| CZ | 306691 B6 * | 5/2017 | |
| DE | 4141889 A1 | 6/1993 | |
| EP | 507272 A1 | 10/1992 | |
| EP | 1304346 A2 | 4/2003 | |
| JP | 4308525 A | 10/1992 | |
| JP | 7236419 A | 9/1995 | |
| JP | 11057314 A | 3/1999 | |
| JP | 2001335698 A | 12/2001 | |
| JP | 2004026785 A | 1/2004 | |
| JP | 2008056615 A | 3/2008 | |
| JP | 2011246461 A | 12/2011 | |
| KR | 2012035285 A | 4/2012 | |
| KR | 101309546 B1 * | 9/2013 | ......... B01D 46/0028 |
| WO | 9630343 A1 | 10/1996 | |
| WO | WO 1999/004764 A1 | 2/1999 | |
| WO | WO 2003/091237 A1 | 11/2003 | |
| WO | WO 2008/092006 A2 | 7/2008 | |
| WO | WO 2009/076618 A2 | 6/2009 | |
| WO | WO 2010/075376 A | 7/2010 | |
| WO | WO 2010/078660 A1 | 7/2010 | |
| WO | WO-2011129230 A1 * | 10/2011 | ............... A61L 9/16 |
| WO | WO 2012/016217 A1 | 2/2012 | |

OTHER PUBLICATIONS

English translation of CN 109395170 A obtained by Espacenet (Year: 2019).*
Beads Formation in Electrospinning, ElectrospinTech, Aug. 19, 2014 (Year: 2014).*
English translation of CZ 306691 B6 obtained from Google Patents (Year: 2017).*
English translation of KR 101309546 B1 obtained from Espacenet (Year: 2013).*
Polycaprolactone, Wikipedia, 2022. (Year: 2022).*
Tannin, Encyclopaedia Britannica, 2022. (Year: 2022).*
Tannic acid, PubChem, 2022. (Year: 2022).*
Furukawa, Ryutaro, et al. "Persimmon-derived tannin has antiviral effects and reduces the severity of infection and transmission of SARS-CoV-2 in a Syrian hamster model." Scientific reports 11.1 (2021): 1-11. (Year: 2021).*
Aadil, K. R., Mussatto, S. I., & Jha, H. (2018). Synthesis and characterization of silver nanoparticles loaded poly (vinyl alcohol)-lignin ESNFs and their antimicrobial activity. *International journal of biological macromolecules*, 120, 763-767.
Abdel-Hady, F., Alzahrany, A., & Hamed, M. (2011). Experimental validation of upward electrospinning process. *ISRN nanotechnology*, 2011.
Agarwal, S., Wendorff, J. H., & Greiner, A. (2008). Use of electrospinning technique for biomedical applications. *Polymer*, 49(26), 5603-5621.

(56) References Cited

OTHER PUBLICATIONS

Al-Omair, M. (2015). Synthesis of antibacterial silver-poly (ε-caprolactone)-methacrylic acid graft copolymer nanofibers and their evaluation as potential wound dressing. *Polymers*, 7(8), 1464-1475.
Alborzi, S., Lim, L. T., & Kakuda, Y. (2014). Release of folic acid from sodium alginatepectin-poly (ethylene oxide) electrospun fibers under in vitro conditions. *LWT-FoodScience and Technology*, 59(1), 383-388.
Angammana, C. J., & Jayaram, S. H. (2011). Analysis of the effects of solution conductivity on electrospinning process and fiber morphology. *IEEE Transactions on industry applications*, 47(3), 1109-1117.
Arce-Urbina, M. E., Hun-Opfer, C., & Mata-Segreda, J. F. (2003). The aqueous extract of Triumfetta semitriloba (Tiliaceae) does not inhibit the in-vitro hydrolytic activity of the major pancreatic enzymes. *Revista de biología tropical*, 51(2), 313-316.
Avila, G., Misch, K., Galindo-Moreno, P., & Wang, H. L. (2009). Implant surface treatment using biomimetic agents. *Implant dentistry*, 18(1), 17-26.
Bauer, A. W., Kirby, W. M. M., Sherris, J. C., & Turck, M. (1966). Antibiotic susceptibility testing by a standardized single disk method. *American journal of clinical pathology*, 45(4_ts), 493-496.
Beecher, Overview of dietary flavonoids: nomenclature, occurrence and intake, J. Nutrition, 2003, 3248S-3254S.
Bhardwaj, N., & Kundu, S. C. (2010). Electrospinning: a fascinating fiber fabrication technique. *Biotechnology advances*, 28(3), 325-347.
Bhattarai, D., Aguilar, L., Park, C., & Kim, C. (2018). A review on properties of natural and synthetic based electrospun fibrous materials for bone tissue engineering. *Membranes*, 8(3), 62.
Blainski, A., Lopes, G., & de Mello, J. (2013). Application and analysis of the folin ciocalteu method for the determination of the total phenolic content from Limonium brasiliense L. *Molecules*, 18(6), 6852-6865.
Blumberg, J. B., Basu, A., Krueger, C. G., Lila, M. A., Neto, C. C., Novotny, J. A., . . . & Toner, C. D. (2016). Impact of cranberries on gut microbiota and cardiometabolic health: Proceedings of the cranberry health research conference 2015. *Advances in Nutrition*, 7(4), 759S-770S.
Bondet, V., Brand-Williams, W., & Berset, C. L. W. T. (1997). Kinetics and mechanisms of antioxidant activity using the DPPH. free radical method. *LWT-Food Science and Technology*, 30(6), 609-615.
Brettmann, B. K., Tsang, S., Forward, K. M., Rutledge, G. C., Myerson, A. S., & Trout, B. L. (2012). Free surface electrospinning of fibers containing microparticles. *Langmuir*, 28(25), 9714-9721.
Brettmann, B. K., Cheng, K., Myerson, A. S., & Trout, B. L. (2013). Electrospun formulations containing crystalline active pharmaceutical ingredients. *Pharmaceutical research*, 30(1), 238-246.
Brettmann, B., Pincus, P., & Tirrell, M. (2017). Lateral structure formation in polyelectrolyte brushes induced by multivalent ions. *Macromolecules*, 50(3), 1225-1235.
Bustamante, M., Oomah, B. D., Rubilar, M., & Shene, C. (2017). Effective Lactobacillus plantarum and Bifidobacterium infantis encapsulation with chia seed (*Salvia hispanica* L.) and flaxseed (*Linum usitatissimum* L.) mucilage and soluble protein by spray drying. *Food chemistry*, 216, 97-105.
Charernsriwilaiwat, N., Rojanarata, T., Ngawhirunpat, T., Sukma, M., & Opanasopit, P. (2013). Electrospun chitosan-based nanofiber mats loaded with Garcinia mangostana extracts. *International journal of pharmaceutics*, 452(1-2), 333-343.
Chaves, M. A., Piati, J., Malacarne, L. T., Gall, R. E., Colla, E., Bittencourt, P. R., . . . & Matsushita, M. (2018). Extraction and application of chia mucilage (*Salvia hispanica* L.) and locust bean gum (*Ceratonia siliqua* L.) in goat milk frozen dessert. *Journal of food science and technology*, 55(10), 4148-4158.
Choi, J.S., Lee, S.W., Jeong, L., Bae, S.H., Min, B.C., Youk, J.H., & Park, W.H. (2004). Effect of organosoluble salts on the nanofibrous structure of electrospun poly(3-hydroxybutyrate-co-3-hydroxyvalerate). *International Journal of Biological Macromolecules*, 34, 249.
Deitzel, J. M., Kleinmeyer, J., Harris, D. E. A., & Tan, N. B. (2001). The effect of processing variables on the morphology of ESNFs and textiles. *Polymer*, 42(1), 261-272.
Dhandayuthapani, B., Yoshida, Y., Maekawa, T., & Kumar, D. S. (2011). Polymeric scaffolds in tissue engineering application: a review. *International journal of polymerscience*, 2011.
Du, L., Xu, H., Zhang, Y., & Zou, F. (2016). Electrospinning of polycaprolatone nanofibers with DMF additive: the effect of solution proprieties on jet perturbation and fiber morphologies. *Fibers and Polymers*, 17(5), 751-759.
Duan, B., Dong, C., Yuan, X., & Yao, K. (2004). Electrospinning of chitosan solutions in acetic acid with poly (ethylene oxide). *Journal of Biomaterials Science, Polymer Edition*, 15(6), 797-811.
Eichhorn, S. J., & Sampson, W. W. (2010). Relationships between specific surface area and pore size in electrospun polymer fibre networks. *Journal of the Royal Society Interface*, 7(45), 641-649.
Elendran, S., Wang, L. W., Prankerd, R., & Palanisamy, U. D. (2015). The physicochemical properties of geraniin, a potential antihyperglycemic agent. *Pharmaceutical biology*, 53(12), 1719-1726.
Ewaldz, E., & Brettmann, B. (2019). Molecular Interactions in Electrospinning: From Polymer Mixtures to Supramolecular Assemblies. *ACS Applied Polymer Materials*, 1(3), 298-308.
Ewaldz, E., Patel, R., Banerjee, M., & Brettmann, B. K. (2018). Material selection in electrospinning microparticles. *Polymer*, 153, 529-537.
Fallahi, D., Rafizadeh, M., Mohammadi, N., & Vahidi, B. (2008). Effect of applied voltage on jet electric current and flow rate in electrospinning of polyacrylonitrile solutions. *Polymer international*, 57(12), 1363-1368.
Fang, Z., & Bhandari, B. (2010). Encapsulation of polyphenols—a review. *Trends in Food Science & Technology*, 21(10), 510-523.
Feldman, M., Tanabe, S., Howell, A., & Grenier, D. (2012). Cranberry proanthocyanidins inhibit the adherence properties of Candida albicans and cytokine secretion by oral epithelial cells. *BMC complementary and alternative medicine*, 12(1), 6.
Feliciano, R. P., Krueger, C. G., & Reed, J. D. (2015). Methods to determine effects of cranberry proanthocyanidins on extraintestinal infections: Relevance for urinary tract health. *Molecular nutrition & food research*, 59(7), 1292-1306.
Feliciano, R. P., Shea, M. P., Shanmuganayagam, D., Krueger, C. G., Howell, A. B., & Reed, J. D. (2012). Comparison of isolated cranberry (Vaccinium macrocarpon Ait.) proanthocyanidins to catechin and procyanidins A2 and B2 for use as standards in the 4-(dimethylamino) cinnamaldehyde assay. *Journal of agricultural and food chemistry*, 60(18), 4578-4585.
Fernandez, A., Torres-Giner, S., & Lagaron, J. M. (2009). Novel route to stabilization of bioactive antioxidants by encapsulation in electrospun fibers of zein prolamine. *Food Hydrocolloids*, 23(5), 1427-19721.
Ferreira, J. L., Gomes, S., Henriques, C., Borges, J. P., & Silva, J. C. (2014). Electrospinning polycaprolactone dissolved in glacial acetic acid: Fiber production, nonwoven characterization, and In Vitro evaluation. *Journal of Applied Polymer Science*, 131(22).
Frenot, A., & Chronakis, I. S. (2003). Polymer nanofibers assembled by electrospinning. *Current opinion in colloid & interface science*, 8(1), 64-75.
Guo, H. F., & Xu, B. G. (2017). Numerical study of Taylor cone dynamics in electrospinning of nanofibers. In *Key Engineering Materials* (vol. 730, pp. 510-515). Trans Tech Publications.
Gupta, K., Chou, M. Y., Howell, A., Wobbe, C., Grady, R., & Stapleton, A. E. (2007). Cranberry products inhibit adherence of p-fimbriated *Escherichia coli* to primary cultured bladder and vaginal epithelial cells. *The Journal of urology*, 177(6), 2357-2360.
Gurlek, A. C., Sevinc, B., Bayrak, E., & Erisken, C. (2017). Synthesis and characterization of polycaprolactone for anterior cruciate ligament regeneration. *Materials Science and Engineering: C*, 71, 820-826.
Hadad, S., & Goli, S. A. H. (2018). Fabrication and characterization of ESNFs using flaxseed (*Linum usitatissimum*) mucilage. *International journal of biological macromolecules*, 114, 408-414.

(56) References Cited

OTHER PUBLICATIONS

Haeri, M., & Haeri, M. (2015). ImageJ plugin for analysis of porous scaffolds used in tissue engineering. *Journal of Open Research Software*, 3(1).

Haider, A., Haider, S., & Kang, I. K. (2018). A comprehensive review summarizing the effect of electrospinning parameters and potential applications of nanofibers in biomedical and biotechnology. *Arabian Journal of Chemistry*, 11(8), 1165-1188.

Haider, S., Al-Zeghayer, Y., Ali, F. A. A., Haider, A., Mahmood, A., Al-Masry, W. A., . . . & Aijaz, M. O. (2013). Highly aligned narrow diameter chitosan ESNFs. *Journal of Polymer Research*, 20(4), 105.

Hani, N. M., Torkamani, A. E., Azarian, M. H., Mahmood, K. W., & Ngalim, S. H. (2017). Characterisation of electrospun gelatine nanofibres encapsulated with Moringa oleifera bioactive extract. *Journal of the Science of Food and Agriculture*, 97(10), 3348-3358.

Hotaling, N. A., Bharti, K., Kriel, H., & Simon Jr, C. G. (2015). DiameterJ: A validated open source nanofiber diameter measurement tool. *Biomaterials*, 61, 327-338.

Howell, A. B. (2007). Bioactive compounds in cranberries and their role in prevention of urinary tract infections. *Molecular nutrition & food research*, 51(6), 732-737.

Howell, A. B., Reed, J. D., Krueger, C. G., Winterbottom, R., Cunningham, D. G., & Leahy, M. (2005). A-type cranberry proanthocyanidins and uropathogenic bacterial antiadhesion activity. *Phytochemistry*, 66(18), 2281-2291.

Huan, S., Liu, G., Han, G., Cheng, W., Fu, Z., Wu, Q., & Wang, Q. (2015). Effect of experimental parameters on morphological, mechanical and hydrophobic properties of electrospun polystyrene fibers. *Materials*, 8(5), 2718-2734.

Huang, C. H., Chi, C. Y., Chen, Y. S., Chen, K. Y., Chen, P. L., & Yao, C. H. (2012). Evaluation of proanthocyanidin-crosslinked electrospun gelatin nanofibers for drug delivering system. *Materials Science and Engineering: C*, 32(8), 2476-2483.

Ikada, Y. (2006). Challenges in tissue engineering. *Journal of the Royal Society Interface*, 3(10), 589-601.

Jahangir, M. A., Rumi, T. M., Wahab, M. A., Khan, M. I., Rahman, M. A., & Sayed, Z. B. (2017). Poly Lactic Acid (PLA) Fibres: Different Solvent Systems and Their Effect on Fibre Morphology and Diameter. *American Journal of Chemistry*, 7(6), 177-186.

Jahani, H., Kaviani, S., Hassanpour-Ezatti, M., Soleimani, M., Kaviani, Z., & Zonoubi, Z. (2012). The effect of aligned and random electrospun fibrous scaffolds on rat mesenchymal stem cell proliferation. *Cell Journal (Yakhteh)*, 14(1), 31.

Kai, D., Jiang, S., Low, Z. W., & Loh, X. J. (2015). Engineering highly stretchable ligninbased ESNFs for potential biomedical applications. *Journal of Materials Chemistry B*, 3(30), 6194-6204.

Kandhasamy, N., Perumal, S., Madhan, B., Umamaheswari, N., Banday, J. A., Perumal, P.T., & Santhanakrishnan, V. P. (2017). Synthesis and fabrication of collagen-coated ostholamide electrospun nanofiber scaffold for wound healing. *ACS applied materials & interfaces*, 9(10), 8556-8568.

Katsogiannis, K. A. G., Vladisavljević, G. T., & Georgiadou, S. (2015). Porous electrospun polycaprolactone (PCL) fibres by phase separation. *European Polymer Journal*, 69, 284-295.

Kaur, M., Kaur, R., & Punia, S. (2018). Characterization of mucilages extracted from different flaxseed (*Linum usitatissiumum* L.) cultivars: A heteropolysaccharide with desirable functional and rheological properties. *International journal of biological macromolecules*, 117, 919-927.

Kayaci, F., & Uyar, T. (2012). Encapsulation of vanillin/cyclodextrin inclusion complex in electrospun polyvinyl alcohol (PVA) nanowebs: Prolonged shelf-life and high temperature stability of vanillin. *Food chemistry*, 133(3), 641-649.

Keat, C.L., Aziz, A., Eid, A.M., & Elmarzugi, N.A. (2015). Biosynthesis of nanoparticles and silver nanoparticles. *Bioresources and Bioprocessing*, 2, 47.

Khajavi, R., & Abbasipour, M. (2012). Electrospinning as a versatile method for fabricating coreshell, hollow and porous nanofibers. *Scientia Iranica*, 19(6), 2029-2034.

Khoo, H.E., Azlan, A., Tang, S.T., & Lim, S.M. (2017). Anthocyanidins and anthocyanins: colored pigments as food, pharmaceutical ingredients, and the potential health benefits. *Food and Nutrition Research*, 61(1), 1361779.

Kim, H. C., Kim, M. H., & Park, W. H. (2018). Polyelectrolyte complex nanofibers from poly (γ-glutamic acid) and fluorescent chitosan oligomer. *International journal of biological macromolecules*, 118, 238-243.

Krishnan, P. (2006). The scientific study of herbal wound healing therapies: Current state of play. *Current Anaesthesia & Critical Care*, 17(1-2), 21-27.

Krueger et al. Matrix-assisted laser desorption/ionization time-of-flight mass spectrometry of heteropolyflavan-3-ols and glucosylated heteropolyflavans in sorghum [*Sorghum bicolor* (L.) Moench], J. Agric. Food Chem. 2003, 51, 538-543.

Kumar, A., Paul, S., Kumari, P., Somasundaram, S. T., & Kathiresan, K. (2015). Antioxidant and free radical scavenging activities of *Ipomoea pes-caprae* (L.) R. Br. extracts. *Int J Curr Pharm Rev Res*, 5, 91-109.

Kurd, F., Fathi, M., & Shekarchizadeh, H. (2017). Basil seed mucilage as a new source for electrospinning: Production and physicochemical characterization. *International journal of biological macromolecules*, 95, 689-695.

Lee, K. Y., Jeong, L., Kang, Y. O., Lee, S. J., & Park, W. H. (2009). Electrospinning of polysaccharides for regenerative medicine. *Advanced drug delivery reviews*, 61(12), 1020-1032.

Li, D., & Xia, Y. (2004). Electrospinning of nanofibers: reinventing the wheel?. *Advanced materials*, 16(14), 1151-1170.

Li, D., McCann, J. T., Xia, Y., & Marquez, M. (2006). Electrospinning: a simple and versatile technique for producing ceramic nanofibers and nanotubes. *Journal of the American Ceramic Society*, 89(6), 1861-1869.

Li, M., Mondrinos, M. J., Gandhi, M. R., Ko, F. K., Weiss, A. S., & Lelkes, P. I. (2005). Electrospun protein fibers as matrices for tissue engineering. *Biomaterials*, 26(30), 5999-6008.

Li, W. R., Xie, X. B., Shi, Q. S., Zeng, H. Y., You-Sheng, O. Y., & Chen, Y. B. (2010). Antibacterial activity and mechanism of silver nanoparticles on *Escherichia coli*. *Applied microbiology and biotechnology*, 85(4), 1115-1122.

Madrigal-Carballo, S., Haas, L., Vestling, M., Krueger, C. G., & Reed, J. D. (2016). Noncovalent pomegranate (*Punica granatum*) hydrolyzable tannin-protein complexes modulate antigen uptake, processing and presentation by a T-cell hybridoma line cocultured with murine peritoneal macrophages. *International journal of food sciences and nutrition*, 67(8), 960-968.

Malafaya, P. B., Silva, G. A., & Reis, R. L. (2007). Natural-origin polymers as carriers and scaffolds for biomolecules and cell delivery in tissue engineering applications. *Advanced drug delivery reviews*, 59(4-5), 207-233.

Malikmammadov, E., Tanir, T. E., Kiziltay, A., Hasirci, V., & Hasirci, N. (2018). PCL and PCL-based materials in biomedical applications. *Journal of Biomaterials science, Polymer edition*, 29(7-9), 863-893.

Maran, J. P., Manikandan, S., Nivetha, C. V., & Dinesh, R. (2017). Ultrasound assisted extraction of bioactive compounds from *Nephelium lappaceum* L. fruit peel using central composite face centered response surface design. *Arabian Journal of Chemistry*, 10, S1145-S1157.

Matabola, K. P., & Moutloali, R. M. (2013). The influence of electrospinning parameters on the morphology and diameter of poly (vinyledene fluoride) nanofibers-effect of sodium chloride. *Journal of Materials Science*, 48(16), 5475-5482.

Matthews, J. A., Wnek, G. E., Simpson, D. G., & Bowlin, G. L. (2002) Electrospinning of collagen nanofibers. *Biomacromolecules*, 3(2), 232-238.

Megelski, S., Stephens, J. S., Chase, D. B., & Rabolt, J. F. (2002). Micro- and nanostructured surface morphology on electrospun polymer fibers. *Macromolecules*, 35(22), 8456-8466.

Merrill, E. W. (1994). Poly (ethylene oxide) star molecules: synthesis, characterization, and applications in medicine and biology. *Journal of Biomaterials Science, Polymer Edition*, 5(1-2), 1-11.

(56) References Cited

OTHER PUBLICATIONS

Miser-Salihoglu, E., Akaydin, G., Caliskan-Can, E., & Yardim-Akaydin, S. (2013). Evaluation of antioxidant activity of various plant-based folk medicines. *Nutrition & Food Sciences*.
Mogoşanu, G. D., & Grumezescu, A. M. (2014). Natural and synthetic polymers for wounds and burns dressing. *International journal of pharmaceutics*, 463(2), 127-136.
Moomand, K., & Lim, L. T. (2015). Properties of encapsulated fish oil in electrospun zein fibres under simulated in vitro conditions. *Food and bioprocess technology*, 8(2), 431-444.
Moradkhannejhad, L., Abdouss, M., Nikfarjam, N., Mazinani, S., & Sayar, P. (2017). Electrospun curcumin loaded poly (lactic acid) nanofiber mat on the flexible crosslinked PVA/PEG membrane film: Characterization and in vitro release kinetic study. *Fibers and Polymers*, 18(12), 2349-2360.
Mueller, M., Čavarkapa, A., Unger, F. M., Viernstein, H., & Praznik, W. (2017). Prebiotic potential of neutral oligo- and polysaccharides from seed mucilage of Hyptis suaveolens. *Food chemistry*, 221, 508-514.
Mulfinger, L., Solomon, S. D., Bahadory, M., Jeyarajasingam, A. V., Rutkowsky, S. A., & Boritz, C. (2007). Synthesis and study of silver nanoparticles. *Journal of chemical education*, 84(2), 322.
Munir, A., & Edwards-Lévy, F. (2011). Encapsulation of natural polyphenolic compounds; a review. *Pharmaceutics*, 3(4), 793-829.
Nagori, B. P., & Solanki, R. (2011). Role of medicinal plants in wound healing. *Research Journal of Medicinal Plant*, 5(4), 392-405.
Natarajan, V., Krithica, N., Madhan, B., & Sehgal, P.K. (2010). Formulation and evaluation of quercetin polycaprolactone microspheres for the treatment of rheumatoid arthritis. *Journal of Pharmaceutical Sciences*, 100(1), 195-205.
Nie, H., He, A., Wu, W., Zheng, J., Xu, S., Li, J., & Han, C. C. (2009). Effect of poly (ethylene oxide) with different molecular weights on the electrospinnability of sodium alginate. *Polymer*, 50(20), 4926-4934.
Noriega, S. E., Hasanova, G. I., Schneider, M. J., Larsen, G. F., & Subramanian, A. (2012). Effect of fiber diameter on the spreading, proliferation and differentiation of 81 chondrocytes on electrospun chitosan matrices. *Cells Tissues Organs*, 195(3), 207-221.
Noruzi, M. (2016). Electrospun nanofibres in agriculture and the food industry: a review. *Journal of the Science of Food and Agriculture*, 96(14), 4663-4678.
Okoro, I. O., Osagie, A., & Asibor, E. O. (2010). Antioxidant and antimicrobial activities of polyphenols from ethnomedicinal plants of Nigeria. *African Journal of Biotechnology*, 9(20).
Okuda, T., & Ito, H. (2011). Tannins of constant structure in medicinal and food plants—hydrolyzable tannins and polyphenols related to tannins. *Molecules*, 16(3), 2191-2217.
Okutan, N., Terzi, P., & Altay, F. (2014). Affecting parameters on electrospinning process and characterization of electrospun gelatin nanofibers. *Food Hydrocolloids*, 39, 19-26.
Oveissi, V., Ram, M., Bahramsoltani, R., Ebrahimi, F., Rahimi, R., Naseri, R., . . . & Farzaei, M. H. (2019). Medicinal plants and their isolated phytochemicals for the management of chemotherapy-induced neuropathy: Therapeutic targets and clinical perspective. *DARU Journal of Pharmaceutical Sciences*, 389-406.
Palanisamy, U. D., Ling, L. T., Manaharan, T., & Appleton, D. (2011). Rapid isolation of geraniin from Nephelium lappaceum rind waste and its anti-hyperglycemic activity. *Food Chemistry*, 127(1), 21-27.
Pan, H., Fan, D., Cao, W., Zhu, C., Duan, Z., Fu, R., . . . & Ma, X. (2017). Preparation and characterization of breathable hemostatic hydrogel dressings and determination of their effects on full-thickness defects. *Polymers*, 9(12), 727.
Pan, H., Li, L., Hu, L., & Cui, X. (2006). Continuous aligned polymer fibers produced by a modified electrospinning method. *Polymer*, 47(14), 4901-4904.

Park, J. C., Ito, T., Kim, K. O., Kim, K. W., Kim, B. S., Khil, M. S., . . . & Kim, I. S. (2010). Electrospun poly (vinyl alcohol) nanofibers: effects of degree of hydrolysis and enhanced water stability. *Polymer journal*, 42(3), 273.
Pathak, D., Pathak, K., & Singla, A. K. (1991). Flavonoids as medicinal agents-recent advances. *Fitoterapia*, 62(5), 371-389.
Pelipenko, J., Kristl, J., Janković, B., Baumgartner, S., & Kocbek, P. (2013). The impact of relative humidity during electrospinning on the morphology and mechanical properties of nanofibers. *International journal of pharmaceutics*, 456(1), 125-134.
Picciani, P. H., Medeiros, E. S., Pan, Z., Orts, W. J., Mattoso, L. H., & Soares, B. G. (2009). Development of conducting polyaniline/poly (lactic acid) nanofibers by electrospinning. *Journal of Applied Polymer Science*, 112(2), 744-753.
Pietta, P., Minoggio, M., & Bramati, L. (2003). Plant polyphenols: Structure, occurrence and bioactivity. In *Studies in Natural Products Chemistry* (vol. 28, pp. 257-312). Elsevier.
Pillay, V., Dott, C., Choonara, Y. E., Tyagi, C., Tomar, L., Kumar, P., . . . & Ndesendo, V. M. (2013). A review of the effect of processing variables on the fabrication of ESNFs for drug delivery applications. *Journal of Nanomaterials*, 2013.
Quideau and Feldman, Ellagitannin Chemistry, Chem. Rev. 1996, 96, 475-503.
Radzig, M. A., Nadtochenko, V. A., Koksharova, O. A., Kiwi, J., Lipasova, V. A., & Khmel, I. A. (2013). Antibacterial effects of silver nanoparticles on gram-negative bacteria: influence on the growth and biofilms formation, mechanisms of action. *Colloids and Surfaces B: Biointerfaces*, 102, 300-306.
Raghavamma, S.T.V., Mothukuri, A.S., Rama, R.N. (2013). Antimicrobial activity of mucilage isolated from Coccinia grandis (L) Fruits, J Voigt, International Journal of Advances in Pharmaceutical Research 4(11) 2497-2502.
Raven, P. H., Evert, R. F., & Eichhorn, S. E. (2005). *Biology of plants*. Macmillan.
Reed et al. MALDI-TOF mass spectrometry of oligomeric food polyphenols, Phytochem. 66(18): 2248-2263 (2005).
Reyes, C. D., Petrie, T. A., Burns, K. L., Schwartz, Z., & García, A. J. (2007). Biomolecular surface coating to enhance orthopaedic tissue healing and integration. *Biomaterials*, 28(21), 3228-3235.
Rieger, K. A., Birch, N. P., & Schiffman, J. D. (2016). Electrospinning chitosan/poly (ethylene oxide) solutions with essential oils: Correlating solution rheology to nanofiber formation. *Carbohydrate polymers*, 139, 131-138.
Sahay, R., Thavasi, V., & Ramakrishna, S. (2011). Design modifications in electrospinning setup for advanced applications. *Journal of Nanomaterials*, 2011, 17.
Santos, C., Silva, C. J., Büttel, Z., Guimarães, R., Pereira, S. B., Tamagnini, P., & Zille, A. (2014). Preparation and characterization of polysaccharides/PVA blend nanofibrous membranes by electrospinning method. *Carbohydrate polymers*, 99, 584-592.
Sarhan, W. A., & Azzazy, H. M. (2015). High concentration honey chitosan ESNFs: Biocompatibility and antibacterial effects. *Carbohydrate polymers*, 122, 135-143.
Sell, S. A., Wolfe, P. S., Garg, K., McCool, J. M., Rodriguez, I. A., & Bowlin, G. L. (2010). The use of natural polymers in tissue engineering: a focus on electrospun extracellular matrix analogues. *Polymers*, 2(4), 522-553.
Shao, C., Kim, H. Y., Gong, J., Ding, B., Lee, D. R., & Park, S. J. (2003). Fiber mats of poly (vinyl alcohol)/silica composite via electrospinning. *Materials Letters*, 57(9-10), 1579-1584.
Shenoy, S.L., Bates, W.D., Frisch, H.L., & Wnek, G.E. (2005). Role of chain entanglements on fiber formation during electrospinning of polymer solutions: good solvent, nonspecific polymer-polymer interaction limit. *Polymer*, 46, 3372.
Singleton, V. L., Orthofer, R., & Lamuela-Raventós, R. M. (1999). Analysis of total phenols and other oxidation substrates and antioxidants by means of folin-ciocalteu reagent. In *Methods in enzymology* (vol. 299, pp. 152-178). Academic press.
Son, W. K., Youk, J. H., Lee, T. S., & Park, W. H. (2005). Effect of pH on electrospinning of poly (vinyl alcohol). *Materials letters*, 59(12), 1571-1575.

(56) References Cited

OTHER PUBLICATIONS

Sousa, A. M., Souza, H. K., Uknalis, J., Liu, S. C., Goncalves, M. P., & Liu, L. (2015). Electrospinning of agar/PVA aqueous solutions and its relation with rheological properties. *Carbohydrate polymers*, 115, 348-355.

Subbiah, T., Bhat, G. S., Tock, R. W., Parameswaran, S., & Ramkumar, S. S. (2005). Electrospinning of nanofibers. *Journal of applied polymer science*, 96(2), 557-569.

Sun, Z., Zussman, E., Yarin, A. L., Wendorff, J. H., & Greiner, A. (2003). Compound core-shell polymer nanofibers by co-electrospinning. *Advanced materials*, 15(22), 1929-1932.

Supaphol, P., & Chuangchote, S. (2008). On the electrospinning of poly (vinyl alcohol) nanofiber mats: a revisit. *Journal of Applied Polymer Science*, 108(2), 969-978.

Tang, C., Saquing, C. D., Harding, J. R., & Khan, S. A. (2009). In situ cross-linking of electrospun poly (vinyl alcohol) nanofibers. *Macromolecules*, 43(2), 630-637.

Tarus, B., Fadel, N., Al-Oufy, A., & El-Messiry, M. (2016). Effect of polymer concentration on the morphology and mechanical characteristics of electrospun cellulose acetate and poly (vinyl chloride) nanofiber mats. *Alexandria Engineering Journal*, 55(3), 2975-2984.

Thilagavathi, G., & Bala, S. K. (2007). Microencapsulation of herbal extracts for microbial resistance in healthcare textiles.

Thitilertdecha, N., Teerawutgulrag, A., & Rakariyatham, N. (2008). Antioxidant and antibacterial activities of *Nephelium lappaceum* L. extracts. *LWT-Food Science and Technology*, 41(10), 2029-2035.

Tsai, S. P., Hsieh, C. Y., Hsieh, C. Y., Chang, Y. N., Wang, D. M., & Hsieh, H. J. (2007). Gamma-poly (glutamic acid)/chitosan composite scaffolds for tissue engineering applications. In *Materials science forum* (vol. 539, pp. 567-572). Trans Tech Publications.

Cranberry proanthocyanidins have anti-biofilm properties against Pseudomonas aeruginosa. *BMC complementary and alternative medicine*, 14(1), 499.

Urena-Saborio, H., Alfaro-Viquez, E., Esquivel-Alvarado, D., Madrigal-Carballo, S., & Gunasekaran, S. (2018). Electrospun plant mucilage nanofibers as biocompatible scaffolds for cell proliferation. *International journal of biological macromolecules*, 115, 1218-1224.

Van der Schueren, L., De Schoenmaker, B., Kalaoglu, Ö. I., & De Clerck, K. (2011). An alternative solvent system for the steady state electrospinning of polycaprolactone. *European Polymer Journal*, 47(6), 1256-1263.

Vanaja, M., Gnanajobitha, G., Paulkumar, K., Rajeshkumar, S., Malarkodi, C., & Annadura, G. (2013). Phytosynthesis of silver nanoparticles by *Cissus quadrangularis*: Influence of physicochemical factors. *Journal of Nanostructure in Chemistry*, 3, 17.

Varoni, E. M., Iriti, M., & Rimondini, L. (2012). Plant products for innovative biomaterials in dentistry. *Coatings*, 2(3), 179-194.

Vineis, C., & Varesano, A. (2018). Natural polymer-based electrospun fibers for antibacterial uses. In *Electrofluidodynamic Technologies (EFDTs) for Biomaterials and Medical Devices* (pp. 275-294). Woodhead Publishing.

Wang, H., Hao, L., Niu, B., Jiang, S., Cheng, J., & Jiang, S. (2016). Kinetics and antioxidant capacity of proanthocyanidins encapsulated in zein electrospun fibers by cyclic voltammetry. *Journal of agricultural and food chemistry*, 64(15), 3083-3090.

Wang, G., Yang, S., Wei, Z., Dong, X., Wang, H., & Qi, M. (2013). Facile preparation of poly (ε-caprolactone)/Fe 3 O 4@ graphene oxide superparamagnetic nanocomposites. *Polymer bulletin*, 70(8), 2359-2371.

Wang, H., Wang, J., Qiu, C., Ye, Y., Guo, X., Chen, G., . . . & Liu, R. H. (2017). Comparison of phytochemical profiles and health benefits in fiber and oil flaxseeds (*Linum usitatissimum* L.). *Food chemistry*, 214, 227-233.

Wang, L. F., & Rhim, J. W. (2016). Grapefruit seed extract incorporated antimicrobial LDPE and PLA films: Effect of type of polymer matrix. *LWT*, 74, 338-345.

Wang, S., Cao, X., Shen, M., Guo, R., Bányai, I., & Shi, X. (2012). Fabrication and morphology control of electrospun poly (γ-glutamic acid) nanofibers for biomedical applications. *Colloids and Surfaces B: Biointerfaces*, 89, 254-264.

Wang, S., Marcone, M. F., Barbut, S., & Lim, L. T. (2012). Fortification of dietary biopolymers-based packaging material with bioactive plant extracts. *Food research international*, 49(1), 80-91.

Wang, S., Marcone, M. F., Barbut, S., & Lim, L. T. (2013). Electrospun soy protein isolatebased fiber fortified with anthocyanin-rich red raspberry (*Rubus strigosus*) extracts. *Food research international*, 52(2), 467-472.

Wang, X., Bazuin, C. G., & Pellerin, C. (2015). Effect of small molecule hydrogen-bond crosslinker and solvent power on the electrospinnability of poly (4-vinyl pyridine). *Polymer*, 57, 62-69.

Wen, P., Zhu, D. H., Wu, H., Zong, M. H., Jing, Y. R., & Han, S. Y. (2016). Encapsulation of cinnamon essential oil in electrospun nanofibrous film for active food packaging. *Food Control*, 59, 366-376.

Woodruff, M. A., & Hutmacher, D. W. (2010). The return of a forgotten polymer Polycaprolactone in the 21st century. *Progress in polymer science*, 35(10), 1217-1256.

World Health Organization (WHO). (2005). National Policy on Traditional Medicine and Regulation of Plant-based Medicines. Geneva: Report of WHO global survey.

Yang, G., Lin, H., Rothrauff, B. B., Yu, S., & Tuan, R. S. (2016). Multilayered polycaprolactone/gelatin fiber-hydrogel composite for tendon tissue engineering. *Acta biomaterialia*, 35, 68-76.

Yuan, W., & Zhang, K. Q. (2012). Structural evolution of electrospun composite fibers from the blend of polyvinyl alcohol and polymer nanoparticles. *Langmuir*, 28(43), 15418-15424.

Zargham, S., Bazgir, S., Tavakoli, A., Rashidi, A. S., & Damerchely, R. (2012). The effect of flow rate on morphology and deposition area of electrospun nylon 6 nanofiber. *Journal of Engineered Fibers and Fabric*, 7(4), 155892501200700414.

Zhang, B., Kang, F., Tarascon, J. M., & Kim, J. K. (2016). Recent advances in electrospun carbon nanofibers and their application in electrochemical energy storage. *Progress in Materials Science*, 76, 319-380.

Zhou, C., Chu, R., Wu, R., & Wu, Q. (2011). Electrospun polyethylene oxide/cellulose nanocrystal composite nanofibrous mats with homogeneous and heterogeneous microstructures. *Biomacromolecules*, 12(7), 2617-2625.

Zhou, T., Wang, N., Xue, Y., Ding, T., Liu, X., Mo, X., & Sun, J. (2016). Electrospun tilapia collagen nanofibers accelerating wound healing via inducing keratinocytes proliferation and differentiation. *Colloids and Surfaces B: Biointerfaces*, 143, 415-422.

Zhu, J., & Marchant, R. E. (2011). Design properties of hydrogel tissue-engineering scaffolds. *Expert review of medical devices*, 8(5), 607-626.

Zong, X.H., Kim, K.S., Fang, D.F., Ran, S.F., Hsiao, B.S., & Chu, B. (2002). Structure and process relationship of electrospun bioabsorbable nanofiber membranes. Polymer, 43, 20 4403.

Aelenei et al., Tannic Acid Incorporation in Chitosan-Based Microparticles and In Vitro Controlled Release, J Mater Sci: Mater Med (2009) 20:1095-1102.

Afaq et al., Anthocyanin- and hydrolysable tannin-rich pomegranate fruit extract modulates MAPK and NF-kappaB pathways and inhibits skin tumorigenesis in CD-1 mice, Int. J. Cancer (2005) 113 (3): 423-433.

Alvarez et al., Influence of the electrical interface properties on the rheological behavior of sonicated soy lecithin dispersions, J. Colloid Interface Sci. (2007) 309(2): 279-82.

Alving et al., Liposomes as vehicles for vaccines, Prog. Clin. Biol. Res. (1980) 47: 339-55.

Alving, Liposomes as earners of Antigens and Adjuvants, J. Immunol. Methods (1991) 140(1): 1-13.

Bala et al., 2013 (Rajni Bala, Pravin Pawar, Sushil Khanna, and Sandeep Arora. Orally dissolving strips; A new approach to oral drug delivery system. Int J Pharm investig. Apr.-Jun. 2013; 3(2): 67-76.

Balde, A, T De Bruyne, L Pieters, H Kolodziej, D Vanden Berghe, M Claeys, A Vlietnck. "Tetrameric Proanthocyanidins Containing a Double Interflavanoid (A-Type) Linkage from Pavetta Owariensis." Phytochemistry, vol. 40, No. 3, 1995, pp. 933-948.

Beecher. (2003) Overview of dietary flavonoids: nomenclature, occurrence and intake, J. Nutrition; 133(10):3248S-3254S.

(56) References Cited

OTHER PUBLICATIONS

Benech et al. Inhibition of *Listeria innocua* in Cheddar cheese by addition of nisin Z in liposomes or by in situ production in mixed culture. Appl. Environ. Microbiol. (2002) 68:3683-90.
Berthold et al., Preparation and characterization of chitosan microspheres as drug carrier for prednisolone sodium phosphate as model for anti-inflammatory, J. Control Release (1996) vol. 39: 17-25.
Blumberg et al., Cranberries and their bioactive constituents in human health, 2013, American Society for Nutrition, Adv. Nutr. 4: 618-632.
Bu et al., Co-delivery of IL-2 or liposomes augment the responses of mice to a DNA vaccine for pseudorabies virus IE180 Comp. Immunol. Microbiol. Infect. Dis. (2003) 26(3): 175-87.
Burleigh et al., Consumption of sweetened, dried cranberries may reduce urinary tract infection incidence in susceptible women—a modified observational study. Nutrition Journal (2013),12:139.
Calvo et al., Novel hydrophilic chitosan-polyethylene oxide nanoparticles as protein earners, J. Appl. Polym. Sci. (1997) vol. 63, 125-132.
Corradin et al., Novel adjuvants for vaccines, Curr. Med. Chem.—Anti-Inflammatory & Anti-Allergy Agents (2005) 4:1-7.
Czochanska et al., Compositional changes in lower molecular weight flavans during grape maturation (1979) : Phytochemistry 18:1819-1822 (Abstract Provided Only).
Gan et al., Modulation of surface charge, particle size and morphological properties of chitosan-TPP nanoparticles intended for gene delivery, Colloids Surf. B. 2005;44(2-3) :65-73.
Garlea et al., Chitosan-Polyphenols Nanostructured Matrices Drug Release Kinetics Studies, Analele Stiintifice ale Universitatii "Al. I. Cuza" din Iaşi (Serie Noua), Tomul IV, Biofizica, Fizica Medicala, Fizica Mediului, (2008), pp. 25-30, ISSN 1841-5318.
Gregoriadis et al., Liposome-mediated DNA vaccination, FEBS Lett. (1997) 402 : 107.
Gregoriadis G. Drug entrapment in liposomes. FEBS Lett. (1973) 36:292-6.
Gregoriadis G., Liposome technology., 2nd ed. Boca Raton, Fla.: CRC Press (1993). (Book—Copy Not Provided).
Gric et al., Mucoadhesive Chitosan-Coated Liposomes: Characteristics and Stability, Journal of Microencapsulation, (2001) vol. 18 No. 1, p. 3-12.
Guo et al., Chitosan-coated liposomes : Characterization and interaction with leuprolide, Int. J. Pharm. (2003) 260: 167-173.
Gupta et al., Adjuvants for human vaccines-current status, problems and future prospects, Vaccine (1995) 13: 1263.
Guzey et al., Formation, stability and properties of multilayer emulsions for application in the food industry. Adv. Colloid Interface Sci. (2006) 130:227-48.
Guzey et al., Impact of electrostatic interactions on formation and stability of emulsions containing oil droplets coated by beta-lactoglobulin-pectin complexes. J. Agric. Food Chem. (2007) 55(2):475-85.
Hedqvist et al., Characterisation of Tannins and In Vitro Protein Digestibility of Several Lotus Corniculatus Varieties, Animal Feed Science and Technology (2000) 87: 41-56.
Henriksen et al. Interactions between liposomes and chitosan II: effect of selected parameters on aggregation and leakage, Int. J. Pharm. (1997) 146:193-204.
Hong and McClements. Modulation of pH sensitivity of surface charge and aggregation stability of protein-coated lipid droplets by chitosan addition. Food Biophys. (2007) 2(1):46-55.
Howell et al., A-type cranberry proanthocyanidins and uropathogenic bacterial anti-adhesion activity, Phytochem. (2005) 66(18): 2281-2291.
Howell et al., Dosage effect on uropathogenic *Escherichia coli* anti-adhesion activity in urine following consumption of cranberry powder standardized for proanthocyanidin content: a multicentric randomized double blind study, BMC Infection Diseases (2010), 10:94.
Howell, Amy; Bioactive compounds in cranberries and their role in prevention of urinary tract infections, Molecular nutrition food Res (2007), 51: 732-737.

Illum et al., Chitosan as a novel nasal delivery system for vaccines, Adv. Drug Deliv. Rev. (2001) 51:81-96.
Illum., Chitosan and its use as a Pharmaceutical Excipient, Pharm. Res. (1998) 15 (vol. 9):1326-31.
Iwanaga et al., Application of Surface-Coated Liposomes for Oral Delivery of Peptide: Effects of Coating the Liposome's Surface on the GI Transit of Insulin, J. Pharm. Sci. (1999) 88:248-52.
Jameela et al., Progesterone-loaded chitosan microspheres: a long acting biodegradable controlled delivery system, J. Control. Release (1998) 52:17-24.
Janes et al., Polysaccharide colloidal particles as delivery systems for Macromolecules, Adv. Drug. Deliv. Rev. (2001) 47:83-97.
Jepson et al., Cranberries for preventing urinary tract infections (Review), 2013, The Cochrane Collaboration, reprint of the Cochrane Library 2012, Issue 10.
Jones et al., Quenched BODIPY dye-Labeled casein substrates for the assay of protease activity by direct fluorescence measurement, Anal. Biochem. (1997) 251:144.
Kato et al., Influence of Liposomes on Tryptic Digestion of Insulin, Biol. Pharm. Bull. (1993) 16: 457.
Khatri et al., Surface modified liposomes for nasal delivery of DNA vaccine, Vaccine (2008) 26: 2225-33.
Kim, S, Me Nimni, Z Yang, B Han. Chitosan/Gelatin-Based Films Crosslinked by Proanthocyanidin, Journal of Biomedial Research Part B: Applied Biomaterials, vol. 75B, 2005, pp. 442-450.
Krueger et al., Quantifying and characterizing proanthocyanidins in cranberries in relation to urinary tract health, Anal Bianal Chem (2013) 405:4385-4395.
Krueger, C.G. et al. Matrix-assisted laser desorption/Ionization time-of-flight mass spectrometry of anthocyanin-polyflavan-3-ol polymers in cranberry fruit [*Vaccinium macrocarpon, Ait.*] and spray dried cranberry juice, ACS Symposium, Uncovering the Mysteries of Red Wine Pigments. (2004) vol. 886: pp. 232-246.
Krueger, C.G. et al. Matrix-assisted laser desorption/ionization time-of-flight mass spectrometry of polygalloyl polyflavan-3-ols in grape seed extract., J Agric. Food Chem. (2000) 47: 3693-3710 and 48:1663-1667.
Kulkarni et al., In Vitro Studies on the Binding, Antioxidant, and Cytotoxic Actions of Punicalagin, Journal of Agricultural and Food Chemistry, (2007) vol. 55, pp. 1491-1500.
Kumar, Rajesh et al., Potential use of chitosan nanoparticles of oral delivery of DNA vaccine in Asian sea bass (*Lates calcarifer*) to protect from Vibrio (*Listonella*) anguillarum; Fish and Shellfish Immunology (2008), 25: 47-56.
Kumar et al. Chitosan chemistry and pharmaceutical perspectives, Chemical Reviews (2004) 104:6017-6084.
Lowry et al., Protein measurement with the folin phenol reagent, J. Biol. Chem. (1951) 193: 265-75.
Madrigal-Carballo et al., An approach to rheological and electro-kinetic behaviour of lipidic vesicles covered with chitosan biopolymer. Colloids Surf., (2008) 323:149-154.
Madrigal-Carballo et al., Chitosomes loaded with cranberry proanthocyanidins attenuate the bacterial lipopolysaccharide-induced expression of iNOS and COX-2 in raw 264.7 macrophages, J. Liposome Res. (2009) 19(3): 189-196.
Manconi et al., Colloids and Surfaces A: Physicochemical and Engineering Aspects, Coll, and Surfaces A: Physicochem. Eng. Aspects. (2005) 270-271 102. (Abstract Provided Only).
Manconi et al., Development and characterization of liposomes containing glycols as carriers for diclofenac, Coll, and Surfaces A: Physicochem. Eng. Aspects. (2009) vol. 342 53-58.
McClements. Theoretical analysis of factors affecting the formation and stability of multilayered colloidal dispersions. Langmuir (2005) 21(21):9777-85.
McNeela et al., Intranasal immunization with genetically detoxified diphtheria toxin induces T cell responses in humans: enhancement of Th2 responses and toxin-neutralizing antibodies by formulation with chitosan, Vaccine. (2004) 22:909-14.
Mills et al., Protective Levels of Diphtheria-Neutralizing Antibody Induced in Healthy Volunteers by Unilateral Priming-Boosting Intranasal Immunization Associated with Restricted Ipsilateral Mucosal Secretory Immunoglobulin A, Infect. Immun. (2003) 71:726-32.

(56) References Cited

OTHER PUBLICATIONS

Mishra et al., Evaluation of uptake and generation of immune response by murine dendritic cells pulsed with hepatitis B surface antigen-loaded elastic liposomes, Vaccine (2007) 25:6939-6944).
Mokarram et al., Preparation and evaluation of chitosan nanoparticles containing Diphteria toxoid as new carriers for nasal vaccine delivery in mice, Archives of Razi Institute (2006) vol. 61, No. 1:13-25.
Muller et al., Nanosuspensions as particulate drug formulations in therapy: Rationale for development and what we can expect for the future, Adv. Drug Deliv. Rev. (2001) 47:3-19.
Nakanishi et al., Positively charged liposome functions as an efficient immunoadjuvant in inducing cell-mediated immune response to soluble proteins, Control. Release. (1999) 61:233-40.
Neto, et al., Maldi-Tof MS characterization of proanthocyanidins from cranberry fruit (*Vacciniummacrocarpon*) that inhibit tumor cell growth and matrix metalloproteinase expression in vitro, J. Sci. Food Agric., (2006) vol. 86, pp. 18-25.
Nishimura et al., Immunological activity of chitin and its derivatives, Vaccine. (1984) 2: 93-9.
Nishimura et al., Stimulation of cytokine production in mice using deacetylated chitin, Vaccine. (1986) 4:151-6.
Onishi, Y. Machida, Biodegradation and distribution of water-soluble chitosan in mice, Biomaterials. (1991) 20:175-82.
Pallandre et al., Improvement of stability of oil-in-water emulsions containing caseinate-coated droplets by addition of sodium alginate., J. Food Sci. (Nov./Dec. 2007) 72(9): E518-E524.
Peek et al., Nanotechnology in vaccine delivery, Adv. Drug Deliv. Rev. (2008) 60:915-928.
Popa, M-I, N Aelenei, VI Popa, D Andrei. Study of the interactions between polyphenolic compounds and chitosan. Reactive & Functional Polymers, vol. 45, 2000, pp. 35-43.
Porporatto et al., Local and systemic activity of the polysaccharide chitosan at lymphoid tissues after oral administration, Journal of Leukocyte Biology (2005), vol. 78:62-69.
Read et al., Effective nasal influenza vaccine delivery using chitosan, Vaccine. (2005) 23: 4367.
Rinaudo. Chitin and chitosan: Properties and applications, Progress in Polymer Science (2006) 31:603-632.
Roussy et al., Treatment of Ink-Containing Wastewater by Coagulation/Flocculation Using Biopolymers, Water SA vol. 31 No. 3 (http://www.wrc.org.za) Jul. 2005, pp. 369-376. ISSN 0378-4738.
Saupe et al., Immunostimulatory colloidal delivery systems for cancer vaccines, Expert Opin. Drug Deliv. (2006) 3:345-54.
Seeram et al., Pomegranate Phytochemicals, Pomegranates Medicinal and Aromatic Plants—Industrial Profiles (2006).
Seferian et al. Immune stimulating activity of two new chitosan containing adjuvant formulations, Vaccine (2000) 19:661-8.
Singla et al., Chitosan: some pharmaceutical and biological aspects an update, J. Pharm. Pharmacol. (2001) 53: 1047.
Stagg et al., The dendritic cell: its role in intestinal inflammation and relationship with gut bacteria, Gut Journal (2003) 52:1522-1529.
Takeuchi et al., Enteral Absorption of Insulin in Rats from Mucoadhesive Chitosan-Coated Liposomes, Pharm. Res. (1996) 13:896-901.
Taylor et al., Liposomal nanocapsules in food science and agriculture. Crit. Rev. Food Sci. Nutr. (2005) 45:1-19.
Tezuka et al., Regulation of IgA production by naturally occurring TNF/iNOS-producing dendritic cells, Nature (2007) 448:929-933.
Van Der Lubben et al., Chitosan for mucosal vaccination, Adv. Drug Deliv. Rev. (2001) 52: 139-144.
Van Der Lubben et al., Chitosan microparticles for oral vaccination: preparation, characterization and preliminary in vivo uptake studies in murine Peyer's patches, Biomaterials (2001) 22:687.
Wahlberg, David; Are cranberries healthy? Probably, but science uncertain; Wisconsin State Journal (2015).
Wharton and Dieguez-Uribeonodo. The biology of Colletotrichum acutatum. Anales del Jardin Botanico de Madrid, 61(1):3-22 (2004).
Were et al., Size, stability, and entrapment efficiency of phospho-lipid nanocapsules containing polypeptide antimicrobials. J. Agric. Food Chem. (2003) 51:8073-9.
Yoshikawa et al., Augmentation of antigen-specific immune responses using DNA-fusogenic liposome vaccine, Biochem. Biophys. Res. Commun. (2004) 325:500.
Yuan, Y, BM Chesnutt, WO Haggard, JD Bumgardner. "Deacetylation of Chitosan: Material Characterization and in vitro Evaluation via Albumin Adsorption and Pre-Osteoblastic Cell Cultures." Materials, vol. 4, 2011, pp. 1399-1416.
Zaharoff et al., Chitosan solution enhances both humoral and cell-mediated immune responses to subcutaneous vaccination, Vaccine (2007) 25:2085-94.
Zhang, L, SL Kosaraju. "Biopolymeric delivery system for controlled release of polyphenolic antioxidants." European Polymer Journal, vol. 43, 2007, pp. 2956-2966.
Zhu et al., Rapid Identification of Gallotannins from Chinese Galls by Matrix-Assisted Laser Desorption/Ionization Time-of-Flight Quadrupole Ion Trap Mass Spectrometry, Rapid Commun. Mass Spec from. (2009); 23:1678-1682.
Sill, T. J., & von Recum, H. A. (2008). Electrospinning: applications in drug delivery and tissue engineering. *Biomaterials*, 29(13), 1989-2006.
Ulrey, R. K., Barksdale, S. M., Zhou, W., & van Hoek, M. L. (2014). Cranberry proanthocyanidins have anti-biofilm properties against Pseudomonas aeruginosa. *BMC complementary and alternative medicine*, 14(1), 499.
Zargham, S., Bazgir, S., Tavakoli, A., Rashidi, A. S., & Damerchely, R. (2012). The effect of flow rate on morphology and deposition area of electrospun nylon 6 nanofiber. *Journal of Engineered Fibers and Fabrics*, 7(4), 155892501200700414.

\* cited by examiner

PAC-based biosensor response to bacteria

TANNIN COMPOSITE FIBERS

STATEMENT REGARDING FEDERALLY SPONSORED RESEARCH

This invention was made with government support under 18-CRHF-0-6055 awarded by the USDA/NIFA. The government has certain rights in the invention.

BACKGROUND

Electrospinning is a fiber production method that uses electrical force to draw up charged threads of polymer solutions with fiber diameters from submicrons to hundreds of nanometers or less. The resulting fibers have large surface area per unit mass, high porosity, high gas permeability, and small interfibrous pore size. These nanofibers are of considerable interest for various kinds of applications in areas such as filtrations, recovery of metal ions, drug release, dental applications, tissue engineering, catalyst and enzyme carriers, wound healing, protective clothing, cosmetics, biosensors, medical implants, and energy storage.

Tannins are a heterogeneous group of high molecular weight, water soluble, polyphenolic compounds, naturally present in cereals, leguminous seeds, and many fruits and vegetables. Tannins offer a variety of activities, including antioxidant and free radical scavenging activity as well as antimicrobial, anti-cancer, anti-nutritional, and cardio-protective properties. They also seem to exert beneficial effects on metabolic disorders and prevent the onset of several oxidative stress-related diseases. Tannins can be classified into two groups: hydrolyzable tannins and proanthocyanidins.

Composite nanofibers that comprise tannins and exhibit the properties of tannins would be a useful advancement in the art.

SUMMARY OF THE INVENTION

The present invention relates to structurally stable nanofibers comprising polymers and tannins, methods of making same, and methods of use. The nanofibers comprise a composite of a polymer, such as a synthetic polymer, and a tannin. The synthetic polymer can include polymers such as polycaprolactone (PCL) and polyaniline (PANI), among others. The tannin can include condensed tannins (proanthocyanidins) and/or hydrolyzable tannins. The nanofibers exhibit a number of structural and functional characteristics. The functional characteristics include enhanced swelling in aqueous liquid, enhanced antibacterial activity, enhanced bacterial adsorption, enhanced fibroblast adhesion, enhanced fibroblast proliferation, and enhanced surface coating of silver nanoparticles, among others.

The nanofibers of the invention can be made by electrospinning a solvent mixture comprising the synthetic polymer and the tannin in a solvent.

The nanofibers can be used in methods of isolating cells, methods of filtration, and methods of detecting cells, among other methods.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10A. PCL 100 mg/mL, FIG. 10B. PAC 6 mg/mL:PCL 100 mg/mL, FIG. 10C. PAC 8 mg/mL:PCL 100 mg/mL, FIG. 10D. PAC 12 mg/mL:PCL 100 mg/mL. Scale bars represent 1 μm. Inserted images correspond to the histograms showing average nanofiber diameter distributions.

FIG. 29A. PCL 100 mg/mL (no RPE added); FIG. 29B. PCL 100 mg/mL:R-134 12 mg/mL; FIG. 29C. PCL 100 mg/mL:Rongrein 12 mg/mL; FIG. 29D. PCL 100 mg/mL:Criollo 12 mg/mL.

FIG. 37A. Hydrated morphology of the nanofibers. FIG. 37B. Scale bar indicates 1 µm, suggesting AgNPs average size of 100 nm. RPE variety R-134.

FIG. 51A. Frequency response of the biosensors to decreasing bacterial concentrations. FIG. 51B. Bacterial culture plates showing the associated bacterial colony forming units as a reference for bacterial dispersions. FIG. 51C. Electrode illustration containing an SEM micrograph showing the bacterial adsorption onto PANI-PAC composite nanofibers.

DETAILED DESCRIPTION OF THE INVENTION

Figure 1:
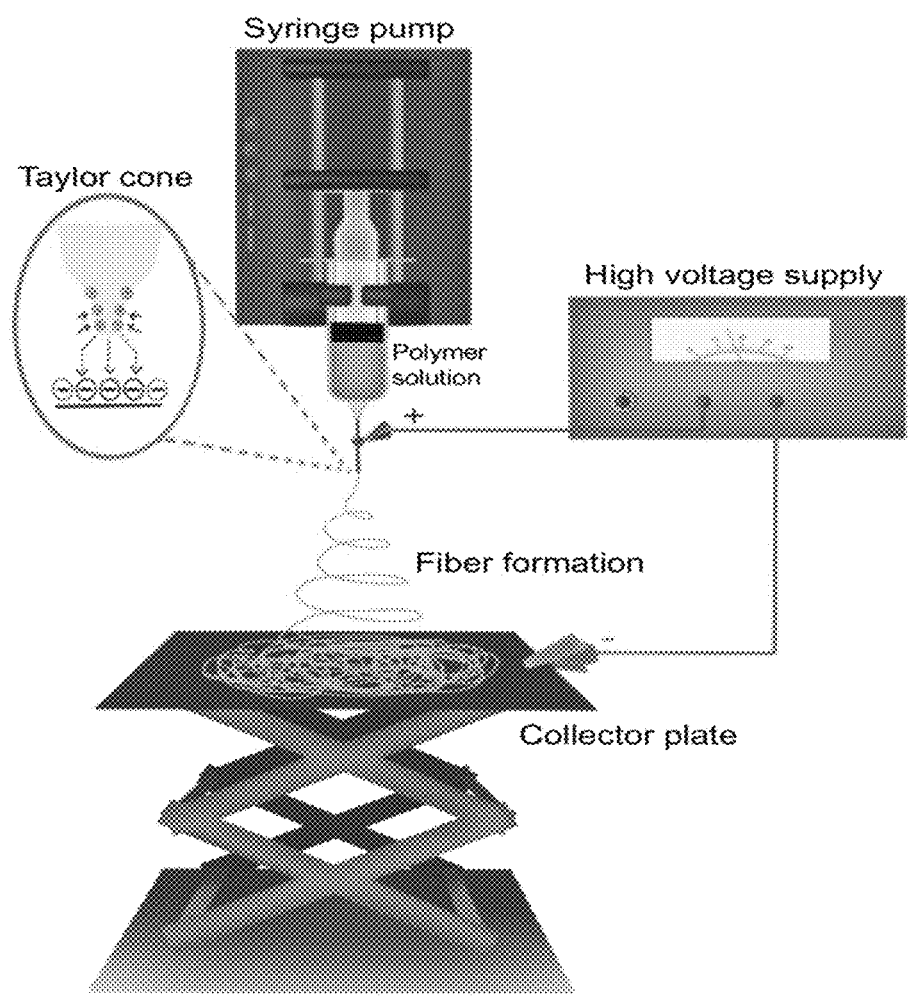
FIG. 1. Schematic diagram showing an exemplary setup up for an electrospinning system.

The invention is directed in part to nanofibers. Nanofibers are threads or filaments having an average cross-sectional diameter from about 1 to about 1000 nm and a length (in a dimension orthogonal to the cross-section) of at least about 5 times the average cross-sectional diameter. Nanofibers can have a form of a beadless fiber (see FIG. 2) (e.g, a substantially uniform cross-sectional diameter), a "bead-on-string" fiber (see FIG. 2), or a combination or hybrid of the two. Nanofibers are distinct from nanoparticles (see FIG. 2), the latter of which have approximately the same diameter regardless of dimension.

The nanofibers of the invention are composites comprising a polymer and a tannin. "Composite" is used herein to refer to a material comprising two or more constituent materials with significantly different physical or chemical properties.

The polymer in the nanofibers of the invention preferably comprises a synthetic polymer. Except for poly-glutamic acid, which is considered herein to constitute a synthetic polymer, synthetic polymers are polymers that are not found in or isolated from nature. Except for poly-glutamic acid, which is considered herein not to constitute a natural polymer, natural polymers are polymers that are found in or isolated from nature.

The synthetic polymer comprised by the nanofibers of the invention can include a polyester, a semi-flexible rod polymer, a polyether, a polyurethane, a vinyl polymer, a poly(alkylene oxide), a polyanhydride, poly-glutamic acid, or any combination thereof. Exemplary polyesters include polycaprolactone (PCL), poly(lactic acid) (PLA), poly(glycolic acid) (PGA), poly(lactic-co-glycolic acid) (PLGA), poly(lactic acid-co-caprolactone) (P(LLA-CL)), and poly(3-hydroxybutyrate-co-3-hydroxyvalerate) (PHBV). Exemplary semi-flexible rod polymers include polyaniline (PANI), poly(p-phenylene oxide) and poly(p-phenylene sulfide). As understood herein, semi-flexible rod polymers include both conductive and non-conductive forms. Exemplary polyethers include aliphatic polyethers and aromatic polyethers. Exemplary aliphatic polyethers include polyoxymethylene (POM), polyethylene oxide, polypropylene oxide (PPOX), and polytetrahydrofuran (PTHF). Exemplary aromatic polyethers include polyphenyl ether (PPE) and poly(p-phenylene oxide) (PPO). Exemplary vinyl polymers include polyethylene, polypropylene, polystyrene, polyvinyl chloride, polyvinyl acetate, polyvinyl alcohol, polyacrylonitrile, and poly(ethylene-co-vinylacetate) (PEVA). Exemplary poly(alkylene oxide) polymers include polymers made from ethylene oxide (EO) (e.g., poly(ethylene oxide)), propylene oxide (PO), butylene oxide (BO), and combinations thereof. As used herein, poly(ethylene glycol), poly(ethylene oxide), and poly(oxyethylene) are used synonymously and refer to polymers of ethylene oxide ($-CH_2-CH_2-O$). Exemplary polyanhydrides include aliphatic polyanhydrides, unsaturated polyanhydrides, and aromatic polyanhydrides, such as poly(p-pentamethylenedibenzoic anhydride), poly(p-tetramethylenedibenzoic anhydride), poly(sebacic anhydride), and poly(azelaic anhydride).

In some versions, the synthetic polymer comprises a weight average molecular weight ($M_w$) from about 25 kDa to about 400 kDa, such as from about 25 kDa to about 250 kDa or from about 50 kDa to about 100 KDa.

The tannin comprised by the nanofibers of the invention can include any tannin. Tannins include oligomeric polyphenols that occur naturally in a variety of plants. Isolated tannins typically form a heterogeneous mixture of tannin compounds. Tannin compounds can be subdivided into two groups: condensed tannins, also known as proanthocyanidins ("PA" or "PAC"), and hydrolyzable tannins (HT). Tannin oligomers typically occur as dimers, trimers, tetramers, pentamers, hexamers, heptamers, octamers, nonamers, or decamers. Oligomers with greater than ten monomeric segments can also be isolated, such as oligomers that include up to 50 units. For a review of tannin nomenclature, see Beecher (*J. Nutrition* 2003, 3248S-3254S), which is incorporated herein by reference. In some embodiments, certain monomerics or tannins with a low degree of polymerization (DP) can be excluded from a particular composition. For example, a composition may exclude catechin, tannic acid, or other monomers, dimeric tannins, trimers, or tetramers, proanthocyanidin tannins, hydrolyzable tannins, tannins having a certain molecular weight range, or any type, class, or specific tannin cited in Beecher.

Proanthocyanidins are polymers of flavan-3-ols and flavans linked through an interflavan bond between carbon 4 of the C ring and carbon 8 of the A ring, as shown in Scheme 1. Scheme 1 illustrates a cranberry polyflavan-3-ol showing structural variation in the nature of interflavan linkage and substitution to an anthocyanin terminal unit through a $CH_3$—CH bridge.

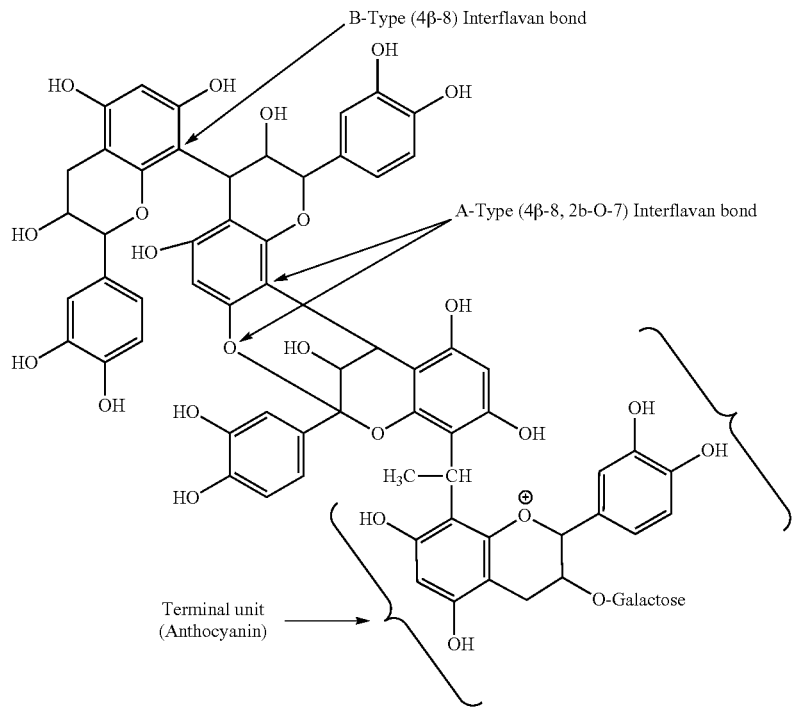

Scheme 1. Representative structures of a proanthocyanidin (PA).

Scheme 2 illustrates two other types of condensed tannins (PAs): procyanidins and prodelphinidins (for the trimer x=1; for the tetramer, x=2; for the pentamer, x=3; for the hexamer, x=4; for the heptamer, x=5; for the octamer, x=6; for the nonamer, x=7; and for the decamer, x=8). Procyanidins (R=H) contain catechin and/or epicatechin (CE) subunits; prodelphinidins (R=OH) contain gallocatechin and/or epigallocatchin (GE) subunits.

Scheme 2. Representative Structures of a Proanthocyanidin (PA). R=H and/or OH.

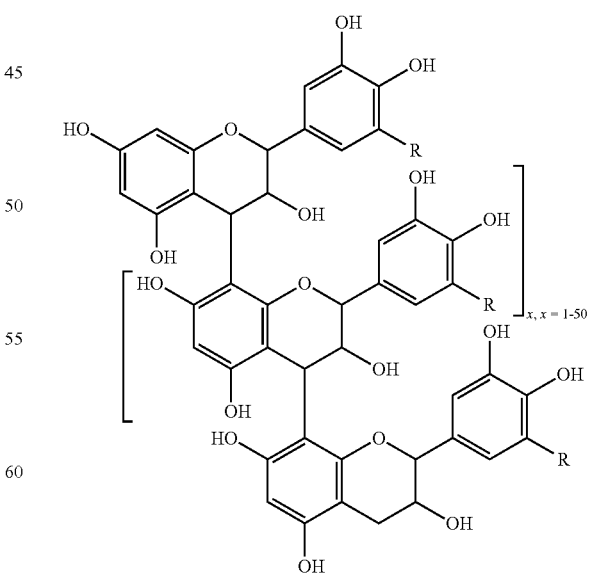

In various proanthocyanidins, the R groups of Scheme 2 can each independently be H or OH. In some embodiments, one or more hydroxyl groups may be glycosylated. In some embodiments, x is 1 to about 50, 1 to about 25, 1 to about 20, 1 to about 12, 1 to about 10, or a range of between any to integers from 1 to 50. The condensed tannins (PAs) can have various interflavanoid linkages (such as A-type 4→8 or 4→6 interflavan bonds, or B-type 4→8, 2→O-7 interflavan bonds, each α or β), cis- or trans-stereochemistry, and one or more hydroxyl groups can optionally be absent on the A-ring, B-ring, C-ring, or a combination thereof.

Other PA tannins include glycosylated heteropolyflavans, such as those illustrated in Scheme 3. Representative compounds shown in Scheme 3 include proluteolinidin ($R^1$=OH); proapigininidin ($R^1$=H); eriodictyol ($R^2$=H); and eriodictyol 5-O-β glucoside ($R^2$=glucose). Krueger et al. has described a variety of known heteropolyflavans-3-ols and glycosylated heteropolyflavans (see *J. Agric. Food Chem.* 2003, 51, 538-543, which is incorporated herein by reference).

Scheme 3. Representative Structures of Proanthocyanidins (PAs).

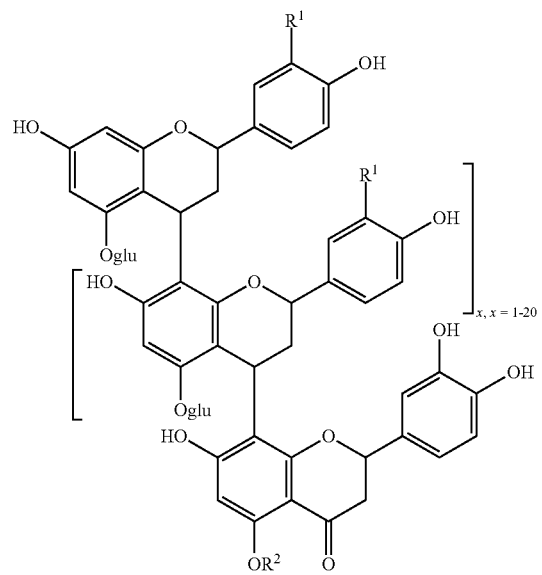

where $R^1$ is H or OH; $R^2$ is H or glucose; and glu is glucose (e.g., a β-glucoside).

In some embodiments, x of Scheme 3 is 1 to about 50, 1 to about 25, 1 to about 20, 1 to about 12, 1 to about 10, or a range of between any to integers from 1 to 50. Several examples of condensed tannins are described in U.S. Pat. No. 7,122,574 (Romanczyk et al.), which is incorporated herein by reference.

A review by Reed et al. (*Phytochem.* 66(18): 2248-2263 (2005)) describes the structural heterogeneity of tannin polyphenols from cranberries, grape seed extracts, sorghum, and pomegranates as characterized by MALDI-TOF MS. Examples of plants that produce proanthocyanidins include cranberries, blueberries, grapes, sorghum, and pine.

Hydrolyzable tannins include gallic acid and ellagic acid esters of polyol core moieties, such as sugars. Scheme 4 illustrates a pomegranate ellagitannin showing structural variation in nature of esterification of the glucose core molecule.

Scheme 4. Representative Structure of a Hydrolyzable Tannin.

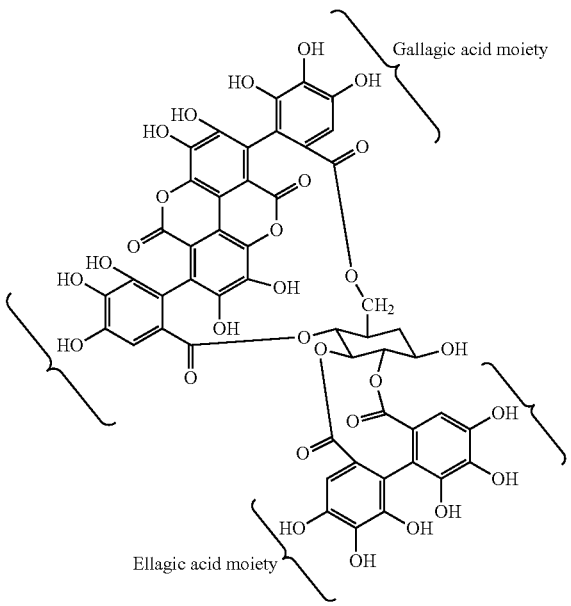

Hydrolyzable tannins, such as the compound shown in Scheme 4, can be isolated in oligomeric forms that include 2 to about 12 hydrolyzable tannin moieties, for example, linked by oxidative C—O coupling between galloyl and hexahydroxydiphenoyl moieties of the monomeric precursors. Common coupling also occurs between two ellagic acid moieties, or by addition of gallic acid moieties to the saccharide core of an oligomer. See Quideau and Feldman, *Chem. Rev.* 1996, 96, 475-503, which is incorporated herein in its entirety.

Accordingly, in some embodiments of compositions described herein, the hydrolyzable tannins employed will be oligomeric hydrolyzable tannins. Thus, in some embodiments, oligomeric hydrolyzable tannins include at least two saccharide core moieties. In some embodiments, a hydrolyzable tannin will include one or more (e.g., 1, 2, 3, 4, 5, or more) ellagic acid moieties, and in some embodiments, a hydrolyzable tannin will include one or more (e.g., 1, 2, 3, 4, 5, or more) gallagic acid moieties.

Examples of plants that produce hydrolyzable tannins include pomegranates, strawberries, raspberries, blackberries, and sumac. Significant quantities of hydrolyzable tannins can be isolated from, for example, pomegranate husks. Specific hydrolyzable tannins include punicalin and punicalagin (the alpha or beta isomer of 2,3-(S)-hexahydroxydiphenoyl-4,6-(S,S)-gallagyl-D-glucose, with a molecular weight of 1084) and stereochemical isomers thereof, as well as the hydrolyzable tannins described by Quideau and Feldman (*Chem. Rev.* 1996, 96, 475-503).

In some versions of the invention, the tannin in the nanofiber comprises a condensed tannin, and the condensed tannin comprises a weight average molecular weight ($M_w$) from about 100 Da to about 100,000 Da, such as from about 500 Da to about 100,000 Da or from about 1,000 Da to about 10,000 Da.

In some versions of the invention, the tannin in the nanofiber comprises a hydrolyzable tannin, and the hydrolyzable tannin comprises a weight average molecular weight ($M_w$) from about 100 Da to about 100,000 Da, such as from about 300 Da to about 30,000 Da or from about 1,000 Da to about 10,000 Da.

In some versions, the nanofibers of the invention comprise the tannin and the synthetic polymer in a ratio by mass (mass tannin:mass synthetic polymer) of about 1:99, about 5:95, about 10:90, about 15:85, about 20:80, about 25:75, about 30:70, about 35:65, about 40:60, about 45:55, about 50:50, about 55:45, about 60:40, about 65:35, about 70:30, or 75:25 or within a range between any two of the foregoing ratios. Exemplary ranges include from about 1:99 (mass tannin:mass synthetic polymer) to about 40:60 (mass tannin:mass synthetic polymer), from about 5:95 (mass tannin:mass synthetic polymer) to about 50:50 (mass tannin:mass synthetic polymer), or from about 10:90 (mass tannin:mass synthetic polymer) to about 50:50 (mass tannin:mass synthetic polymer).

In some versions, the nanofibers of the invention have an average diameter in dry form of at least about 1 nm, at least about 5 nm, at least about 10 nm, at least about 25 nm, at least about 50 nm, at least about nm, at least about 75 nm, at least about 100 nm, at least about 125 nm, at least about 150 nm, at least about 175 nm, at least about 200 nm, at least about 225 nm, at least about 250 nm, at least about 275 nm, at least about 300 nm, at least about 325 nm, at least about 350 nm, or at least about 375 nm. In some versions, the nanofibers of the invention have an average diameter in dry form of up to about 200 nm, up to about 225 nm, up to about 250 nm, up to about 275 nm, up to about 300 nm, up to about 325 nm, up to about 350 nm, up to about 375 nm, up to about 400 nm, up to about 425 nm, up to about 450 nm, up to about 475 nm, up to about 500 nm, up to about 525 nm, up to about 550 nm, up to about 575 nm, up to about 600 nm, or more. "Dry form" refers to a form of the nanofiber after electrospinning and in the absence of hydration with an aqueous liquid after the electrospinning.

In some versions, the nanofiber of the invention is present in the form of a nanofiber mat. In some versions, the nanofiber mat in dry form has a mean pore size of at least about 400 $nm^2$, at least about 425 $nm^2$, at least about 450 $nm^2$, at least about 475 $nm^2$, at least about 500 $nm^2$, at least about 525 $nm^2$, at least about 550 $nm^2$, at least about 575 $nm^2$, at least about 600 $nm^2$, at least about 625 $nm^2$, at least about 650 $nm^2$, at least about 675 $nm^2$, at least about 700 $nm^2$, at least about 725 $nm^2$, at least about 750 $nm^2$, at least about 775 $nm^2$, at least about 800 $nm^2$, at least about 825 $nm^2$, at least about 850 $nm^2$, at least about 875 $nm^2$, or at least about 900 $nm^2$. In some versions, the nanofiber mat in dry form has a mean pore size of up to about 550 $nm^2$, up to about 575 $nm^2$, up to about 600 $nm^2$, up to about 625 $nm^2$, up to about 650 $nm^2$, up to about 675 $nm^2$, up to about 700 $nm^2$, up to about 725 $nm^2$, up to about 750 $nm^2$, up to about 775 $nm^2$, up to about 800 $nm^2$, up to about 825 $nm^2$, up to about 850 $nm^2$, up to about 875 $nm^2$, up to about 900 $nm^2$, or up to about 925 $nm^2$.

In some versions of the invention, the tannin forms nodes on and/or in the nanofiber. The term "node" refers to an area of a higher concentration of tannin that is surrounded by an area of a lower concentration of tannin. In other words, "node" refers to a cluster or collection of tannin on and/or within the nanofiber. The term "node" does not necessarily imply a physical "bump" on the nanofiber itself. Thus, the nanofiber can take a fairly uniform beadless form and still have nodes of tannin thereon.

In some versions of the invention, the composite nanofiber is in the form of a matrix comprising the synthetic polymer and the tannin. "Matrix" in this context refers to a solid form in which at least a portion of the constituent members of the matrix are mutually embedded and distributed throughout (e.g., as opposed to one or more of the constituent members being present only on a surface). The term "matrix" does not necessarily imply that that the constituent members of the matrix are each evenly distributed throughout. The tannin, for example, can form a matrix with the synthetic polymer when electrospun therewith but still form nodes.

In some versions, the composite nanofiber in the form of a matrix comprising the synthetic polymer without the tannin, and the tannin is adsorbed only to the outer surface of the matrix. Such a nanofiber can be generated, for example, by electrospinning a nanofiber with the synthetic polymer in the absence of the tannin and then adsorbing the tannin to the outer surface of the pre-formed nanofiber.

In some versions, the tannin is non-covalently bound to the synthetic polymer. Such versions can be made by electrospinning the synthetic polymer together with the tannin under conditions that promote non-covalent interactions between the synthetic polymer and the tannin or by contacting a pre-formed synthetic polymer nanofiber with the tannin under conditions that promote non-covalent interactions between the synthetic polymer and the tannin.

In some versions, the tannin is covalently bound to the synthetic polymer. Such versions can be made by electrospinning the synthetic polymer together with the tannin under conditions that promote covalent interactions between the synthetic polymer and the tannin or by contacting a pre-formed synthetic polymer nanofiber with the tannin under conditions that promote covalent interactions between the synthetic polymer and the tannin. Such covalent interactions do not need to be direct and can include or be mediated by linkers.

In some versions, the nanofiber exhibits, compared to a corresponding nanofiber lacking the tannin, one or more of: enhanced swelling in aqueous liquid; enhanced antibacterial activity; enhanced bacterial adsorption; enhanced fibroblast adhesion; enhanced fibroblast proliferation; and enhanced surface coating of silver nanoparticles. Exemplary methods for determining an absolute or relative level of swelling in aqueous liquid, antibacterial activity, bacterial adsorption, fibroblast adhesion, fibroblast proliferation, and surface coating of silver nanoparticles are provided in the following examples. The term "aqueous liquid" refers to a liquid comprising at least 70% w/w water.

In some versions, the nanofiber is included as a filtration medium in a filter housing. A filter housing is any solid structure configured to direct a fluid (such as liquid) to and through the filtration medium without bypassing the filtration medium.

In some versions, the nanofiber is included as a surface coating on a medical device. "Medical device" in this context refers to any device configured to and/or intended to enter, be implanted in, or directly contact an animal body, such as a mammalian body. Non-limiting examples of medical devices include pacemakers, syringes, catheters, thermometers, sutures, scalpels, dressings, intrauterine devices, tracheal tubes, gauze, insulin pumps, feeding tubes, adhesive bandages, surgical mesh, elastic bandages, gastric bands, speculums, and stents, among others. The nanofiber is preferably coated on a portion of the medical device that contacts a portion of the animal (e.g., mammalian) body. The medical device can be plastic, metal, made of organic materials, or a combination thereof.

In some versions, the nanofiber is included as a surface coating on a biosensor. See, e.g., the following examples.

In some versions, the nanofiber is devoid of natural polymer or comprises natural polymer less than 50% w/w, less than 45% w/w, less than 40% w/w, less than 35% w/w, less than 30% w/w, less than 25% w/w, less than 20% w/w, less than 15% w/w, less than 10% w/w, less than 5% w/w, less than 1% w/w.

The invention also provides methods of producing the nanofibers of the invention. Some methods include providing a solvent mixture comprising nanofiber components and a solvent and electrospinning the solvent mixture into a nanofiber.

In some versions, the nanofiber components comprise the synthetic polymer and the tannin, and the electrospinning generates a composite nanofiber comprising the synthetic polymer and the tannin.

In some versions, the nanofiber components comprise the synthetic polymer and the tannin, the synthetic polymer comprises polycaprolactone, the tannin comprises a condensed tannin, and the electrospinning generates a matrix comprising the synthetic polymer and the tannin, wherein: the nanofiber components are present in the solvent mixture in a concentration from about 4 to about 14 mg/mL; the solvent mixture has a viscosity from about 90 mPa s to about 130 mPa s; the solvent mixture has a conductivity from about 1.0 µS/cm to about 5.0 µS/cm, such as from about 1.2 µS/cm to about 3 µS/cm; the electrospinning is performed at an applied voltage from about 10 kV to about 25 kV, such as from about 16 kV to about 20 kV; the electrospinning is performed at a flow rate from about 0.5 mL/h to 1.5 mL/h, such as from about 0.8 mL/h to about 1.2 mL/h; and/or the electrospinning is performed with a needle-collector distance from about 8 cm to about 30 cm, such as about 8 cm to about 20 cm or from about 8 cm to about 12 cm.

In some versions, the nanofiber components comprise the synthetic polymer and the tannin, the synthetic polymer comprises polycaprolactone, the tannin comprises a hydrolyzable tannin, and the electrospinning generates a matrix comprising the synthetic polymer and the tannin, wherein: the nanofiber components are present in the solvent mixture in a concentration from about 8 to about 14 mg/mL; the solvent mixture has a viscosity from about 115 mPa s to about 155 mPa s; the solvent mixture has a conductivity from about 0.5 µS/cm to about 3.0 µS/cm, such as from about 0.5 µS/cm to about 1.0 µS/cm; the electrospinning is performed at an applied voltage from about 10 kV to about 20 kV, such as from about 10 kV to about 14 kV; the electrospinning is performed at a flow rate from about 0.5 mL/h to about 2.0 mL/h, such as from about 0.8 mL/h to about 1.2 mL/h; and/or the electrospinning is performed with a needle-collector distance from about 8 cm to about 20 cm, such as from about 8 cm to about 12 cm.

In some versions, the nanofiber components comprise the synthetic polymer without the tannin, the electrospinning generates a matrix comprising the synthetic polymer without the tannin, and, after the electrospinning, the tannin is adhered to the matrix to thereby form a composite nanofiber comprising the synthetic polymer and the tannin. The tannin in such a version can be covalently or non-covalently adhered to the matrix to thereby form the composite nanofiber.

The invention also provides methods of isolating cells. The methods comprise contacting a cell-containing medium with a nanofiber as described herein, wherein cells in the cell-containing medium adhere to the nanofiber.

In some versions, the cells comprise bacteria. In some versions, the cells comprise fibroblasts.

In some versions, the cell-containing medium is a fluid. In some versions, the fluid is a liquid. Exemplary liquids include bodily fluids, such as blood, serum, plasma, lymph, etc.; cellular growth media or other media requiring sterilization; among others. In some versions, the fluid is a gas.

In some versions, the nanofiber is in the form of a nanofiber mat. The contacting can comprise flowing the cell-containing medium through the nanofiber mat.

In some versions, the nanofiber is included as a surface coating on a medical device. In some versions, the cells adhering on the nanofiber include bacteria, and the adherence reduces bacterial growth. In some versions, the cells adhering on the nanofiber include fibroblasts, and the adherence can stimulate fibroblast proliferation.

The invention also provides methods of filtration. These methods include flowing a fluid through a nanofiber mat, wherein the nanofiber mat comprises a nanofiber as described herein. The fluid can be a liquid or a gas, for example.

The invention also provides methods of detecting a cell. These methods comprise contacting a medium suspected of containing the cell with a biosensor, wherein the biosensor is coated with a nanofiber as described herein. The cell can comprise a bacterium.

In any version of the invention described herein, a natural polymer can be used in addition to or in place of the synthetic polymer.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure from 1 to 10 should be construed as supporting a range from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Bioactive Plant-Based Electrospun Nanofibers and their Applications

In the following examples, multi-component electrospun nanofibers (ESNFs) incorporating bioactive compounds were produced and evaluated for various applications. Different bioactive compounds, such as polysaccharides and polyphenols, were used to prepare ESNFs in conjunction with biocompatible polymers. The ESNFs were extensively characterized and evaluated for applications such as potential scaffolding biomaterials for tissue engineering, as bacterial-attachment coating agents of medical devices, and as drug delivery systems.

INTRODUCTION

Overview

Over the previous 100 years, the expansion and mass manufacture of chemically synthesized drugs have transformed health care in most parts of the world. However, large portions of the population in developing countries still rely on traditional practitioners and plant-based medicines for their primary care (WHO 2005). Nevertheless, the use of traditional medicine is not restricted to developing countries, and through the past two decades, public attention in natural therapies has augmented significantly in industrialized countries, with intensifying use of ethnobotanicals (Wachtel-Galor and Benzie, 2011). Although plant-based extracts come in numerous forms, they have one shared feature. Extracts represent naturally occurring phytochemicals (plant-produced chemical compounds) that have been obtained from the inert structural fraction of the plant that produced them. The leading benefit of using extracts over raw herb is that once obtained from the plant matrix, the phytochemicals avoid the necessity of digestion and are furthermore readily absorbable. As indicated by the World Health Organization, approximately 20,000 medicinal plants exist in 91 countries (WHO 2005). Thousands of phytochemicals from plants, such as polyphenols, tannins, and polysaccharides, among others, have been recognized as harmless and broadly effective alternatives with less adverse effects. Several advantageous biological effects, such as anticancer, antimicrobial, antioxidant, antidiarrheal, analgesic, and wound healing activity, have been reported (Kumar et al. 2015; Oveissi et al. 2019).

Bioactive Plant-Based Extracts in Biomedical Engineering

Recently, there has been an augment in the number of studies in the area of bioactive plant-based extracts and their potential applications in biomedical engineering. Bioactive plant-based extracts demonstrate advantages relative to other synthetic functional components in that they have minimal health and ecological concerns, whereas they possess diverse bioactive capacitates and generally recognized as safe ingredients. Bioactive plant-based extracts have been proved to be able to fortify polymer-based biomaterials via modifying their physicochemical properties and further extend their applications (Madrigal-Carballo et al. 2016). More encouragingly, plant-based extracts can also impart polymeric biomaterials with certain biological properties such as antioxidant capacities or antimicrobial properties (Thilagavathi and Bala, 2007; Wang et al. 2013).

The therapeutic efficiency of plant-based extracts have been limited by various factors, including the lack of targeting capacity and poor bioavailability. Biomaterials composed by hydrophilic polymer networks may be able to act as suitable loading and delivery systems for bioactive plant-based extracts. They are biocompatible and may enable sustained drug release. Polymeric biomaterials, therefore, have attracted extensive studies in biomedical engineering for encapsulating bioactive plant-based extracts (Malafaya et al. 2007; Kayaci and Uyar, 2012; Alborzi et al. 2014).

Nanotechnology Approaches to Bioactive Plant-Based Extracts

Nanotechnology-based biomaterials and natural products represent two growing research fields, revealing bioactive plant-based extract compounds may play a role not only as nutraceuticals in affecting human health but also in improving physical-chemical properties of biomaterials used in biomedical engineering (Varoni et al. 2012; Noruzi, 2016). As the popularity of multicomponent polymer-based biomaterials containing bioactive plant-based extracts has increased, various techniques have been attempted to retain better or maximize their functionalities. However, the selection of matrix polymers and plant-based extracts, in various combinations, have been limited to biofilm casting technique (Wang et al. 2012; Wang and Rhim, 2016). New methodologies, such as nanotechnology, are rising as promising techniques in promoting developments in this area. Nanomaterials are considered promising carriers for bioactive plant-based extracts, as they offer a much larger surface area to volume ratio as compared to their micro counterparts. Amongst the many different loading techniques for fabrication of nanomaterials containing plant-based extracts, electrospinning approaches have recently gained considerable attention due to their simplicity, versatility, and cost-effectiveness (Moomand and Lim, 2015; Wen et al. 2016; Hani et al. 2017). Application of the electrospinning method in filtration, electronics, tissue engineering, enzyme immobilization, and textiles has been well studied. However, not many studies have addressed the fabrication of multicomponent electrospun nanofibers (ESNFs) loaded with crude plant-based extracts within a biomedical grade polymeric matrix for applications in biomedical engineering.

Furthermore, biomaterial surface properties regulate host cell and tissue responses to biomedical devices, as well as biological integration of biomedical prostheses and tissue-engineered constructs (Varoni et al. 2012). Consequently, the biomaterial-host interface represents a key-point in biocompatibility and functionality of devices or products interacting with the human body and greatly depends on biomaterial composition and surface properties. This interface can be modulated through different surface coatings in order to improve the biomaterial-cell/tissue interactions for cell proliferation and differentiation (Reyes et al. 2007, Avila et al. 2009). Only recently, plant-based extracts composed by polysaccharides, polyphenols, and proteins rich in bioactive phytochemicals have been investigated in enhancing the performance of medical biomaterials. However, this approach is a real challenge for biomedical engineering researchers, being just a new-born field, still to be thoroughly investigated.

The present examples show the nanoencapsulation process of bioactive plant-based extracts within different biopolymer matrixes via electrospinning technique, allowing fabricating multicomponent electrospun nanofiber (ESNF) templates with encapsulated plant-based extracts. In addition, improvement in chemical and biological properties of multicomponent ESNF templates containing bioactive plant-based extracts was evaluated against ESNF templates containing no plant-based extracts; properties such as chemical interactions, plant-based compound release, antioxidant properties, antibacterial properties, bacterial attachment, cell attachment and proliferation, were evaluated in vitro. Overall, the examples show the development of polymer-based ESNF as carriers of bioactive plant-based extracts and shows the relationships between ESNF properties and carrier performance.

The present examples show the fabrication of multicomponent electrospun nanofiber (ESNF) templates that incorporate bioactive plant-based extracts for applications, for example, in biomedical engineering. Different sources of bioactive plant-based extracts, such as polysaccharides and polyphenols were selected according to their well-known biological properties. The addition of plant-based extracts to synthetic polymer-based ESNF templates increases hydrophilicity, promotes cell attachment and proliferation (associated with wound healing), induces antibacterial properties (bacterial attachment and bacteriostatic effects), and improves biocompatibility when compared to the polymeric ESNF templates alone.

Different multicomponent ESNF systems containing plant-based extracts were developed covering the different approaches. One ESNF system contained polyphenols extracted from cranberry (*Vaccinium macrocarpon*) and can be applied, for example, as biomaterial surface coating agent for preventing proliferation of bacterial infections associated with catheters and similar medical devices. Another ESNF system contained polyphenols extracted from rambutan (*Nephelium lappaceum*) and can be applied, for example, in the fabrication of antibacterial and antioxidant multicomponent ESNF templates, in incorporating antibacterial silver nanoparticles (AgNP), and in applications in chronic wound management.

Background

Electrospinning

Electrospinning is a technique for fabrication of nanofibers based on electrostatic interactions that have been widely used because of its versatility for applications in diverse scientific fields. Successful applications of electrospinning technique have been reported in the fields like nanofiltration, drug delivery, tissue engineering, wound healing, and biosensors, among others (Frenot and Chronakis, 2003). One of the major advantages of electrospinning technique, over other available methods for fabrication of nanofibers, is its ability to fabricate fibers in the nanoscale, from a wide variety of polymer matrixes, with consistent reproducibility and homogeneity, challenging to achieve by using standard mechanical fiber-formation techniques.

The term "electrospinning" is derived from "electrostatic spinning" and has been spread exponentially since 1994 (Bhardwaj and Kundu, 2010). This technique involves the use of a high voltage to induce the formation of a liquid jet and has been considered as a variant of the electrostatic spraying (or electrospray) method. In the electrospinning process, a solid fiber is generated as the electrified jet composed of a highly viscous polymer solution is continuously stretched due to electrostatic repulsions between surface charges and solvent evaporation. By contrast, electrospray produces small droplets or particles that are formed as a result of the break-up of the electrified jet that is often dissolved in a low viscosity solution (Li and Xia, 2004; Agarwal, 2008).

Electrospinning Setup and Principles for Nanofibers Fabrication

A typical electrospinning setup usually includes a syringe pump to control the flow rate of polymer solution, a metallic spinneret for ejecting fibers, which is connected to a high voltage supply to apply an electric current between the nozzle positively charged and a collector grounded or charged to a negative voltage, as illustrated in FIG. 1 (Pan et al. 2016; Zhang et al. 2016). The setup of the electrospinning system provides a straightforward electro-hydrodynamical mechanism allowing fabricating nanofibers with average diameters in the range from 500 nm to even 5 nm (Khajavi and Abbasipour, 2012).

A standard setup for producing randomly oriented electrospun nanofibers is shown in FIG. 1. This setup constitutes the most simple, easy to use and less expensive arrangement based only on a single nozzle with a metal plate collector that can be placed in either a vertical or horizontal position, with the positive and negative electrodes connected to the spinneret and collector, respectively (Li et al. 2006).

The process involved in the fabrication of polymeric ESNFs begins when electric charges are moving into the polymer solution via the metallic needle, inducing instability within the polymer solution as a result of the induction of charges on the polymer droplet. This process is simultaneously accompanied by the mutual repulsion of charges that yields to a force that opposes the surface tension, causing the polymer solution to flow in the direction of the electric field. As the electric field is increased, the spherical droplet will deform and assume a conical droplet shape known as a "Taylor cone," allowing the formation of ultrafine nanofibers that will be collected in a metallic collector located at an optimal distance from the metallic needle. A stable charge jet can only be formed when the polymer solution has sufficient cohesive forces. During the process, both internal and external electrical forces will promote the movement of the liquid jet in the direction of the collector, allowing the polymer chains within the solution to stretch and slide past each other, resulting in the formation of nanofibers (Haider et al. 2018).

Although the most abundant work in the field of electrospinning has been of an experimental nature, some theoretical studies had shown that the driving force behind the bending instability of electrospun jet and fiber formation is the electrostatic forces, becoming responsible for the increase in nanofiber diameter and the production of randomly aligned nanofibers, thus suggesting that manipulation of electric field lines will help to control the trajectory of the electrospun jet and the architecture of the final electrospun nanofiber membranes (Sahay et al. 2011).

Based on an understanding of the role played by the electrical field in electrospinning process, a large number of modifications have been incorporated into the basic design for fabricating different nanostructures with a variety of nanofiber orientations and configurations. Most of those modifications are based on modifications in the spinnerets and collectors, allowing preparing nanofibers with random, aligned, twisted, or core-shell structures (Zhang et al. 2016). However, fabrication of aligned ESNFs requires a modification in the collector design by the substitution of the metal plate with a high-speed rotating metal drum collector, that will collect and align the fibers by rotational speed as they are formed at the spinneret (Matthews et al. 2002). In another modification of the basic setup, the addition of coaxial nozzles provide a simple way to produce continuous core-shell structured nanofibers composed by two different solutions filled into the outer and inner nozzles (Sun et al. 2003).

Parameters Affecting Electrospinning

The production of nanofibers via electrospinning is affected by many operating parameters associated with the process, such as solution (polymer concentration, viscosity, solvent and solution conductivity), environment (relativity humidity and temperature), applied electric field, space between the needle and collector as well as needle diameter, and flow rate (Haider et al. 2018).

Figure 2:
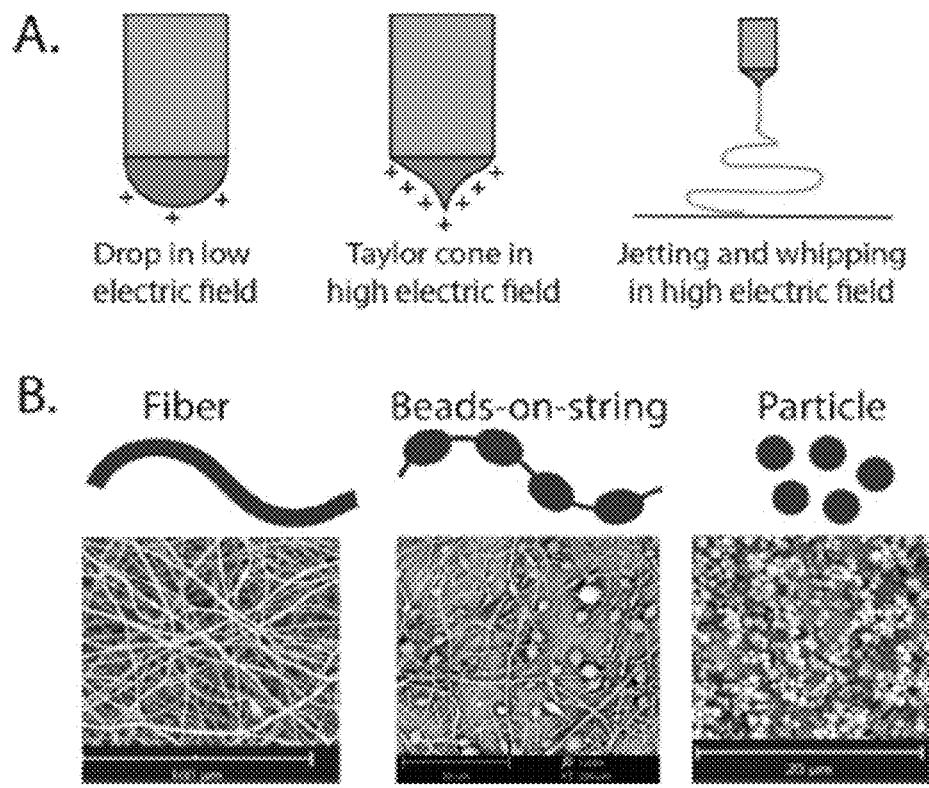
FIG. 2. Illustration of the Taylor cone and jetting formation during electrospinning process (A) and scanning electron microscopy showing the principal morphologies formed (B) from left to right: beadless fibers, beads-on-strings, and particles (Ewaldz and Brettmann 2019).

The mechanical integrity of nanofibers plays an essential role in their applicability in many promising fields. For electrospun nanofiber mats, the chosen solution and process parameters, are accompanied by a certain level of mechanical and morphological properties. Effective control of these parameters would enable one to achieve optimal nanofiber mats (Tarus et al. 2016). Depending on the electro-processing parameters, three primary morphologies can be formed: beadless fibers, beads-on-string fibers, or particles, as shown in FIG. 2.

Process parameters affecting homogeneous nanofiber formation during the electrospinning process include:

Effect of voltage: The flow of current from a high-voltage power supply into a solution via a metallic needle will cause a spherical droplet to deform into a Taylor cone and form ultrafine nanofibers at a critical voltage (Haider et al. 2018). This critical value of applied voltage varies from polymer to polymer. The formation of smaller-diameter nanofibers with an increase in the applied voltage is attributed to the stretching of the polymer solution in correlation with the charge repulsion within the polymer jet (Sill and von Recum, 2008). An increase in the applied voltage beyond the critical value will result in the formation of beads or beaded nanofibers, attributed to the decrease in the size of the Taylor cone and increase in the jet velocity for the same flow rate (Deitzel et al. 2001).

Effect of flow rate: The flow of the polymeric solution through the metallic needle tip determines the morphology of the ESNFs. Uniform beadless ESNFs could be prepared via a critical flow rate for a polymeric solution. This critical value varies with the polymer system. Increasing the flow rate above the critical value could lead to the formation of beads. Because increases and decreases in the flow rate affect the nanofiber formation and diameter, a minimum flow rate is preferred to maintain a balance between the leaving polymeric solution and replacement of that solution with a new one during jet formation (Megelski et al., 2002). This will also allow the formation of a stable jet cone and sometimes a receded jet (a jet that emerges directly from the inside of the needle with no apparent droplet or cone) (Zargham et al. 2012).

Effect of surface charge density: Any change in the surface charge density may also affect the morphology of the nanofiber. An increase in the flow rate simultaneously increased the electric current and decreased surface charge density. Likewise, a reduction in the surface charge density will allow the merging of ESNFs during their flight toward the collector. This merging of nanofibers facilitates the formation of garlands (Fallahi et al. 2008; Haider et al. 2018).

Effect of needle-collector distance: The distance between the metallic needle tip and collector plays an essential role in determining the morphology of an electrospun nanofiber. Similar to the applied electric field, viscosity, and flow rate, the distance between the metallic needle tip and collector also varies with the polymer system. The nanofiber morphology could be easily affected by the distance because it depends on the deposition time, evaporation rate, and whipping or instability interval (Matabola and Moutloali 2013). Hence, a critical distance needs to be maintained to prepare smooth and uniform ESNFs, and any changes on either side of the critical distance will affect the morphology of the nanofibers (Abdel-Hady et al. 2011).

There are also some properties of the solution that can determine the efficiency in the electrospinning process:

Effect of polymer concentration and solution viscosity: The electrospinning process relies on the phenomenon of the uniaxial stretching of a charged jet. The stretching of the charged jet is significantly affected by changing the concentration of the polymeric solution. For example, when the concentration of the polymeric solution is low, the applied electric field and surface tension cause the entangled polymer chains to break into fragments before reaching the collector (Haider et al. 2013). These fragments cause the formation of beads or beaded nanofibers. Increasing the concentration of the polymeric solution will lead to an augment in the viscosity, which then intensifies the chain entanglement between the polymer chains. These chain entanglements overcome the superficial tension and finally result in uniform beadless ESNFs (Pillay et al. 2013).

Effect of solution conductivity: Solution conductivity not only affects the Taylor cone formation but also helps in controlling the diameter of the nanofibers. In solutions with lower conductivity, the surface of the droplet will have no charge to form a Taylor cone; as a result, no electrospinning will take place. Increasing the conductivity of the solution to a critical value will not only increase the charge on the surface of the droplet to form a Taylor cone but also cause a decrease in the fiber diameter. Increasing the conductivity beyond a critical value will again hinder the Taylor cone formation and electrospinning (Angammana and Jayaram, 2011).

Effect of humidity and temperature: Besides the electrospinning and solution parameters, it has recently been reported that environmental (ambient) factors such as relative humidity and temperature also affect the diameter and morphology of the nanofibers (Huan et al. 2015). Humidity causes changes in the diameter of the nanofibers by controlling the solidification process of the charged jet. This phenomenon is, however, dependent on the chemical nature of the polymer (Pelipenko et al. 2013). On the other hand, temperature causes two opposing effects to change the average diameter of the nanofibers; first it increases the rate of evaporation of the solvent, and second, it decreases the viscosity of the solution. The increase in the evaporation of the solvent and the decrease in the viscosity of the solution lead to a decrease in the mean fiber diameter (Haider et al. 2018).

Application of ESNFs

The manufacture of ultrafine fibers in the nanometer to the sub-micrometer range has opened up new applications in which fibrous materials can be used. Many techniques for ultrafine fiber production exist, from which electrospinning has been outstanding. Materials fabricated through electrospinning have found their way into numerous applications, including food packaging, tissue engineering, wound dressing, protective clothing, high-efficiency filtration, and many more (Tarus et al. 2016). The process is quite economical and straightforward, thus has become the preferred method of choice for many in nanofiber fabrication.

Some bioactive plant-based extracts are susceptible to degradation under physiological conditions. Therefore, these bioactive compounds need to be protected using encapsulation techniques. The immobilization by encapsulation of functional and added-value components from plant-based extracts is an area of great interest for the design of bioactive medical devices (Alborzi et al. 2014). The nonwoven nanofibrous mats fabricated by the techniques described herein can mimic extracellular matrix constituents. The submicron range spun fibers formed by these processes offer several advantages like a high surface area to volume ratio, tunable porosity, and the capacity to handle nanofiber compositions in order to get required properties and function. Throughout the years, more than 200 polymers have been electrospun for various purposes, and the quantity is still rising progressively with time (Bhardwaj et al. 2010).

An optimized design of carriers might provide a controlled release of active compounds during the application of the desired biomaterial. Encapsulation for controlled release or fixation of functional plant-based extracts in nanofibers might provide unexplored means to stabilize and release, allowing designing more effective functionalized biomaterials due to the unique characteristics of the nanofibers (Fernandez et al. 2009). Due to their submicron diameter, the electrospun fibers are advantageous for applications where strong surface activity is needed to promote the residence time of carrier at physiological conditions to enhance the absorption. The ultrafine fibers also confer desirable organoleptic properties such as product transparency and smoothness, which may not be achievable with typical microcapsules that are larger in size (Alborzi et al. 2014).

Polymeric Matrix for Electrospinning

For over approximately 70 years, polymers have transformed the global economy, manufacturing and, predominantly, the fields which involve biocompatible materials, such as food technology and packaging, controlled drug delivery, tissue engineering, regenerative medicine, wound dressing, anti-allergy textiles, and personal care. Several prerequisite criteria for an effective design of proper polymer-based ESNFs for biomedical engineering purposes are: three-dimensional structure and conducive mechanical properties for physical support, high surface area for cellular attachment, biomimetic framework for guiding new tissue formation, and biocompatibility for complying host responses towards the construct nanofiber mats (Bhattarai et al. 2018). Until now, ESNFs have been prepared from approximately 200 different polymers with both synthetic and natural origins (Haider et al. 2018). Natural polymers are more capable of mimicking an extracellular matrix, whereas synthetic polymers can be easier electrospun than natural ones (Sharma et al. 2015).

Natural Polymers

In recent years, nanofibrous mats derived from natural polymers have attracted increasing attention for biomedical applications thanks to their biocompatibility, biodegradation, and low toxicity. Natural polymers are usually challenging to be transformed into nanofibers, and therefore a synthetic polymer is often used in a blend with the natural polymer, or the natural polymer is chemically modified to be processed via high-voltage electric forces (Vineis and Varesano 2018).

Natural polymers such as collagen, gelatin, elastin, fibrinogen, and polysaccharides (chitosan, hyaluronic acid, alginate, or dextran) represent most of the body's native extracellular matrix (ECM). This ECM offers structure and mechanical integrity to tissues, as well as interconnection with the cellular components (Sell et al. 2010). One limitation of ESNFs fabricated with natural polymers is the high fiber density and the resultant fishnet effect, with the fiber density in electrospun mats is often too high to allow for ingrowth of cells. Other disadvantages associated with the use of natural polymers are its low availability, the batch-to-batch variation, and the expensiveness of the material. Furthermore, a significant drawback of natural polymer-based nanofibers is the need for crosslinking in order to prevent rapid hydrolysis of the delicate fibers (Li et al. 2005).

Synthetic Polymers

The advantages in the use of synthetic polymers are their high availability, inexpensiveness, homogeneity, and reactivity, allowing easy chemical modification and controlled properties. Table 1 summarizes the main characteristics of synthetic polymers, making them useful for electrospinning processes. Overall, the use of polyesters, polyanhydrides, and polyurethanes for the fabrication of ESNFs has been well established. Some of the main polymers used for electrospinning are discussed as follows.

Polycaprolactone (PCL): PCT has gotten much attention in biomedical applications due to its biocompatibility and biodegradability (Woodruff and Hutmacher, 2010). PCL is a U.S. Food and Drug Administration approved polymer for implantable materials such as sutures. Electrospinning of PCL, its blends and composites have been tried by many workers for tissue engineering scaffolds (Van der Schueren et al. 2011; Katsogiannis et al. 2015; Malikmammadov et al. 2018). PCL has been electrospun by several research groups investigating nerve repair, tendon regeneration, and tissue engineering of skin (Yang et al. 2016; Gurlek et al. 2017). However, the solvent systems used between research groups vary; for example, PCL can be electrospun with several solvents including, dichloromethane (DCM), trifluoroethanol (TFE) and hexafluoro-2-propanol (HFP). Consequently, the electrospinning parameters required to fabricate fibers of appropriate dimensions and morphologies repeatedly will vary from one solvent system to another because of the variability in conductivity, surface tension and dielectric constant between solvents (Ferreira et al. 2014; Du et al. 2016).

Polyethylene oxide (PEO): PEO is a polyether compound with many applications from industrial manufacturing to medicine (Merrill, 1994). PEO is recognized for aiding the electrospinning of biopolymer solutions that are otherwise not electrospun. Biopolymers have been electrospun into fibers for food and biomedical uses due to their biodegradability and biocompatibility (Zhou et al. 2011). Nevertheless, in aqueous systems, electrospinning of low-molecular biopolymers, like proteins and carbohydrates, dissolved in aqueous solutions has been ineffective in most situations (Nie et al. 2009). To facilitate the electrospinning of aqueous biopolymer systems, a spinning aid polymer such as poly (ethylene oxide) is commonly added. For example, chitosan, keratin, alginate, eggshell membrane, and soy protein fibers have been effectively electrospun from aqueous solutions when PEO is added to the aqueous polymer solution (Duan et al. 2004). There have been numerous works applying PEO as a matrix for electrospinning. Rieger et al. (2016), fabricated chitosan/PEO composite nanofibers for delivery of essential oils (cinnamaldehyde and hydrocinnamic alcohol). The correlations determined for electrospinning plant-derived oils could potentially be applied to other hydrophobic molecules, thus broadening the delivery of therapeutics from electrospun nanofiber mats (Zhou et al. 2011).

Polylactic Acid (PLA): PLA is one of the highest extensively used aliphatic polyesters in tissue engineering and drug delivery applications, due to its biodegradability and excellent biocompatibility (Moradkhannejhad et al. 2017). PLA is mechanically robust and environmentally stable and has therefore attracted interest in applications such as biomedical implants, controlled drug delivery, and other kitchen variety commodity products. Commercial PLA has a hard-grainy morphology but is readily soluble in organic solvents and can be cast into thin films, fibers, foams, or other forms (Picciani et al. 2009). Among all of the biodegradable polymer, PLA is particularly meaningful on biomedical and biocompatible field. For the selection of a suitable non-hazardous solvent or solvent system, it is critical to define the rheological properties and electrospinnability of the solution and the morphology of nanofibers (Jahangir et al. 2017).

Polyvinyl alcohol (PVA): PVA is a very hydrophilic, and biocompatible semicrystalline polymer with exceptional properties such as strength, water solubility, gas permeability, and thermal features. This polymer forms excellent nanofibers through electrospinning, with applications in the field of bio-drugs and tissue engineering (Supaphol and Chuangchote, 2008). PVA is offered in a variety of degrees of hydrolysis (DH) since it is resulting from the hydrolysis or alcoholysis of polyvinyl acetate (PVAc). The properties of PVA are consequently disturbed by DH. A PVA with DH around 87 and 89% has lower mechanical and water resistance than a PVA with DH among 98 and 99.9%. Therefore, the possibility of interacting with other polar polymers would be likely to vary as a function of DH (Park et al. 2010). The electrospinning of PVA solution has been broadly studied for the formulation of biodegradable mats, and inorganic fibers, among others. The dissolution of PVA varies depending on the solvent nature, the extent of hydrolysis in the polymer, and the temperature. Various solution parameters affect the morphology and diameter of electrospun PVA fibers, such as the solution concentration, molecular weight, pH, salt, and surfactant molecules (Son et al. 2005). Also, PVA forms outstanding nanofibers through electrospinning, but its purposes are limited by its high hydrophilicity, which leads to an immediate dissolve on contact with water. Consequently, PVA fibers have been improved by either chemical or physical crosslinking to increase their mechanical properties and water resistance (Tang et al. 2009).

Poly-glutamic acid (PGA): PGA is a natural polymer, non-toxic for human and environment, which is secreted by *Bacillus subtilis* strains. This hydrophilic polymer can be further modified by disulfide crosslinking to prevent solubility in water (Wang et al. 2012). PGA includes of D- and L-glutamic acid units by amide linkages and γ-carboxylic acid pendants. This anionic polypeptide has potential applications as a drug carrier, a biological adhesive, a food additive, and a hydrogel. PGA/chitosan composite scaffolds, due to their better hydrophilicity, cytocompatibility, and mechanical strength, are very promising biomaterials for tissue engineering applications (Tsai et al. 2007; Kim et al. 2018).

TABLE 1

List of exemplary electrospinning polymers for fabricating ESNFs containing bioactive plant-based extracts.

| Molecule | Characteristics |
|---|---|
| Polycaprolactone (PCL) | PCL is an FDA approved, biocompatible polymer that is cost-efficient and therefore commonly used within research, electrospun by itself or within blends to aid in thee lectrospinning of more difficult polymers. |
| Poly ethylene oxide (PEO) | Derivative from PEG, showing fair water solubility and biocompatibility. |
| Poly lactic acid (PLA) | Biodegradable and bioactive thermoplastic aliphatic polyester. Is water insoluble and it degrades slightly in aqueous media. |
| Poly vinyl alcohol (PVA) | Is a water-soluble synthetic polymer prepared from polyvinyl acetate. Intermediate biocompatibility. |
| Poly glutamic acid (PGA) | Is water-soluble, anionic, biodegradable, and edible biopolymer. |

Plant-Based Extracts

Plants enclose a large variety of substances holding antioxidant activity, such as vitamin C, vitamin E, xanthophylls, carotenes, tannins and phenolics. Sources of natural antioxidants are primarily plant-based phenolics that can be found in all parts of the plant (Miser-Salihoglu et al. 2013). The plant-based phenolic compounds, such as flavonoids, exhibit antioxidant properties due to their high redox potential. Some plant-based extracts also exhibit a wide range of antimicrobial activities, anti-carcinogenicity and antiproliferation properties, among many other biological activities that allow considering them as medicinal plants (Krishnan, 2006; Nagori and Solanki, 2011).

Plant Polyphenols for Bioactive Plant-Based Extracts

Polyphenols are secondary metabolites existent in all vascular plants and represent a large family of ubiquitous and diverse substances, from simple molecules to complex structures. These natural substances have in common the presence of one or several benzenic cycles bearing one or several hydroxy functions, originating from the metabolism of shikimic acid and/or polyacetate. To the present-day, several thousands of polyphenolic compounds have been identified in plants and are grouped in various classes. Inside each of these classes, the distinctions around the basic chemical skeleton mainly concern the degrees of oxidation, hydroxylation, methylation, glycosylation, and the possible connections to other molecules (Munir and Edwards-Levy 2011).

Tannins are polyphenols found in plants that can bind and precipitate macromolecules. Although the term tannin was initially derived from the use of tannins in tanning animal skins to make leather, the term is broadly applied to any polyphenolic compound that forms strong complexes with proteins. The molecular weight of tannins varies from 500 Da to more than 3000 Da (Fang and Bhandari, 2010). Furthermore, tannins are divided in two types; condensed tannins and hydrolyzable tannins. Condensed tannins are extensively spread in plants and can affect the quality of foods. They are known as proanthocyanidins and are polymers of 2-50 (or more) flavonoid units, which are not susceptible to hydrolysis. In contrast, hydrolyzable tannins contain carbohydrates such as D-glucose at the center. In the carbohydrate, the hydroxyl groups are partially or entirely esterified with phenolic acids like gallic acid in gallotannins. Hydrolyzable tannins can be hydrolyzed by weak acids or weak bases to produce carbohydrate and phenolic acids (Pietta et al. 2003; Okuda and Ito, 2011; Munir and Edwards-Levy 2011).

Cranberry (*Vaccinium macrocarpon* Ait.) Proanthocyanidin Extract

Cranberry (*Vaccinium macrocarpon* Ait.) consumption has long been associated with prevention of urinary tract infections. The favorable mechanism was historically assumed to be due to the fruit acids causing a bacteriostatic effect in the urine (Howell, 2007). Clinical, epidemiological, and mechanistic studies support the role of cranberry in maintaining urinary tract health. Cranberry proanthocyanidins contain A-type linkages and have been associated with preventing adhesion of P-fimbriated uropathogenic *Escherichia coli* to uroepithelial cells (Howell et al. 2005). Recent advances in cranberry research have expanded the evidence for the role of this *Vaccinium* berry fruit in modulating gut microbiota function and cardiometabolic risk factors (Gupta et al. 2007).

Figure 3:
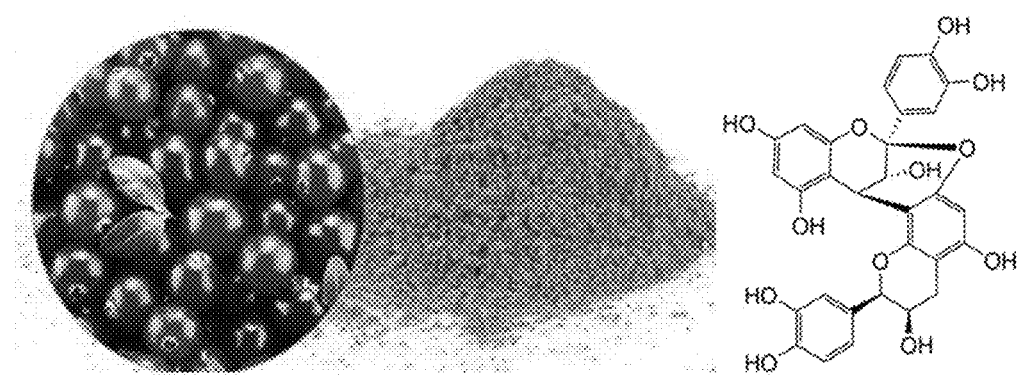
FIG. 3. Illustrative representation of the physical appearance of cranberry (*Vaccinium macrocarpon*) proanthocyanidin extract and the general chemical structure of proanthocyanidins showing A-type interflavonyl linkages (Adapted from Ulrey et al. 2014).

The main active compound in cranberries is the condensed tannin A-type proanthocyanidins (PACs), which covers about 65% of cranberry non-dialyzable material (Ulrey et al. 2014). This oligomer is composed of several types of alpha-linked flavan-3-ols that are replaced with hydroxyls along with the aromatic and fused oxytane rings, as shown in FIG. 3. The A-type structure of cranberry proanthocyanidins seems to be responsible for much of this fruit's efficacy as a natural antimicrobial. Cranberry proanthocyanidins interfere with the colonization of the gut by extraintestinal pathogenic *Escherichia coli* in vitro and attenuate gut barrier dysfunction caused by dietary insults in vivo (Blumberg et al. 2016).

Rambutan (*Nephelium lappaceum* L) Polyphenolic Extract

Figure 4:
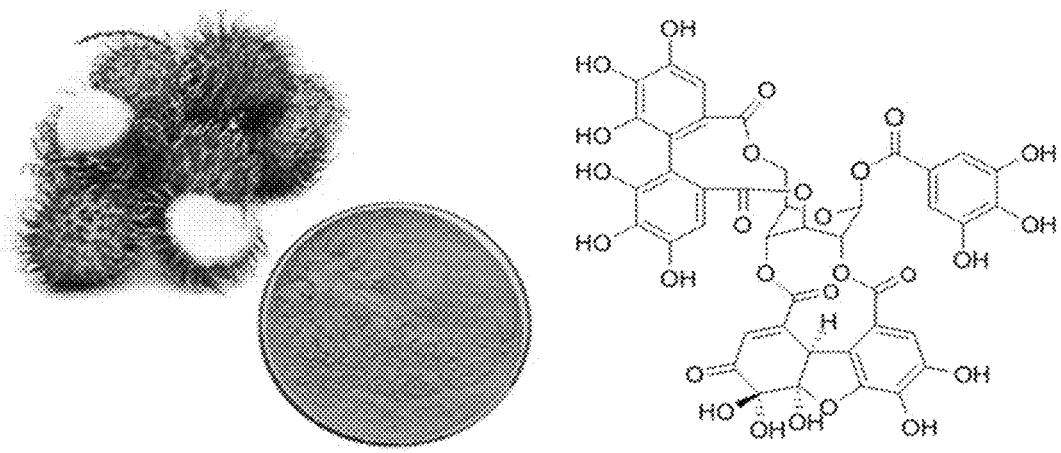
FIG. 4. Illustrative representation of the physical appearance of rambutan (*Nephelium lappaceum*) polyphenolic extract and the general chemical structure of geraniin, the major hydrolyzable tannin found in rambutan polyphenolic extract (Adapted from Elendran et al. 2015).

*Nephelium lappaceum* L. family Sapindaceae, commonly known as rambutan, is an attractive tropical fruit originally from South-East Asia and introduced a couple of decades ago in different Central American countries such as Costa Rica. The estimated annual harvest capacity of rambutan is half a million tons, and its consumption results in vast amounts of waste from seeds and peels of the fruit (Thitilertdecha et al. 2010). The peel contains antioxidant and antimicrobial activity such as tannins and phenolic compounds (Okoro et al. 2010). The antioxidant and microbial capacities associated with plant extracts are primarily due to the presence of associated phenolic compounds (Pathak et al. 1991). These secondary metabolites are located in different parts of the plant, and their quantities are variable according to the vegetative cycle (Maran et al. 2017). Geraniin (FIG. 4), an ellagitannin, was identified as the primary compound in the ethanolic extracts of rambutan rind, with yields of almost 30% by weight and a molecular weight of 952 g/mol (Palanisamy et al., 2011). Geraniin possess a range of bioactive properties, which include antioxidant and free radical scavenging activity, anticancer, antimicrobial, antiviral, and anti-hyperglycemic activity. Corilagin, ellagic acid, and gallic acid are the primary metabolites of geraniin (Elendran et al. 2015).

Polymer Plant-Based Extract Interaction Mechanisms

Electrospinning is growing as a production technology for many applications, particularly in membranes and tissue engineering. However, the materials typically considered electrospinnable are limited to high molecular weight polymers mixed with limited quantities of small molecules, and nanoparticles (Wang et al. 2015). This restriction holds back the technology for applications including filtration, structural materials, and electronic devices. An elevated concentration of high molecular weight polymers is necessary to prevent a breakup of the fiber into droplets during the electrospinning process, where the entanglements of the polymer chains provide the cohesion of the fiber during jetting. An alternative to entanglements that has been pursued is using molecular interactions such as hydrophobic and hydrogen bonding to provide jet cohesion instead of entanglements (Ewaldz and Brettmann 2019).

Molecular Interactions and its Effect on Electrospun Nanofiber Morphology

Molecular interactions can be exploited to broaden applications by enabling the use of a wider variety of materials, for example, nanoparticles, surfactants, cells, and bioactive plant-based extracts, among others. Demand for functionalized devices has led to new technologies being developed, with advanced functions such as flexibility, controlled biodegradation, improved hydrophilicity, cell attachment antibacterial properties, and biological compatibility (Brettmann et al. 2013).

As described above, three morphologies can be formed during the electrospinning process, depending on the operational parameters selected. There is a drive for the thin jet to break into droplets due to the instability, and there must be sufficient stabilizing forces in the polymer solution to maintain the continuous fiber shape until solvent evaporation provides a stiff skin that prevents breakup. Entanglements between polymer chains contribute to the morphology transition from electrosprayed particles to beads-on-string to smooth fibers (Ewaldz and Brettmann 2019).

Physical molecular interactions between polymer units or other molecules in the spinning solutions may provide similar resistance to the breakup of the jet as polymer entanglements and so may also provide stabilization and allow for electrospinning without high molecular weight polymers or at lower concentrations. Hydrogen bonding interactions are strong molecular attractions, and many different polymers and small molecules can participate in hydrogen bonding. The strength of the interactions can be tuned through both molecular design or external stimuli, such as specific functional groups, or temperature, among others. Polymer self-interactions, such as through hydrogen bonding, can increase solution viscosity and elasticity and stabilize the electrospinning jet (Shenoy et al. 2005). A particularly strong molecular interaction is electrostatic, which can be tuned using charge density, specific functional groups, and ionic strength. These are some of the major interactions encountered in advanced electrospinning formulations and are core to designing systems to replace traditional high molecular weight polymer entanglements fibers (Ewaldz and Brettmann 2019).

Figure 5:
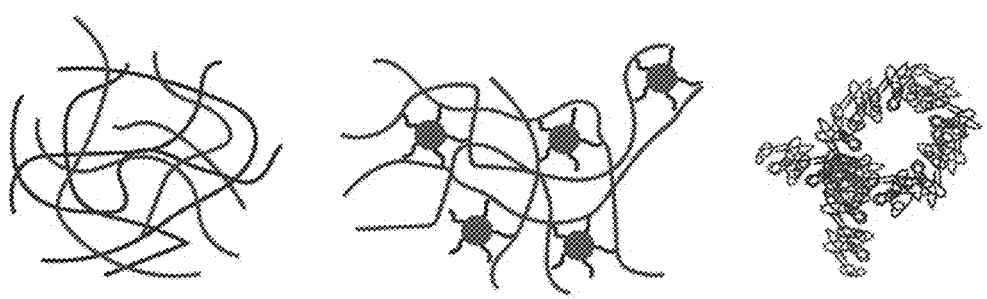
FIG. 5. Illustrative representation of the general categories of molecular interaction during electrospinning process (Ewaldz and Brettmann 2019).

There are three general categories of molecular interactions driving electrospinning: polymer-polymer interactions, polymer-small molecule interactions, and supramolecular polymers from small molecules, as shown in FIG. 5.

Polymer-Small Molecule Interactions

Some of the simplest small molecules used to induce interactions between polymer chains are multivalent ions. Oppositely charged multivalent ions can form bridges between charged polymer chains, driving behavior such as precipitation from solution and collapse of charged polymer brushes (Brettmann et al. 2017). This same phenomenon has been used to maintain jet stability during electrospinning, attributed to the balance between providing sufficient cross-links to maintain jet stability and providing too many cross-links and inducing gelation, which prevents molecular chains from moving independently (Wang et al. 2015).

Some particles have been shown to self-assemble into certain morphologies during the electrospinning process due to interactions such as particle-particle, particle-polymer, and particle-solvent. This can be driven by polar attractions, hydrogen bonding, wetting ability, among others. Studies on large particles (~10 μm) at various loadings have shown that uniform fibers can be produced with proper distribution of particles throughout, but when the processing time is prolonged or at high concentrations, the particles form aggregates within the solution. They create an uneven dispersion of particles in final fibers, showing a node-like aggregate morphology along the fibers (Ewaldz et al. 2018).

Particles have been used to alter the viscosities of polymer solutions as a mechanism to increase the range of polymer concentrations able to be used. It was also found that different concentrations of polymer and polymer-nanoparticle weight ratios produced variant structures due to the viscoelasticity of the solution. When very high amounts of particles are added, the viscoelasticity is not sufficient to form uniform fibers (Bretmann et al. 2012). Though particle-polymer or particle-particle interactions may provide stabilizing forces for the jet, very high concentrations can decrease jet elasticity significantly and prevent electrospinning (Yuan et al. 2012).

Small molecules have been shown to alter how the polymers act in solution as well as the final fiber form. Multivalent ions can be used to form bridges or ionically cross-link chains as a way of balancing the need for sufficient cross-links to maintain jet stability and using low concentrations or low molecular weight polymers. Other small molecule cross-linkers have also been used to tune morphology and stability, including chemical cross-linking (Ewaldz and Brettmann, 2019).

Cranberry Proanthocyanidins-PCL Composite Electrospun Nanofibers

Extraction of Cranberry Proanthocyanidins

Cranberry proanthocyanidins (PAC) were extracted from cranberries according to the methods developed by the Reed Research Group (UW-Madison) involving nitrogen blending, solvent extraction, column chromatography and freeze drying to obtain a freeze-dried powder (Feliciano et al. 2012), which was characterized by HPLC and mass spectroscopy and quantified by the 4-(Dimethylamino)cinnamaldehyde (DMAC) method.

Fabrication of PAC-PCL ESNF

PAC dissolved in dimethylformamide (DMF) was combined with PCL dissolved in organic solvent mixture composed of (7:3 v/v) chloroform and DMF at different concentration ratios (PCL 100 mg/mL, PAC 6 mg/mL:PCL 100 mg/mL, PAC 8 mg/mL:PCL 100 mg/mL and PAC 12 mg/mL:PCL 100 mg/mL). For the process of electrospinning, the PAC-PCL composite solutions, prepared in chloroform and DMF, were placed in a 10 mL syringe fitted with an 18-G needle. An 18-kV electric field using a high voltage power (Gamma High Voltage Research, Ormond Beach, Fla., USA) was applied. The distance between the aluminum foil covering a copper plate and the needle tip was 20 cm to create a 0.9-kV/cm charge density on the composite solution. After 3 mL of the solution was electrospun the mat was removed, placed in a vacuum chamber for at 24 h to remove organic solvent residue, and then stored in a desiccator.

Characterization of ESNF

ESNFs were characterized using attenuated total reflectance Fourier-transform infrared spectroscopy (Nicolet 4700 ATR FT-IR, Thermo Scientific, Gran Island, N.Y., USA), and thermal properties by thermogravimetric analysis (TGA, Q100, TA Instruments, Lindon, Utah, USA). TGA analyses were performed at 20° C./min over a temperature scan range of 50 to 400° C. in a nitrogen atmosphere (20 mL/min). The morphology of nanofibers was observed by using scanning electron microscope (SEM, Leo 1530-FE, Zeiss, Cambridge, UK). The average fiber diameter was determined by analyzing at least 20 fibers in the SEM images using ImageJ software (LOCI, Madison Wis.) according to the method previously reported by Haeri 2015.

Viscosity of the feed solution was measured by stress-sweep test in a programmable rheometer (DV-III ULTRA, Brookfield, UK) with a fixed shear rate of 100 s$^{-1}$ at room temperature. The swelling property of the nanofibers was studied by immersing the samples in PBS 1× at 37° C. for 5, 15, 30, 45, 60, 120, 240 min. Swelling percentage was determined as:

$$\text{Swelling \%} = \frac{W_{Wet} - W_{Dry}}{W_{Dry}} \times 100$$

Where $W_{Dray}$ and $W_{Wet}$ are dry and wet weight respectively (Zhou et al. 2016; Kandhasamy et al. 2017).

Pore area of the ESNFs membranes was calculated from SEM imaging of the ESNFs by ImageJ software combined with DiameterJ package (LOCI, Madison Wis.), this package allows obtaining pixel-based segmented pictures useful for calculation of membrane average pore area (nm$^2$). Segmented pictures contain only black and white pixels, with black pixels representing background and white pixels representing nanofibers. Black pixels were analyzed using the analyze particles command in ImageJ. This algorithm essentially finds discrete clusters of black pixels, counts the number of pixels in each cluster and then reports their area (Hotaling et al. 2015).

Determination of In Vitro Bacterial Attachment

The antibacterial activity of PAC-PCL electrospun biomaterials were tested by the Kirby-Bauer disk diffusion method (Bauer et al. 1966). Nanofibers were cut into ~14 mm diameter circular discs. These discs were put on the surface of agar culture media, after that 25 µL of bacteria (ExPEC 5011) was added to the nanofiber area on the surface of the agar. The plates were incubated at 37° C. The diameters of the growth zones were measured in diameter with transparent ruler. The zones of bacteria growth were estimated after 0-14 days. PCL nanofiber discs was placed as negative control.

Bacterial Attachment Assay

Bacterial attachment assay (Feldman et al. 2012) was conducted using 50 µL of bacteria (ExPEC 5011) stock solution of 1.0×10$^{10}$ colony forming units (CFU)/mL were added to the cuvettes, resulting in a final concentration of 5.0×10$^8$ CFU/mL. Then 45 mg of 8 mm diameter nanofibers were added to each bacterial inoculum cuvette. The cuvettes were gently mixed to ensure that the nanofibers were completely mixed with the bacterial suspension. Light transmission through the cuvettes was measured at 600 nm at 5, 15, 30, 60 min on a DU 640-spectrophotometer equipped with a six-position cuvette holder (Beckman Coulter, Brea, CA). The transmittance (%) and the area under the transmittance curve (AUC) of the normalized data was calculated as a function of the ability of PAC-PCL to attach ExPEC from 0 to 60 min.

Nanofibers were cut into appropriate pieces and primary fixation was done with 2.5% gluteraldehyde (Sigma-Aldrich, St. Louis, Mo.) buffered with 0.01 M phosphate buffered saline (Sigma-Aldrich, St. Louis, Mo.) for 6 h. Post fixation with 1% aqueous solution of osmium tetroxide (TEDPELLA, Inc., CA, USA) overnight. Samples were dehydrated with 20%, 40%, 60%, 80%, 100% ethanol (Sigma-Aldrich, St. Louis, Mo.) 5 min each.

Fluorescent PAC-PCL Composite ESNFs

PCL solution at 100 mg/mL was prepared by dissolving 1 g of PCL into 10 mL of organic solvent (9 mL chloroform+1 mL methanol) and stirring for 4 h at room temperature. Fluorescently labeled PAC (F-PAC) was dissolved in methanol to prepare a stock solution of 5 mg/mL. The samples for electrospinning were then prepared by blending a constant volume of PCL 100 mg/mL (2 mL) with different aliquots of the F-PAC stock solution obtaining three final concentrations of PAC, 250 µg/mL, 500 µg/mL and 1000 µg/mL.

The F-PAC-PCL blends were collected directly onto a microscope glass slide. The distance between the needle and the collector was 10 cm, 12 kV power supply and a flow rate of 1 mL/h were used. The collected ESNFs were then kept at dark in a desiccator. Imaging of the slides containing F-PAC-PCL ESNF was carried out in a fluorescent microscope (Axio Imager 2, Zeiss, Thornwood, N.Y.) at 40× magnification and using Texas Red fluorescent filter.

Fluorescent Imaging of F-PAC:PCL ESNFs and GFP-Labeled *Escherichia coli*

To confirm the previously identified interactions between cranberry PAC and pathogenic *Escherichia coli*, we decided to apply fluorescent microscopy imaging to follow co-localization of both fluorescently labeled PAC (Texas Red) and *E. coli* (Green fluorescent protein, GFP). ESNF membranes were fabricated by combining PCL with F-PAC at three concentrations of 250, 500 and 1000 µg/mL. The membranes were cut in 11 mm diameter circles and placed in a syringe filter. To keep the membranes in position a nylon membrane filter of 0.45 µm was also placed together with the membrane. Fluorescently labeled *E. coli* (GFP-*E. coli*)

was grown for 72 h in culture media and then diluted to a concentration range of $1\times10^9$ to $1\times10^5$ CFU/mL. An aliquot of 4.5 mL of each bacterial dilution was placed in a 5 mL syringe and approximately 1 mL volume was passed through the filter containing ESNF membranes to promote interaction of bacteria with PAC loaded into the ESNFs. Bacteria attached ESNF membranes were then placed in 1 mL glutaraldehyde solution (2.5% v/v) for 4 h to fix and kill the bacteria, followed by rinsing with PBS 1×, pH 7 for 12 h. After fixing and washing bacterial attached ESNF membranes were let to dry and fixed in a glass slide using 500 μL of fluoromount G and then kept at dark in a desiccator. For fluorescent imaging, the samples were visualized in a fluorescent microscope (Zeiss Axio Imager 2) at 40× magnification using Texas Red and GFP fluorescent filters.

Surface Functionalization of Medical Devices (Catheters)

A plastic, biomedical grade PVC, instillation catheter was used as standard reference material for studying surface coating properties of ESNFs onto medical devices. ESNF were collected directly onto the catheter's surface by placing it in the top of the electrospinning system collector. After 3 mL of the feed PAC-PCL blend solution was electrospun on all catheter surface, the sample was removed and placed in a vacuum chamber for 24 h to remove any organic solvent residues, and then stored in a desiccator.

The presence of ESNFs on the surface of the catheter was analyzed using optical microscopy and the morphology of nanofibers was observed by SEM microscopy (Leo 1530-FE, Zeiss, Cambridge, UK). The catheters were cut in square pieces and added to previously inoculated cuvettes containing ExPEC 5011 strain bacterial solution at ($1\times10^8$ CFU/mL). The cuvettes were gently mixed to promote complete immersion of the surface coated catheter section and let it interact with the bacterial solution for 8 h to finally apply the methodology described earlier to fix the bacteria onto nanofibers, followed by SEM imaging as previously described as well.

Data and Statistical Analysis

All data are reported as mean±standard deviation of at least three replicates. Statistical analysis was done using JMP Pro (Version 10.0.0; SAS Institute Inc., Cary, N.C., USA), the differences were considered statistically significant at $p<0.05$. Results were analyzed with two-way ANOVA models with interaction between the independent variables "sample" and "bacterial attached transmittance" to assess significant differences, followed by Tukey's multiple comparison test (n=5). Statistical significances were represented with asterisks denoting statistical highly significative (**, $p<0.01$) and statistically significant (*, $p<0.05$).

Characterization of PAC-PCL ESNF

Figure 6:
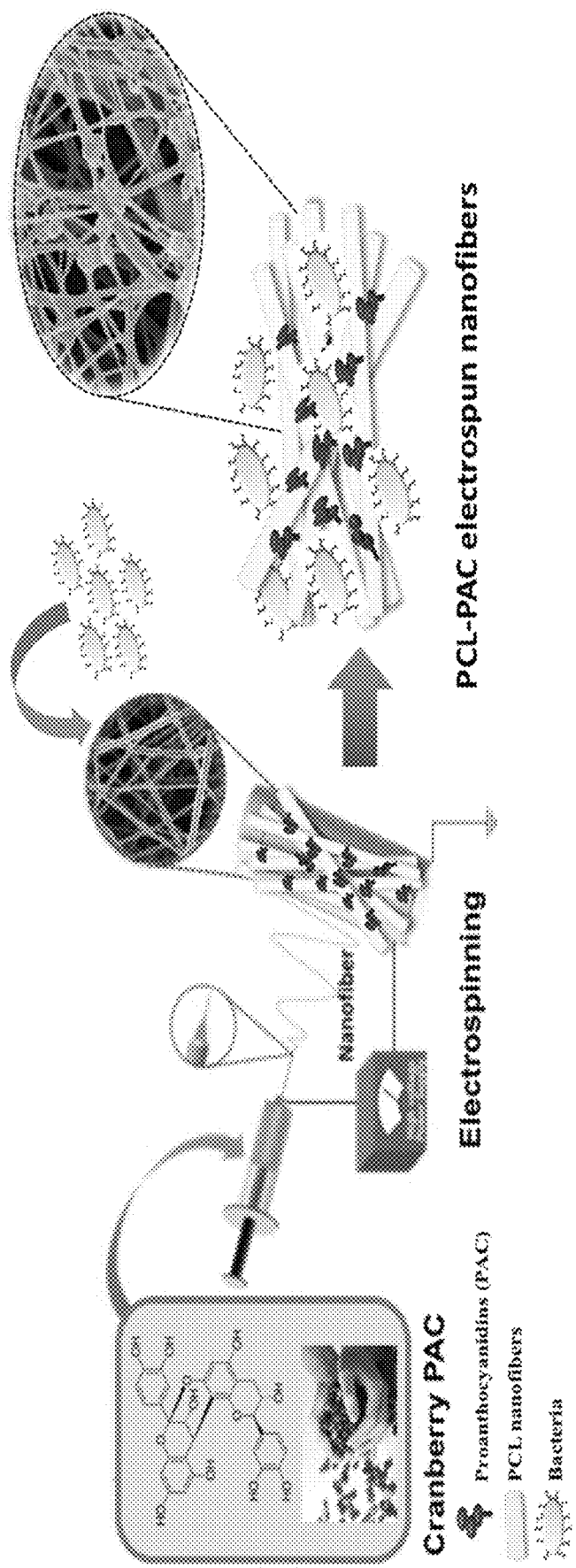
FIG. 6. Scheme for attachment bacteria in electrospun proanthocyanidin-polycaprolactone (PAC-PCL) nanofibers.

Cranberry proanthocyanidins have become a widely used bioactive compounds due to their well-known effects against urinary tract infections. Cranberry PAC seems to interact with surface virulence factors of pathogenic bacteria, especially extra-intestinal pathogenic *E. coli* (ExPEC), limiting mobility and colonization properties of ExPEC by a mechanism involving bacterial attachment when interacting with A-type interflavan linkages present in oligomeric PAC extracts. We predicted that loading cranberry PAC into polymeric ESNFs will provide a functionalized biomaterial for applications where bacterial adsorption or attachment is required, such as prevention of catheter-associated infections, food coating or nanocoating of medical devices. FIG. 6 shows an illustration of the mechanism for functionalization of ESNFs with cranberry PAC bioactive plant-based extract.

Figure 7:
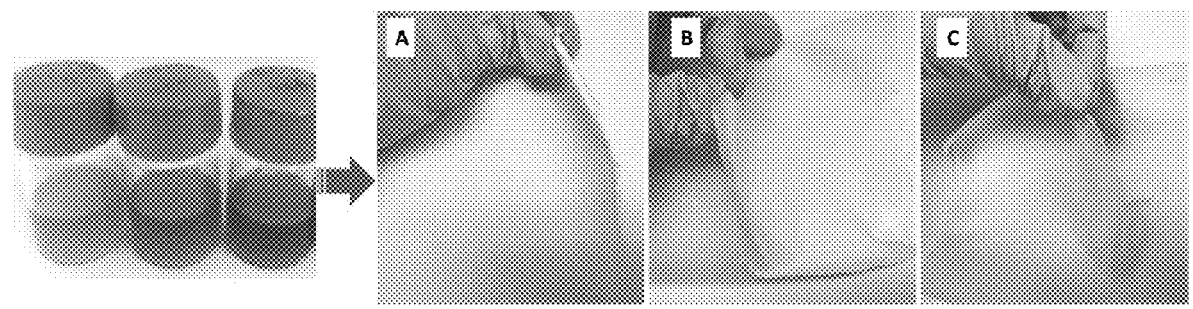
FIG. 7. Photographs showing the physical appearance of PAC-PCL electrospun nanofibers (ESNFs) A. PAC 6 mg/mL:PCL 100 mg/mL, B. PAC 8 mg/mL:PCL 100 mg/mL, C. PAC 12 mg/mL:PCL 100 mg/mL.

Electrospun nanocoatings based on PAC-PCL mixtures were prepared at increasing concentrations of PAC (6, 8 and 12 mg/mL) in a fixed concentration of PCL (100 mg/mL). The resulting nanofiber mats showed slightly reddish coloration and were easily peeled from the collector's parafilm surface, as shown in FIG. 7.

Characterization of the PAC-PCL polymeric blends prior to the electrospinning process was conducted by viscosity and conductivity measurements, as shown in Table 2. Results suggest addition of PAC to PCL polymeric solution reduces viscosity as an effect of a dilution phenomenon but does not seem to significantly affect overall viscosity required for suitable electrospinning process. On the other hand, as PAC concentration increases in the PAC-PCL polymeric blend, solution conductivity shows an increase associated to the higher conductivity of PAC when compared to the one of PCL alone. Since conductivity of the polymeric solution is an important parameter for electrospinning process, as discussed above, addition of PAC to PCL will improve efficacy of the electrospinning process and will allow to obtain PAC-loaded ESNFs with improved physical and morphological properties.

TABLE 2

Correlation between viscosity (measured at a shear rate of $100\ s^{-1}$) and conductivity of cranberry PAC and the PAC-PCL blends before electrospinning. Results are reported as mean ± SD (n = 5).

| PAC-PCL Blend | Viscosity (mPa s) | Conductivity (μS/cm) |
|---|---|---|
| PAC (20 mg/mL) (No PCL) | 3.67 ± 0.09 | 3.12 ± 0.2 |
| PCL (100 mg/mL) (No PAC) | 137.8 ± 2.25 | 1.02 ± 0.8 |
| PAC (6 mg/mL): PCL | 123.3 ± 2.69 | 2.11 ± 0.1 |
| PAC (8 mg/mL): PCL | 121.7 ± 1.94 | 2.33 ± 0.3 |
| PAC (12 mg/mL): PCL | 109.3 ± 1.21 | 2.19 ± 0.1 |

Figure 8:
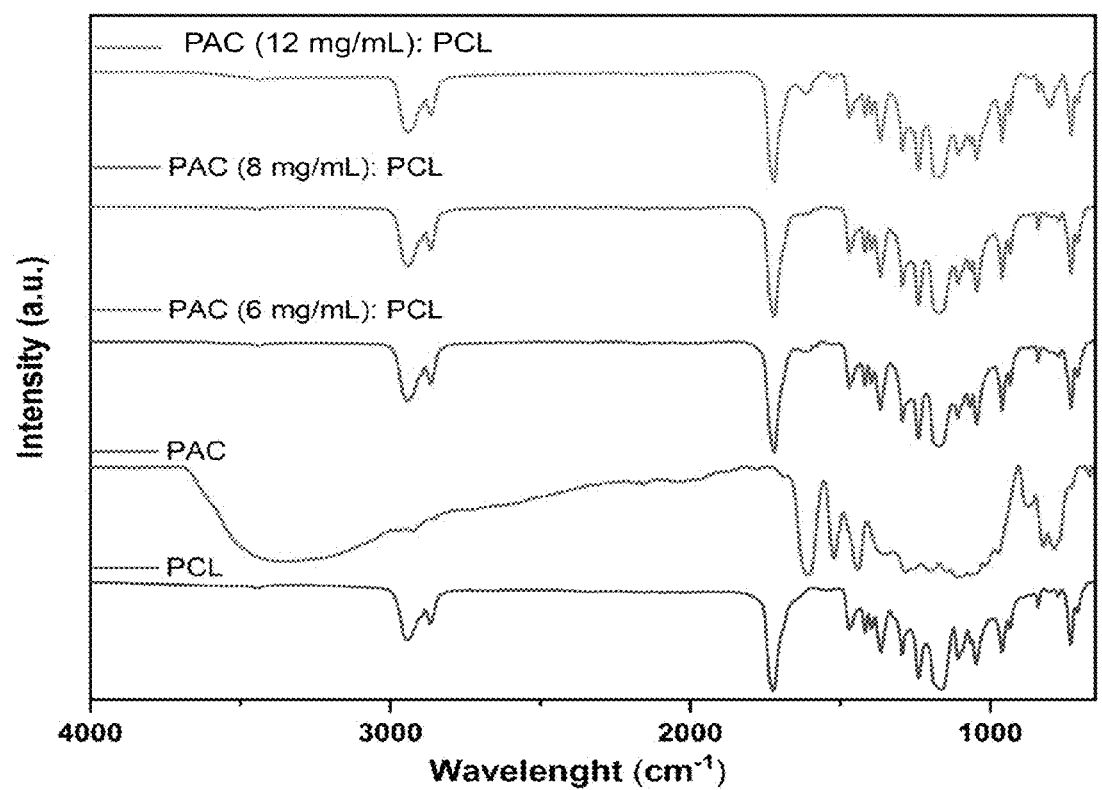
FIG. 8. Attenuated total reflection Fourier transform infrared spectroscopy (ATR-FTIR) spectra of different PAC-PCL ESNFs.

FIG. 8 shows infrared spectra for PAC-PCL composite nanofibers at increasing concentration of PAC added to a fixed percentage of PCL (100 mg/mL). The spectra showed a peak around 2800 $cm^{-1}$ and a very sharp signal at 1750 $cm^{-1}$, corresponding to hydroxyl and ester groups, respectively. The FTIR spectrum for PAC showed a group of characteristic peaks associated to phenolic groups in the range between 1250 to 1500 $cm^{-1}$, together with the large bump around 3000 $cm^{-1}$ associated to the extensive distribution of hydroxyl groups. The spectra for different samples of PCL-PAC show an increase in the characteristic peaks of PAC as the concentration of PAC loaded into the ESNF increases from 6 to 12 mg/mL.

The PCL-related absorption bands at 3500, 1729.6, 1185.9 cm', which indicate carbonyl stretching and axial deformation of C—C, (C=O)—O, are present in the FTIR spectra of the PCL ESNFs. Likewise, as the concentration of PAC increases in the nanofiber matrix, a reduction in the 3500 $cm^{-1}$ band is seen as a result of the interaction between polyphenol moieties from PAC and carbonyl groups in PCL, together with an increase in the phenolic stretching bands around 1700 $cm^{-1}$. No other appreciable changes were found in the comparative FTIR spectra.

Figure 9:
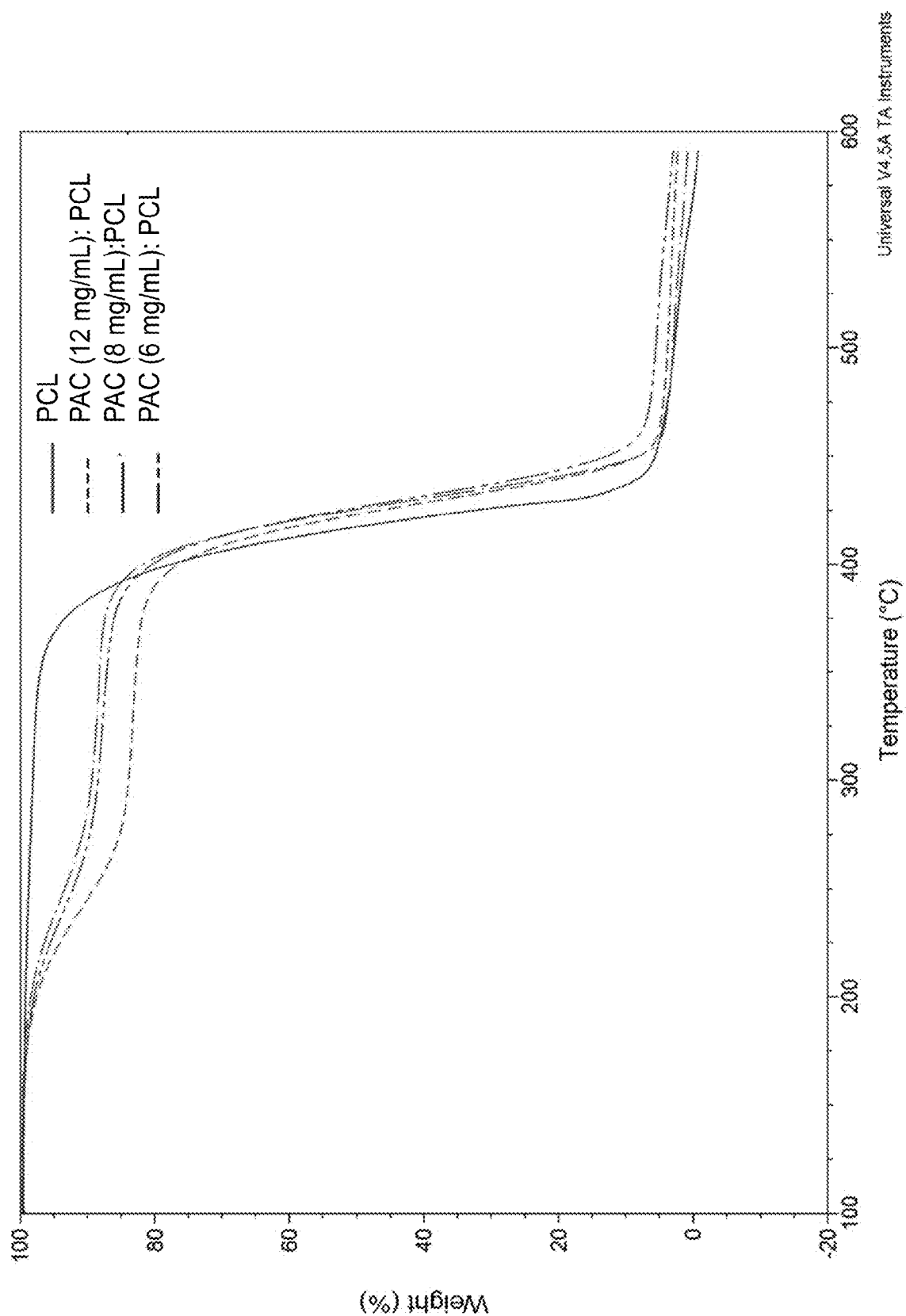
FIG. 9. TGA of PAC-loaded ESNFs membranes fabricated at increasing concentrations of cranberry PAC (6, 8 and 12 mg/mL) and compared against PCL ESNFs alone.
Figure 10A:
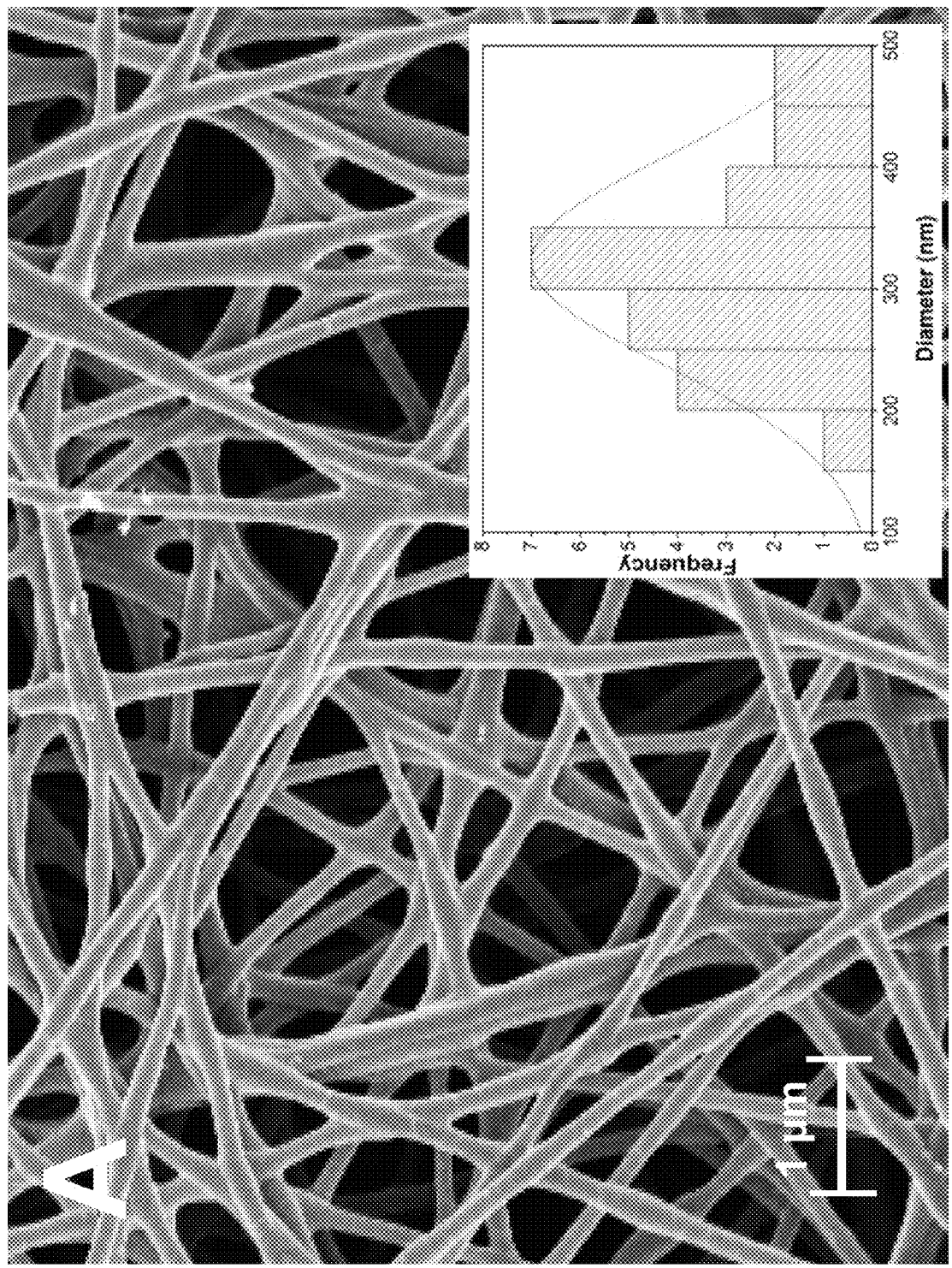
FIGS. 10A-10D. Scanning electron micrographs of PAC-loaded ESNFs.
Figure 10B:
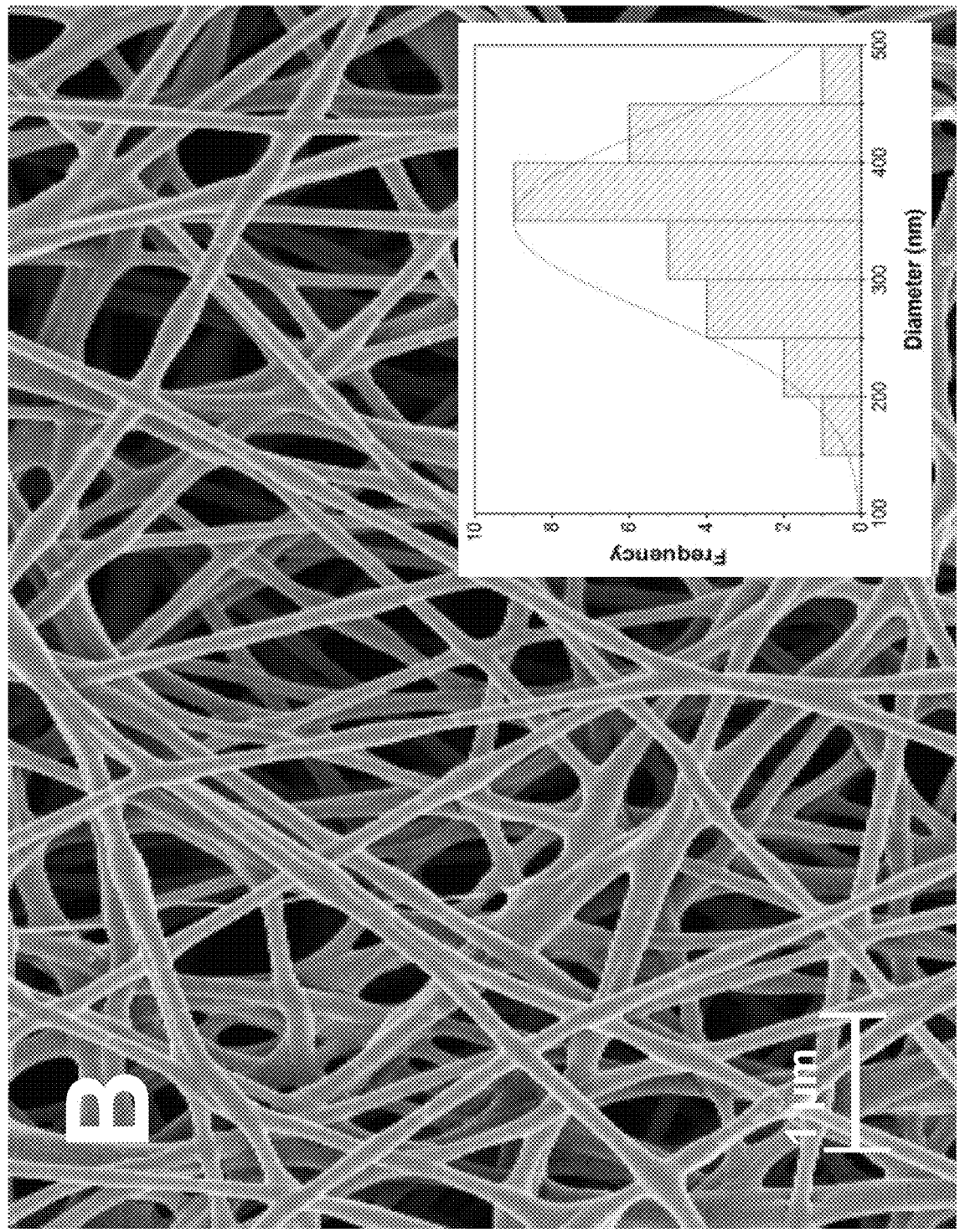
Figure 10C:
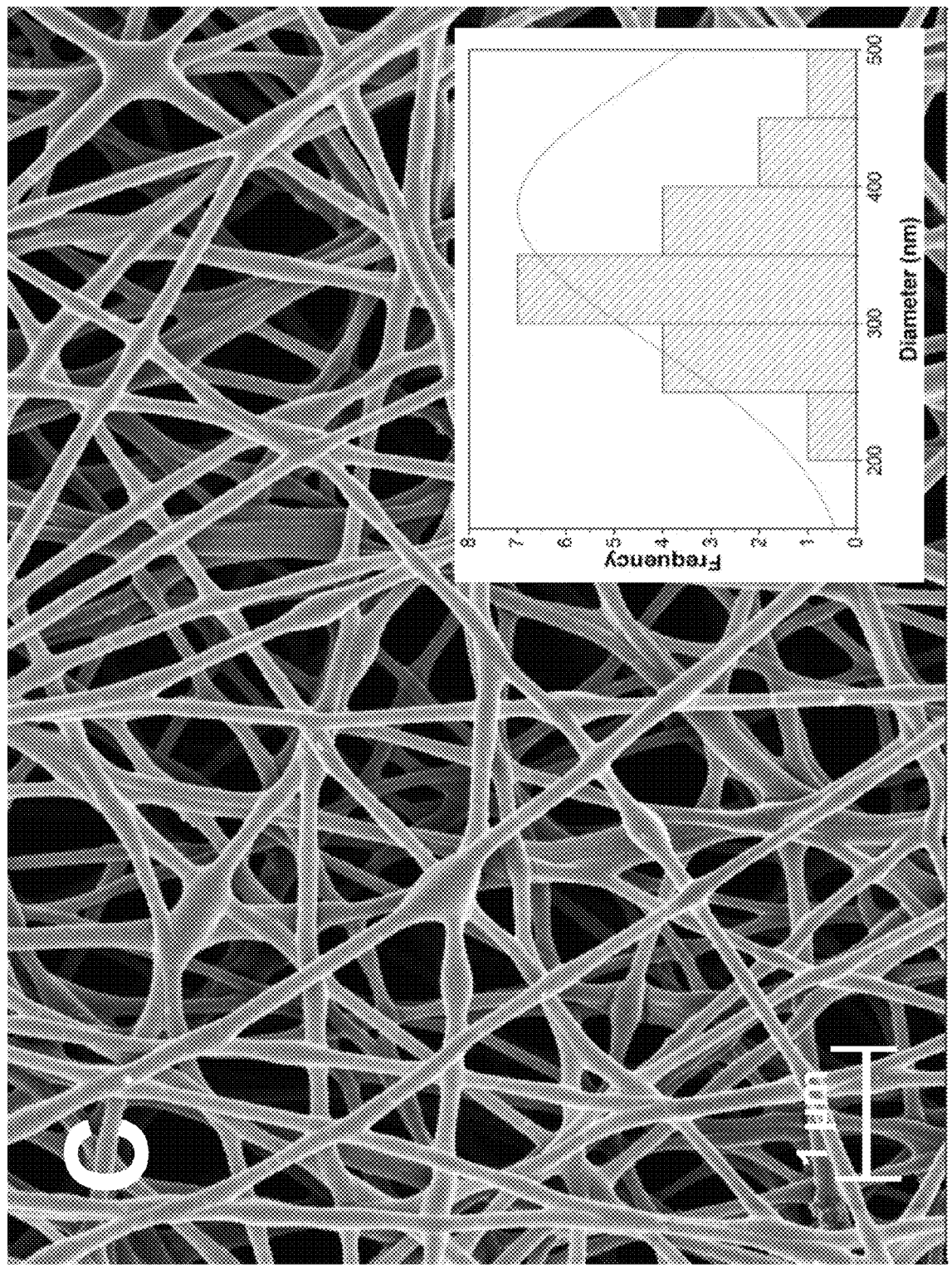
Figure 10D:
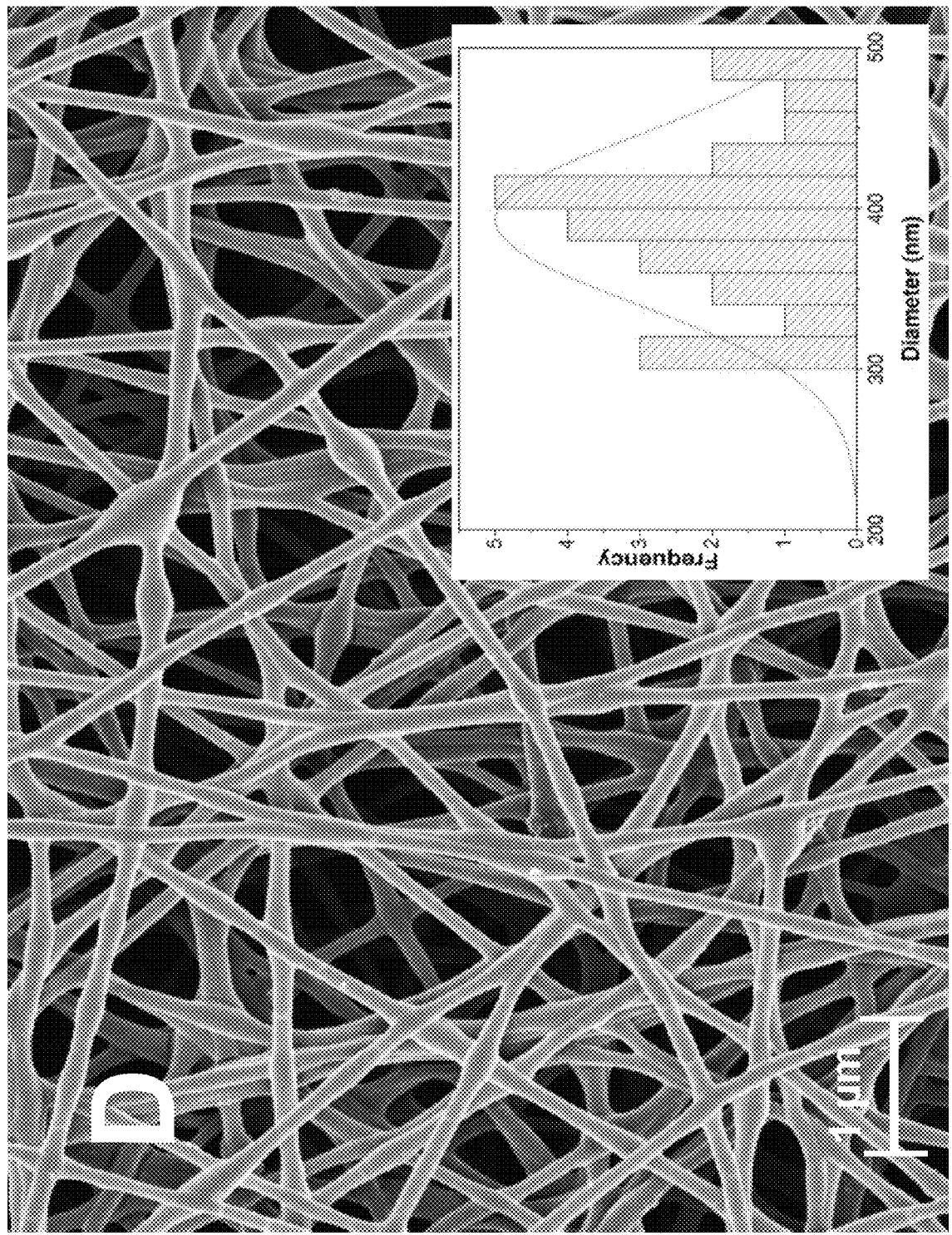

Thermal analysis of the ESNFs by thermogravimetry (TGA) with and without addition of cranberry PAC, presented in FIG. 9, shows a single thermal transition for thermogram of PCL-ESNFs (without addition of PAC) starting around 350° C. and corresponding to >90% the total weight of the membrane; whereas for PAC-loaded ESNFs two thermal transitions can be easily identify, with the first one corresponding to the degradation of cranberry PAC starting slightly below 200° C. and showing a dose-dependent trend for the degraded mass percentage ranging PAC 6 mg/mL (10%)<PAC 8 mg/mL (12%)<PAC 12 mg/mL (20%). The second transition clearly corresponds to the thermal degradation of PCL in each ESNF membrane system, starting around 350° C. and not showing appreciable differences among the different PAC-loaded ESNFs membranes. Thermogram for PCL ESNFs alone is consistent with previously reported TGA analysis (Wang et al. 2013). Results from TGA analysis support the efficacy of the PAC-loading process into the PCL ESNFs.

FIGS. 10A-D show the surface morphology of PAC-PCL ESNF. The fairly uniform nanofibers are formed into a network suitable for attachment pathogenic bacteria. Results also suggest that there is a slightly increase in nanofiber diameter from PCL ESNFs to the ones loaded with PAC, as the concentration of PAC added to the PCL matrix increases from 6 mg/mL to 12 mg/mL PAC nanofiber diameter increases. The inserted histograms in each image shows a trend to higher nanofiber diameters as the concentration of PAC increase in the matrix as well, suggesting the efficacy for PAC attachment among the ESNFs matrix. However, there were no appreciable differences in morphology between the different PAC-containing ESNFs. These results suggest that the addition of PAC can affect the nanofiber matrix morphology and surface area.

Additionally, Table 3 shows the correlation between mean nanofiber diameter and mean pore area of PAC-loaded ESNFs, important parameters for promoting bacterial adsorption and attachment during surface functionalization of medical devices. Results show an increasing trend in average nanofiber diameter, consistent with the decreasing trend showed by porosity, as the concentration of PAC loaded into the ESNFs increases. It is expected that PAC loading into the PCL ESNFs will increase the average nanofiber diameter, since PAC will become additional components in the nanofiber matrix, thus expecting a dose response in average nanofiber diameter as PAC concentration increases. Likewise, an increase in nanofiber size, mean pore area decreased as a function of increase in concentration of PAC loaded. Even though pore area in ESNFs membranes will be directly influenced by the density of ESNFs collected, the trend in decreasing the total pore area with increasing nanofiber thickness can be explained by the formation of more compressed structure during collection of the ESNFs membranes (Eichhorn and Sampson 2010).

TABLE 3

Correlation between average nanofiber diameter and ESNFs membrane pore area as function of the increasing in cranberry PAC concentration. Results are reported as mean ± SD (n = 20).

| PAC-PCL ESNF | Mean Nanofiber diameter (nm) | Mean Pore Area (nm$^2$) |
|---|---|---|
| PCL (100 mg/mL) | 313.94 ± 98.77 | 767.83 ± 96.55 |
| PAC (6 mg/mL): PCL | 360.19 ± 75.20 | 731.69 ± 87.53 |
| PAC (8 mg/mL): PCL | 378.87 ± 102.09 | 650.22 ± 71.26 |
| PAC (12 mg/mL): PCL | 391.45 ± 57.66 | 574.12 ± 85.07 |

Figure 11:
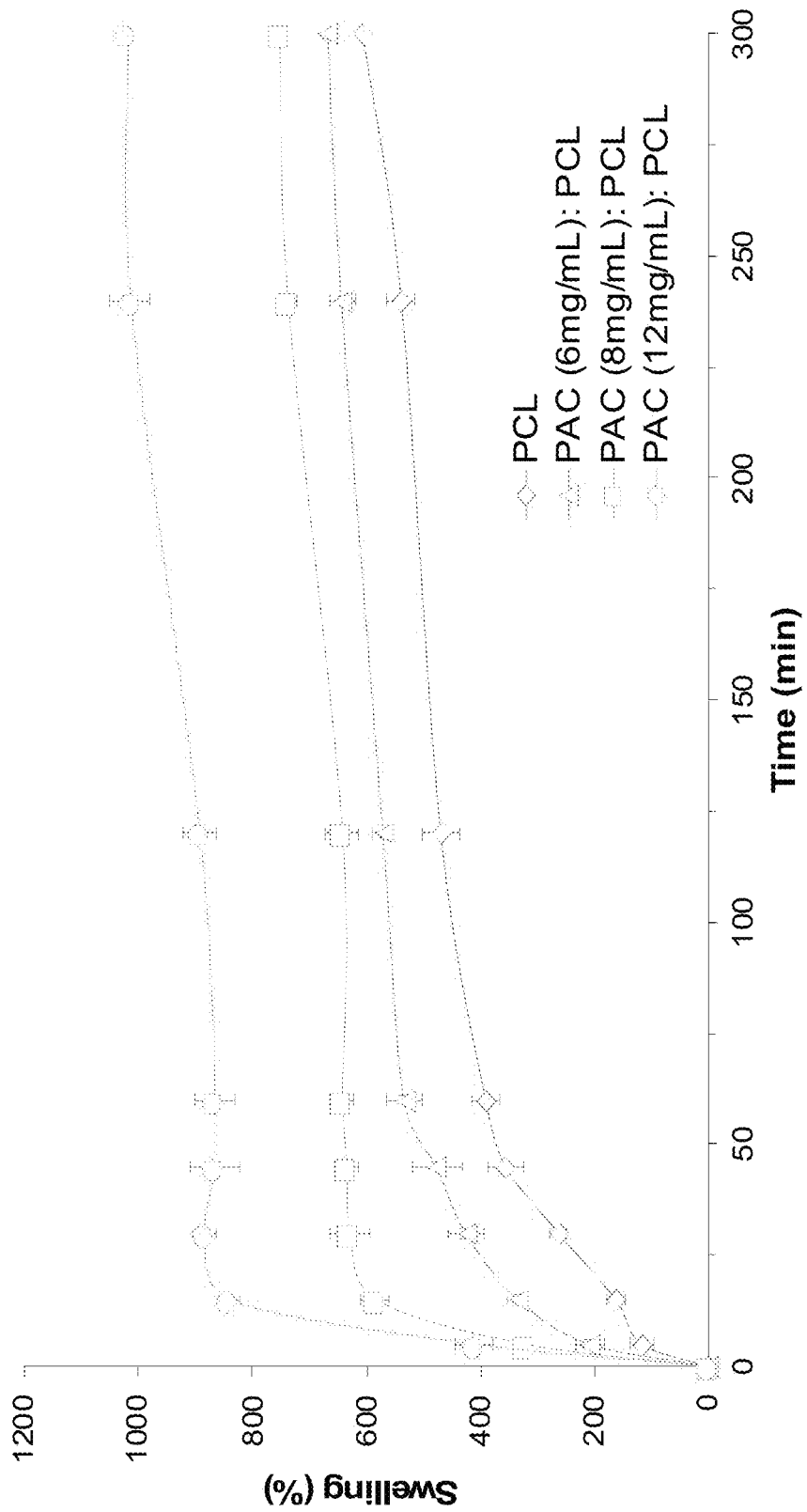
FIG. 11. Swelling behavior of PAC-PCL nanofibers formulated at increased concentrations of cranberry PAC. Results are reported as mean±SD (n=3).

PCL is an amphipathic matrix that can interact with water through its sterically blocked carbonyl groups. Addition of PAC to PCL matrix creates a more hydrophilic environment due to the increase in hydrogen bonding spots along the PAC moieties, thus increasing swelling properties. FIG. 11 shows the swelling behavior for the PAC-PCL composite ESNF coatings, results suggest addition of PAC to the PCL matrix increased the nanofibers hydrophilicity in a dose-dependent manner, from PAC 0 to 12 mg/mL. Suitable swelling properties are required for promoting nanofiber disentanglement allowing increasing surface area for potential bacterial attachment.

PAC-PCL ESNF Bacterial Attachment

Figure 12:
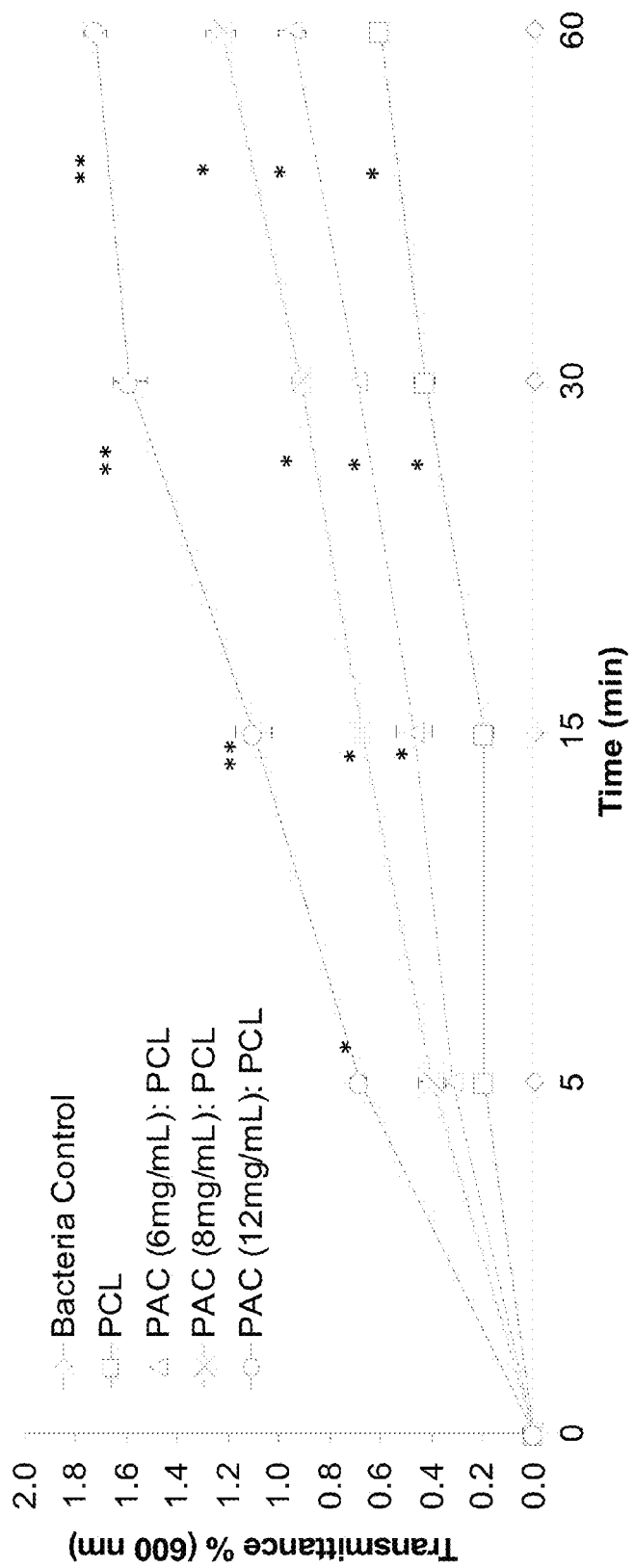
FIG. 12. Attachment of extra-intestinal pathogenic *E. coli* (ExPEC) (strain 5011) by cranberry PAC loaded ESNFs formulated at increasing concentrations of PAC. Results are reported as mean±SD (n=3). One asterisk indicates an effect that is statistically significant p<0.05 and two asterisks indicate an effect that is statistically highly significant p<0.01, compared to the corresponding control.
Figure 13:
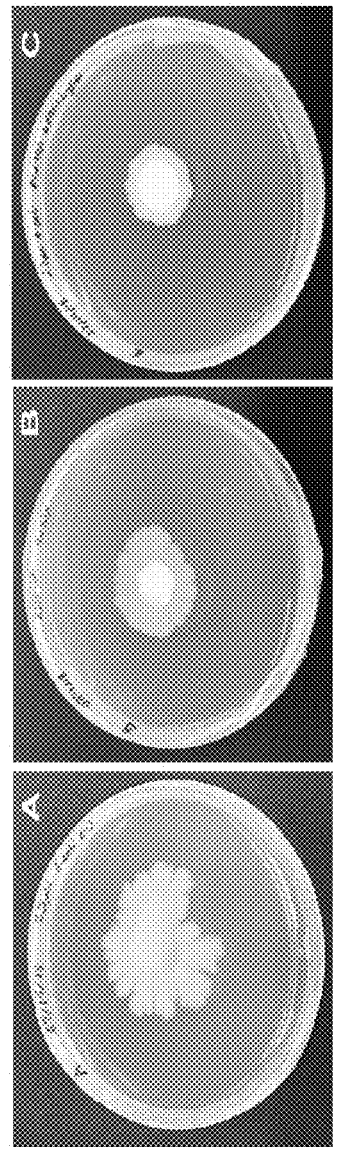
FIG. 13. Prevention of bacterial growth by PAC loaded ESNFs, A. Control, B. PCL 100 mg/mL, C. PAC 12 mg/mL: PCL 100 mg/mL, after incubation at 37° C. for seven days.

Cranberry PAC are known by its properties to agglutinate and attach to bacteria and more specifically ExPEC. The effect of the PAC-PCL ESNF on bacterial attachment in vitro, is shown in FIGS. 12 and 13. Results indicate there is a dose-response for bacterial attachment as the concentration of PAC increases in the composite ESNFs. The trends in FIG. 12 allow concluding the positive effect of adding cranberry PAC to the nanofiber matrix to promote surface bacterial adsorption and attachment. Results also show that PCL itself has some attachment effect against ExPEC strain 5011, may be associated with the inter-porosity of the ESNFs, but addition of cranberry PAC clearly enhances bacterial attachment close to 2-fold when compared to control for the highest PAC concentration loaded into the ESNFs (12 mg/mL) after 60 min incubation at 37° C. Recent research showed that higher attachment of ExPEC and reduced bacterial invasion are correlated with higher number of "A-type" bonds and higher degree of polymerization of PAC (Feliciano et al. 2015). However, there always been concerns regarding PAC efficacy as antibacterial due to its poor absorption and easy degradation in vivo. The efficacy showed by our process for loading PAC into ESNFs provides a novel carrier system for cranberry PAC, allowing effective dosing, improved stability, and localized bioactivity, suitable for potential applications as nanocoating with antibacterial properties.

The bacterial plating experiment were conducted by seeding the bacterial solution (ExPEC strain 5011) onto a culture plate followed by incubation for one week. The effect of ESNFs coatings on preventing bacterial growth was also followed by plate imaging, as shown in FIG. 13. Results agreed with the bacterial attachment assay, in this case ExPEC 5011 strain continuously grew along the control plate, whereas for the plates containing PCL and PAC-PCL ESNF the bacterial growth rate seems to be modified, showing a reduction in bacterial growth for PCL alone and the lowest bacterial growth for the ESNF membrane containing PCL and PAC 12 mg/mL.

Figure 14:
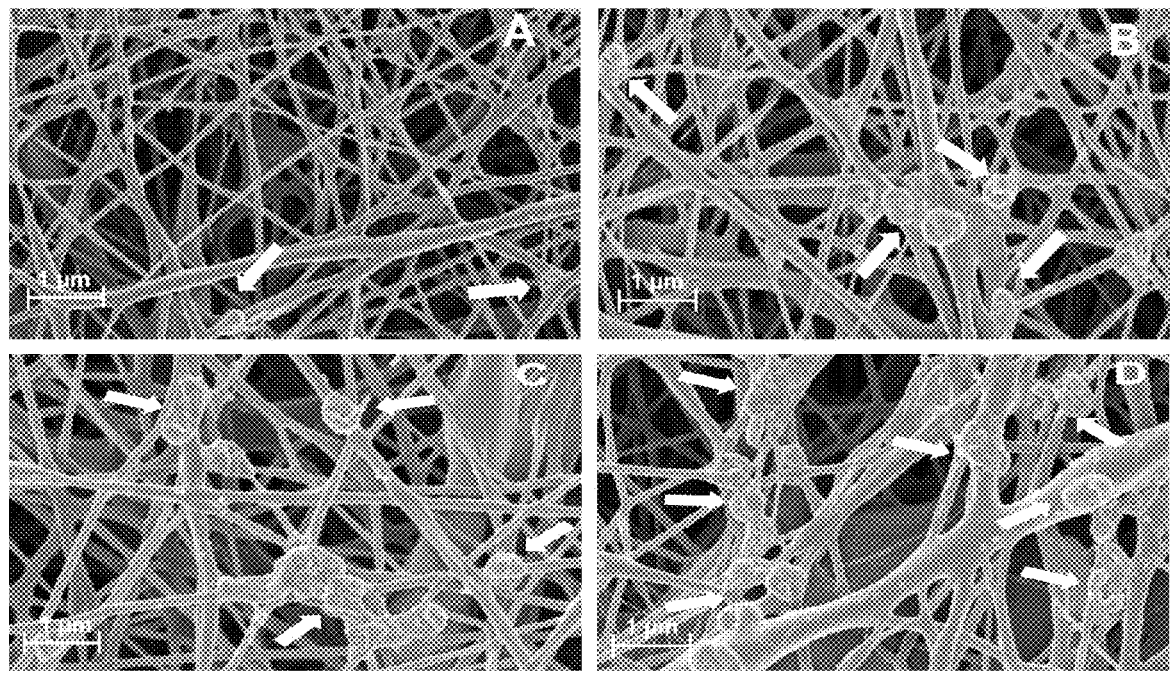
FIG. 14. Scanning electron microscopy (SEM) imaging showing bacterial adsorption effect of cranberry PAC-loaded electrospun nanocoatings against extra-intestinal pathogenic *Escherichia coli* (ExPEC strain 5011). A. PCL 100 mg/mL, B. PAC 6 mg/mL: PCL 100 mg/mL, C. PAC 8 mg/mL: PCL 100 mg/mL, D. PAC 12 mg/mL: PCL 100 mg/mL. Arrows are pointing to ExPEC strain 5011 cells.

SEM imaging was performed on the ESNFs coatings in order to identify the surface adsorption of ExPEC strain 5011 onto the PAC-loaded ESNFs, as shown in FIG. 14. Results suggest there is an increase in bacterial attachment to the surface of the nanofibers as the concentration of PAC increases.

Imaging of Fluorescent PAC-PCL ESNFs

Figure 15:
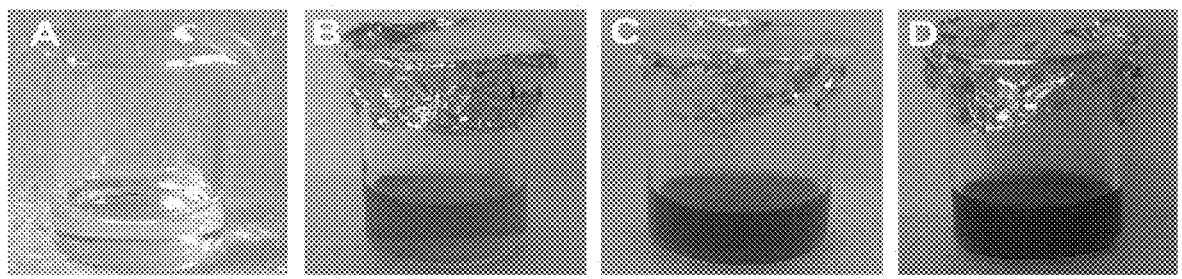
FIG. 15. The physical appearance of fluorescently labeled PAC (F-PAC):PCL blends used for electrospinning. A. PCL 100 mg/mL, B. PAC 250 μg/mL:PCL 100 mg/mL, C. PAC 500 μg/mL:PCL 100 mg/mL and D. PAC 1000 μg/mL:PCL 100 mg/mL.

The mixture of PCL and PAC show a complete fairly uniform solution in the three different concentrations of F-PAC added (FIG. 15).

Figure 16:
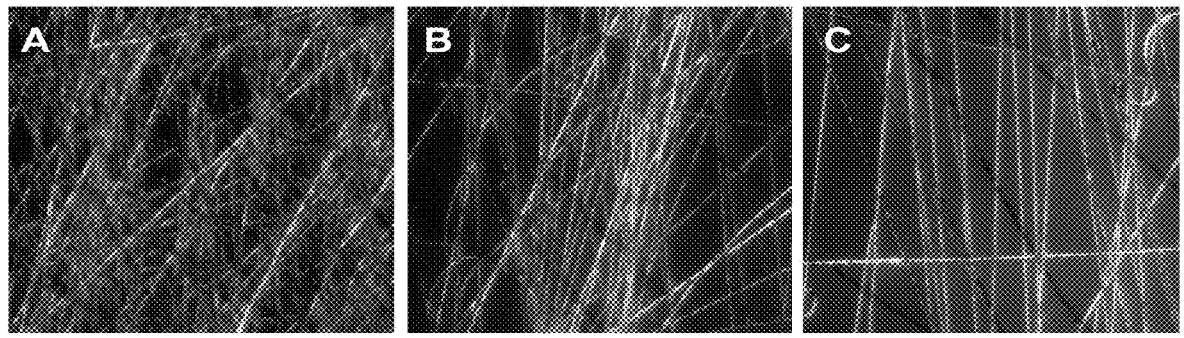
FIG. 16. Fluorescent microscopy images showing the distribution of F-PAC loaded into PCL 100 mg/mL ESNFs at different densities of collected nanofibers at A. High density ESNFs, B. Medium density ESNFs, C. Low density ESNFs. (Magnification 40×)

Fluorescent microscopy imaging of the F-PAC loaded into PCL matrix ESNFs allowed following up the location of the PAC distributed along the nanofibers. Results indicated that the distribution of F-PAC in the PCL ESNFs is not homogeneous and trend to accumulate forming nodes or clusters along the ESNFs surface, creating sections of high PAC density (FIG. 16).

Figure 17:
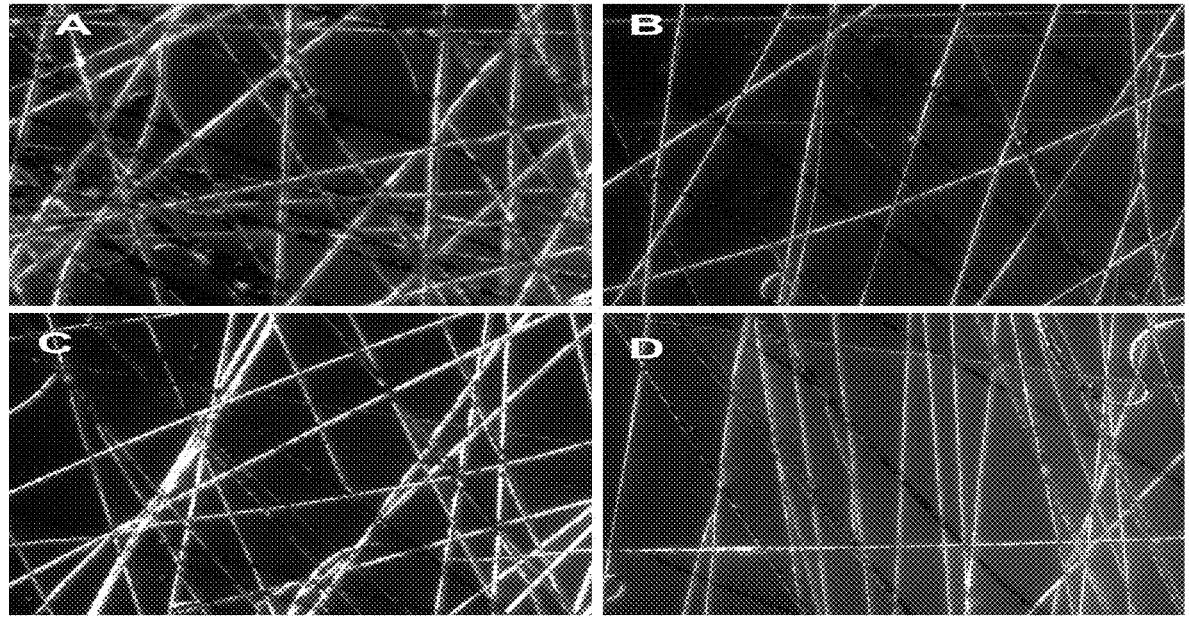
FIG. 17. Fluorescent microscopy imaging showing the distribution of fluorescently labeled PAC loaded into PCL 100 mg/mL ESNFs at different concentration of PAC. A. PCL 100 mg/mL, B. PAC 250 µg/mL:PCL 100 mg/mL, C. PAC 500 µg/mL:PCL 100 mg/mL, D. PAC 1000 µg/mL:PCL 100 mg/mL. (Magnification 40×)

Increasing the amount of F-PAC in the blends for PCL leads to an increase of fluorescent response observed in the ESNFs, suggesting a dose response behavior for the ESNFs loaded with a higher amount of F-PAC, as shown in FIG. 17. Results indicate no fluorescence was observed in the ESNFs composed solely by the PCL matrix, and a dose dependent increase in the detected red fluorescence as the concentration of F-PAC was increased from 250 µg/mL to 500 µg/mL.

Figure 18:
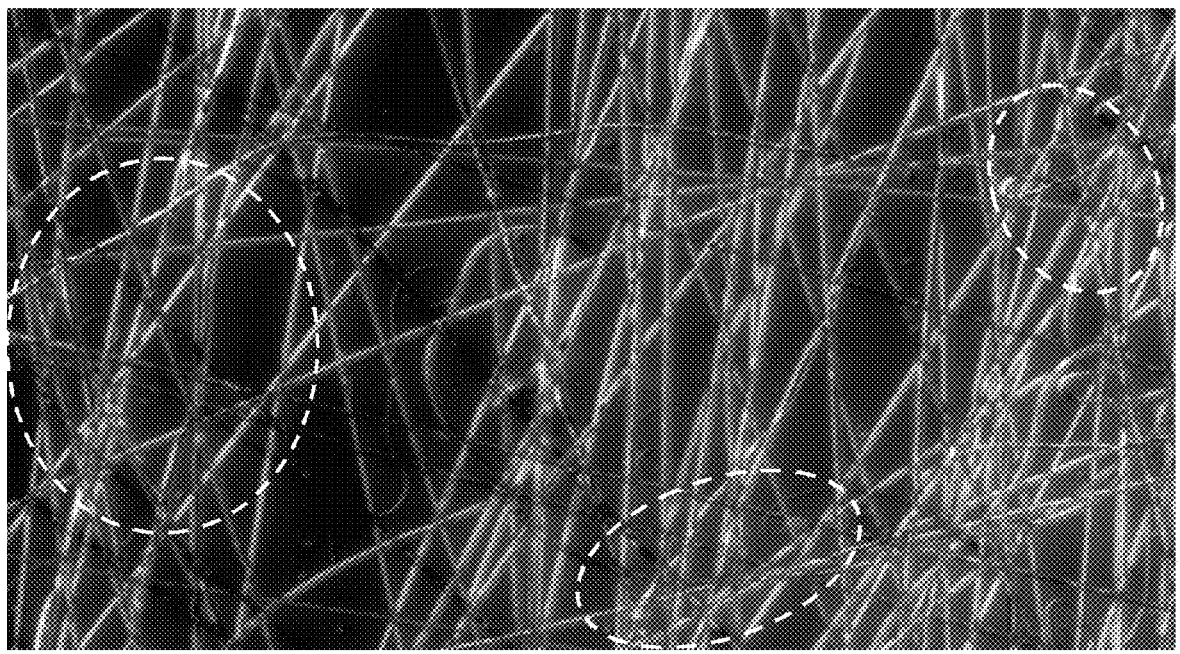
FIG. 18. Fluorescent microscopy image showing the expected areas for higher bacterial adhesion in PAC-loaded ESNFs. (Magnification 40×)

As FIG. 14 suggests, ExPEC 5011 strain seems to adhere to the PAC-loaded ESNFs in specific locations that may correspond to the observed locations of the F-PAC nodes or clusters indicated by the fluorescent imaging experiments, generating areas of higher PAC density suitable for favorable bacterial adhesion, as indicated in FIG. 18.

Figure 19:
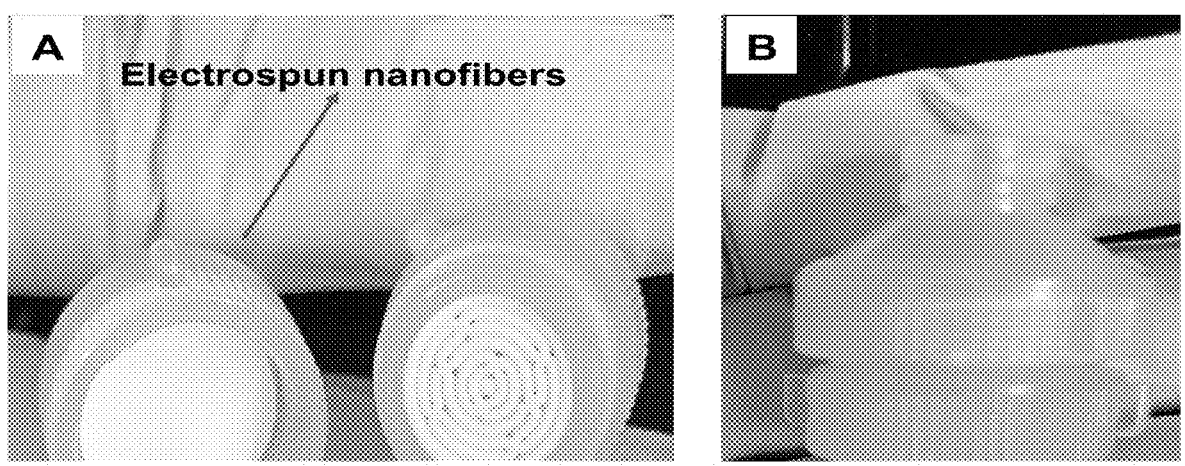
FIG. 19. Filter used for bacteria attachment. A. the electrospun nanofiber membrane placed inside the filter and B. the final filter assembly.

Fluorescent Imaging Study of the Interaction Between Fluorescently Labeled Proanthocyanidins Loaded into PCL ESNFs and GFP-Labeled E. coli To determine attachment distribution of fluorescently labeled E. coli (ExPEC) onto PAC-PCL ESNFs by means of filtration attachment process followed by fluorescent imaging. First F-PAC/PCL ESNF membranes cut in 11 mm diameter circles and placed in syringe filter as shown in FIG. 19.

Figure 20:
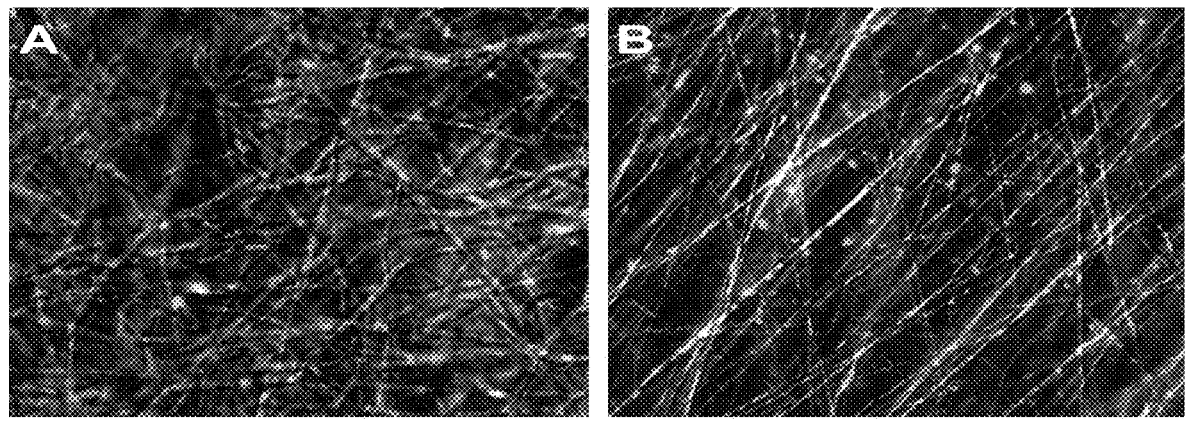
FIG. 20. Fluorescent microscopy images of ESNF membranes treated with florescent GFP-$E.$ $coli$ at $1\times10^5$ CFU/mL. A. PCL 10% ESNF, no F-PAC added, and B. PCL 10% ESNF, loaded with PAC 500 µg/mL. (Magnification 40×).
Figure 21:
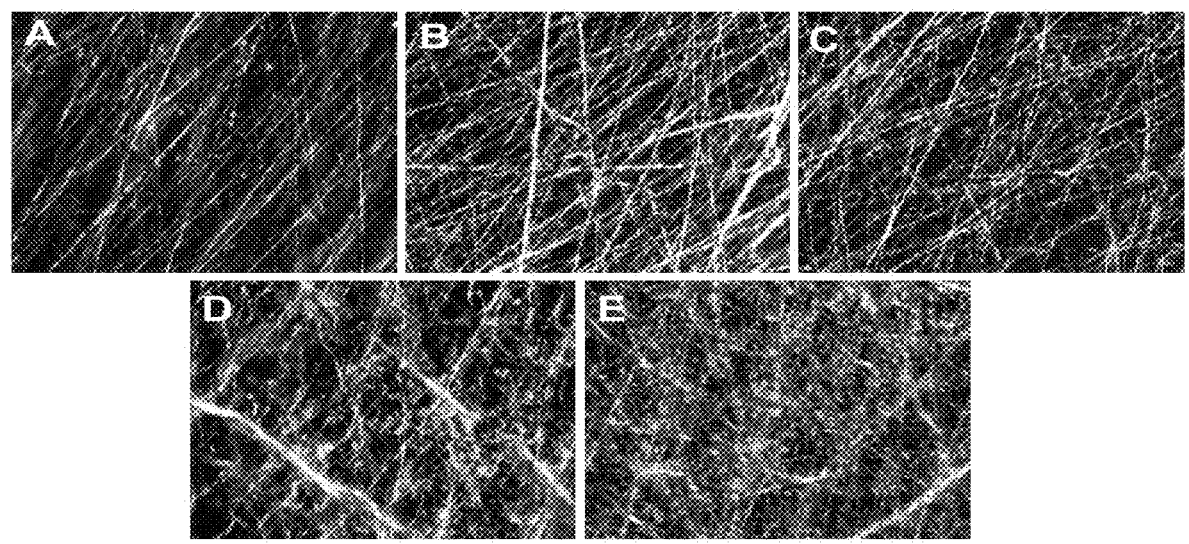
FIG. 21. Fluorescent microscopy imaging of ESNF membranes loaded with F-PAC at 500 µg/mL and treated with different concentrations of fluorescent GFP-$E.$ $coli$. A. $1\times10^5$ CFU/mL, B. $1\times10^6$ CFU/mL, C. $1\times10^7$ CFU/mL, D. $1\times10^8$ CFU/mL and E. $1\times10^9$ CFU/mL. (Magnification 40×).

Fluorescent imaging showed that ESNF membranes loaded with F-PAC showed higher attachment that membranes fabricated without F-PAC, as shown in FIG. 20. Results allow concluding that F-PAC (500 µg/mL) play an important role in GFP-E. coli attachment onto the ESFN membranes after the filtration process. The ESFN membrane composed solely by the PCL barely show adsorption of bacteria, as evidenced by the few green spots in FIG. 20, panel A. It is easy to identify the presence of both fluorescent PAC (red) and bacteria (green) along the ESNF shown in FIG. 20, panel B, suggesting retention of the bacteria may be influenced by the addition of PAC to the ESNF membrane. Furthermore, fluorescent microscopy imaging of the F-PAC-loaded ESNF membranes treated with different concentrations of fluorescently-labeled GFP-E. coli, showed a dose-dependent trend for bacteria adsorption onto ESNF membranes loaded with PAC at 500 µg/mL, as shown in FIG. 21.

Figure 22:
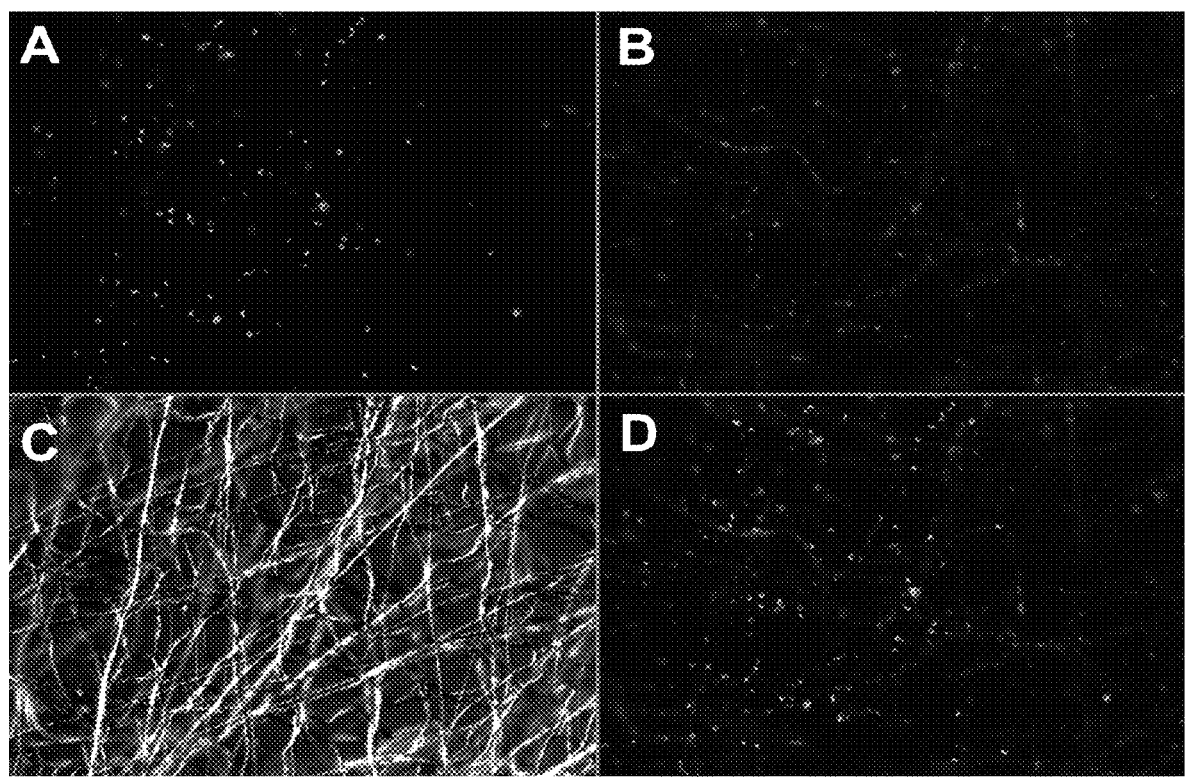
FIG. 22. Fluorescent microscopy image showing the areas for higher bacterial adhesion found in ESNF membranes loaded with F-PAC (500 µg/mL) and treated with GFP-labeled $E.$ $coli$ ($1\times10^5$ CFU/mL). A. GFP filter, B. Texas Red filter, C. DIC filter, D. GFP and TexasRed filter (Magnification 40×).

The results indicate that E. coli seems to adhere to the PAC-loaded into ESNF membranes in specific locations that correspond to the observed locations of the F-PAC nodes indicated by previous fluorescent imaging experiments, generating areas of higher PAC density suitable for a more favorable bacterial adhesion, as showed in FIG. 22. The accumulation of the PAC as nodes or clusters along the ESNF membranes creates areas of high PAC density associated to a higher tendency for attachment bacteria, as previously shown by SEM image with ExPEC 5011 strain.

However, the filtration requires that the ESNF membranes are at least 0.03 mm in thickness affecting light transmission during fluorescent microscopy visualization, which leads to problems for focusing on the nanofibers and making difficult take clear and good images. It may be useful to culture the bacteria directly onto the ESNF membranes for a predetermined time allowing enough time for the bacteria to interact with PAC in the membrane, generating a reliable attachment process, since filtration is a mechanical process were the bacteria is forced to pass thought the ESNF membranes. It is also recommended to rinse the ESNF membranes with PBS through the filter once the bacteria have been adsorbed to confirm efficacy of the bacterial attachment onto the PAC-loaded ESNF.

Efficacy of Catheter Surface Electrospun Nanocoating

Figure 23:
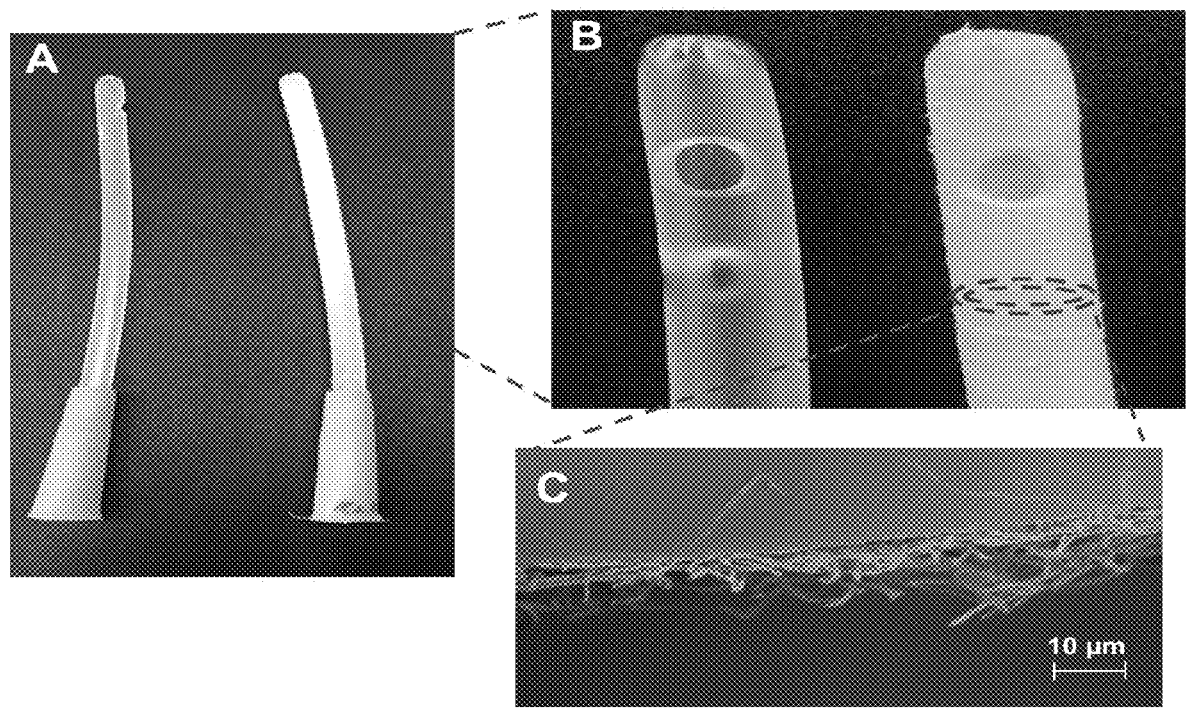
FIG. 23. Photograph and scanning electron micrograph showing the effect of PAC-PCL electrospun nanocoatings on surface functionalization of model catheter biomedical devices. A. an uncoated catheter (left) and a nanocoated catheter (right). B. Magnified view of un-coated and nanocoated catheters. C. Cross-section of the catheter-nanocoating interface showing the nanofibers tangling from the PVC catheter smooth surface.
Figure 24:
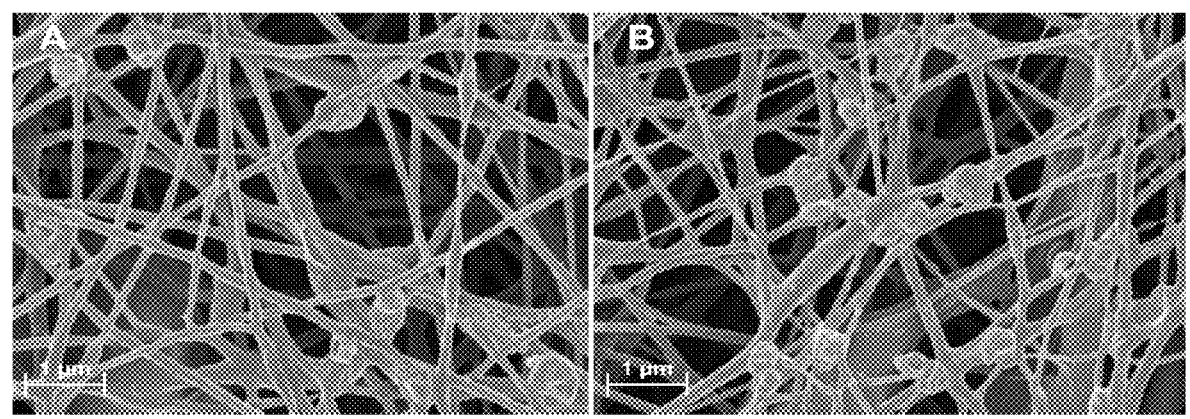
FIG. 24. SEM image showing the effect of surface functionalization of catheters with PAC-loaded electrospun nanocoatings on the bacterial adsorption of extra-intestinal pathogenic $Escherichia$ $coli$ (ExPEC strain 5011). A. PCL 100 mg/mL, B. PAC 12 mg/mL:PCL 100 mg/mL.

After completion of the characterization and efficacy studies on the PAC-loaded electrospun as potential antibacterial surface coating agent, we initiated experimental trials for surface functionalization of model medical devices (biomedical grade PVC catheters) by surface functionalization of PAC-loaded ESNFs directly onto model catheter biomaterials, as shown in FIG. 23. Once we optimized the catheter coating protocol on the electrospinning system, we decided to evaluate the effect of the electrospun nanocoatings loaded with PAC at different concentrations against pathogenic bacteria. We were not able to conduct attachment or bacterial growth studies with the surface functionalized catheters, but we treated the nanocoated catheters with ExPEC 5011 strain and visualized the adsorption of the bacteria by SEM, as shown in FIG. 24.

Results agreed with the previously observed trends regarding an increase in bacterial adsorption for the PAC-loaded electrospun nanocoatings. This study contains a robust proof-of-concept for the potential application of electrospun technology in the development of antibacterial surface functionalized nanocoatings for preventing catheter-associated bacterial infections.

Conclusions

Cranberry PAC were successfully loaded into PCL ESNFs. PAC-loaded ESNFs were successfully bioengineered under parameters (solution concentration 6 to 12 mg/mL, applied voltage 18 kV, flow-rate 1 mL/h, needle-collector distance 10 cm), showing fairly uniform nanofiber diameters, pore sizes, and random nanofiber distribution with average diameters around 350 nm.

The efficacy of PAC loading into the nanofibers was confirmed by spectroscopy (FTIR), thermal analysis (TGA), electron microscopy (SEM) and fluorescent microscopy analysis, showing a random distribution of PAC along the ESNFs and the formation of nodes where PAC seems to be accumulated and thus conferring higher bioactivity spots, especially for bacterial attachment.

Microscopy imaging by both SEM and fluorescent microscopy allowed identifying the efficacy of PAC-loaded into ESNFs for preventing bacterial infections, as suggested by the attachment of model pathogenic bacterial strain ExPEC 5011 and fluorescent E. coli into the PAC nodes randomly distributed along the ESNFs.

Finally, surface coating of a model medical device (biomedical grade PVC catheter) was successfully accomplished by PAC-loaded ESNFs, conferring the model functionalized catheter bacterial attachment properties against EXPEC 5011 strain, as previously shown by SEM imaging of PAC-loaded ESNFs.

Silver Nanoparticles Coated Electrospun Nanofibers Loaded with Polyphenolic Extract from Rambutan Materials Rambutan (*Nephelium lappaceum* L.) samples from grafted varieties (R-134, Rongrein and Criollo) were kindly provided by the Laboratory of Phytochemistry (LAFIT) at the School of Chemistry, National University, Costa Rica. Polycaprolactone (PCL), acetone and alamarBlue solution were purchased from Thermo Fisher Scientific (Waltham, Mass., USA) and used without further purification.

Polyphenol Extraction and Characterization

Rambutan exocarp samples from three varieties R-134, Rongrein, and Criollo were frozen and lyophilized (Labconco 2.5 L plus, Kansas City, MO). The dried samples were milled and sieved with a 1.0-mm pore size sieve. To determine the most efficient extraction solvent for rambutan samples the following solvents were used, acetone:methanol:HCl 5% (4:4:2), acetone:HCl 5% (7:3), acetone:ethanol:HCl 5% (4:5:1) and ethanol 95%:HCl 5% (95:5) (all expressed as volume ratios). Efficacy of solvent extraction was followed by the Folin-Ciocalteau assays for total polyphenol content. The optimal number of extractions with the best extracting solution was determined by quantifying total polyphenolic content after each extraction step using the Folin-Ciocalteau assay (Singleton et al. 1999; Blainski et al. 2013). After, completing the optimal number of successive extractions (25 mL/each) with 1 g of sample, most of the phenolic compounds were extracted. The extracts were then filtered (Whatman 42, Sigma-Aldrich, St. Louis, MO) and concentrated in a rotary evaporator (Büchi R200, New Castle, DE) under reduced pressure (100 psi) and temperature not higher than 40° C. for three hours and lyophilized. The final lyophilized powder was stored in a desiccator and labeled as crude rambutan polyphenolic extract (RPE).

Total polyphenol content in each sample was quantified by the Folin-Ciocalteu method, as previously described by Singleton, et al. (1999) and adapted for a microplate reader (Synergy HT Multi-Mode, Biotek, Vinooski, VT). A total of 200 µL of water, 15 µL of Folin-Ciocalteu reagent, 30 µL of sample and 50 µL of sodium carbonate solution (20% w/v) were added to a 96-well plate and programed for microplate shaking after the addition of the calcium carbonate solution. The measures were performed with a thermal incubation program at 40° C., subsequent stirring and absorbance reading at 20 min from the addition of the carbonate solution, allowing developing of color in the sample. The absorbance was determined by UV-Vis as a wavelength of 755 nm and gallic acid was used as the standard.

Electrospinning of Crude Rambutan Polyphenols Extracts (RPE)

The crude RPE was dissolved in methanol and then combined with PCL solution, previously prepared in organic solvent mixture composed by chloroform and methanol (9:1 v/v) at a concentration ratio of 12 mg/mL RPE:100 mg/mL PCL. The RPE-PCL blends were characterized by measuring their viscosity by a stress-sweep test in a programmable rheometer (DV-III ULTRA, Brookfield, UK) at a shear rate of 100 (1/s). Their electrical conductivity was measured at 25° C. with a conductivity meter (Orion Star A215, Thermo Fisher, Waltham, Mass.) with an electrode conductivity constant of 0.7265 $cm^{-1}$.

The RPE-PCL blended solutions were loaded into a 5 mL syringe fitted with 18-G needle and connected to an electrospinning setup as indicated in FIG. 1. A 12-kV electric field was applied using a high voltage power source (Gamma High Voltage Research, Ormond Beach, FL) and the distance between the needle tip and the aluminum foil-coated copper collector was fixed at 10 cm, creating a 1.2 kV/cm charge density (voltage/distance) on the blended solution. After 3 mL of the solution was collected onto the aluminum foil the samples were kept in a vacuum chamber for 24 h to remove any residual of organic solvent, and then stored in a desiccator for further experiments.

Surface Coating of RPE-Loaded ESNF with Silver Nanoparticles

The silver nanoparticles (AgNPs) were directly formed on the surface of the RPE-ESNFs according to a previously described chemical reduction method (Mulfinger et al. 2007). Briefly, aqueous solutions of $AgNO_3$ (100 M) and $NaBH_4$ (100 M) were prepared. To load the un-reduced silver ions the REP-ESNFs were cut into 8 mm circles and dipped into the $AgNO_3$ solution for 5, 15 and 30 min at room temperature. Consecutively, the silver-containing samples were dipped into reducing solution of $NaBH_4$ for 5 min at room temperature, to reduce silver ions to elemental silver, inducing the spontaneous formation of AgNPs, as shown by the change in color of the ESNFs mat. Once the reduction reaction was completed, each sample was washed thoroughly with denoized (DI) water to remove any remaining AgNPs that were not attached directly onto the ESNFs. The samples were dried in a vacuum chamber at room temperature for 12 h, labeled as AgNPs/RPE-ESNFs and then stored in a desiccator for further analyses. Furthermore, the effect on the size of AgNPs surface coated onto RPE-ESNFs as result of dipping into the $AgNO_3$ solution for different time periods (5, 15 and 30 min) and then dipped into reducing solution of $NaBH_4$ for 5 min was analyzed by the collection of 1.5 mL of the solution containing AgNPs after the dipping process and quantified the average hydrodynamic diameter determined by dynamic light scattering measurements (90 Plus Particle size analyzer, Brookhaven Instruments Corporation, Holtsville, NY).

Characterization of RPE and AgNPs/RPE ESNFs

The RPE-ESNFs and AgNPs/RPE-ESNFs were characterized for their chemical profile using attenuated total reflectance Fourier-transform infrared spectroscopy (Nicolet 4700 ATR FT-IR, Thermo Scientific, Gran Island, N.Y.), and thermal properties by thermogravimetric analysis (TGA, Q100, TA Instruments, Lindon, Utah). TGA analyses were performed at a programmed heating rate of 20° C./min over a temperature scan range between 50 to 400° C. in a nitrogen atmosphere (20 mL/min). The morphology of nanofibers was examined using scanning electron microscope (SEM, Leo 1530-FE, Zeiss, Cambridge, UK). The average fiber diameter was determined by analyzing at least 20 nanofibers from SEM images using ImageJ software (NIH, Bethesda, Md.). Statistical analysis was performed using Assistat VR software (Statistics, Arlington, Tex.). The swelling property and mean pore area of the ESNF were studied as previously described in above.

Determination of the RPE Release and Antioxidant Activity of RPE-Loaded ESNFs

Release of RPEs from loaded ESNFs was carried out by immersing previously cut ESNFs membrane discs (8 mm diameter) into 5 mL phosphate buffer saline solution (PBS, lx), followed by incubation at 37° C. and sampling 1 mL of media solution at different time intervals (6, 12, 24, 48 and 72 h) and returning 1 mL PBS into each sample container. Released RPEs were quantified by the Folin-Ciocalteu method as previously described in section 5.1.2.

Antioxidant capacity was determined by the DPPH assay, briefly a solution of 2,2-Diphenyl-1-picrylhydrazyl (DPPH) was prepared by the method described by Bondet et al. (1997). A 96-wells plate was filled with a blank solution composed of 30 µL of a methanol:water solution (80:20 v/v), 30 µL of gallic acid (0.0215 mg/mL) was used as standard. Samples were dipped into the blank solution for 1 min and 30 µL of each sample extract was added into each sample. Finally, a 270 µL aliquot of the DPPH solution (0.042 mg/mL) was added to complete the redox reaction. A characteristic color change developed in the samples after 30 min incubation at 25° C., which was monitored using a microplate reader (Synergy HT Multi-Mode, Biotek, Vinooski, VT) at a wavelength of 515 nm.

Determination of In Vitro Antibacterial Activity

Microbial susceptibility assay measured as zone-of-inhibition (ZoI) was employed to qualitatively evaluate the antimicrobial activity of RPE-ESNFs and AgNPs/RPE-ESNFs. Samples were tested against three different human pathogens: *Escherichia coli* ATCC 25992 (Ec), *Staphylococcus aureus* ATCC 25923 (Sa), and *Pseudomonas aeruginosa* PAO1 (Pa). Negative controls were composed by PCL 100 mg/mL and 6 mm filter of Whatman sterile filter, while positive control was composed by a standard antibiotic solution (kanamycin 6 mg/mL). Firstly, a loopful of each tested bacterium was inoculated into 50 mL of nutrient broth and incubated at 37° C. overnight. Subsequently, 1 mL of this culture was diluted to a concentration of $10^7$ CFU/mL using 10-fold dilution method and then 100 μL of diluted solution was spread on nutrient agar plates. After spreading was completed, different samples discs of RPE-ESNFs and AgNPs/RPE-ESNFs were cut into 8 mm diameter samples and sterilized under ultraviolet irradiation in a laminar flow hood for 1 h (30 min each side) and then placed on the inoculated nutrient agar plates. Positive control (5 μL), was added into a sterilized filter disk and placed on the inoculated nutritional agar. The ZoI diameter of each inoculated plate was measured after incubation at 37° C. for 24 h. The tests were carried out in triplicates.

Cell Adhesion and Proliferation Assays

Samples of RPE-ESNFs and AgNPs/RPE-ESNFs were cut into disc-shaped 8 mm diameter discs and both sides of the discs were sterilized by UV irradiation as indicated above. Sample discs were placed into different wells in a sterile cell culture plate with media and 3 mL of fibroblast cell suspension (3T3 Mouse embryonic fibroblast, 1.56 Å~$10^5$) were added into each treatment well. Firstly, the adhesion assay was carried by incubated the cells with the membranes for 40 min with a stirring of 2 rpm at room temperature. Each of the membranes was relocated in different wells of the same plate without cell suspension and were left incubating for 15 min at 37° C. and 5% $CO_2$. Next, alamarBlue cell viability reagent (10 μM) was added and incubate for 2 h at 37° C. and 5% $CO_2$, fluorescence was measured at 540/590 nm using a microplate reader (SpectraMax Plus, Molecular Devices, Sunnyvale, CA, USA).

Meanwhile, the membranes were coated with DMEM medium culture medium and placed in an incubator at 37° C. for 3, 7 and 14 days. After each incubation period, media was removed and alamarBlue 10 μM solution was added into each treatment well in a 1:10 dilution with fresh media. Plates were subsequently incubated at 37° C. for 4 h and fluorescence was measured at 540/590 nm using a microplate reader (Synergy HT Multi-Mode, Biotek, Vinooski, VT).

Data and Statistical Analysis

All data are reported as mean±standard deviation of at least three replicates. Statistical analysis was done using JMP Pro (Version 10.0.0; SAS Institute Inc., Cary, N.C., USA), the differences were considered statistically significant at $p<0.05$. Results were analyzed with two-way ANOVA models with interaction between the independent variables "sample" and "bacterial attachment transmittance" to assess significant differences, followed by Tukey's multiple comparison test (n=5). Statistical significances were represented with asterisks denoting statistical highly significative (**, $p<0.01$) and statistically significant (*, $p<0.05$).

Characterization of Rambutan Polyphenolic Extract (RPE)

Figure 25:
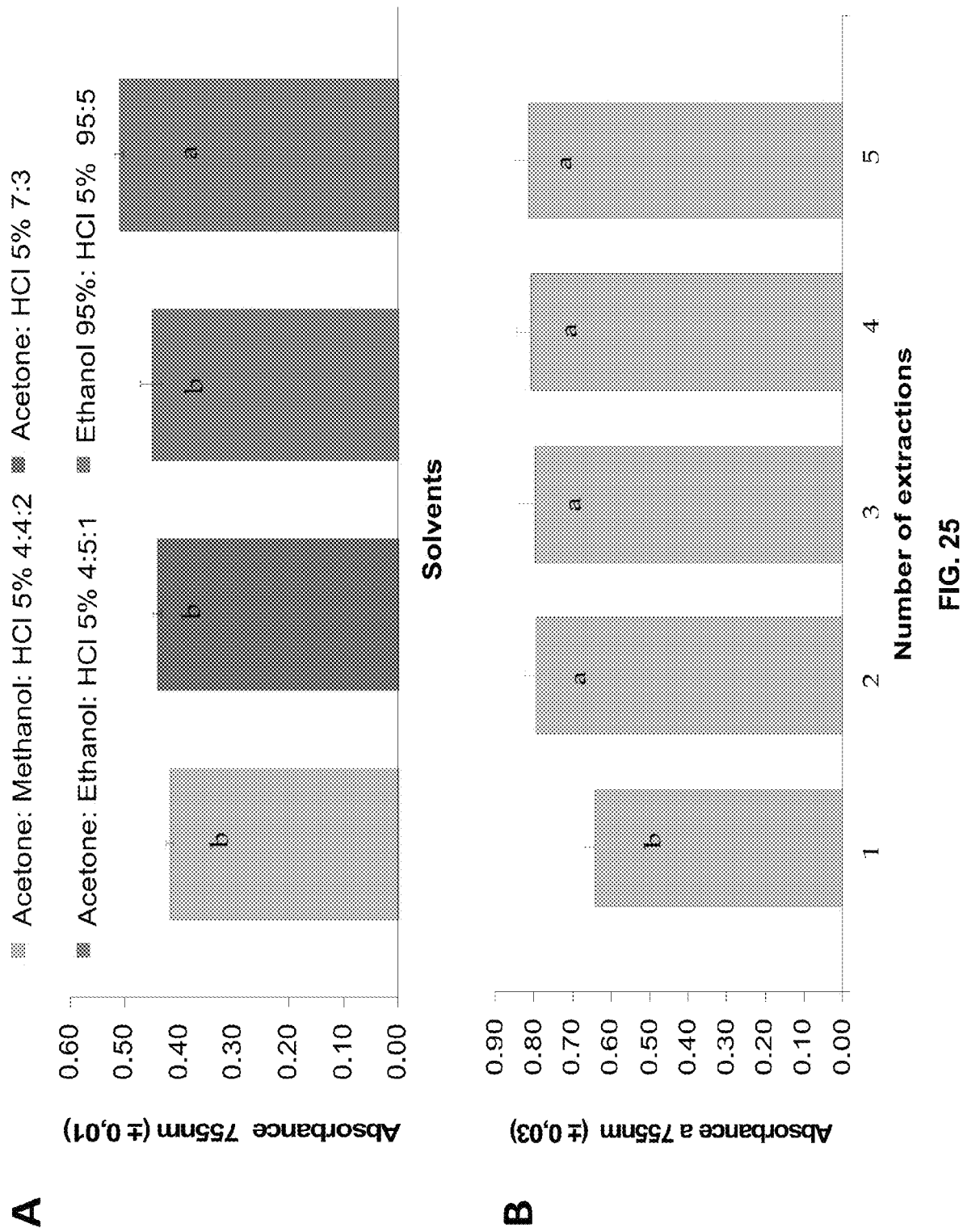
FIG. 25. Polyphenols raw extractions from rambutan, A. Evaluation of solvents in the extraction of the total polyphenol content. B. Determination of the number of extractions to be made using ethanol 95%: HCl 5% (95:5). Same letter in the bars (e.g., "a" or "b") represent no significant difference, using the statistical test of Tukey ($P \leq 0.01$).

A total of four solvent systems, as indicated above, were tested to be certain of the ideal extracting solution to be used for isolation of crude polyphenolic extract from rambutan rind samples (varieties R-134, Rongrein and Criollo). The Folin-Ciocalteu method was applied to measure total polyphenol content in the extracted samples, as an indicative of efficacy in polyphenol extraction. All extracting solvent systems contained HCl (5% v/v), the acidic medium has been previously described as important for polyphenol extraction, since it prevents premature decomposition of some secondary metabolites, such as anthocyanidins and anthocyanins (Khoo et al 2017). Extraction efficacy results shown in FIG. 25, panel A, indicate that the best solvent for the extraction of polyphenols from all varieties of rambutan was ethanol:HCl (95:5% v/v) allowing extracting the highest number of total polyphenols and showing a statistically significant difference compared to the other solvent systems applied. The efficacy of the solvent system for extracting polyphenols from rambutan can be associated to the polar nature of the phenolic compounds extracted from this plant-based material. The other three solvent systems applied showed no significant differences in the amount of extracted phenolic compounds, indicating ethanol:HCl (95:5% v/v) solvent system was the more suitable for producing RPEs from the three rambutan varieties selected for this study. Likewise, Folin-Ciocalteu method was applied to determine the optimal number of successive extractions to be conducted in a fixed mass sample of rambutan powder to achieve maximum extraction of polyphenols, until the next extraction showed no statistically significant differences in the content of these secondary metabolites. As shown in FIG. 25, panel B, there were non-significant changes in the sample's absorbance at 755 nm after the second successive extraction, suggesting the maximum polyphenol content is fully extracted in two successive extractions using ethanol: HCl (95:5% v/v) as the solvent.

Characterization of Rambutan-PCL ESNFs

Results shown in Table 4 summarize the values for viscosity and conductivity obtained for the RPE-PCL blends prior to electrospinning processing. Increasing the conductivity of the solution has been shown to improve the quality of the fibers in cases where beaded fibers are formed. This is due to increased stretching of the solution jet as a result of higher level of charges carried by the solution. The same factor also encourages the reduction of fiber diameter (Zhong et al. 2002). Another way to look at it is that increased bending instability due to greater conductivity lengthens the jet path as evident from the larger deposition area (Choi et al. 2004). Another important solution property to consider is its viscosity. For highly viscous solution, the electrical charges may not generate sufficient strength to stretch the solution to form fibers. If a solution is so viscous that it is almost "gel-like", it may be necessary to reduce the concentration of the solution. However, below a certain concentration, the electrospinning jet may break up into droplets and no fiber is formed. In the preparation of the solution for electrospinning, it is useful to predict whether the solution has sufficient viscosity to be stretched into fibers. For a polymer solution, the viscosity of the solution is determined by the chain entanglements of the polymer molecules. In a dilute solution, the distance between polymer chains are sufficiently far apart such that there is no overlap in the molecules (Shenoy et al. 2005).

TABLE 4

Viscosity (measured at a shear rate of 100 $s^{-1}$) and conductivity of rambutan polyphenol extracts (RPE) and the RPE-PCL blends before electrospinning. Results arer eported as mean ± SD (n = 5).

| Physical properties of RPE samples at a fixed concentration (96 mg/mL) | | |
|---|---|---|
| Rambutan Variety | Viscosity (mPa · s) | Conductivity (μS/cm) |
| R-134 | 1.87 ± 0.4 | 0.52 ± 0.02 |
| Rongrein | 2.13 ± 0.5 | 0.54 ± 0.03 |
| Criollo | 1.87 ± 0.8 | 0.51 ± 0.028 |
| Physical properties of RPE-PCL blends (12: 100 mg/mL) | | |
| RPE-PCL Blend | Viscosity (mPa · s) | Conductivity (μS/cm) |
| PCL (No RPE) | 136.7 ± 5.8 | 1.05 ± 0.1 |
| R-134: PCL | 135.5 ± 8.9 | 0.74 ± 0.4 |
| Rongrein: PCL | 136.8 ± 5.6 | 0.76 ± 0.8 |
| Criollo: PCL | 134.3 ± 5.5 | 0.72 ± 0.3 |

TABLE 4-continued

Viscosity (measured at a shear rate of 100 s$^{-1}$) and conductivity
of rambutan polyphenol extracts (RPE) and
the RPE-PCL blends before electrospinning.
Results arer eported as mean ± SD (n = 5).

Figure 26:
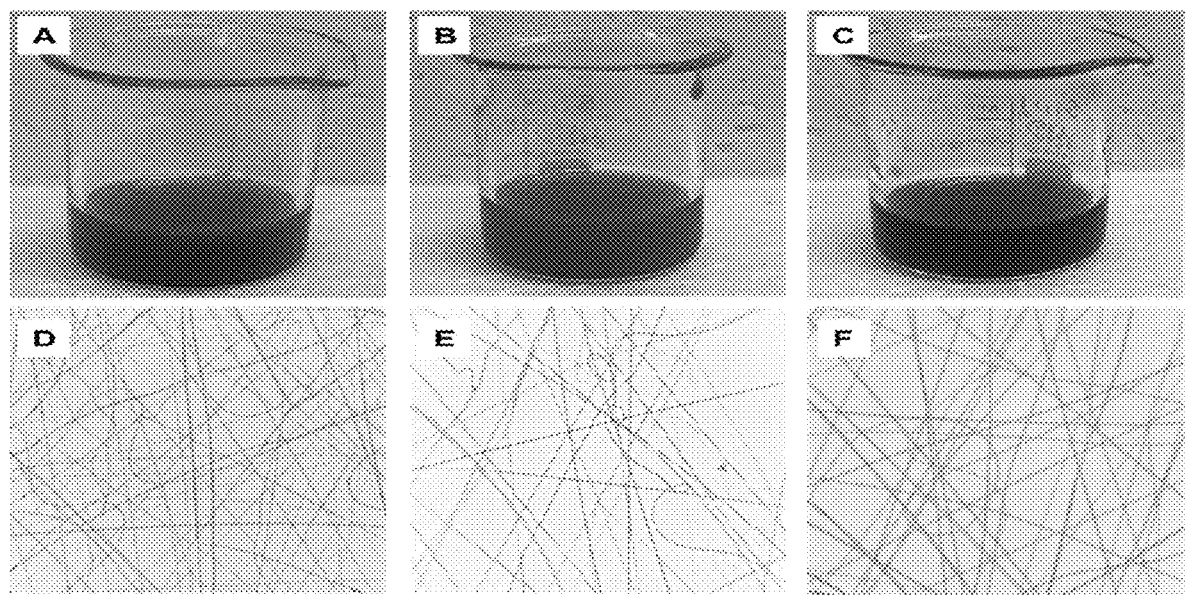
FIG. 26 Physical appearance of the rambutan polyphenolic extract (RPE)-PCL blends used for electrospinning (upper images) and optical microscopy images (40× magnification) showing the physical appearance of RPE-ESNFs. A and D: PCL 100 mg/mL:R-134 12 mg/mL; B and E: PCL 100 mg/mL:Rongrein 12 mg/mL; C and F: PCL 100 mg/mL: Criollo 12 mg/mL.

Viscosity and conductivity values for RPE-PCL blends at the concentration selected in the present study seem to be suitable for electrospinning processing, as shown below by following up the efficacy of the electrospinning process through optical microscopy imaging. The physical appearance of RPE-PCL blends and the efficacy of electrospinning for the fabrication of RPE-ESNFs is shown in FIG. 26. The pictures show the homogeneity and color difference between the viscous RPE-PCL blends prepared with the three varieties of rambutan samples selected for this study. Optical microscopy images show the efficacy of the electrospinning under the optimal parameters determined for the fabrication of fairly uniform RPE-ESNFs.

Figure 27:
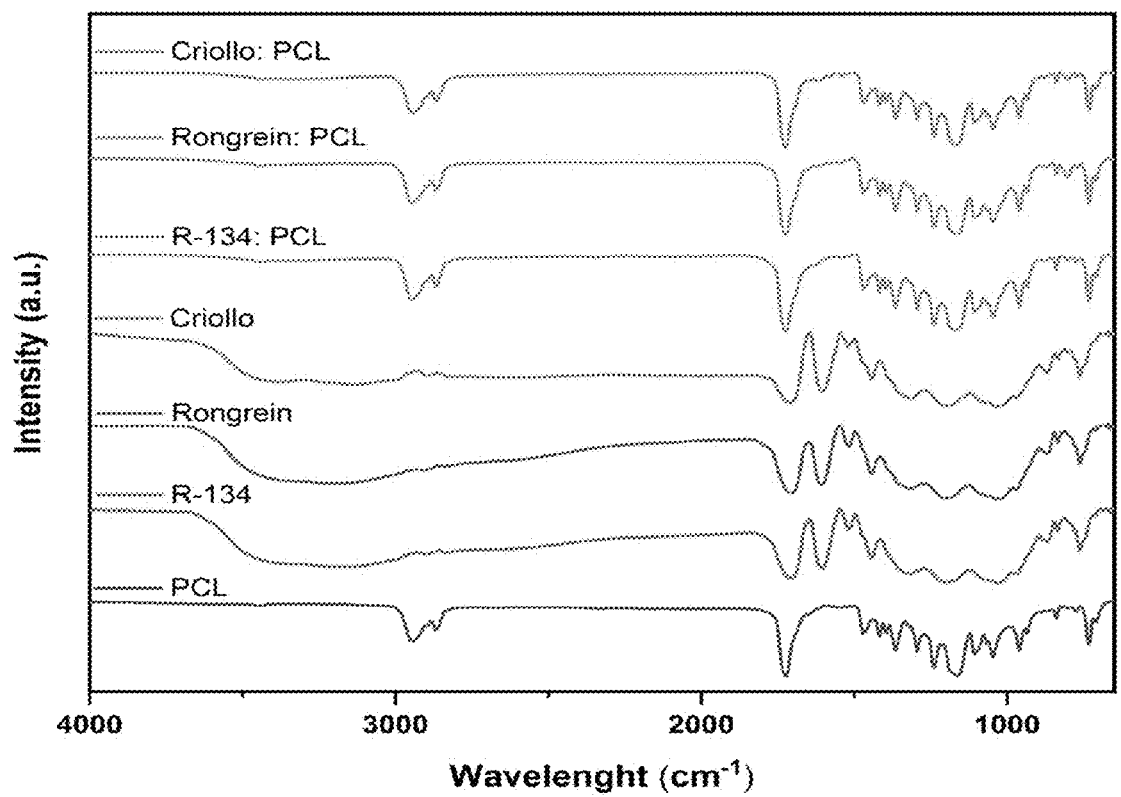
FIG. 27 ATR-FTIR spectra of RPE-PCL blends with RPE from three varieties of rambutan rind powder.

The surface chemistries of the RPE-ESNFs membranes were evaluated using FTIR-ATR, and the resulting spectra are shown in FIG. 27. It was shown that the graph derived from PCL ESNFs with no RPE added was significantly different from that of the RPE-loaded PCL ESNFs showing different peaks in different regions. FTIR spectra obtained could confirm the chemical stability of RPE in the ESNFs. FTIR of the different RPE showed no significant differences between varieties, all spectra showed broad phenolic —OH band centered around 3400 cm$^{-1}$, characteristic —CO stretching at 1665 cm$^{-1}$, aromatic bending and stretching around 1100 and 1600 cm$^{-1}$, —OH phenolic bending around 1200 and 1400 cm$^{-1}$. On the other hand, FTIR spectrum of PCL shows prominent peak at 1730 cm$^{-1}$, which corresponds to the —CO (stretching), whereas the peaks at 2868 and 2947 cm$^{-1}$ are related to the C—H bond of saturated carbons. Finally, FTIR spectrum of RPE-loaded PCL ESNFs showed additional peaks due to the presence of RPE in the blend matrix. The characteristic 1665 cm$^{-1}$ of RPE's —CO stretching is seen as small shoulder due to the overlapping of the dominant —CO stretching of PCL (1730 cm$^{-1}$), but the phenolic —OH corresponding to RPE is seen around 3400 cm$^{-1}$ for the RPE-loaded PCL ESNFs. The spectral analysis showed that the all RPE varieties loaded were stable in the PCL blended ESNFs. Similar results were previously reported by Natarajan et al. (2010), for a system composed by quercetin, a common polyphenol, encapsulated in PCL microspheres.

Figure 28:
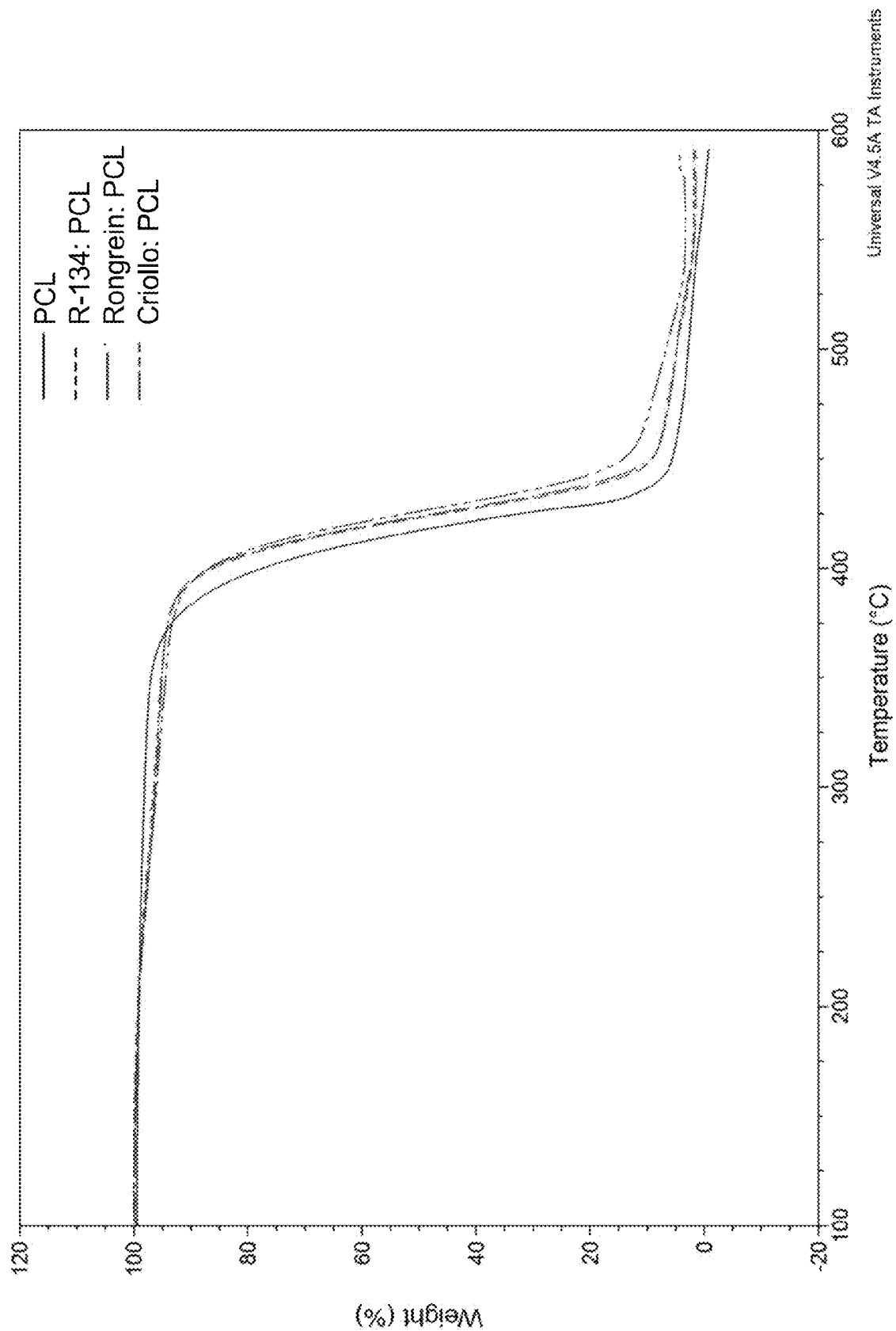
FIG. 28. Thermogravimetric analysis (TGA) of RPE-loaded ESNFs membranes fabricated with RPE from different rambutan varieties (Rongrein, Criollo and R-134) and compared against PCL ESNFs alone.
Figure 29A:
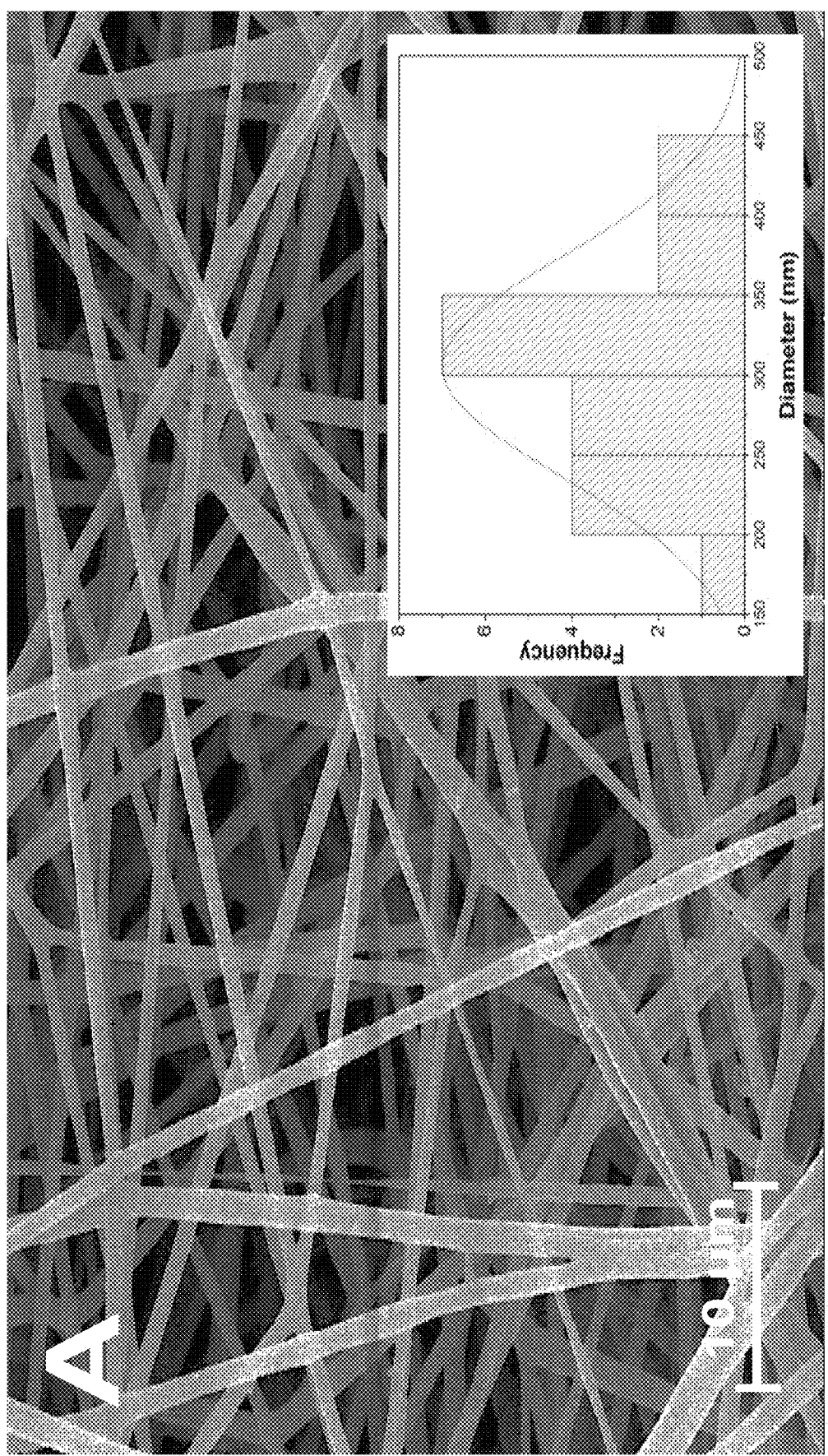
FIGS. 29A-29D. Scanning electron micrographs showing the surface morphology of RPE-ESNFs.
Figure 29B:
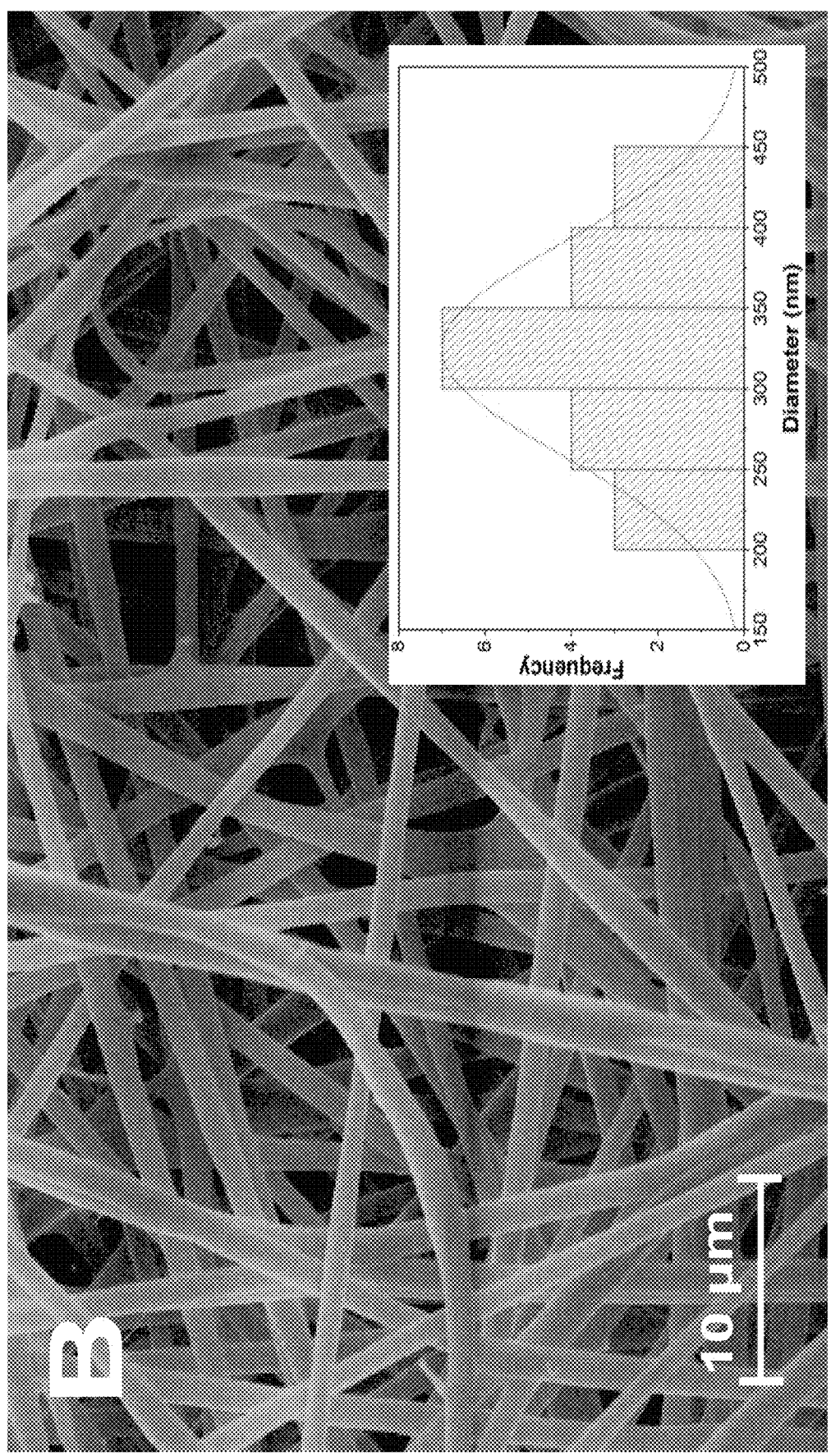
Figure 29C:
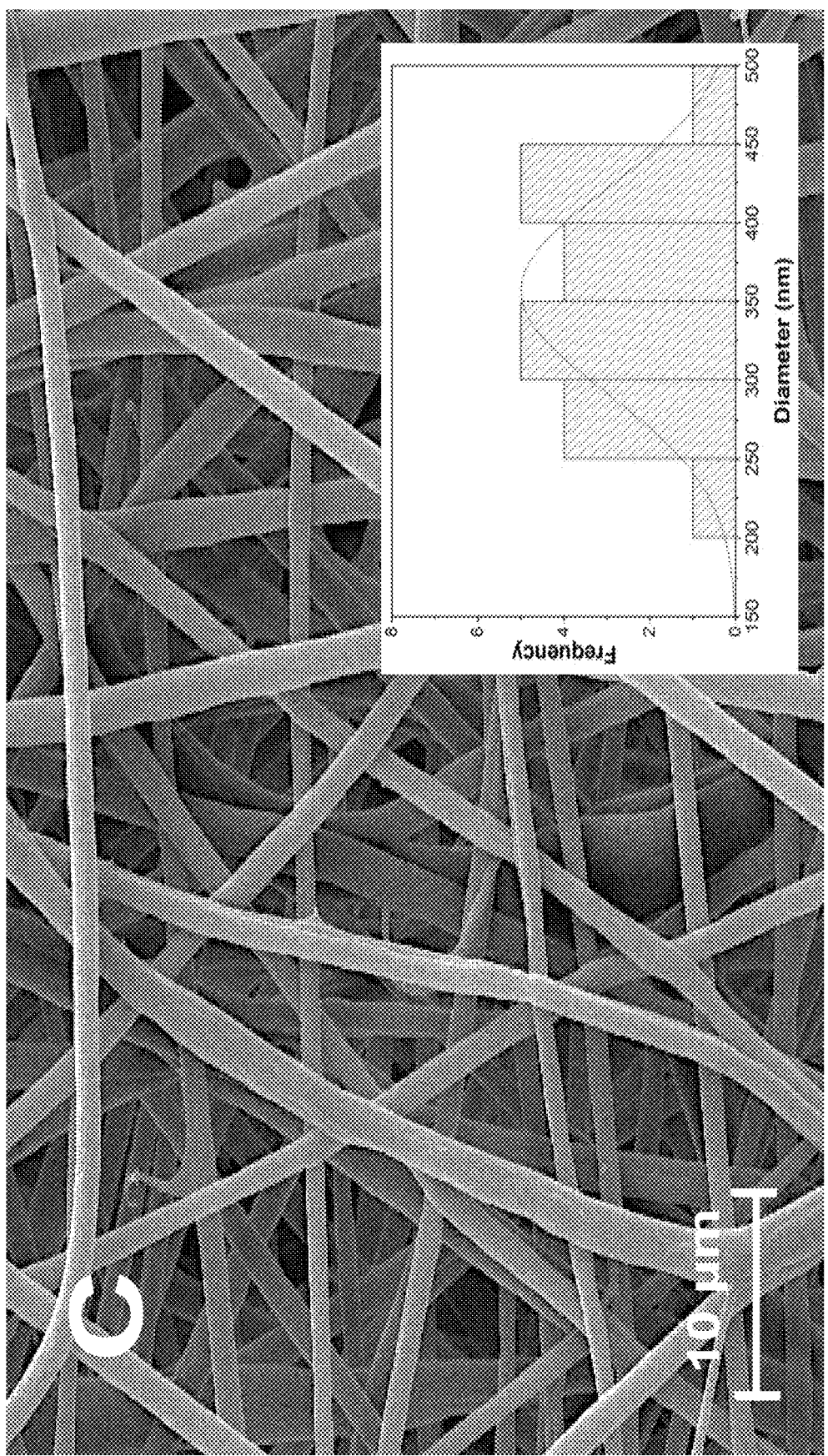
Figure 29D:
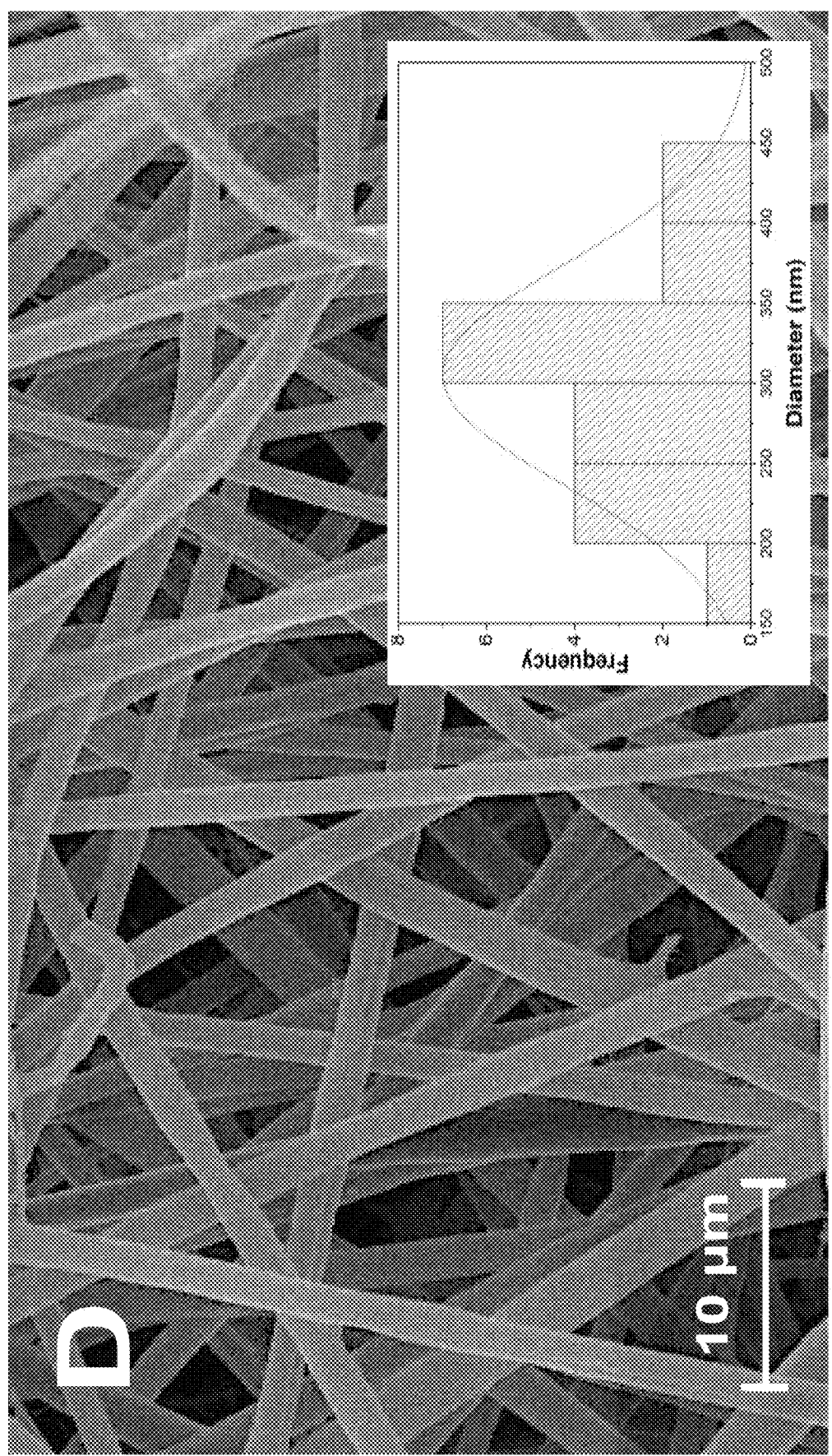

Efficacy of RPE-loading process into ESNFs was successfully confirmed by thermal analysis by thermogravimetry (TGA) as shown in FIG. 28. Thermogram for PCL ESNFs alone agrees with previously shown TGA thermogram shown in FIG. 9, showing a single thermal transition event associated with PCL thermal degradation starting around 350° C. On the other hand, ESNFs containing different RPEs showed two thermal transition events, with the first one starting around 200° C. for all rambutan varieties, corresponding to RPE degradation and a second thermal event starting around 350° C., corresponding to PCL matrix degradation. No differences were observed among the different varieties of rambutan rind RPEs loaded into ESNFs, with all varieties showing weight reduction of about 4%, suggesting efficacy and homogeneity in RPE loading during electrospinning process.

Surface morphology of the RPE-ESNFs was characterized by SEM, as shown in FIGS. 29A-29D. The results indicate electrospinning process succeeded in fabricating ESNFs with an average diameter of about 300 nm and a fairly uniform fiber distribution. Results also suggest that, as the concentration of RPE loaded into the ESNFs increases, the nanofiber diameter also increases. Different varieties of RPE extracts did not show significant differences between their respective RPE-ESNFs.

The correlation between nanofiber diameter and mean pore area of RPE-loaded ESNFs is shown in Table 5. Similar to the results reported above for cranberry PAC-loaded ESNFs, the nanofibers loaded with rambutan extracts seem increases average nanofiber size with addition of RPE. When compared to PCL ESNFs with no RPE added (305 nm), RPE-loaded ESNFs showed an increase in nanofiber diameter of 50-fold. Nanofibers obtained from different rambutan varieties showed no significant differences (Table 5). Pore area analysis of the RPE-loaded ESNFs membranes also showed a trend similar to that for cranberry PAC discussed above, with a reduction in pore area of the ESNFs membranes when loaded with RPEs, associated to the increase in ESNFs average diameter. The results for pore area testing are consistent with the results of nanofiber diameter, showing inverse correlation but not significantly different among rambutan varieties.

TABLE 5

Correlation between average nanofiber diameter and ESNFs
membrane pore area with three varieties of rambutan.
Results are reported as mean ± SD (n = 20).

| RPE-PCL ESNF | Fiber diameter (nm) | Mean Pore Area (nm$^2$) |
| --- | --- | --- |
| PCL | 305.29 ± 68.75 | 996.94 ± 106.51 |
| R-134: PCL | 337.34 ± 66.86 | 652.29 ± 98.69 |
| Rongrein: PCL | 356.63 ± 64.29 | 629.31 ± 102.47 |
| Criollo: PCL | 353.81 ± 97.86 | 647.17 ± 85.07 |

Figure 30:
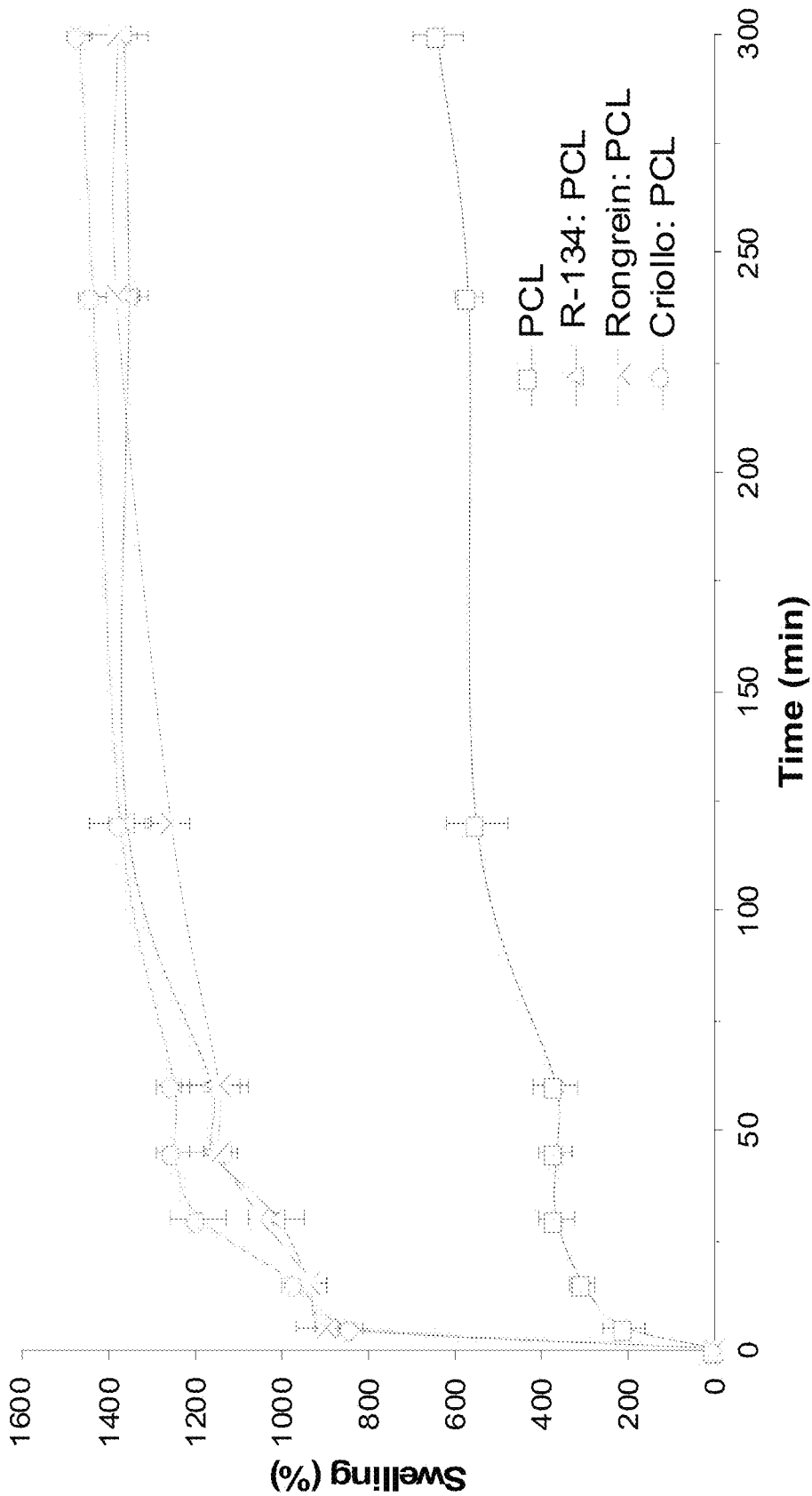
FIG. 30. Swelling behavior of RPE-PCL nanofibers formulated with three varieties of rambutan. Results are reported as mean±SD (n=3).

Swelling properties of the RPE-loaded ESNFs are shown in FIG. 30. Results indicate addition of RPE into PCL ESNFs significantly improves swelling behavior of polymeric membranes by about 600-fold, suggesting RPE increases hydrophilicity of the polymeric membrane and physical performance as well, allowing the membrane to support higher amounts of water as well as increasing flexibility in the swelled 3D nanofiber network.

Effect of RPE Concentration in the Fabrication of RPE-Loaded ESNFs

Figure 31:
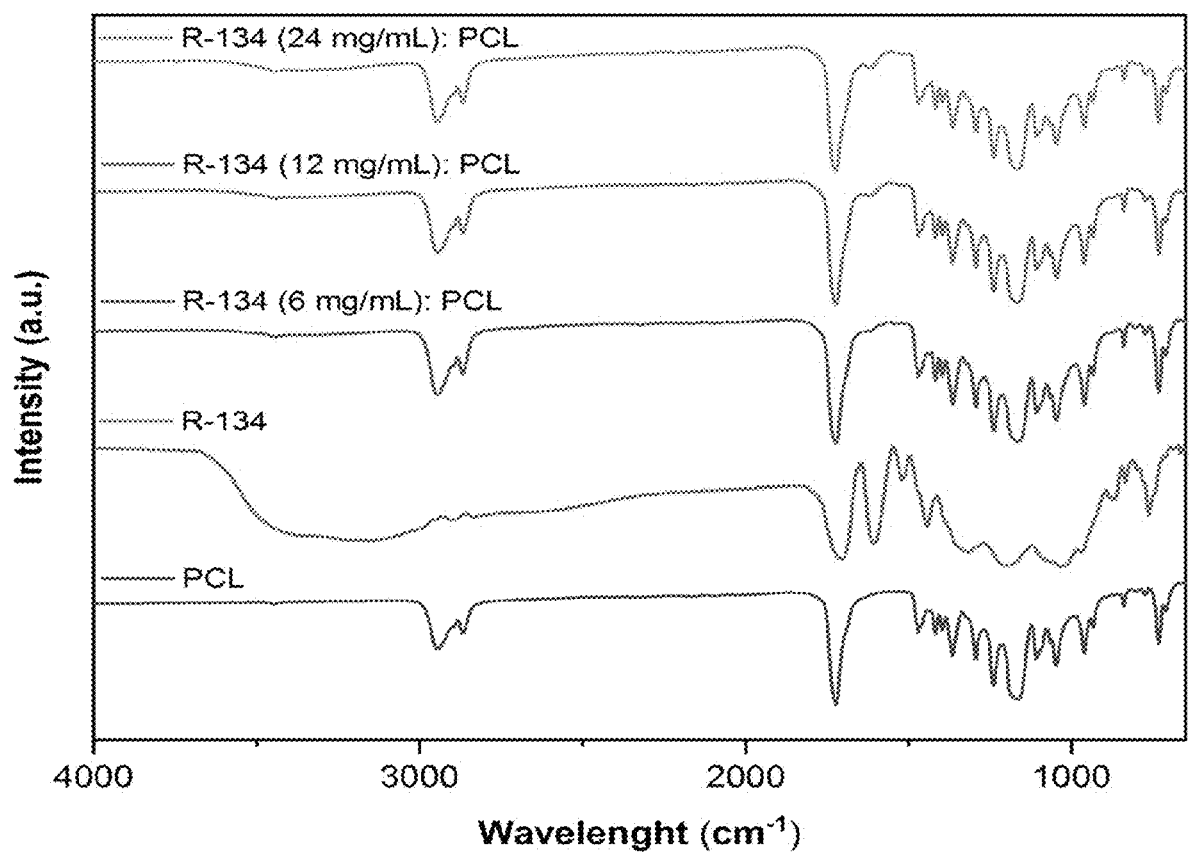
FIG. 31. ATR-FTIR spectra for RPE-loaded ESNFs formulated at increasing concentrations of RPE variety R-134 (0, 6, 12 and 24 mg/mL). PCL (100 mg/mL) ESNFs were used as control with no RPE added.

Results obtained so far showed the positive effect of adding RPE, extracted from different varieties of rambutan rind, to PCL ESNFs, especially in improving hydrophilicity and swelling properties. In a following approach, we decided to study the effect of increasing RPE concentration, for one variety of rambutan (R-134). FIG. 31 shows the infrared spectra for ESNFs prepared at increasing concentrations of RPE (R-134), results allowed identifying an increase in the intensity of the characteristic phenolic —CO stretching peak appearing at 1665 cm$^{-1}$ as a result of the increase in the concentration of RPE loaded into the PCL ESNFs, supporting the success in functionalization of ESNFs with RPE in a dose dependent manner.

Figure 32:
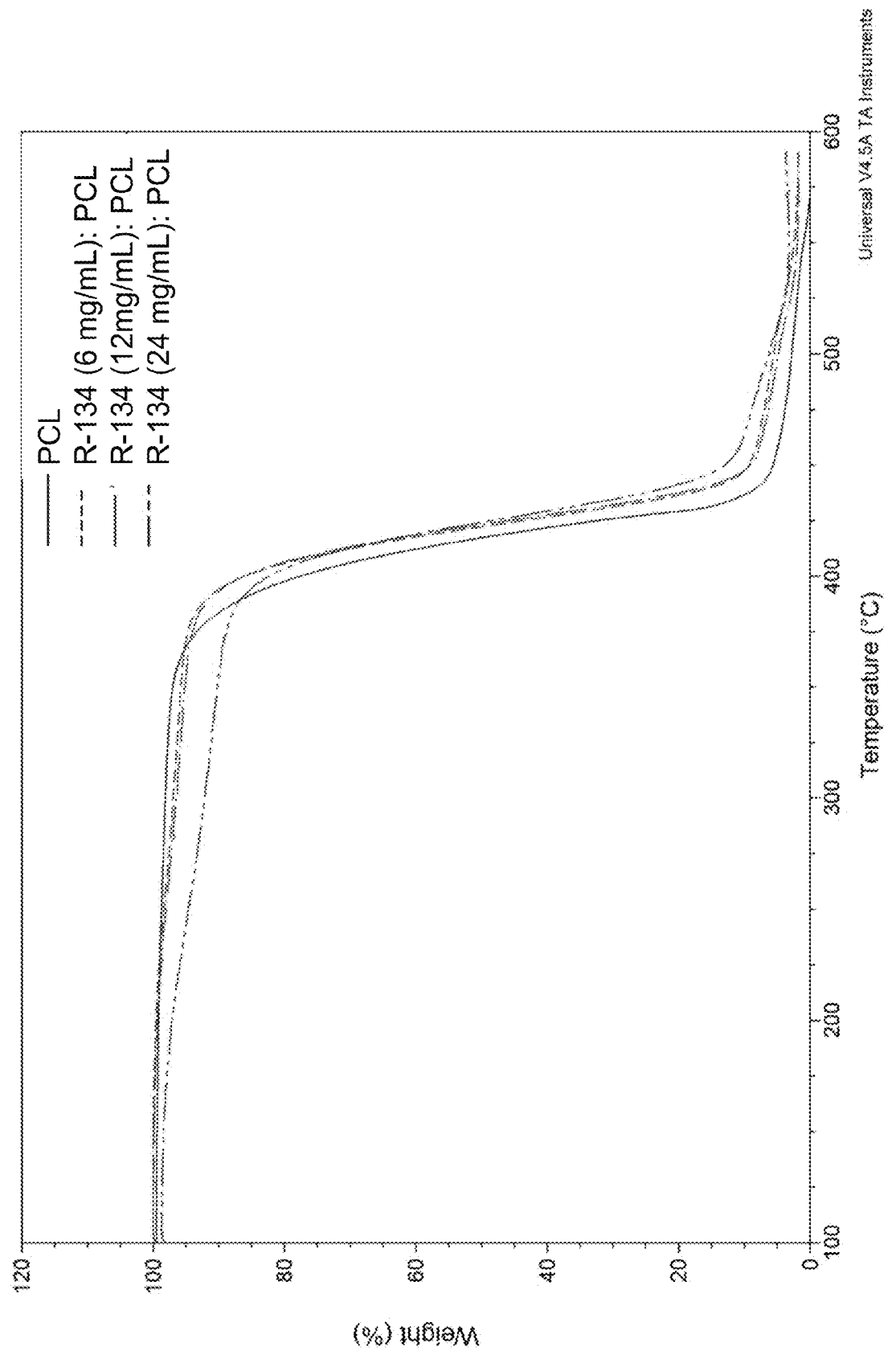
FIG. 32 TGA of RPE-loaded ESNFs membranes fabricated at increasing concentrations of RPE from variety R-134 and compared against PCL ESNFs alone.

Similarly, FIG. 32 shows the thermal behavior of RPE-loaded ESNFs formulated at increasing concentrations of RPE from variety R-134. Thermograms for R-134 RPE-loaded ESNFs showed a similar behavior than the one previously observed in FIG. 28, but this time the thermal event starting around 200° C. and corresponding to the thermal degradation of RPE shows a dose-response behavior with increasing weight loss percentage as the concentration of R-134 RPE increases in the respective ESNFs membrane tested, ranging as follows R-134 24 mg/mL (17%)>R-134 12 mg/mL (8%)>R-134 6 mg/mL (5%).

Figure 33:
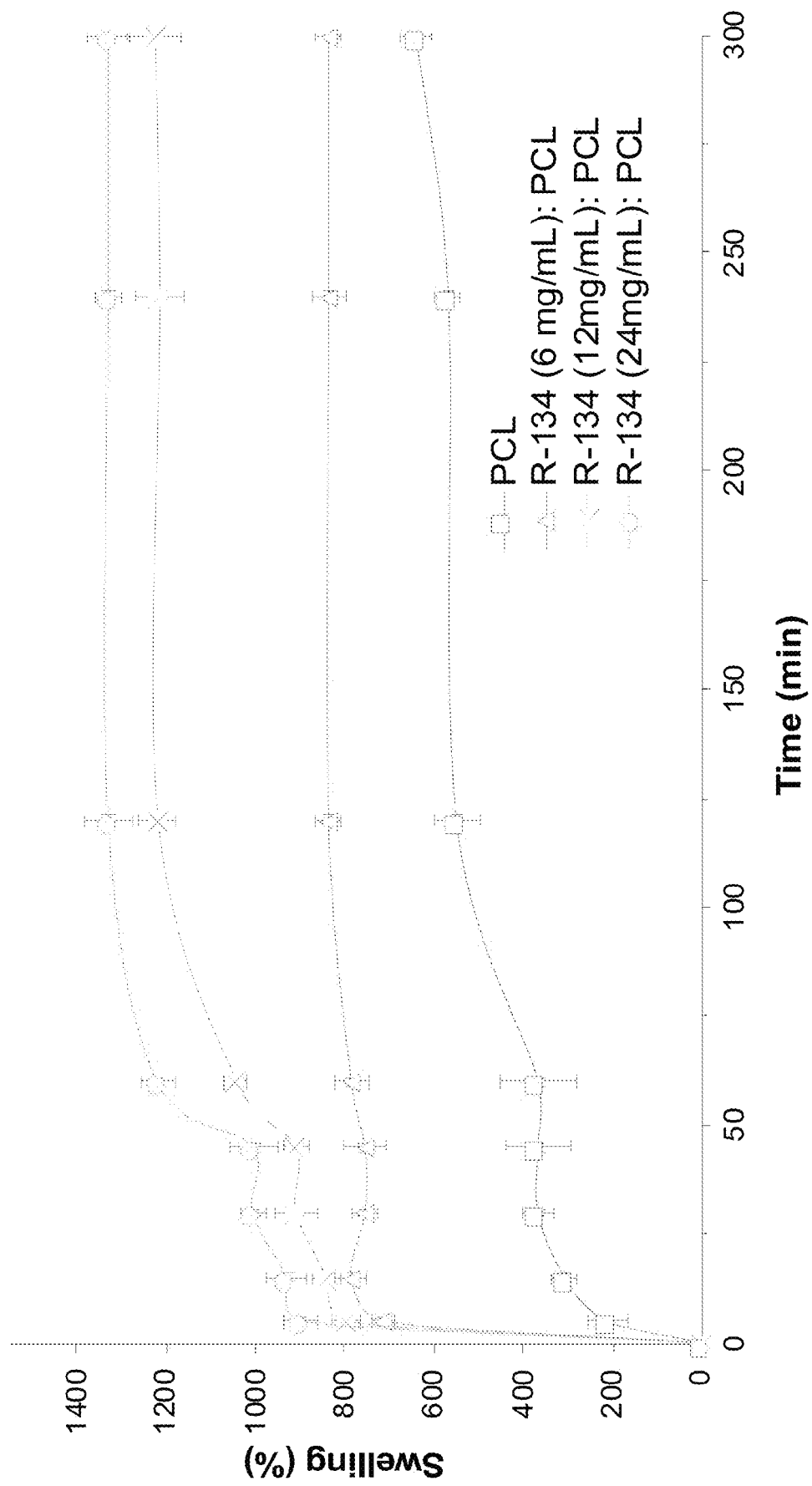
FIG. 33 Swelling behavior of RPE-loaded ESNFs formulated at increasing concentrations of RPE from variety R-134. Results are reported as mean±SD (n=3).

Effect of loading different concentrations of R-134 RPE into ESNFs on swelling properties of the fabricated nanofiber membrane is shown in FIG. 33. Similar to the results reported in FIG. 30 for different varieties of rambutan, addition of RPEs into PCL ESNFs depict in an increase in nanofiber hydrophilicity, thus results show an increase in swelling of the ESNFs as the concentration of RPE increases reaching values higher than 600-fold for the highest concentration of RPE loaded into ESNFs (24 mg/mL). The swelling percentage for PCL ESNFs alone was about 200%, whereas addition of R-134 RPE increases swelling as follows R-134 RPE 24 mg/mL (900%)>R-134 12 mg/mL (800%)>R-134 6 mg/mL (700%).

Characterization of Rambutan-PCL/AgNPs ESNFs

Figure 34:
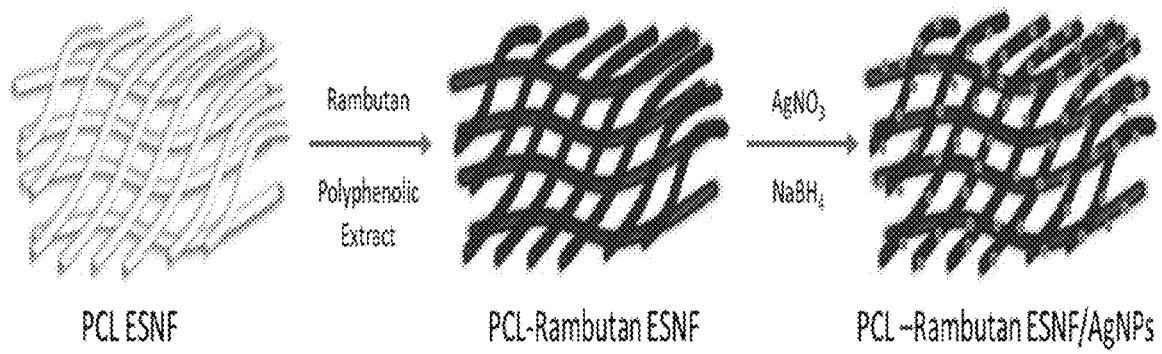
FIG. 34. Illustration of RPE-ESNF surface coated by silver nanoparticles via dipping reduction reaction.

The antibacterial effects of AgNPs have been used to control bacterial growth in a variety of applications, including dental work, surgery applications, wounds and burns treatment, and biomedical devices. It is well known that silver ions and silver-based compounds are highly toxic to microorganisms. Introduction of AgNPs into bacterial cells can induce a high degree of structural and morphological changes, which can lead to cell death (Keat et al. 2015). The illustration shown in FIG. 34 summarizes the proposed mechanism for the surface coating of PCL-RPE ESNFs with AgNPs via reduction dipping technique.

Figure 35:
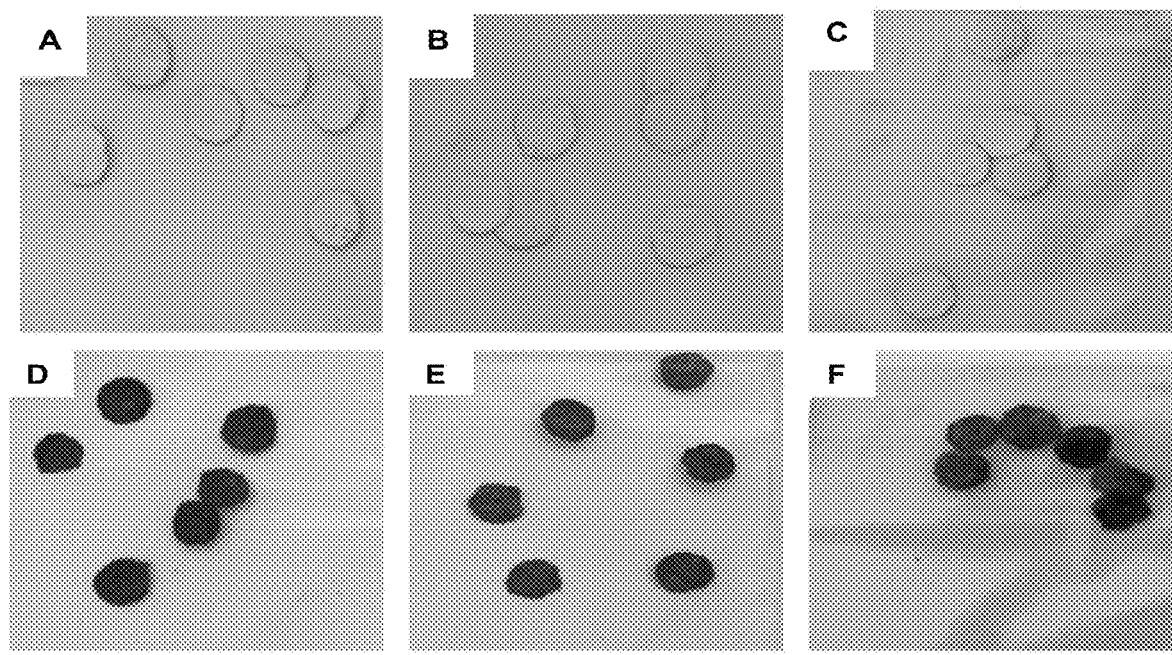
FIG. 35 RPE-ESNFs discs containing RPEs isolated from different varieties of rambutan rind powder. A. PCL100 mg/mL:R-134 12 mg/mL; B. PCL100 mg/mL:Rongrein 12 mg/mL; C. PCL100 mg/mL:Criollo 12 mg/mL), and silver nanoparticles (AgNPs) surface coated RPE-ESNFs discs fabricated via dipping reduction reaction for 5 min. D. AgNPs:PCL100 mg/mL:R-134 12 mg/mL; E. AgNPs:PCL 100 mg/mL:Rongrein 12 mg/mL; F. AgNPs:PCL100 mg/mL:Criollo 12 mg/mL.

As mentioned above, the surface coating of RPE-loaded ESNFs was completed by successive dipping of the membranes in a silver nitrate solution followed by reduction of the entrapped silver ions to elemental silver nanoparticle nuclei by sodium borohydride. FIG. 35 shows the physical appearance of the RPE-ESNFs after surface coated by AgNPs via reduction dipping reaction. As shown by the pictures, the color of the ESNFs membranes turned from white to dark brown after immersion into reaction solutions, which indicated the formation of AgNPs (Vanaja et al. 2013), as will be confirmed later by the SEM analyses.

Figure 36:
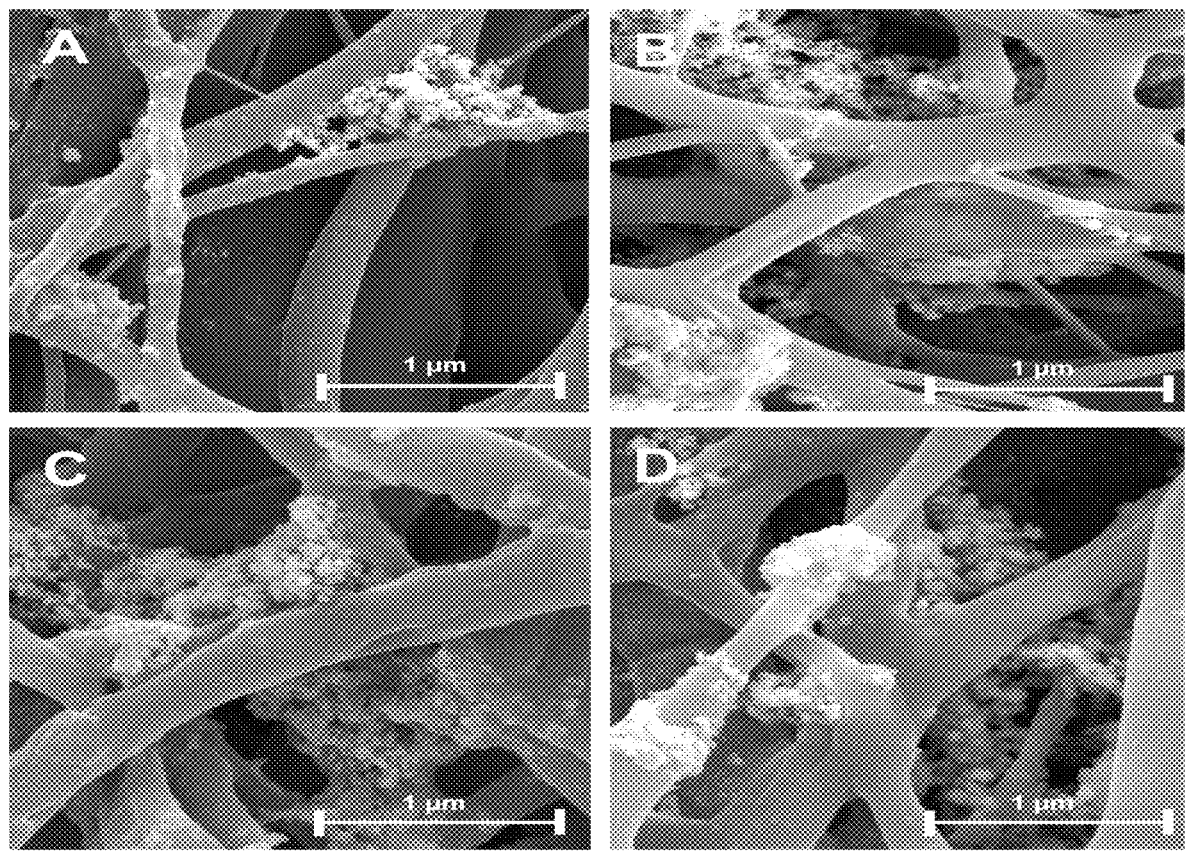
FIG. 36 Scanning electron micrograph showing RPE-ESNF surface coated by silver nanoparticles via dipping reduction reaction after 5 min A. PCL 100 mg/mL, B. PCL 100 mg/mL:R-134 12 mg/mL, C. PCL 100 mg/mL:Rongrein 12 mg/mL, D. PCL 100 mg/mL:Criollo 12 mg/mL.

Surface morphology analysis of the surface coated AgNPs/RPE-ESNFs in FIG. 36 showed the presence of AgNPs randomly distributed among the nanofiber's surface of both RPE-loaded and non-RPE-loaded ESNFs. However, comparative analysis of SEM images clearly suggests a higher density of AgNPs in the RPE-loaded ESNFs independent of the variety selected, may be associated to the higher ion-dipole interactions and hydrophilicity of the RPE-loaded ESNFs when compared to the PCL-ESNFs alone.

Figure 37A:
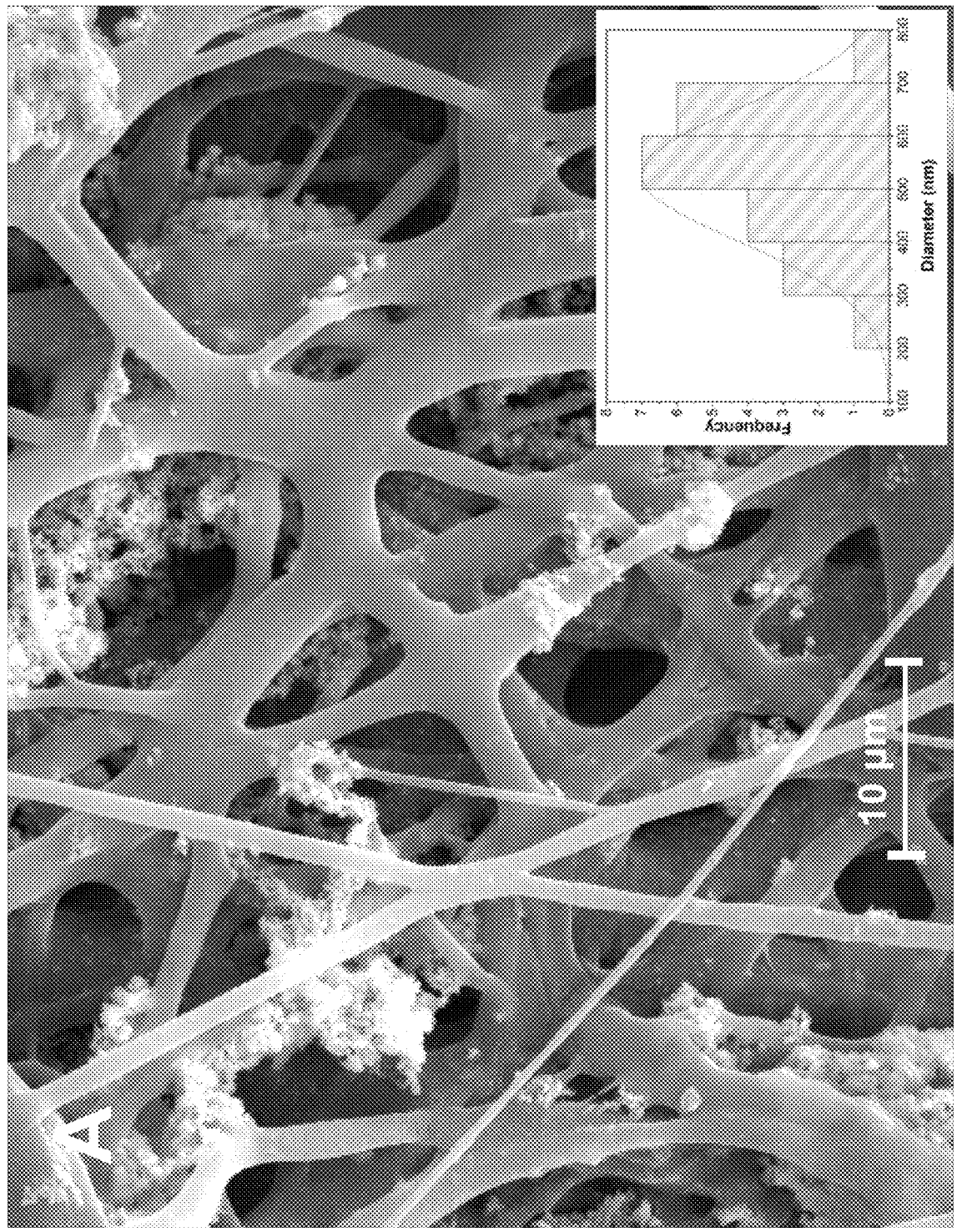
FIGS. 37A-37B Scanning electron micrographs showing the morphology of surface coated AgNPs/RPE-ESNFs after 5 min dipping reduction reaction.
Figure 37B:
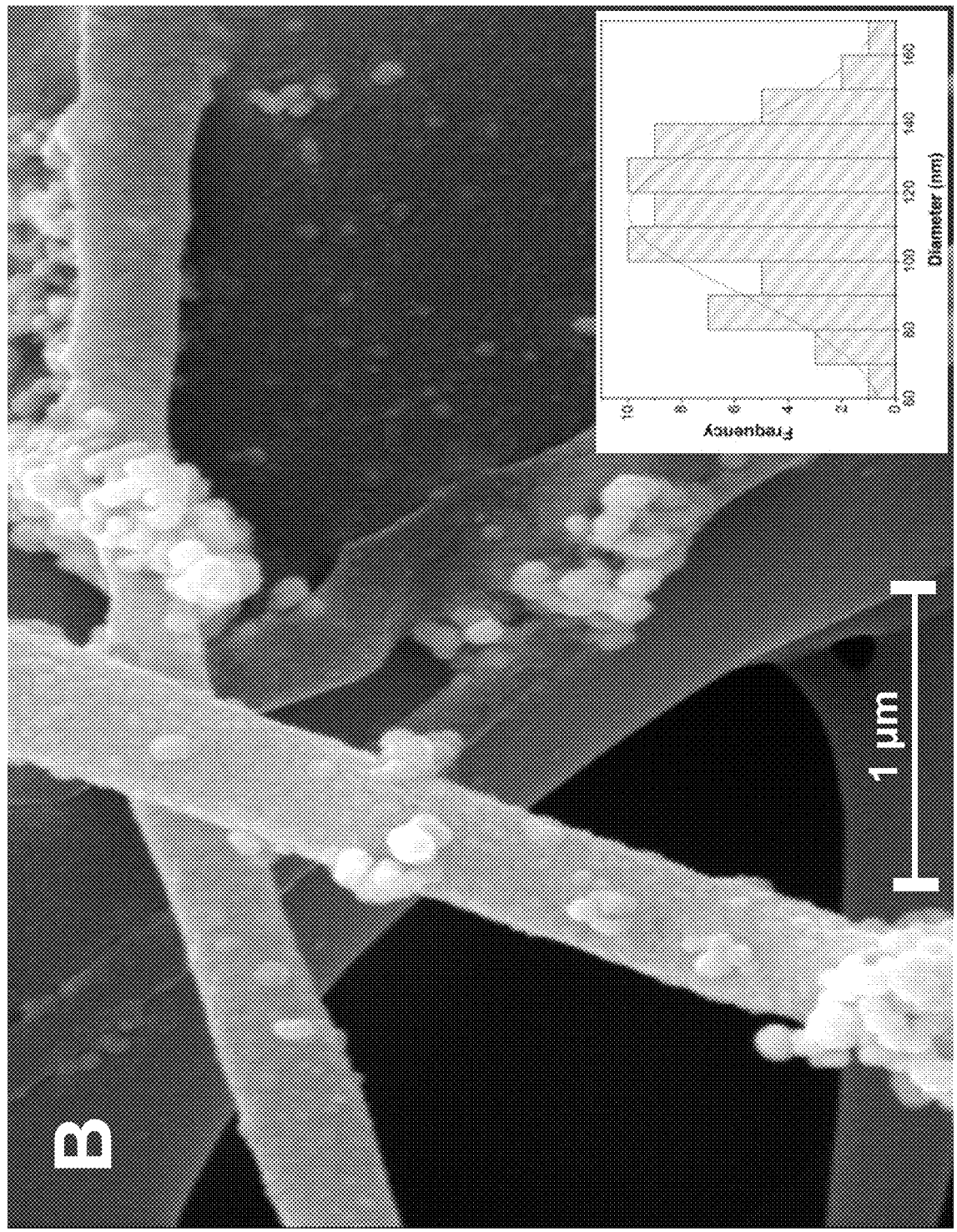

As indicated in Table 6 the RPE-ESNF surface coated by AgNPs via dipping reduction reaction after 5 min show an increase in nanofiber diameter of 100-fold that can be associated to a hydration process of the nanofibers after being dipped in the aqueous solutions of $AgNO_3$ and $NaBH_4$. This observation is consistent with the swelling properties showed by the functionalized nanofibers, where RPE increases the hydrophilicity of the polymeric membrane, as shown in FIG. 30. Results also suggest the pore size is reduced 300-fold which is around half of the initial mean pore for the RPE-loaded ESNFs, this reduction can be related to the deposition of the AgNPs, principally in the pores and edges of the ESNFs membranes as shown in FIG. 36 and FIGS. 37A and 37B. Correspondingly, there is a trend indicating that as nanofiber size increases, mean pore area decreased, showing an inverse correlation as previously explained, due to more free space occupied by the bigger ESNFs.

TABLE 6

Average nanofiber diameter and ESNFs membrane pore area of surface coated AgNPs/RPE-ESNFs fabricated at dipping reduction reaction time of 5 min. Results are reported as mean ± SD (n = 20).

| RPE-PCL/AgNPs ESNF | Fiber diameter (nm) | Mean Pore Area ($nm^2$) |
|---|---|---|
| PCL | 419.68 ± 151.45 | 898.71 ± 130.96 |
| R-134: PCL | 526.12 ± 99.39 | 362.03 ± 84.50 |
| Rongrein: PCL | 569.49 ± 125.22 | 351.15 ± 123.72 |
| Criollo: PCL | 594.04 ± 116.26 | 341.19 ± 119.63 |

Likewise, FIG. 37B shows a magnified SEM micrograph of the AgNPs/RPE-ESNFs from variety R-134, for illustrative purposes, confirming a completed surface coating of the nanofibers by silver nanoparticles, as suggested by the bubble-like surface morphology, and the formation of clusters of nanoparticles with individual sizes ranging around 100 nm along the surface of the supporting nanofibers, indicating the successful reduction dipping AgNPs coating of the ESNFs.

Figure 38:
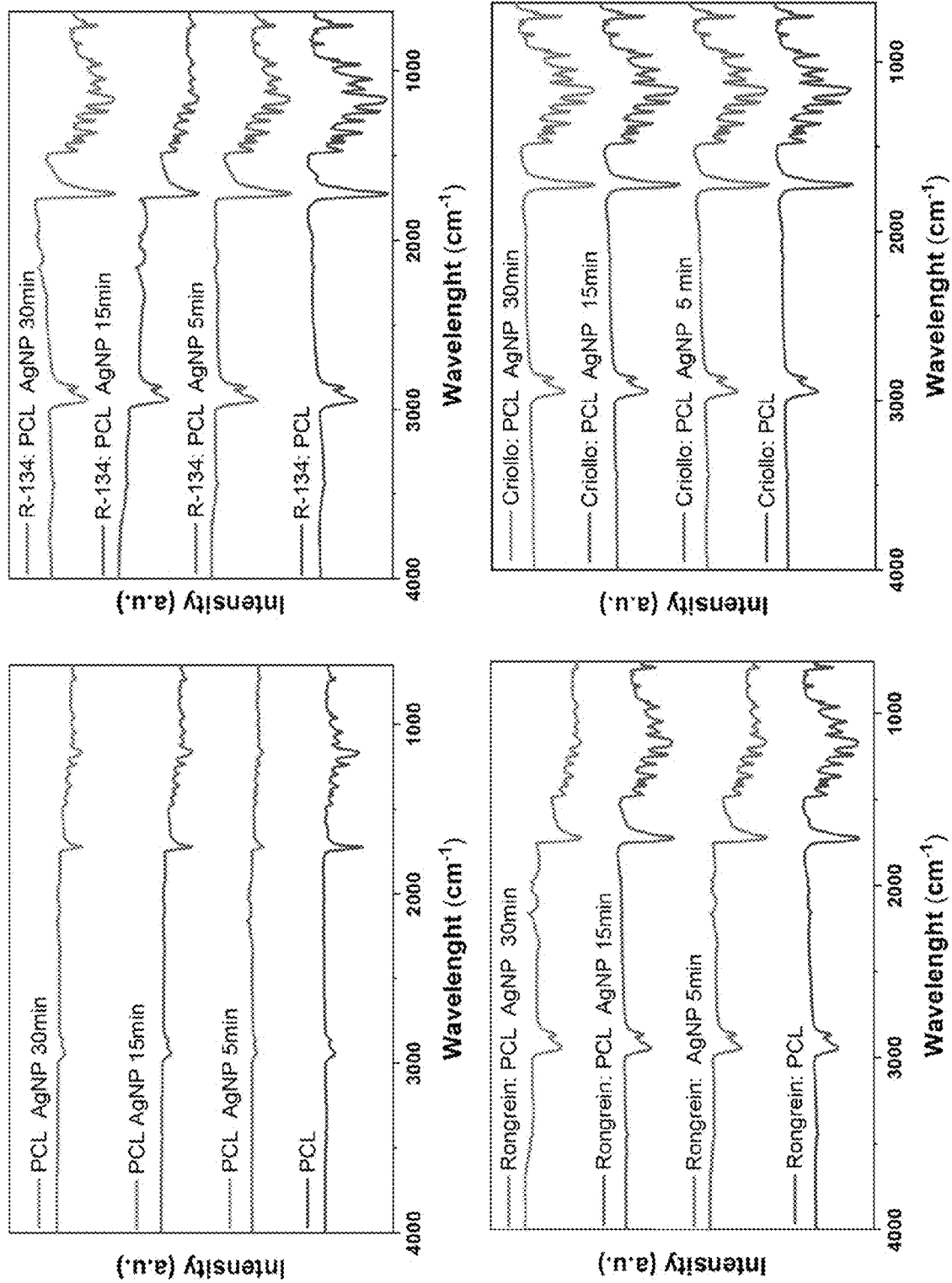
FIG. 38. ATR-FTIR spectra for surface coated AgNPs/RPE-ESNFs fabricated at different dipping reduction reaction times (5, 15 and 30 min).

Chemical surface analysis of the AgNPs/RPE-ESNFs by ATR-FTIR in FIG. 38 showed changes in the spectra of the AgNPs surface coated samples containing no RPE, when compared with nanofibers loaded with RPE, suggesting a more efficient surface coating of the ESNFs by AgNPs, that may be associated to the previously described higher hydrophilicity and suitability for stronger ion-dipole interactions.

Figure 39:
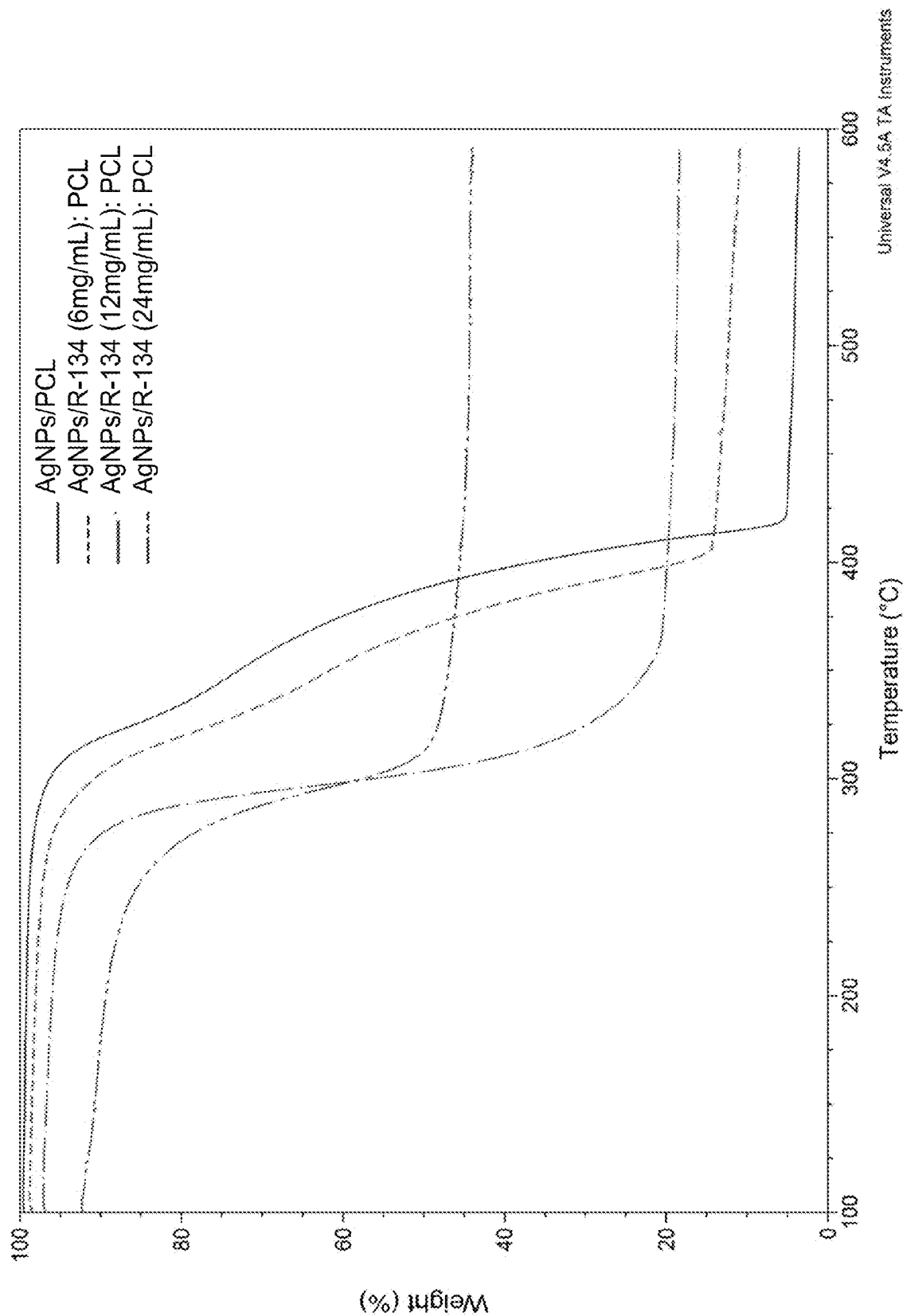
FIG. 39 TGA of RPE-loaded ESNFs membranes surface coated by AgNPs and fabricated at increasing concentrations of RPE from variety R-134.

FIG. 39 shows the thermal behavior of R-134 RPE-loaded ESNFs formulated at increasing concentration of RPE and surface coated by AgNPs, results clearly show a significant change in the trends followed by the RPE-ESNFs membranes after coated by AgNPs when compared with the thermal behavior showed by RPE-loaded ESNFs with no addition of AgNPs in FIG. 32. Addition of AgNPs into the system seems to strongly modify the thermal behavior of both RPE and PCL components of the ESNFs membrane matrix. The individual thermal event expected for PCL alone at 350° C. is now composed by a two-transition event with points of inflection at 325 and 400° C., potentially associated to AgNPs-PCL complex and PCL alone degradation, respectively. On the other hand, RPE-loaded ESNFs showed a behavior associated to the increased concentration of R-134 RPEs in each of the ESNFs membranes, with R-134 (6 mg/mL) showing a similar behavior than AgNPs/PCL alone but slightly displaced to lower temperature ranges, may be due to lower thermal stability of RPEs from R-134. ESNFs membranes coated with AgNPs loaded with higher concentrations of R-134 RPEs (12 mg/mL and 24 mg/mL) showed appreciable changes on their TGA thermograms suggesting a higher thermal destabilization of the hybrid silver-RPEs-PCL system, probably due to strong ion-dipole interactions that seem to be also associated to the increase in RPE, as suggested by the reduction in the percentage weight loss showed by the thermal event starting at 275° C., ranging as follows R-134, 6 mg/mL (90%)>R-134, 12 mg/mL (80%) >R-134 24 mg/mL (55%).

Figure 40:
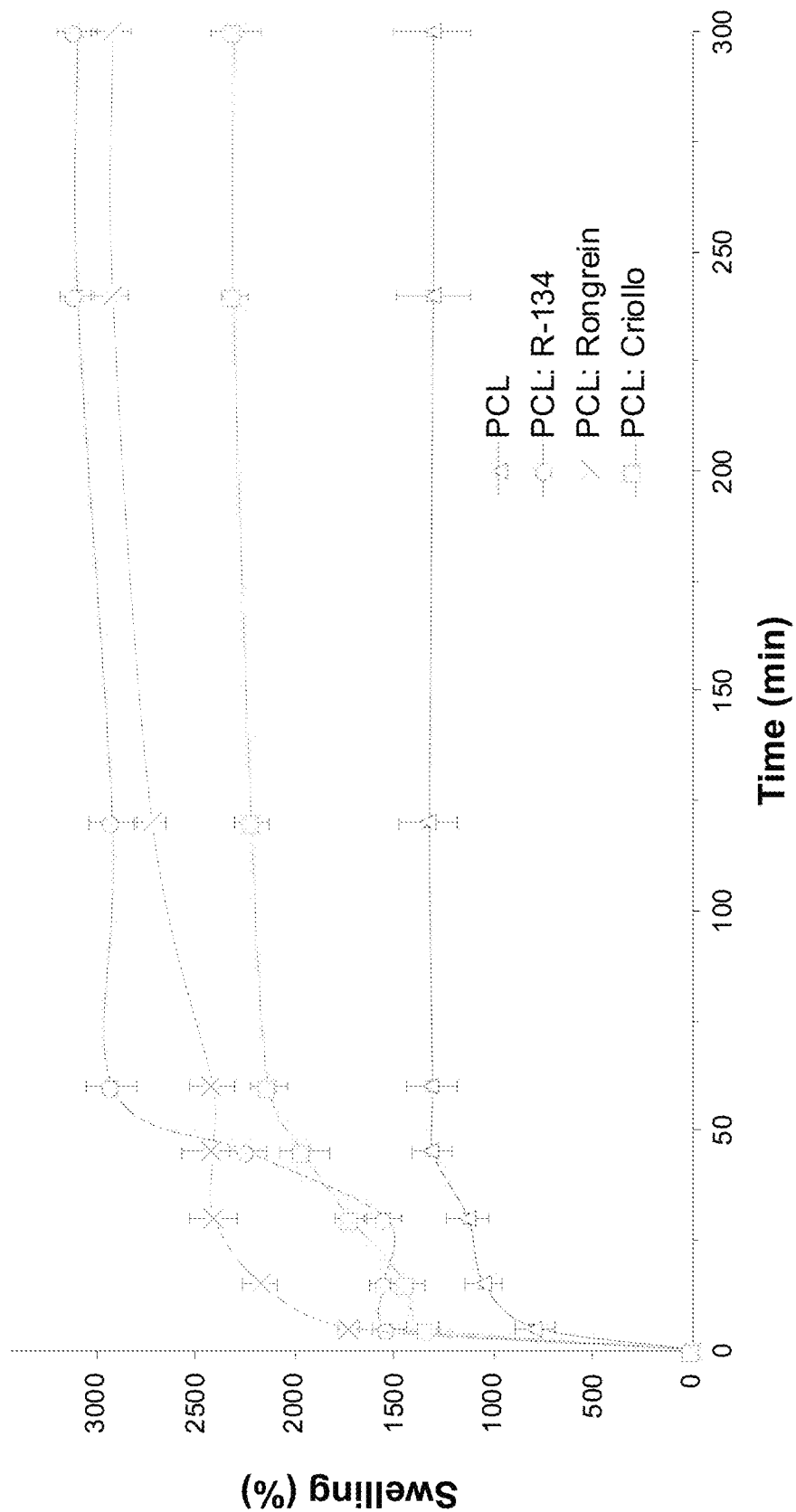
FIG. 40. Swelling behavior for surface coated AgNPs/RPE-ESNFs fabricated at dipping reduction reaction time of 5 min. Results are reported as mean±SD (n=3).

Hydrophilicity of the AgNPs/RPE-loaded ESNFs was confirmed by swelling studies on the sample discs dipped for 5 min, as shown in FIG. 40. Results indicate AgNPs coated ESNFs loaded with RPE from different rambutan varieties showed significant ($p<0.05$) water absorption properties than the AgNPs/PCL-ESNFs. The increase in ESNFs swelling by addition of RPE averages 600% more than AgNPs surface coated PCL-ESNFs along the runtime of the experiment (300 min), suggesting an increase in water absorption properties and hydrophilicity with the addition of RPE, as suggested by the burst-like behavior seen in the swelling curves for all rambutan varieties.

Figure 41:
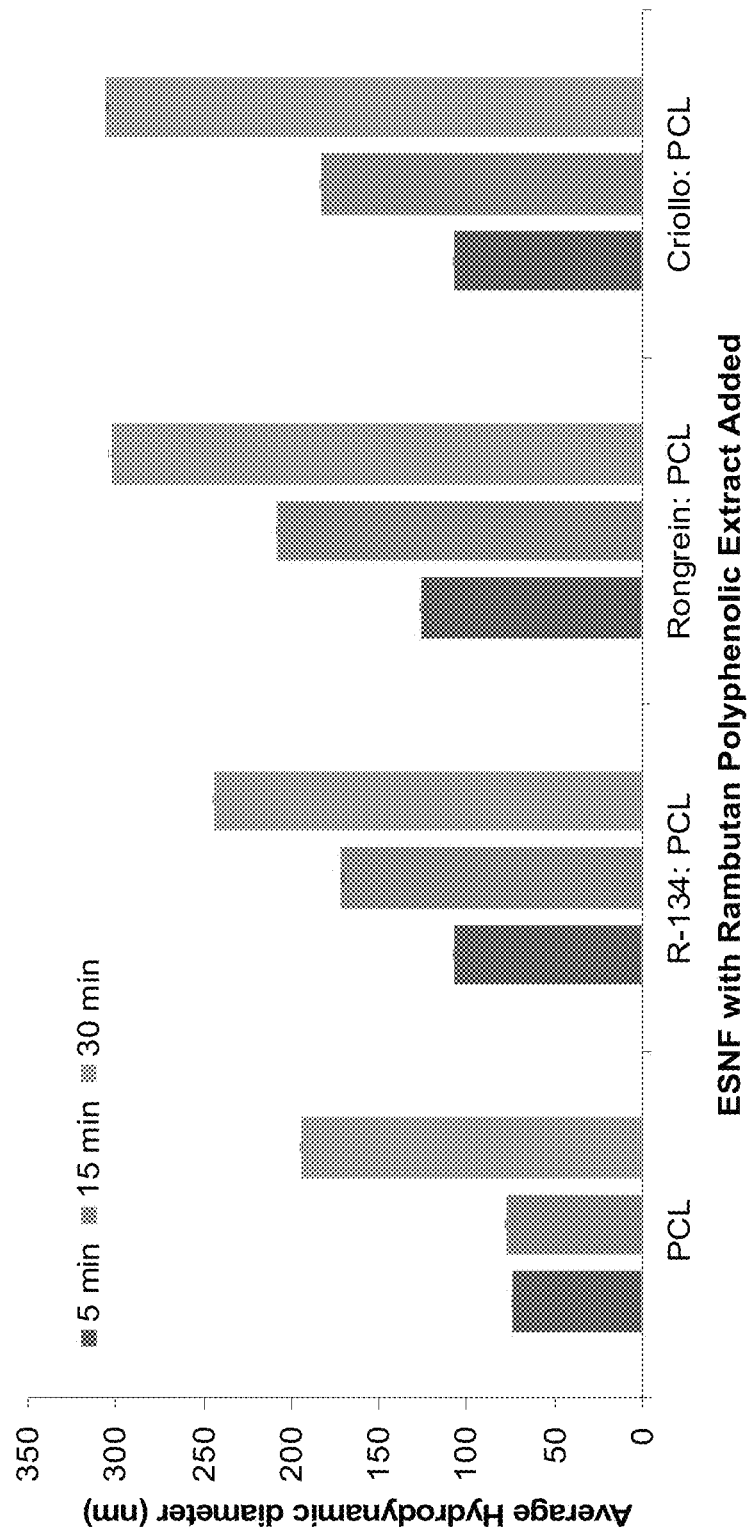
FIG. 41. Effect of dipping reduction reaction time (5, 15 or 30 min) on size of AgNPs surface coated onto RPE-ESNFs. Average hydrodynamic diameter determined by dynamic light scattering measurements. All results are reported as mean±SD (n=5).

Average size of the AgNPs-coated fibers was reported as apparent hydrodynamic diameter (nm), from light scattering measurements in the released nanoparticles collected in solution media (FIG. 41). Results show an increasing trend in average nanoparticle size as the time of immersion in the silver nitrate solution increases from 5 to 30 min. Significant differences ($p<0.05$) were observed between the longer reaction time (30 min) and the intermediate (15 min) and shorter (5 min) reaction times, for the AgNPs released from the RPE-loaded ESNFs, with average nanoparticle sizes ranging 100 nm, 200 nm and 300 nm, respectively. Silver nanoparticles released from RPE-ESNFs loaded with rambutan varieties Rongrein and Criollo showed close variation in nanoparticle size at all dipping reaction times, whereas the sample containing variety R-134 showed slightly lower nanoparticle sizes. All AgNPs released from RPE-loaded ESNFs showed higher average nanoparticle sizes than PCL-ESNFs with no RPE loaded, confirming the formation of nanoparticle clusters previously observed by SEM and may be associated to an excess of AgNPs on the RPE-ESNFs surface.

Release of RPEs from Electrospun Nanofiber Membranes

Figure 42:
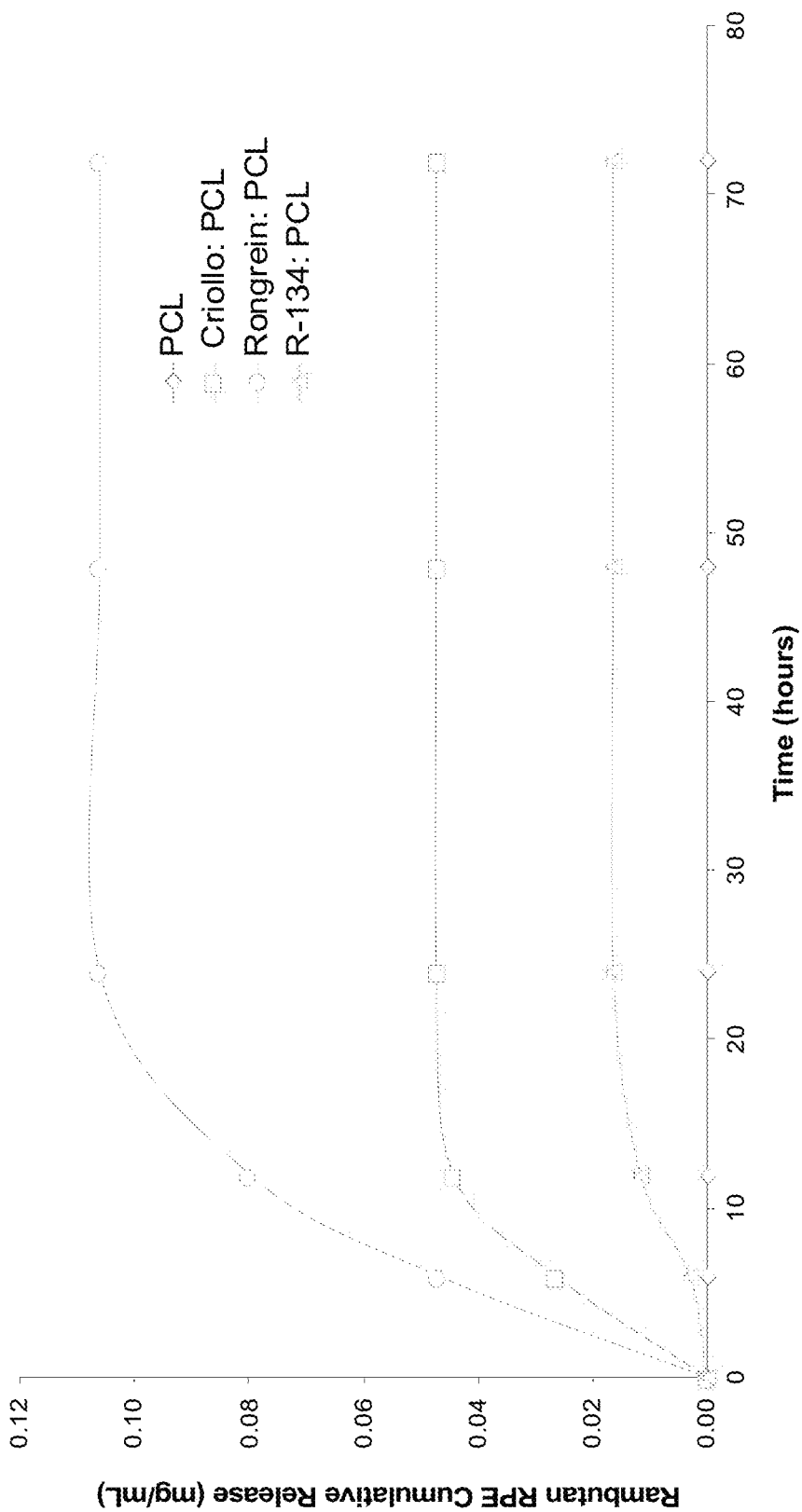
FIG. 42. Comparative RPEs release profiles from PCL (100 mg/ml) ESNFs loaded with 12 mg/mL of different varieties of RPEs. Data are reported as mean±SD (n=4).

Electrospun nanofibers loaded with bioactive extracts can act as carriers, promoting direct or controlled delivery of active compounds, but can also maintain the bioactive compounds attached to the nanofiber's surface conferring functional properties to the ESNFs membranes, suitable for applications as surface nanocoating, wound dressing or 3D scaffold for tissue engineering. We conducted a kinetic release study on RPE-loaded ESNFs, following RPEs release from the ESNFs membrane by the Folin-Ciocalteau assay for quantification of total phenolics. Results for different varieties of RPEs are shown in FIG. 42. All samples tested contained the same concentration of RPEs, allowing a comparative analysis of release profiles. Release of RPEs from ESNFs membranes showed appreciable differences between the different rambutan varieties, with Rongrein variety showing less retention into the ESNFs membrane, showing a burst-like behavior in a shorter time (first 24 h) and reaching a steady state between 24 to 72 h. On the contrary, R-134 variety showed a typical behavior of a controlled release system, with a smooth release of RPEs in the first 24 h and keeping most of the remained RPEs retained into the ESNFs membrane network for a longer period of time when compared to the other rambutan varieties. The third variety Criollo, showed an intermediate behavior between the fast release Rongrein and the controlled release R-134 varieties. Since the Folin-Ciocalteau assay is specific for quantification of polyphenol compounds, no response was obtained when testing PCL ESNFs control membrane with no RPEs added.

Figure 43:
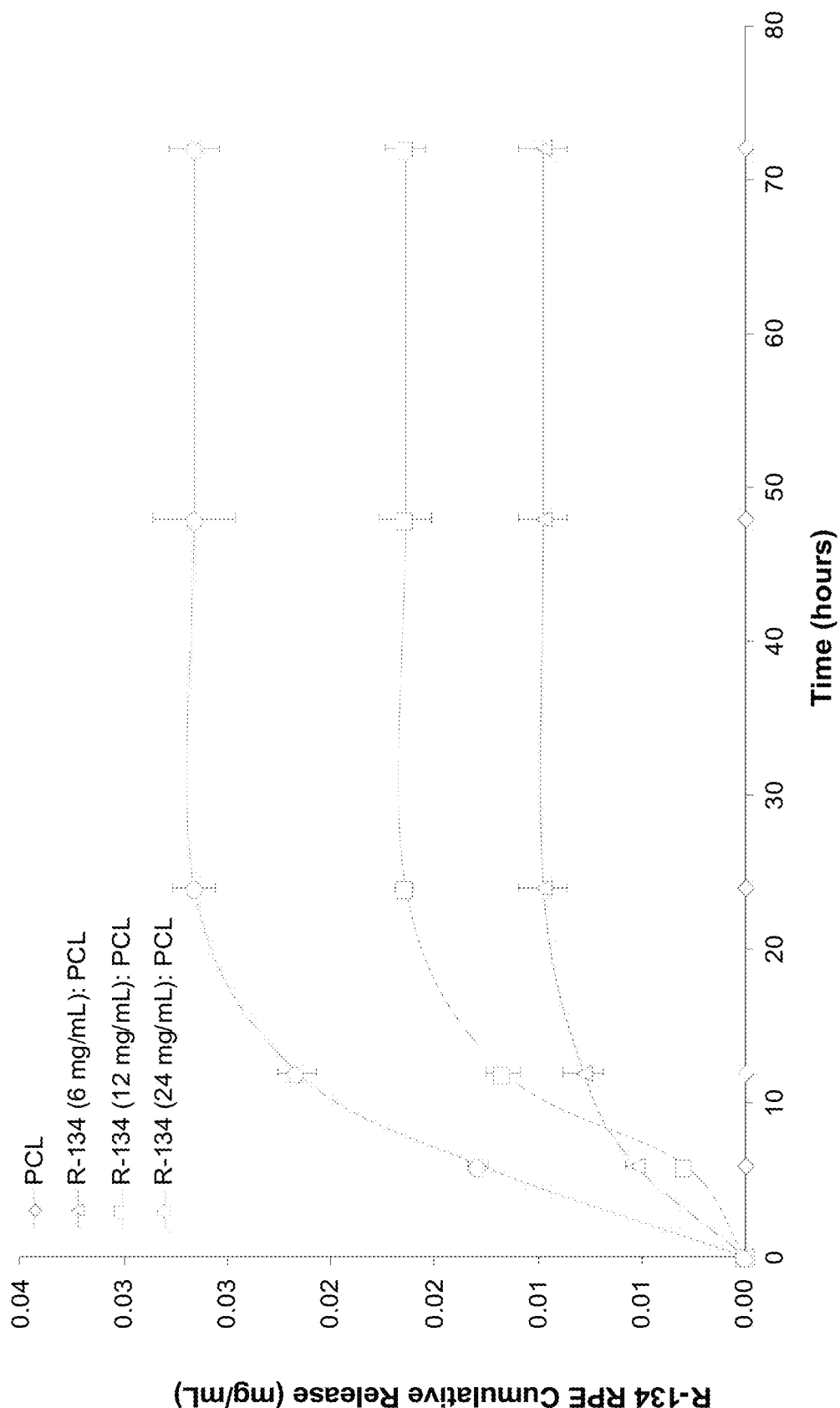
FIG. 43. Comparative release profiles for RPEs from variety R-134 loaded into PCL ESNFs at different concentrations (6, 12 and 24 mg/mL). Data is reported as mean±SD (n=4).

Likewise, FIG. 43 shows the release profiles of RPEs from ESNFs formulated at increasing concentration of R-134 RPEs. Results clearly show a concentration-driven response, with the highest concentration of R-134 RPEs (24 mg/mL) showing the faster release as a function of incubation time at 37° C. Meanwhile, the lowest concentration of R-134 RPEs (6 mg/mL) showed a slower release and the middle concentration of R-134 RPEs (12 mg/mL) showed intermediate behavior. The faster release of R-134 RPEs at the higher concentration loaded into the ESNFs could be associated to a saturation phenomenon, where the ESNFs got the maximum absorption of RPEs into the nanofibers network structure and then the overloaded concentration of RPEs gets exposed in the surface of the ESNFs, allowing a faster release then ESNFs system loaded with the lowest concentration of RPEs, easy to absorb and entrap along the ESNFs network.

Antibacterial Assays

Figure 44:
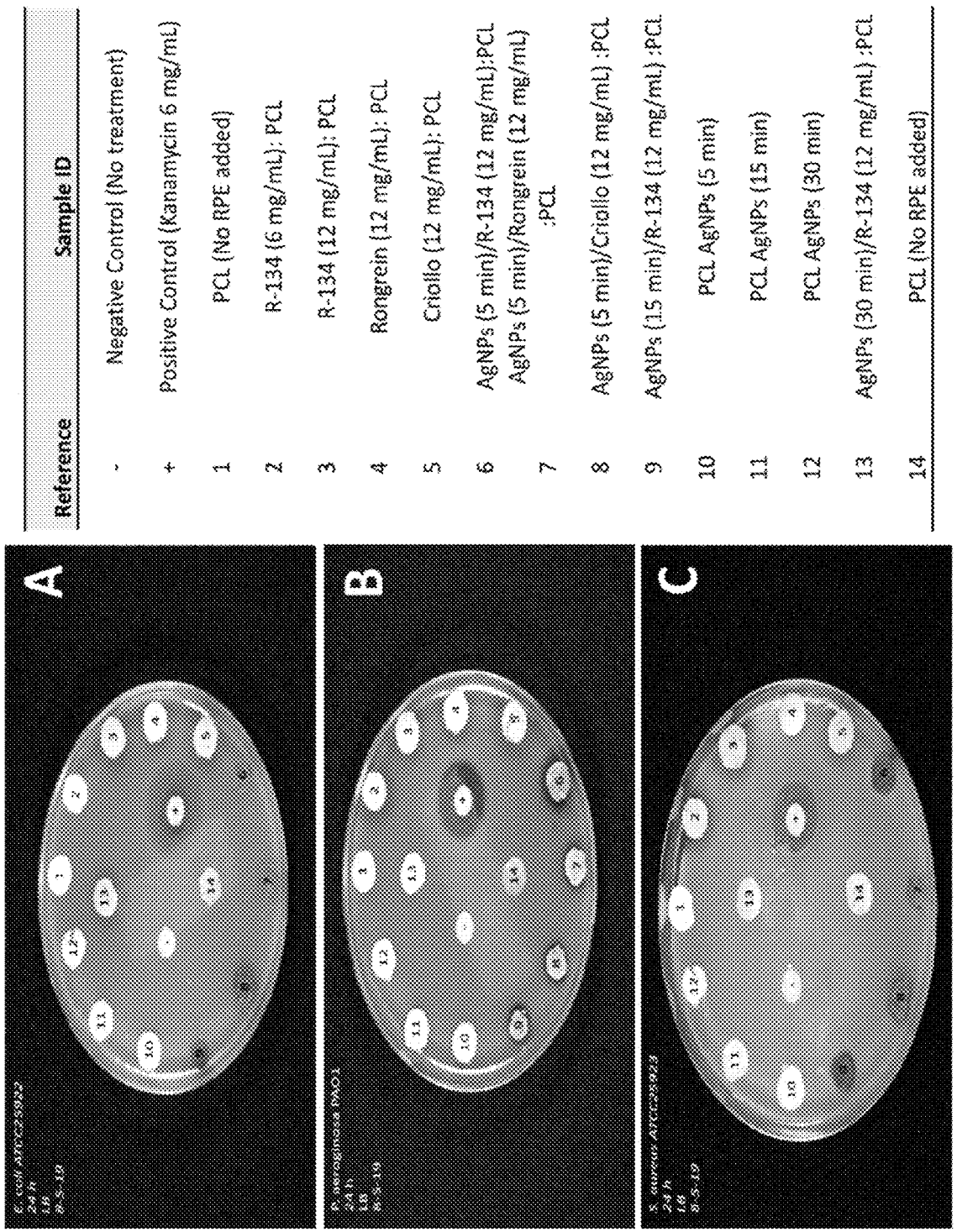
FIG. 44. Antimicrobial activity of RPE-loaded ESNFs with and without surface coating by silver nanoparticles (AgNPs) A. $Escherichia$ $coli$ (ATCC 25992), B. $Pseudomonas$ $aeruginosa$ (PAO1) and C. $Staphylococcus$ $aureus$ (ATCC 25923), after incubation at 37° C. for 24 h in Luria Bertani medium.

As previously discussed above, the plant phenolic compounds found in plant-based extracts from rambutan rind present a wide range of biological activities including antioxidant, antimicrobial and antiallergic activity. We evaluated the antimicrobial activities of RPE-loaded ESNFs against three strains of pathogenic bacteria *Escherichia coli* (ATCC 25992), *Pseudomonas aeruginosa* (PAO1) and *Staphylococcus aureus* (ATCC 25923), qualitative results for bacterial susceptibility testing are summarized in Table 7. Results indicate ESNFs loaded with different varieties of RPEs showed a broad spectrum of antimicrobial susceptibility, showing mild inhibition zones (+), when co-cultured with pathogenic bacteria. Similarly, addition of silver nanoparticles (AgNPs) as surface coating of the RPE-ESNFs showed an increase in bacterial susceptibility reaching moderate inhibition zones (++), suggesting a synergistic effect when AgNPs and RPEs are combined in a single ESNFs membrane (FIG. 44).

TABLE 7

Comparative qualitative analysis of antimicrobial activity of RPE-loaded ESNFs with and without surface coating by silver nanoparticles (AgNPs).

| Sample ID | E. coli (ATCC 25992) | P. aeruginosa (PAO1) | S. aureus (ATCC 25923) |
|---|---|---|---|
| PCL (No RPE) | — | — | — |
| R-134: PCL | + | + | + |
| Rongrein: PCL | + | + | + |
| Criollo: PCL | + | + | + |
| AgNPs/PCL (No RPE) | + | + | + |
| AgNPs/R-134: PCL | + | ++ | ++ |
| AgNPs/Rongrein:PCL | + | ++ | ++ |
| AgNPs/Criollo: PCL | + | ++ | ++ |

(Activity coding, +: zone of mild inhibition; ++: zone of moderate inhibition; +++: zone of high inhibition).

Figure 45:
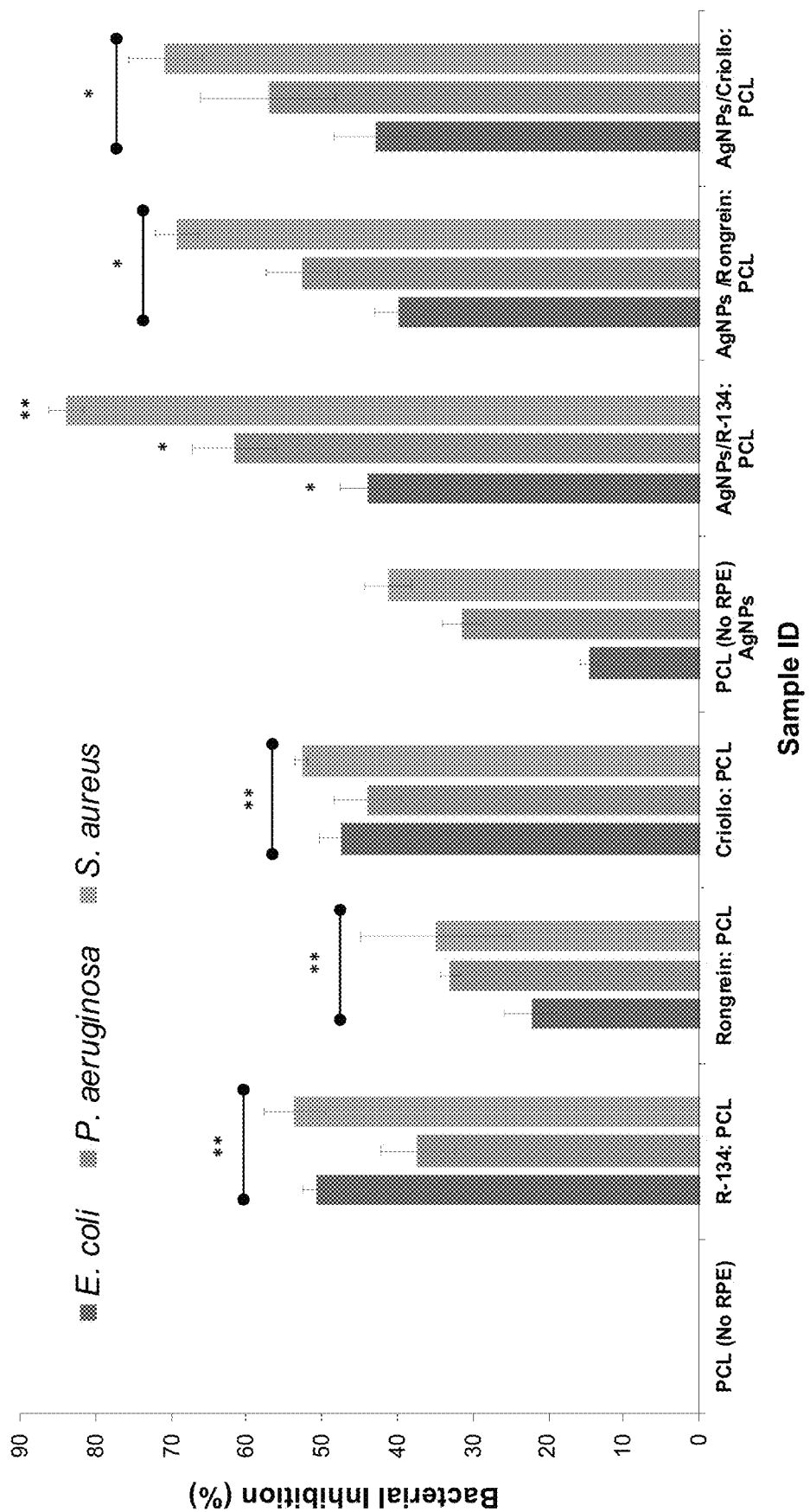
FIG. 45 Comparative quantitative analysis of antimicrobial activity of RPE-loaded ESNFs with and without surface coating by silver nanoparticles (AgNPs). Data is reported as bacterial inhibition percentage standardized to positive control (kanamycin 6 mg/mL) from annular radius calculations performed at the culture plate images using ImageJ software. All results are reported as mean±SD (n=3). The differences were considered statistically significant at p<0.05. One asterisk indicates an effect that is statistically significant p<0.05 and two asterisks indicate an effect that is statistically highly significant p<0.01, compared to the corresponding control.

To provide a more robust comparison of the results generated from the bacterial susceptibility assay, ImageJ software was applied for calculating annular radius of each zone of inhibition. At least three sections of each zone of inhibition was calculated for annular radius and the values obtained where used for calculating the percentage of bacterial inhibition in comparison with the positive control (kanamycin 6 mg/mL), as shown in FIG. 45. Results are in agreement with qualitative observation of the zones of inhibition, showing a statistically significant increase ($p<0.05$) in antimicrobial activity for all RPE-loaded ESNFs when compared to control synthetic PCL ESNFs, suggesting functionalization of synthetic ESNFs with bioactive plant-based extracts significantly improves the performance of PCL ESNFs membranes as antibacterial nanocoatings. Among different rambutan varieties tested, only Rongrein sample showed slightly lower bioactivity against all bacterial strains tested.

Similarly, AgNPs coated RPE-ESNFs showed statistically significant differences in antimicrobial bioactivity when compared with AgNPs coated PCL-ESNFs in all bacterial strains tested. Previous research have reported the low activity of AgNPs against *E. coli* (Li et al. 2010; Aadil et al. 2018), results for our AgNPs/PCL ESNF membranes with no added RPEs show significant lower activity than any of the RPE-loaded ESNFs coated with AgNPs, suggesting not only a synergistic effect between AgNPs and RPE, but also a potential effect of AgNPs against *E. coli* when co-cultured together with RPEs. Compared with other metals, silver exhibits higher toxicity to microorganisms while it exhibits lower toxicity to mammalian cells. Silver ion ($Ag^-$) inhibits phosphate uptake and exchange in bacteria and causes efflux of accumulated phosphate as well as of mannitol, succinate, glutamine, and proline (Li et al. 2010). The silver nanoparticles (AgNPs) are effective against bacteria resistant to antibiotics, as well as against fungi and viruses. The antibacterial mechanisms of silver ion action have been studied for a long time; however, they are only partially understood. Mechanisms of the AgNPs action on bacteria are even less clear. Silver ions can interact with the bases in DNA, rather than with the phosphate groups, and affect the DNA ability to replicate. AgNPs can release silver ions and this mechanism plays a significant role in AgNPs antimicrobial effects (Radzig et al. 2013). The microbiological results obtained by Aadil et al. (2018) showed that the presence of AgNPs in nanostructured membranes has significant antimicrobial activity for the Gram-positive bacteria *Propionibacterium acnes* and less effect in the gram-negative *E. coli*. The result from Al-Omair, M. (2015) also demonstrated that nanofibers containing AgNPs had excellent antimicrobial activity against the Gram-positive bacteria *Bacillus thuringiensis* and *Staphylococcus aureus*, with a clear inhibition zone with a diameter between 22 and 53 mm; moreover, ESNFs sustained the release of AgNP into water over 72 h. Our results are in agreement with these findings and furthermore, the system composed by AgNPs/RPE-ESNFs from variety R-134 showed highly significance ($p<0.01$) when compared to AgNPs/PCL-ESNFs, suggesting addition of RPE significantly improved antibacterial properties of AgNPs when loaded together into ESNFs membranes. More importantly, quantitative analysis allows identifying moderate (30 to 50%) to high (>60%) bacterial inhibition compared to control (100% inhibition), suggesting addition of RPE will significantly improve the performance of ESNFs membranes for potential application as antibacterial coating or as wound healing template. Likewise, the hybrid ESNFs system developed, combining the well-known antibacterial properties of AgNPs together with RPE, will depict in an innovative antibacterial ESNFs membrane showing superior synergistic activity than each of the individual ESNFs membrane systems.

Cell Adhesion and Proliferation Studies

Figure 46:
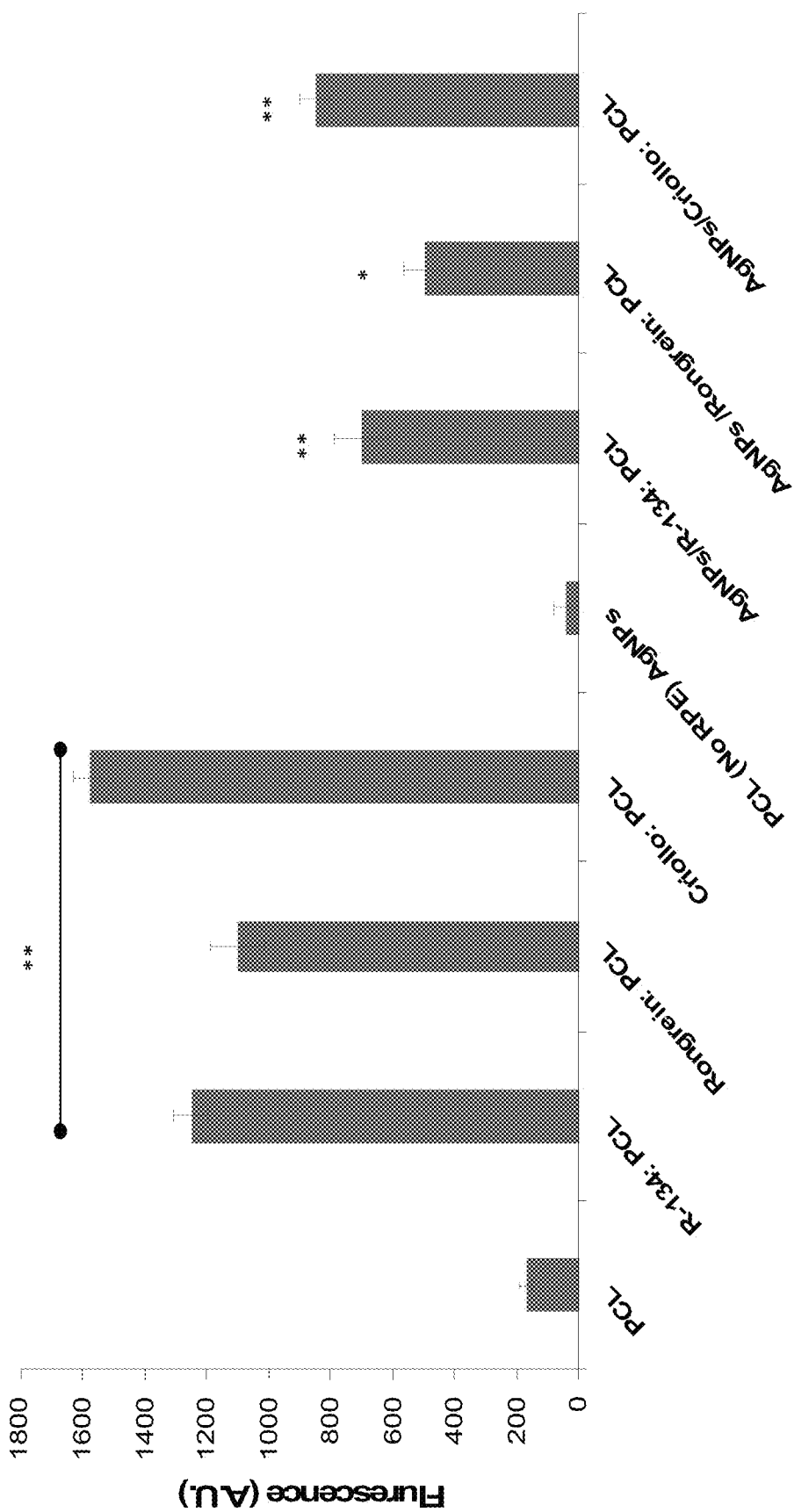
FIG. 46. Comparative analysis of cell adhesion activity of RPE-loaded ESNFs with and without surface coating by silver nanoparticles (AgNPs). Data is reported as fluorescence emitted by adhered cells into the ESNFs membranes. All results are reported as mean±SD (n=3). The differences were considered statistically significant at p<0.05. One asterisk indicates an effect that is statistically significant p<0.05 and two asterisks indicate an effect that is statistically highly significant p<0.01, compared to the corresponding control.

Finally, the effect of functionalizing synthetic ESNFs with RPE on cell adhesion and proliferation properties was tested in vitro using 3T3 fibroblast cells isolated from mouse embryo. The adhesion properties of the ESNFs membranes was tested by adding the cells into cell culture media incorporating the ESNFs membrane discs (8 mm) and incubate the systems under continuous stirring for 4 h to promote cell attachment to the ESNFs that was followed by fluorescence emission, results are reported in FIG. 46. All RPE-loaded ESNFS from different varieties of rambutan showed a highly significant increase in cell adhesion ($p<0.01$) when compared to PCL-ESNFs alone, suggesting functionalization of synthetic ESNFs membranes with significantly improve biocompatibility, providing a suitable environment for cell adhesion, the first step for key biological processes such as wound healing and tissue regeneration. Additionally, ESNFs loaded with RPEs from Criollo variety showed slightly higher bioactivity than the other two rambutan varieties tested.

On the other hand, formulation of hybrid systems composed by RPE-loaded ESNFs surface coated by AgNPs showed lower cell adhesion than the systems containing only RPEs, suggesting addition of AgNPs depicts in reduction of cell adhesion, may be due to a blocking effect of the functional groups in RPEs that promote cell adhesion into the surface of the ESNFs membranes. However, when compared to the AgNPs/PCL ESNFs control, hybrid systems containing RPEs showed a highly significant increase ($p<0.01$) in cell adhesion for varieties R-134 and Criollo and a significant increase ($p<0.05$) for variety Rongrein, showing a similar trend than the one observed for RPE-ESNFs with no AgNPS added. The lower bioactivity showed by Rongrein variety may be associated to its low retention in the ESNFs network, as shown by RPEs release studies in FIG. 42.

Figure 47:
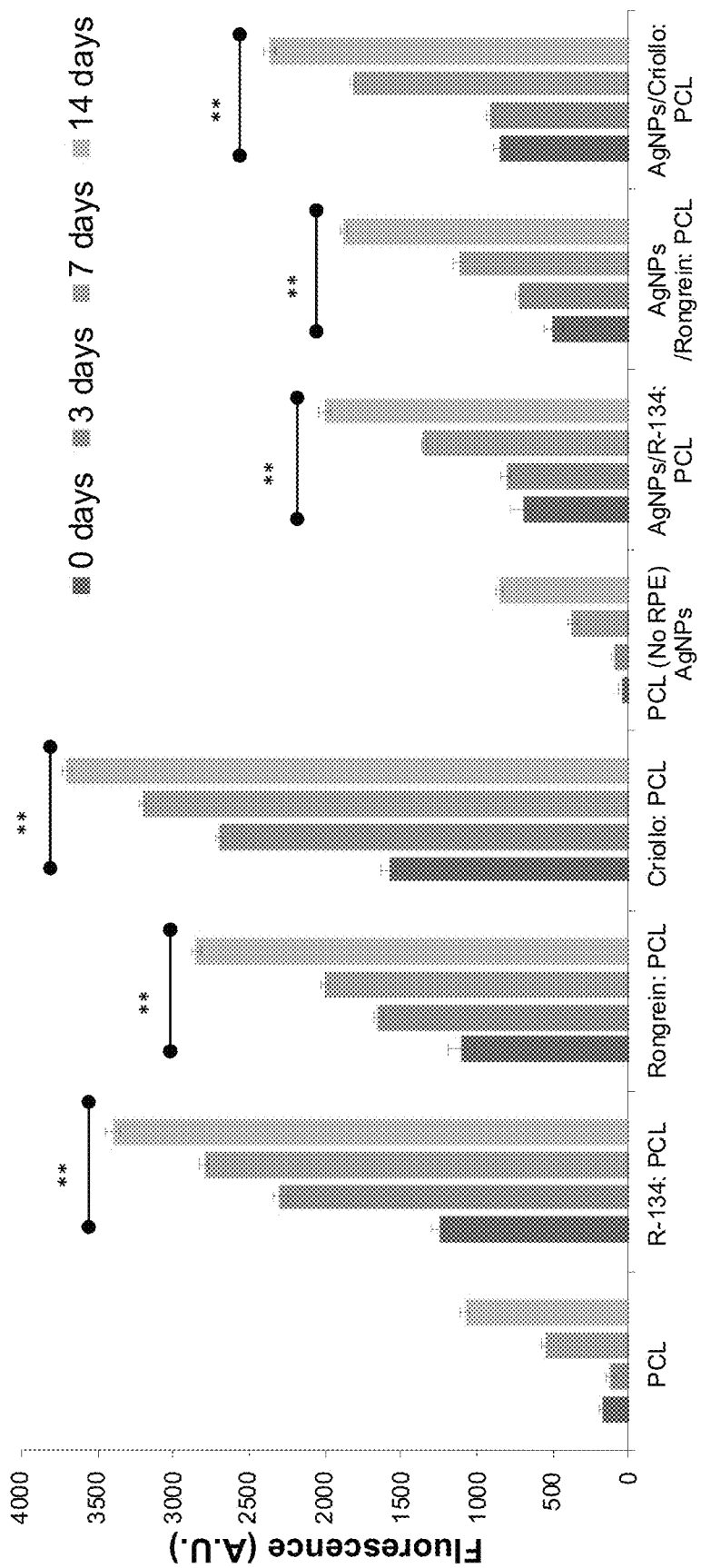
FIG. 47. Comparative analysis of cell proliferation activity of RPE-loaded ESNFs with and without surface coating by silver nanoparticles (AgNPs). Data is reported as fluorescence emitted by growing cells into the ESNFs membranes. All results are reported as mean±SD (n=3). The differences were considered statistically significant at p<0.05. One asterisk indicates an effect that is statistically significant p<0.05 and two asterisks indicate an effect that is statistically highly significant p<0.01, compared to the corresponding control.

After cellular adhesion was tested, the ESNFs membranes with cell adhered were placed in a fresh cell culture media and incubated for 14 days to monitor cell proliferation of 3T3 fibroblasts followed by fluorescent emission. Results reported in FIG. 47 suggests functionalization of synthetic ESNFs membranes with bioactive plant-based extracts from rambutan rind showed a highly significant ($p<0.01$) improvement in cell proliferation in a timely manner, over the extension of the experiment, in comparison with a synthetic PCL-ESNFs membrane with no RPEs added. Similar to results obtained from cell adhesion experiments, RPEs from variety Rongrein showed slightly lower cell proliferation than varieties Criollo and R-134, may be due to less cell count initially attached to the RPE-ESNFs membrane during adhesion stage. Likewise, coating of RPE-ESNFs with AgNPs did not positively impact bioactivity of hybrid ESNFs membranes for cell proliferation. Incorporation of RPEs into hybrid systems containing AgNPs still showing a highly significant improvement on cell proliferation ($p<0.01$) for all rambutan varieties in the time intervals of incubation tested, reinforcing that functionalization of synthetic ESNFs membranes with bioactive plant-based extracts from rambutan will significantly improve biocompatibility, cell attachment and proliferation properties, becoming a suitable system for nanocoating of poor biocompatible biomaterials.

Conclusions

Electrospinning process succeeded in fabricating RPE-loaded under parameters (solution concentration 12 mg/mL, applied voltage 12 kV, flow-rate 1 mL/h, needle-collector distance 10 cm), showing average diameters around 350 nm.

The efficacy of RPE loading into the nanofibers was confirmed by spectroscopy (FTIR), thermal analysis (TGA), electron microscopy (SEM) and swelling studies, suggesting functionalization of synthetic ESNFs with RPEs will increase average nanofiber size, reduce overall membrane pore area, and increase hydrophilicity.

Swelling and release studies conducted in RPE-loaded ESNFs showed that RPEs can be successfully entrapped in the ESNFs network promoting a controlled release of RPEs to the media, which showed to be dependent of the rambutan variety loaded into the ESNFs with rambutan variety R-134 showing the better controlled release properties and variety Rongrein showing the fastest release.

Functionalization of synthetic ESNFs with RPE succeeded in providing and improving antibacterial, cell adhesion and cell proliferation properties of ESNFs membranes, becoming a suitable composite system for applications as functionalized nanocoating for biomaterials, depicting in enhanced biocompatibility and antibacterial properties.

Combination of RPEs with AgNPs succeeded in providing a hybrid ESNFs system showing synergistic properties against pathogenic bacteria. Results also suggested that RPEs significantly improved well-known properties of AgNPs as a broad-spectrum antibacterial agent. However, the hybrid AgNPs/RPE-ESNFs system showed lower cellular adhesion and proliferation properties than the RPE-loaded ESNFs without surface coating by AgNPs, suggesting a different approach must be followed for fabricating hybrid ESNFs containing both AgNPS and RPEs to sustain both antibacterial and cell proliferation properties.

Conclusions

The foregoing examples showed a feasible and cost-effective process for manufacturing of bioengineered ESNF membranes containing bioactive plant-based extracts after the evaluation of several electrospinning parameters including, determination of the adequate solution viscosity and concentration. As well as system parameters including applied voltage, flow rate, and distance between needle and collector for each of the three types of plant-based extract used. Moreover, results of this project indicate that bioactive compounds can be successfully incorporated into ESNFs as carrier system or functionalized device, in combination with synthetic biomedical grade polymers, allowing fabricating fairly uniform and beadless nanofibers of average diameter around 300 nm. Addition of bioactives to ESNFs have proven to increase swelling properties of synthetic-based nanofibers by increasing hydrophilicity of the functionalized ESNFs and also showed improved antibacterial and cell proliferation properties than non-functionalized synthetic ESNFs.

Results from these examples also showed that addition of AgNPs to ESNFs functionalized with bioactives can significantly improve overall antimicrobial activity against pathogenic bacteria, showing a synergistic effect when AgNPs and bioactives are combined in hybrid ESNFs membranes.

These systems constitute a suitable composite biomaterial for potential applications in surface coating of medical devices, fabrication of biosensors, scaffolds for tissue engineering or as wound dressings for chronic wounds.

Ultra-Sensitive Sensor Based in Cranberry Proanthocyanidin-PANI Composite Nanofibers for Pathogenic Bacteria Detection Some small molecules, including carbohydrates, lectin, and vancomycin, have emerged as important recognition elements on nanomaterials for the detection of bacteria. Due to their enhanced stability to temperature and pH variations, these small molecules have attracted attention for mediating interactions between nanomaterials and bacterial cells. These small recognition elements have a strong affinity to bind a broad range of bacterial cells, which are suitable for the detection of unanticipated bacteria. Compared with antibodies or aptamers, these small molecules have much higher recognition element densities on the surface of nanomaterials, providing strong affinity for the capture of bacterial cells. The present example shows that adsorption of PAC onto polyaniline (PANI) nanofibers allows detection of extra-intestinal pathogenic bacteria.

Sensor Preparation

Figure 48:
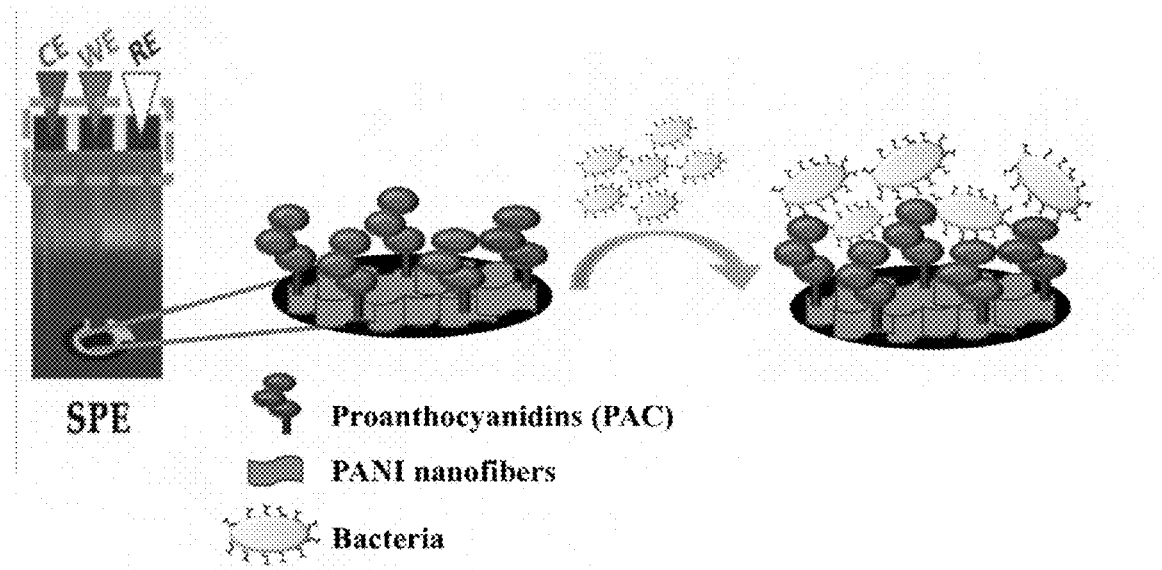
FIG. 48. Illustration of a polyaniline (PANI)-PAC composite nanofiber surface plasmon electrode (SPE) electrochemical assay for pathogenic bacteria detection.

To prepare a sensor, we followed the methodology described by Prathap et al. 2018. Briefly, the electrode pattern in the surface plasmon electrode (SPE) includes a 3-mm diameter carbon working electrode, a carbon counter electrode, and a silver/silver chloride reference electrode, as shown in FIG. 48. The SPE was coated with 2 µL polyaniline nanofibers dropped-casted onto the working surface of the electrode and left to air dry for 3 h. Then the electrode was activated with 0.5 M carbonyldiimidazole (CDI) for 3 h at room temperature. Next, 1 µL of PAC 20 mg/mL dissolved in DMF was immobilized on the activated PANI modified electrode surface and incubated overnight at 4° C. The electrochemical detection was conducted in the presence of 5 mM $K_3[Fe(CN)_6]/K_4[Fe(CN)_6]$ (1:1) solution in 0.1M KCl (pH 7). Dead *E. coli* 5011 were added in a dose dependent manner (1, 10, 100, 1000 CFU) and the plot of current potential was measured.

EXPERIMENTAL RESULTS

Figure 49:
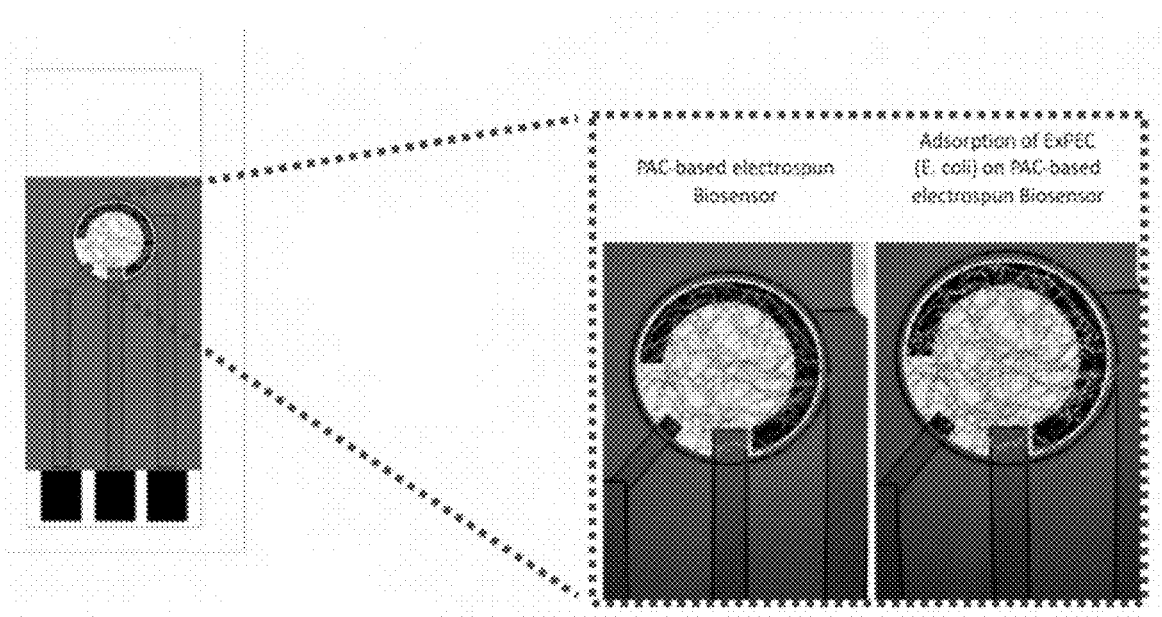
FIG. 49. Schematic illustration of the detection mechanisms for SPE electrodes functionalized by PANI-PAC composite nanofibers.

The proposed mechanism of action of the SPE electrodes functionalized by PANI-PAC composite nanofibers is shown in FIG. 49. We predict that adsorption of PAC onto PANI nanofibers increases efficacy for detecting pathogenic bacteria, by means of the well-known mechanism of interaction between PAC A-type interflavan bonds and surface virulence factors in extra-intestinal pathogenic *Escherichia coli* (ExPEC) and related bacteria.

Figure 50:
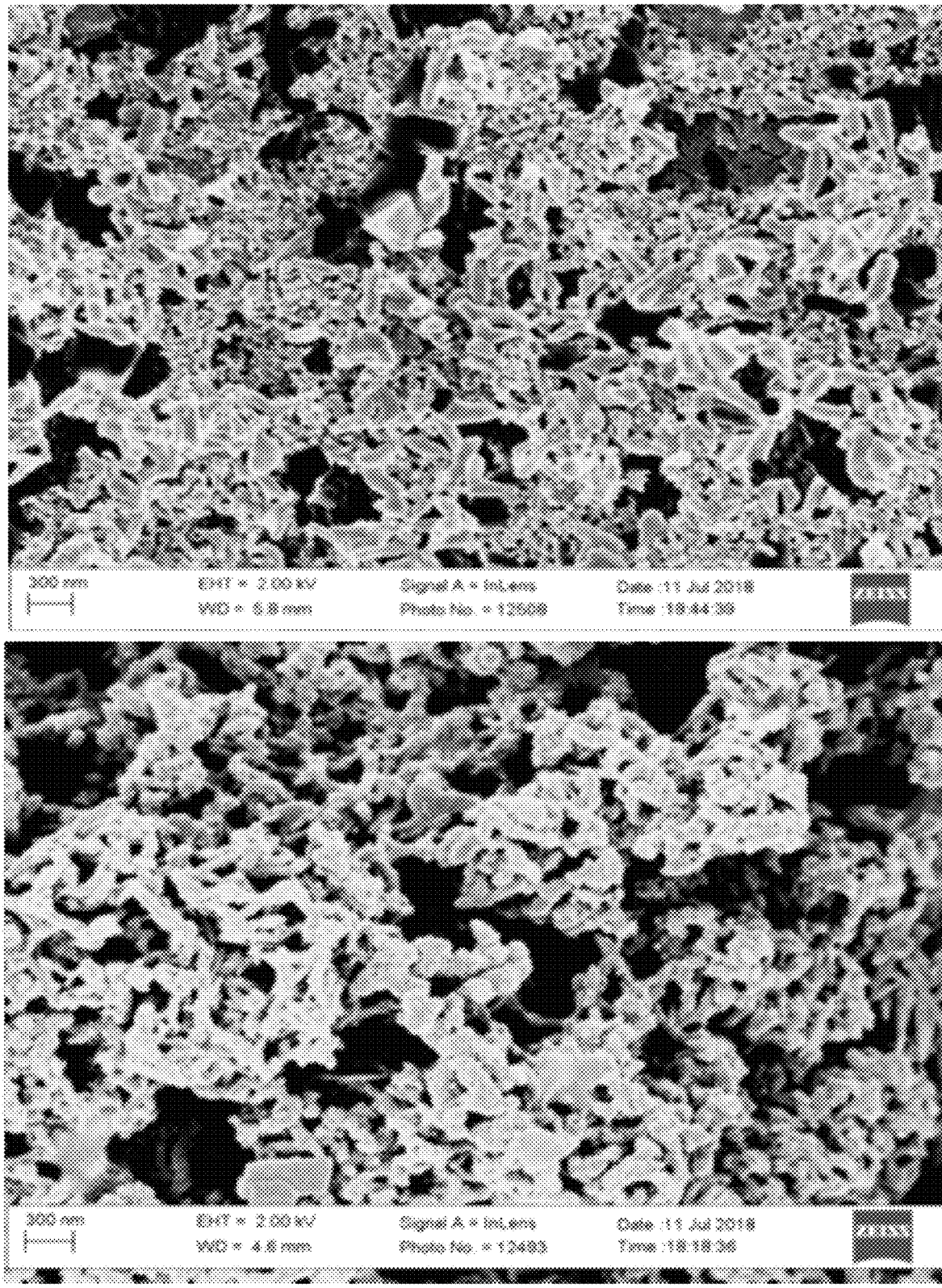
FIG. 50. Scanning electron micrographs showing the surface morphology of modified electrodes functionalized by PANI (top panel) and PANI-PAC composite (bottom panel) nanofibers.

Functionalization of the electrode by PANI and PANI-PAC composite nanofibers was characterized by scanning electron microscopy, as shown in FIG. 50. SEM micrographs showed a change in the surface morphology of PANI nanofibers when PAC had been adsorbed on its surface, showing an apparent surface functionalization of the nanofibers by addition of PAC.

Figure 51A:
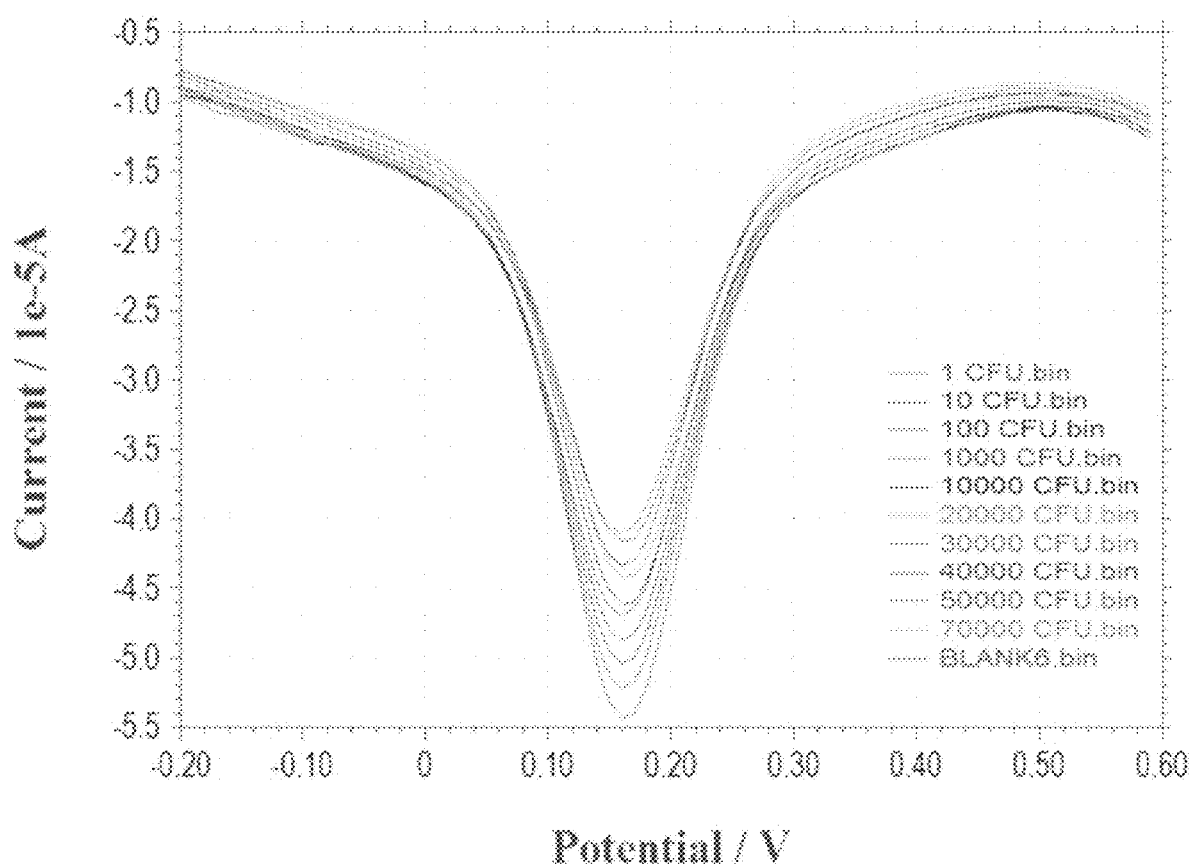
FIG. 51A-51C. Biological response of SPE biosensors functionalized with PANI-PAC composite nanofibers to bacterial cultures prepared at different concentrations (CFU).
Figure 51B:
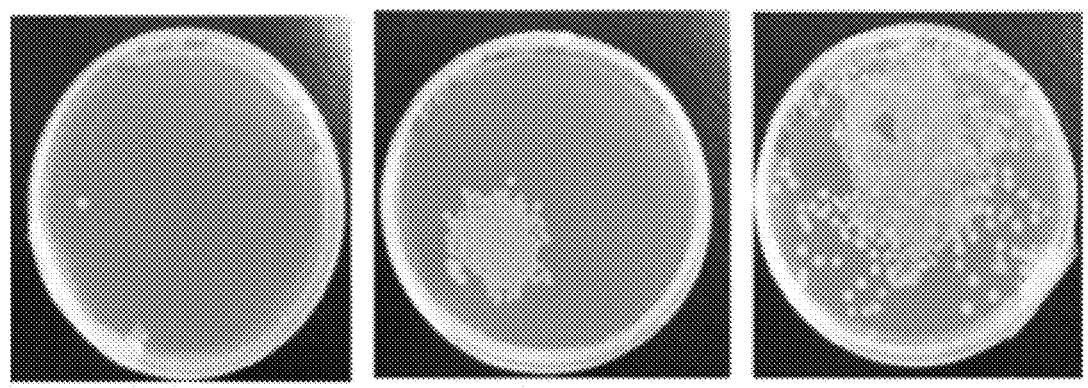
Figure 51C:
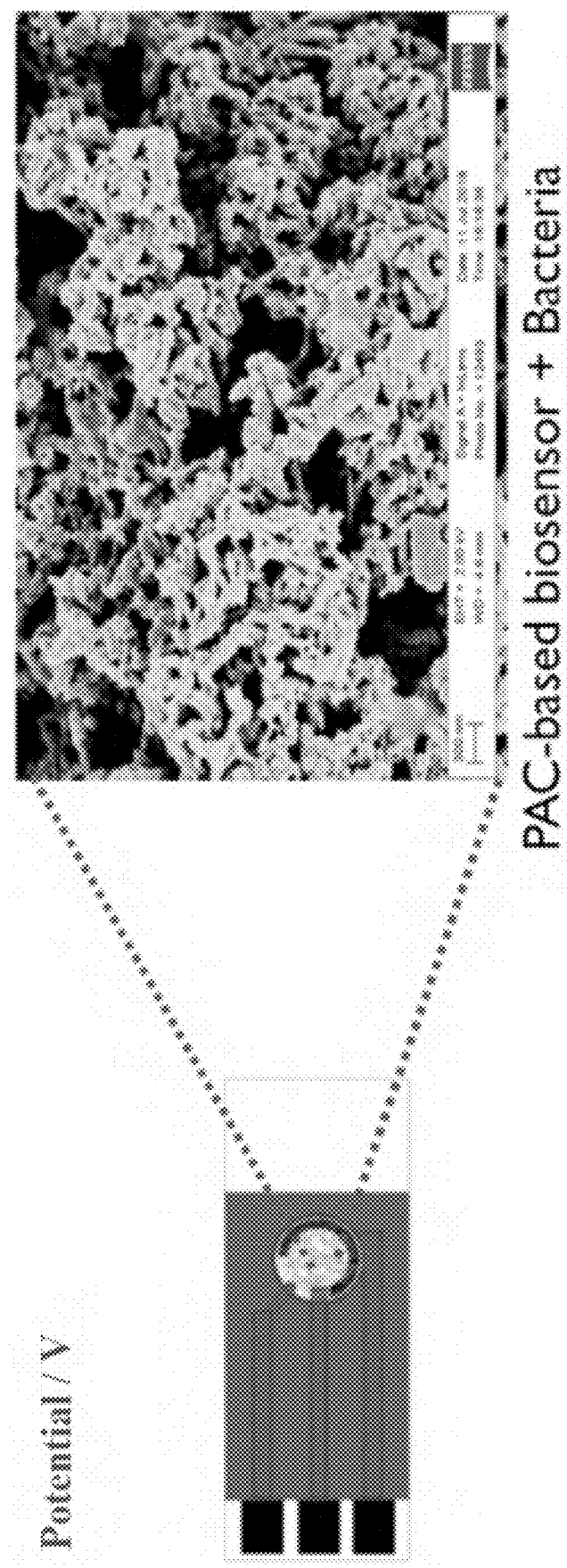

Efficacy of the functionalized biosensor for detecting pathogenic bacteria was assessed by measuring the frequency response of the SPE biosensor to the adsorption of the third layer of bacteria, as shown in FIGS. 51A-C. Results suggest the SPE biosensor functionalized by PANI-PAC composite nanofiber was able to detect the adsorption of bacteria at decreasing concentrations ranging between 70000 CFU and to 1 CFU, demonstrating good sensitivity for biosensing applications (FIG. 51A). Culture plates (FIG. 51B) corresponded to the bacterial concentrations used for the frequency response study. SEM (FIG. 51C), showed the surface adsorption of the bacteria onto PANI-PAC nanofibers in the functionalized SPE biosensor. Similar results were obtained for *S. agona*.

REFERENCES

Aadil, K. R., Mussatto, S. I., & Jha, H. (2018). Synthesis and characterization of silver nanoparticles loaded poly (vinyl alcohol)-lignin ESNFs and their antimicrobial activity. *International journal of biological macromolecules*, 120, 763-767.

Abdel-Hady, F., Alzahrany, A., & Hamed, M. (2011). Experimental validation of upward electrospinning process. *ISRN nanotechnology*, 2011.

Agarwal, S., Wendorff, J. H., & Greiner, A. (2008). Use of electrospinning technique for biomedical applications. *Polymer*, 49(26), 5603-5621.

Al-Omair, M. (2015). Synthesis of antibacterial silver-poly (ε-caprolactone)-methacrylic acid graft copolymer nanofibers and their evaluation as potential wound dressing. *Polymers*, 7(8), 1464-1475.

Alborzi, S., Lim, L. T., & Kakuda, Y. (2014). Release of folic acid from sodium alginate-pectin-poly (ethylene oxide)

electrospun fibers under in vitro conditions. *LWT-Food Science and Technology,* 59(1), 383-388.

Alborzi, S., Lim, L. T., & Kakuda, Y. (2014). Release of folic acid from sodium alginate-pectin-poly (ethylene oxide) electrospun fibers under in vitro conditions. *LWT-Food Science and Technology,* 59(1), 383-388.

Angammana, C. J., & Jayaram, S. H. (2011). Analysis of the effects of solution conductivity on electrospinning process and fiber morphology. *IEEE Transactions on industry applications,* 47(3), 1109-1117.

Arce-Urbina, M. E., Hun-Opfer, C., & Mata-Segreda, J. F. (2003). The aqueous extract of Triumfetta semitriloba (Tiliaceae) does not inhibit the in-vitro hydrolytic activity of the major pancreatic enzymes. *Revista de biologia tropical,* 51(2), 313-316.

Avila, G., Misch, K., Galindo-Moreno, P., & Wang, H. L. (2009). Implant surface treatment using biomimetic agents. *Implant dentistry,* 18(1), 17-26.

Bauer, A. W., Kirby, W. M. M., Sherris, J. C., & Turck, M. (1966). Antibiotic susceptibility testing by a standardized single disk method. *American journal of clinical pathology,* 45(4_ts), 493-496.

Bhardwaj, N., & Kundu, S. C. (2010). Electrospinning: a fascinating fiber fabrication technique. *Biotechnology advances,* 28(3), 325-347.

Bhattarai, D., Aguilar, L., Park, C., & Kim, C. (2018). A review on properties of natural and synthetic based electrospun fibrous materials for bone tissue engineering. *Membranes,* 8(3), 62.

Blainski, A., Lopes, G., & de Mello, J. (2013). Application and analysis of the folin ciocalteu method for the determination of the total phenolic content from *Limonium brasiliense* L. *Molecules,* 18(6), 6852-6865.

Blumberg, J. B., Basu, A., Krueger, C. G., Lila, M. A., Neto, C. C., Novotny, J. A., ... & Toner, C. D. (2016). Impact of cranberries on gut microbiota and cardiometabolic health: Proceedings of the cranberry health research conference 2015. *Advances in Nutrition,* 7(4), 759S-770S.

Bondet, V., Brand-Williams, W., & Berset, C. L. W. T. (1997). Kinetics and mechanisms of antioxidant activity using the DPPH. free radical method. *LWT-Food Science and Technology,* 30(6), 609-615.

Brettmann, B. K., Cheng, K., Myerson, A. S., & Trout, B. L. (2013). Electrospun formulations containing crystalline active pharmaceutical ingredients. *Pharmaceutical research,* 30(1), 238-246.

Brettmann, B. K., Tsang, S., Forward, K. M., Rutledge, G. C., Myerson, A. S., & Trout, B. L. (2012). Free surface electrospinning of fibers containing microparticles. *Langmuir,* 28(25), 9714-

Brettmann, B., Pincus, P., & Tirrell, M. (2017). Lateral structure formation in polyelectrolyte brushes induced by multivalent ions. *Macromolecules,* 50(3), 1225-1235.

Bustamante, M., Oomah, B. D., Rubilar, M., & Shene, C. (2017). Effective *Lactobacillus plantarum* and *Bifidobacterium infantis* encapsulation with chia seed (*Salvia hispanica* L.) and flaxseed (*Linum usitatissimum* L.) mucilage and soluble protein by spray drying. *Food chemistry,* 216, 97-105.

Charernsriwilaiwat, N., Rojanarata, T., Ngawhirunpat, T., Sukma, M., & Opanasopit, P. (2013). Electrospun chitosan-based nanofiber mats loaded with Garcinia mangostana extracts. *International journal of pharmaceutics,* 452(1-2), 333-343.

Chaves, M. A., Piati, J., Malacarne, L. T., Gall, R. E., Colla, E., Bittencourt, P. R., . . . & Matsushita, M. (2018). Extraction and application of chia mucilage (*Salvia hispanica* L.) and locust bean gum (*Ceratonia siliqua* L.) in goat milk frozen dessert. *Journal of food science and technology,* 55(10), 4148-4158.

Choi, J. S., Lee, S. W., Jeong, L., Bae, S. H., Min, B. C., Youk, J. H., & Park, W. H. (2004). Effect of organosoluble salts on the nanofibrous structure of electrospun poly(3-hydroxybutyrate-co-3-hydroxyvalerate). *International Journal of Biological Macromolecules,* 34, 249.

Deitzel, J. M., Kleinmeyer, J., Harris, D. E. A., & Tan, N. B. (2001). The effect of processing variables on the morphology of ESNFs and textiles. *Polymer,* 42(1), 261-272.

Dhandayuthapani, B., Yoshida, Y., Maekawa, T., & Kumar, D. S. (2011). Polymeric scaffolds in tissue engineering application: a review. *International journal of polymer science,* 2011.

Du, L., Xu, H., Zhang, Y., & Zou, F. (2016). Electrospinning of polycaprolatone nanofibers with DMF additive: the effect of solution proprieties on jet perturbation and fiber morphologies. *Fibers and Polymers,* 17(5), 751-759.

Duan, B., Dong, C., Yuan, X., & Yao, K. (2004). Electrospinning of chitosan solutions in acetic acid with poly (ethylene oxide). *Journal of Biomaterials Science, Polymer Edition,* 15(6), 797-811.

Eichhorn, S. J., & Sampson, W. W. (2009). Relationships between specific surface area and pore size in electrospun polymer fibre networks. *Journal of The Royal Society Interface,* 7(45), 641-649.

Elendran, S., Wang, L. W., Prankerd, R., & Palanisamy, U. D. (2015). The physicochemical properties of geraniin, a potential antihyperglycemic agent. *Pharmaceutical biology,* 53(12), 1719-1726.

Ewaldz, E., & Brettmann, B. (2019). Molecular Interactions in Electrospinning: From Polymer Mixtures to Supramolecular Assemblies. *ACS Applied Polymer Materials,* 1(3), 298-308.

Ewaldz, E., Patel, R., Banerjee, M., & Brettmann, B. K. (2018). Material selection in electrospinning microparticles. *Polymer,* 153, 529-537.

Fallahi, D., Rafizadeh, M., Mohammadi, N., & Vahidi, B. (2008). Effect of applied voltage on jet electric current and flow rate in electrospinning of polyacrylonitrile solutions. *Polymer international,* 57(12), 1363-1368.

Fang, Z., & Bhandari, B. (2010). Encapsulation of polyphenols—a review. *Trends in Food Science & Technology,* 21(10), 510-523.

Feldman, M., Tanabe, S., Howell, A., & Grenier, D. (2012). Cranberry proanthocyanidins inhibit the adherence properties of *Candida albicans* and cytokine secretion by oral epithelial cells. *BMC complementary and alternative medicine,* 12(1), 6.

Feliciano, R. P., Krueger, C. G., & Reed, J. D. (2015). Methods to determine effects of cranberry proanthocyanidins on extraintestinal infections: Relevance for urinary tract health. *Molecular nutrition & food research,* 59(7), 1292-1306.

Feliciano, R. P., Shea, M. P., Shanmuganayagam, D., Krueger, C. G., Howell, A. B., & Reed, J. D. (2012). Comparison of isolated cranberry (*Vaccinium macrocarpon* Ait.) proanthocyanidins to catechin and procyanidins A2 and B2 for use as standards in the 4-(dimethylamino) cinnamaldehyde assay. *Journal of agricultural and food chemistry,* 60(18), 4578-4585.

Fernandez, A., Torres-Giner, S., & Lagaron, J. M. (2009). Novel route to stabilization of bioactive antioxidants by encapsulation in electrospun fibers of zein prolamine. *Food Hydrocolloids,* 23(5), 1427-19721.

Ferreira, J. L., Gomes, S., Henriques, C., Borges, J. P., & Silva, J. C. (2014). Electrospinning polycaprolactone dissolved in glacial acetic acid: Fiber production, nonwoven characterization, and In Vitro evaluation. *Journal of Applied Polymer Science*, 131(22).

Frenot, A., & Chronakis, I. S. (2003). Polymer nanofibers assembled by electrospinning. *Current opinion in colloid & interface science*, 8(1), 64-75.

Guo, H. F., & Xu, B. G. (2017). Numerical study of Taylor cone dynamics in electrospinning of nanofibers. In *Key Engineering Materials* (Vol. 730, pp. 510-515). Trans Tech Publications.

Gupta, K., Chou, M. Y., Howell, A., Wobbe, C., Grady, R., & Stapleton, A. E. (2007). Cranberry products inhibit adherence of p-fimbriated *Escherichia coli* to primary cultured bladder and vaginal epithelial cells. *The Journal of urology*, 177(6), 2357-2360.

Gurlek, A. C., Sevinc, B., Bayrak, E., & Erisken, C. (2017). Synthesis and characterization of polycaprolactone for anterior cruciate ligament regeneration. *Materials Science and Engineering: C*, 71, 820-826.

Hadad, S., & Goli, S. A. H. (2018). Fabrication and characterization of ESNFs using flaxseed (*Linum usitatissimum*) mucilage. *International journal of biological macromolecules*, 114, 408-414.

Haeri, M., & Haeri, M. (2015). ImageJ plugin for analysis of porous scaffolds used in tissue engineering. *Journal of Open Research Software*, 3(1).

Haider, A., Haider, S., & Kang, I. K. (2018). A comprehensive review summarizing the effect of electrospinning parameters and potential applications of nanofibers in biomedical and biotechnology. *Arabian Journal of Chemistry*, 11(8), 1165-1188.

Haider, S., Al-Zeghayer, Y., Ali, F. A. A., Haider, A., Mahmood, A., Al-Masry, W. A., . . . & Aijaz, M. O. (2013). Highly aligned narrow diameter chitosan ESNFs. *Journal of Polymer Research*, 20(4), 105.

Hani, N. M., Torkamani, A. E., Azarian, M. H., Mahmood, K. W., & Ngalim, S. H. (2017). Characterisation of electrospun gelatine nanofibres encapsulated with *Moringa oleifera* bioactive extract. *Journal of the Science of Food and Agriculture*, 97(10), 3348-3358.

Hotaling, N. A., Bharti, K., Kriel, H., & Simon Jr, C. G. (2015). Diameter J: A validated open source nanofiber diameter measurement tool. *Biomaterials*, 61, 327-338.

Howell, A. B. (2007). Bioactive compounds in cranberries and their role in prevention of urinary tract infections. *Molecular nutrition & food research*, 51(6), 732-737.

Howell, A. B., Reed, J. D., Krueger, C. G., Winterbottom, R., Cunningham, D. G., & Leahy, M. (2005). A-type cranberry proanthocyanidins and uropathogenic bacterial anti-adhesion activity. *Phytochemistry*, 66(18), 2281-2291.

Huan, S., Liu, G., Han, G., Cheng, W., Fu, Z., Wu, Q., & Wang, Q. (2015). Effect of experimental parameters on morphological, mechanical and hydrophobic properties of electrospun polystyrene fibers. *Materials*, 8(5), 2718-2734.

Huang, C. H., Chi, C. Y., Chen, Y. S., Chen, K. Y., Chen, P. L., & Yao, C. H. (2012). Evaluation of proanthocyanidin-crosslinked electrospun gelatin nanofibers for drug delivering system. *Materials Science and Engineering: C*, 32(8), 2476-2483.

Ikada, Y. (2006). Challenges in tissue engineering. *Journal of the Royal Society Interface*, 3(10), 589-601.

Jahangir, M. A., Rumi, T. M., Wahab, M. A., Khan, M. I., Rahman, M. A., & Sayed, Z. B. (2017). Poly Lactic Acid (PLA) Fibres: Different Solvent Systems and Their Effect on Fibre Morphology and Diameter. *American Journal of Chemistry*, 7(6), 177-186.

Jahani, H., Kaviani, S., Hassanpour-Ezatti, M., Soleimani, M., Kaviani, Z., & Zonoubi, Z. (2012). The effect of aligned and random electrospun fibrous scaffolds on rat mesenchymal stem cell proliferation. Cell Journal (Yakhteh), 14(1), 31.

Kai, D., Jiang, S., Low, Z. W., & Loh, X. J. (2015). Engineering highly stretchable lignin-based ESNFs for potential biomedical applications. *Journal of Materials Chemistry B*, 3(30), 6194-6204.

Kandhasamy, S., Perumal, S., Madhan, B., Umamaheswari, N., Banday, J. A., Perumal, P. T., & Santhanakrishnan, V. P. (2017). Synthesis and fabrication of collagen-coated ostholamide electrospun nanofiber scaffold for wound healing. *ACS applied materials & interfaces*, 9(10), 8556-8568.

Katsogiannis, K. A. G., Vladisavljević, G. T., & Georgiadou, S. (2015). Porous electrospun polycaprolactone (PCL) fibres by phase separation. *European Polymer Journal*, 69, 284-295.

Kaur, M., Kaur, R., & Punia, S. (2018). Characterization of mucilages extracted from different flaxseed (*Linum usitatissiumum* L.) cultivars: A heteropolysaccharide with desirable functional and rheological properties. *International journal of biological macromolecules*, 117, 919-927.

Kayaci, F., & Uyar, T. (2012). Encapsulation of vanillin/cyclodextrin inclusion complex in electrospun polyvinyl alcohol (PVA) nanowebs: Prolonged shelf-life and high temperature stability of vanillin. *Food chemistry*, 133(3), 641-649.

Keat, C. L., Aziz, A., Eid, A. M., & Elmarzugi, N. A. (2015). Biosynthesis of nanoparticles and silver nanoparticles. *Bioresources and Bioprocessing*, 2, 47.

Khajavi, R., & Abbasipour, M. (2012). Electrospinning as a versatile method for fabricating coreshell, hollow and porous nanofibers. *Scientia Iranica*, 19(6), 2029-2034.

Khoo, H. E., Azlan, A., Tang, S. T., & Lim, S. M. (2017). Anthocyanidins and anthocyanins: colored pigments as food, pharmaceutical ingredients, and the potential health benefits. *Food and Nutrition Research*, 61(1), 1361779.

Kim, H. C., Kim, M. H., & Park, W. H. (2018). Polyelectrolyte complex nanofibers from poly (γ-glutamic acid) and fluorescent chitosan oligomer. *International journal of biological macromolecules*, 118, 238-243.

Krishnan, P. (2006). The scientific study of plant-based wound healing therapies: Current state of play. *Current Anaesthesia & Critical Care*, 17(1-2), 21-27.

Kumar, A., Paul, S., Kumari, P., Somasundaram, S. T., & Kathiresan, K. (2015). Antioxidant and free radical scavenging activities of Ipomoea pes-caprae (L.) R. Br. extracts. *Int J Curr Pharm Rev Res*, 5, 91-109.

Kurd, F., Fathi, M., & Shekarchizadeh, H. (2017). Basil seed mucilage as a new source for electrospinning: Production and physicochemical characterization. *International journal of biological macromolecules*, 95, 689-695.

Lee, K. Y., Jeong, L., Kang, Y. O., Lee, S. J., & Park, W. H. (2009). Electrospinning of polysaccharides for regenerative medicine. *Advanced drug delivery reviews*, 61(12), 1020-1032.

Li, D., & Xia, Y. (2004). Electrospinning of nanofibers: reinventing the wheel?. *Advanced materials*, 16(14), 1151-1170.

Li, D., McCann, J. T., Xia, Y., & Marquez, M. (2006). Electrospinning: a simple and versatile technique for producing ceramic nanofibers and nanotubes. *Journal of the American Ceramic Society*, 89(6), 1861-1869.

Li, M., Mondrinos, M. J., Gandhi, M. R., Ko, F. K., Weiss, A. S., & Lelkes, P. I. (2005). Electrospun protein fibers as matrices for tissue engineering. *Biomaterials*, 26(30), 5999-6008.

Li, W. R., Xie, X. B., Shi, Q. S., Zeng, H. Y., You-Sheng, O. Y., & Chen, Y. B. (2010). Antibacterial activity and mechanism of silver nanoparticles on *Escherichia coli*. *Applied microbiology and biotechnology*, 85(4), 1115-1122.

Madrigal-Carballo, S., Haas, L., Vestling, M., Krueger, C. G., & Reed, J. D. (2016). Non-covalent pomegranate (*Punica granatum*) hydrolyzable tannin-protein complexes modulate antigen uptake, processing and presentation by a T-cell hybridoma line co-cultured with murine peritoneal macrophages. *International journal of food sciences and nutrition*, 67(8), 960-968.

Malafaya, P. B., Silva, G. A., & Reis, R. L. (2007). Natural-origin polymers as carriers and scaffolds for biomolecules and cell delivery in tissue engineering applications. *Advanced drug delivery reviews*, 59(4-5), 207-233.

Malikmammadov, E., Tanir, T. E., Kiziltay, A., Hasirci, V., & Hasirci, N. (2018). PCL and PCL-based materials in biomedical applications. *Journal of Biomaterials science, Polymer edition*, 29(7-9), 863-893.

Maran, J. P., Manikandan, S., Nivetha, C. V., & Dinesh, R. (2017). Ultrasound assisted extraction of bioactive compounds from *Nephelium lappaceum* L. fruit peel using central composite face centered response surface design. *Arabian Journal of Chemistry*, 10, S1145-S1157.

Matabola, K. P., & Moutloali, R. M. (2013). The influence of electrospinning parameters on the morphology and diameter of poly (vinyledene fluoride) nanofibers-effect of sodium chloride. *Journal of Materials Science*, 48(16), 5475-5482.

Matthews, J. A., Wnek, G. E., Simpson, D. G., & Bowlin, G. L. (2002). Electrospinning of collagen nanofibers. *Biomacromolecules*, 3(2), 232-238.

Megelski, S., Stephens, J. S., Chase, D. B., & Rabolt, J. F. (2002). Micro- and nanostructured surface morphology on electrospun polymer fibers. *Macromolecules*, 35(22), 8456-8466.

Merrill, E. W. (1994). Poly (ethylene oxide) star molecules: synthesis, characterization, and applications in medicine and biology. *Journal of Biomaterials Science, Polymer Edition*, 5(1-2), 1-11.

Miser-Salihoglu, E., Akaydin, G., Caliskan-Can, E., & Yardim-Akaydin, S. (2013). Evalution of antioxidant activity of various plant-based folk medicines. *Nutrition & Food Sciences*.

Mogoşanu, G. D., & Grumezescu, A. M. (2014). Natural and synthetic polymers for wounds and burns dressing. *International journal of pharmaceutics*, 463(2), 127-136.

Moomand, K., & Lim, L. T. (2015). Properties of encapsulated fish oil in electrospun zein fibres under simulated in vitro conditions. *Food and bioprocess technology*, 8(2), 431-444.

Moradkhannejhad, L., Abdouss, M., Nikfarjam, N., Mazinani, S., & Sayar, P. (2017). Electrospun curcumin loaded poly (lactic acid) nanofiber mat on the flexible crosslinked PVA/PEG membrane film: Characterization and in vitro release kinetic study. *Fibers and Polymers*, 18(12), 2349-2360.

Mueller, M., Čavarkapa, A., Unger, F. M., Viernstein, H., & Praznik, W. (2017). Prebiotic potential of neutral oligo- and polysaccharides from seed mucilage of Hyptis suaveolens. *Food chemistry*, 221, 508-514.

Mulfinger, L., Solomon, S. D., Bahadory, M., Jeyarajasingam, A. V., Rutkowsky, S. A., & Boritz, C. (2007). Synthesis and study of silver nanoparticles. *Journal of chemical education*, 84(2), 322.

Munin, A., & Edwards-Lévy, F. (2011). Encapsulation of natural polyphenolic compounds; a review. *Pharmaceutics*, 3(4), 793-829.

Nagori, B. P., & Solanki, R. (2011). Role of medicinal plants in wound healing. *Research Journal of Medicinal Plant*, 5(4), 392-405.

Natarajan, V., Krithica, N., Madhan, B., & Sehgal, P. K. (2010). Formulation and evaluation of quercetin poly-caprolactone microspheres for the treatment of rheumatoid arthritis. *Journal of Pharmaceutical Sciences*, 100(1), 195-205.

Nie, H., He, A., Wu, W., Zheng, J., Xu, S., Li, J., & Han, C. C. (2009). Effect of poly (ethylene oxide) with different molecular weights on the electrospinnability of sodium alginate. *Polymer*, 50(20), 4926-4934.

Noriega, S. E., Hasanova, G. I., Schneider, M. J., Larsen, G. F., & Subramanian, A. (2012). Effect of fiber diameter on the spreading, proliferation and differentiation of chondrocytes on electrospun chitosan matrices. *Cells Tissues Organs*, 195(3), 207-221.

Noruzi, M. (2016). Electrospun nanofibres in agriculture and the food industry: a review. *Journal of the Science of Food and Agriculture*, 96(14), 4663-4678.

Okoro, I. O., Osagie, A., & Asibor, E. O. (2010). Antioxidant and antimicrobial activities of polyphenols from ethnomedicinal plants of Nigeria. *African Journal of Biotechnology*, 9(20).

Okuda, T., & Ito, H. (2011). Tannins of constant structure in medicinal and food plants—hydrolyzable tannins and polyphenols related to tannins. *Molecules*, 16(3), 2191-2217.

Okutan, N., Terzi, P., & Altay, F. (2014). Affecting parameters on electrospinning process and characterization of electrospun gelatin nanofibers. *Food Hydrocolloids*, 39, 19-26.

Oveissi, V., Ram, M., Bahramsoltani, R., Ebrahimi, F., Rahimi, R., Naseri, R., . . . & Farzaei, M. H. (2019). Medicinal plants and their isolated phytochemicals for the management of chemotherapy-induced neuropathy: Therapeutic targets and clinical perspective. *DARU Journal of Pharmaceutical Sciences*, 1-18.

Palanisamy, U. D., Ling, L. T., Manaharan, T., & Appleton, D. (2011). Rapid isolation of geraniin from Nephelium lappaceum rind waste and its anti-hyperglycemic activity. *Food Chemistry*, 127(1), 21-27.

Pan, H., Fan, D., Cao, W., Zhu, C., Duan, Z., Fu, R., . . . & Ma, X. (2017). Preparation and characterization of breathable hemostatic hydrogel dressings and determination of their effects on full-thickness defects. *Polymers*, 9(12), 727.

Pan, H., Li, L., Hu, L., & Cui, X. (2006). Continuous aligned polymer fibers produced by a modified electrospinning method. *Polymer*, 47(14), 4901-4904.

Park, J. C., Ito, T., Kim, K. O., Kim, K. W., Kim, B. S., Khil, M. S., . . . & Kim, I. S. (2010). Electrospun poly (vinyl alcohol) nanofibers: effects of degree of hydrolysis and enhanced water stability. Polymer journal, 42(3), 273.

Pathak, D., Pathak, K., & Singla, A. K. (1991). Flavonoids as medicinal agents-recent advances. *Fitoterapia*, 62(5), 371-389.

Pelipenko, J., Kristl, J., Janković, B., Baumgartner, S., & Kocbek, P. (2013). The impact of relative humidity during electrospinning on the morphology and mechanical properties of nanofibers. *International journal of pharmaceutics,* 456(1), 125-134.

Picciani, P. H., Medeiros, E. S., Pan, Z., Orts, W. J., Mattoso, L. H., & Soares, B. G. (2009). Development of conducting polyaniline/poly (lactic acid) nanofibers by electrospinning. *Journal of Applied Polymer Science,* 112(2), 744-753.

Pietta, P., Minoggio, M., & Bramati, L. (2003). Plant polyphenols: Structure, occurrence and bioactivity. In *Studies in Natural Products Chemistry* (Vol. 28, pp. 257-312). Elsevier.

Pillay, V., Dott, C., Choonara, Y. E., Tyagi, C., Tomar, L., Kumar, P., . . . & Ndesendo, V. M. (2013). A review of the effect of processing variables on the fabrication of ESNFs for drug delivery applications. *Journal of Nanomaterials,* 2013.

I. Radzig, M. A., Nadtochenko, V. A., Koksharova, O. A., Kiwi, J., Lipasova, V. A., & Khmel, I. A. (2013). Antibacterial effects of silver nanoparticles on gram-negative bacteria: influence on the growth and biofilms formation, mechanisms of action. *Colloids and Surfaces B: Biointerfaces,* 102, 300-306.

Raghavamma, S. T. V., Mothukuri, A. S., Rama, R. N. (2013). Antimicrobial activity of mucilage isolated from *Coccinia grandis* (L) Fruits, J Voigt, International Journal of Advances in *Pharmaceutical Research* 4(11) 2497-2502.

Raven, P. H., Evert, R. F., & Eichhorn, S. E. (2005). *Biology of plants.* Macmillan.

Reyes, C. D., Petrie, T. A., Burns, K. L., Schwartz, Z., & Garcia, A. J. (2007). Biomolecular surface coating to enhance orthopaedic tissue healing and integration. *Biomaterials,* 28(21), 3228-3235.

Rieger, K. A., Birch, N. P., & Schiffman, J. D. (2016). Electrospinning chitosan/poly (ethylene oxide) solutions with essential oils: Correlating solution rheology to nanofiber formation. *Carbohydrate polymers,* 139, 131-138.

Sahay, R., Thavasi, V., & Ramakrishna, S. (2011). Design modifications in electrospinning setup for advanced applications. *Journal of Nanomaterials,* 2011, 17.

Santos, C., Silva, C. J., Büttel, Z., Guimāres, R., Pereira, S. B., Tamagnini, P., & Zille, A. (2014). Preparation and characterization of polysaccharides/PVA blend nanofibrous membranes by electrospinning method. *Carbohydrate polymers,* 99, 584-592.

Sarhan, W. A., & Azzazy, H. M. (2015). High concentration honey chitosan ESNFs: Biocompatibility and antibacterial effects. *Carbohydrate polymers,* 122, 135-143.

Sell, S. A., Wolfe, P. S., Garg, K., McCool, J. M., Rodriguez, I. A., & Bowlin, G. L. (2010). The use of natural polymers in tissue engineering: a focus on electrospun extracellular matrix analogues. *Polymers,* 2(4), 522-553.

Shao, C., Kim, H. Y., Gong, J., Ding, B., Lee, D. R., & Park, S. J. (2003). Fiber mats of poly (vinyl alcohol)/silica composite via electrospinning. *Materials Letters,* 57(9-10), 1579-1584.

Shenoy, S. L., Bates, W. D., Frisch, H. L., & Wnek, G. E. (2005). Role of chain entanglements on fiber formation during electrospinning of polymer solutions: good solvent, non-specific polymer-polymer interaction limit. *Polymer,* 46, 3372.

Sill, T. J., & von Recum, H. A. (2008). Electrospinning: applications in drug delivery and tissue engineering. *Biomaterials,* 29(13), 1989-2006.

Singleton, V. L., Orthofer, R., & Lamuela-Raventós, R. M. (1999). Analysis of total phenols and other oxidation substrates and antioxidants by means of folin-ciocalteu reagent. In *Methods in enzymology* (Vol. 299, pp. 152-178). Academic press.

Son, W. K., Youk, J. H., Lee, T. S., & Park, W. H. (2005). Effect of pH on electrospinning of poly (vinyl alcohol). *Materials letters,* 59(12), 1571-1575.

Sousa, A. M., Souza, H. K., Uknalis, J., Liu, S. C., Goncalves, M. P., & Liu, L. (2015). Electrospinning of agar/PVA aqueous solutions and its relation with rheological properties. *Carbohydrate polymers,* 115, 348-355.

Subbiah, T., Bhat, G. S., Tock, R. W., Parameswaran, S., & Ramkumar, S. S. (2005). Electrospinning of nanofibers. *Journal of applied polymer science,* 96(2), 557-569.

Sun, Z., Zussman, E., Yarin, A. L., Wendorff, J. H., & Greiner, A. (2003). Compound core-shell polymer nanofibers by co-electrospinning. *Advanced materials,* 15(22), 1929-1932.

Supaphol, P., & Chuangchote, S. (2008). On the electrospinning of poly (vinyl alcohol) nanofiber mats: a revisit. *Journal of Applied Polymer Science,* 108(2), 969-978.

Tang, C., Saquing, C. D., Harding, J. R., & Khan, S. A. (2009). In situ cross-linking of electrospun poly (vinyl alcohol) nanofibers. *Macromolecules,* 43(2), 630-637.

Tarus, B., Fadel, N., Al-Oufy, A., & El-Messiry, M. (2016). Effect of polymer concentration on the morphology and mechanical characteristics of electrospun cellulose acetate and poly (vinyl chloride) nanofiber mats. *Alexandria Engineering Journal,* 55(3), 2975-2984.

Thilagavathi, G., & Bala, S. K. (2007). Microencapsulation of plant-based extracts for microbial resistance in healthcare textiles.

Thitilertdecha, N., Teerawutgulrag, A., & Rakariyatham, N. (2008). Antioxidant and antibacterial activities of *Nephelium lappaceum* L. extracts. *LWT-Food Science and Technology,* 41(10), 2029-2035.

Tsai, S. P., Hsieh, C. Y., Hsieh, C. Y., Chang, Y. N., Wang, D. M., & Hsieh, H. J. (2007). Gamma-poly (glutamic acid)/chitosan composite scaffolds for tissue engineering applications. In *Materials science forum* (Vol. 539, pp. 567-572). Trans Tech Publications.

Ulrey, R. K., Barksdale, S. M., Zhou, W., & van Hoek, M. L. (2014). Cranberry proanthocyanidins have anti-biofilm properties against *Pseudomonas aeruginosa. BMC complementary and alternative medicine,* 14(1), 499.

Urena-Saborio, H., Alfaro-Viquez, E., Esquivel-Alvarado, D., Madrigal-Carballo, S., & Gunasekaran, S. (2018). Electrospun plant mucilage nanofibers as biocompatible scaffolds for cell proliferation. *International journal of biological macromolecules,* 115, 1218-1224.

Van der Schueren, L., De Schoenmaker, B., Kalaoglu, Ö. I., & De Clerck, K. (2011). An alternative solvent system for the steady state electrospinning of polycaprolactone. *European Polymer Journal,* 47(6), 1256-1263.

Vanaja, M., Gnanajobitha, G., Paulkumar, K., Rajeshkumar, S., Malarkodi, C., & Annadura, G. (2013). Phytosynthesis of silver nanoparticles by *Cissus quadrangularis:* Influence of physicochemical factors. Journal of Nanostructure in Chemistry, 3, 17.

Varoni, E. M., Iriti, M., & Rimondini, L. (2012). Plant products for innovative biomaterials in dentistry. *Coatings,* 2(3), 179-194.

Vineis, C., & Varesano, A. (2018). Natural polymer-based electrospun fibers for antibacterial uses. In *Electrofluidodynamic Technologies (EFDTs) for Biomaterials and Medical Devices* (pp. 275-294). Woodhead Publishing.

Wachtel-Galor, S., & Benzie, I. F. F. (2011). Chapter 1: Plant-based Medicine: An Introduction to Its History, Usage, Regulation, Current Trends, and Research Needs. In: *Plant-based Medicine: Biomolecular and Clinical Aspects*. I. F. F. Benzie and S. Wachtel-Galor Editors. 2nd edition. CRC Press/Taylor & Francis.

Wang, H., Hao, L., Niu, B., Jiang, S., Cheng, J., & Jiang, S. (2016). Kinetics and antioxidant capacity of proanthocyanidins encapsulated in zein electrospun fibers by cyclic voltammetry. *Journal of agricultural and food chemistry*, 64(15), 3083-3090.

Wang, G., Yang, S., Wei, Z., Dong, X., Wang, H., & Qi, M. (2013). Facile preparation of poly (ε-caprolactone)/Fe 3 O 4@ graphene oxide superparamagnetic nanocomposites. *Polymer bulletin*, 70(8), 2359-2371.

Wang, H., Wang, J., Qiu, C., Ye, Y., Guo, X., Chen, G., . . . & Liu, R. H. (2017). Comparison of phytochemical profiles and health benefits in fiber and oil flaxseeds (*Linum usitatissimum* L.). *Food chemistry*, 214, 227-233.

Wang, L. F., & Rhim, J. W. (2016). Grapefruit seed extract incorporated antimicrobial LDPE and PLA films: Effect of type of polymer matrix. *LWT*, 74, 338-345.

Wang, S., Cao, X., Shen, M., Guo, R., Bányai, I., & Shi, X. (2012). Fabrication and morphology control of electrospun poly (γ-glutamic acid) nanofibers for biomedical applications. *Colloids and Surfaces B: Biointerfaces*, 89, 254-264.

Wang, S., Marcone, M. F., Barbut, S., & Lim, L. T. (2012). Fortification of dietary biopolymers-based packaging material with bioactive plant extracts. *Food research international*, 49(1), 80-91.

Wang, S., Marcone, M. F., Barbut, S., & Lim, L. T. (2013). Electrospun soy protein isolate-based fiber fortified with anthocyanin-rich red raspberry (*Rubus strigosus*) extracts. *Food research international*, 52(2), 467-472.

Wang, X., Bazuin, C. G., & Pellerin, C. (2015). Effect of small molecule hydrogen-bond crosslinker and solvent power on the electrospinnability of poly (4-vinyl pyridine). *Polymer*, 57, 62-69.

Wen, P., Zhu, D. H., Wu, H., Zong, M. H., Jing, Y. R., & Han, S. Y. (2016). Encapsulation of cinnamon essential oil in electrospun nanofibrous film for active food packaging. *Food Control*, 59, 366-376.

Woodruff, M. A., & Hutmacher, D. W. (2010). The return of a forgotten polymer Polycaprolactone in the 21st century. *Progress in polymer science*, 35(10), 1217-1256.

World Health Organization (WHO). (2005). National Policy on Traditional Medicine and Regulation of Plant-based Medicines. Geneva: Report of WHO global survey.

Yang, G., Lin, H., Rothrauff, B. B., Yu, S., & Tuan, R. S. (2016). Multilayered polycaprolactone/gelatin fiber-hydrogel composite for tendon tissue engineering. *Acta biomaterialia*, 35, 68-76.

Yuan, W., & Zhang, K. Q. (2012). Structural evolution of electrospun composite fibers from the blend of polyvinyl alcohol and polymer nanoparticles. *Langmuir*, 28(43), 15418-15424.

Zargham, S., Bazgir, S., Tavakoli, A., Rashidi, A. S., & Damerchely, R. (2012). The effect of flow rate on morphology and deposition area of electrospun nylon 6 nanofiber. *Journal of Engineered Fibers and Fabrics*, 7(4), 155892501200700414.

Zhang, B., Kang, F., Tarascon, J. M., & Kim, J. K. (2016). Recent advances in electrospun carbon nanofibers and their application in electrochemical energy storage. *Progress in Materials Science*, 76, 319-380.

Zhong, X. H., Kim, K. S., Fang, D. F., Ran, S. F., Hsiao, B. S., & Chu, B. (2002). Structure and process relationship of electrospun bioabsorbable nanofiber membranes. *Polymer*, 43, 4403.

Zhou, C., Chu, R., Wu, R., & Wu, Q. (2011). Electrospun polyethylene oxide/cellulose nanocrystal composite nanofibrous mats with homogeneous and heterogeneous microstructures. *Biomacromolecules*, 12(7), 2617-2625.

Zhou, T., Wang, N., Xue, Y., Ding, T., Liu, X., Mo, X., & Sun, J. (2016). Electrospun tilapia collagen nanofibers accelerating wound healing via inducing keratinocytes proliferation and differentiation. *Colloids and Surfaces B: Biointerfaces*, 143, 415-422.

Zhu, J., & Marchant, R. E. (2011). Design properties of hydrogel tissue-engineering scaffolds. *Expert review of medical devices*, 8(5), 607-626.

EXEMPLARY EMBODIMENTS OF THE INVENTION

Embodiment 1. A nanofiber comprising a synthetic polymer and a tannin configured in the form of a composite nanofiber.

Embodiment 2. The nanofiber of embodiment 1, wherein the synthetic polymer comprises a polyester, a semi-flexible rod polymer, a polyether, a polyurethane, a vinyl polymer, a poly(alkylene oxide), a polyanhydride, poly-glutamic acid, or a combination thereof.

Embodiment 3. The nanofiber of any prior embodiment, wherein the synthetic polymer comprises a polyester, a semi-flexible rod polymer, or a combination thereof.

Embodiment 4. The nanofiber of any prior embodiment, wherein the synthetic polymer comprises polycaprolactone, polyaniline, or a combination thereof.

Embodiment 5. The nanofiber of any prior embodiment, wherein the synthetic polymer comprises a weight average molecular weight ($M_w$) from about 25 KDa to about 400 KDa.

Embodiment 6. The nanofiber of any prior embodiment, wherein the tannin comprises a condensed tannin.

Embodiment 7. The nanofiber of embodiment 6, wherein the condensed tannin comprises a weight average molecular weight ($M_w$) from about 100 Da to about 100,000 Da.

Embodiment 8. The nanofiber of any prior embodiment, wherein the tannin comprises a hydrolyzable tannin.

Embodiment 9. The nanofiber of embodiment 8, wherein the hydrolyzable tannin comprises a weight average molecular weight ($M_w$) from about 100 Da to about 30,000 Da.

Embodiment 10. The nanofiber of any prior embodiment, wherein the nanofiber comprises the tannin and the synthetic polymer in a ratio by mass (mass tannin:mass synthetic polymer) from about 1:99 to about 60:40.

Embodiment 11. The nanofiber of any prior embodiment, wherein the nanofiber has an average diameter in dry form from about 300 nm to about 450 nm.

Embodiment 12. The nanofiber of any prior embodiment, wherein the nanofiber is in the form of a beadless fiber.

Embodiment 13. The nanofiber of any prior embodiment, wherein the nanofiber is in the form of a nanofiber mat.

Embodiment 14. The nanofiber of embodiment 13, wherein the nanofiber mat in dry form has a mean pore area from about 300 $nm^2$ to about 750 $nm^2$.

Embodiment 15. The nanofiber of any prior embodiment, wherein the tannin forms nodes on and/or in the nanofiber.

Embodiment 16. The nanofiber of any prior embodiment, wherein the nanofiber is in the form of a matrix comprising the synthetic polymer and the tannin.

Embodiment 17. The nanofiber of any one of embodiments 1-15, wherein the nanofiber is in the form of a matrix comprising the synthetic polymer without the tannin, and the tannin is adsorbed only to the outer surface of the matrix.

Embodiment 18. The nanofiber of any prior embodiment, wherein the tannin is non-covalently bound to the synthetic polymer.

Embodiment 19. The nanofiber of any prior embodiment, wherein the tannin is covalently bound to the synthetic polymer.

Embodiment 20. The nanofiber of any prior embodiment, further comprising silver nanoparticles coated on an outer surface of the nanofiber.

Embodiment 21. The nanofiber of any prior embodiment, wherein the nanofiber exhibits, compared to a corresponding nanofiber lacking the tannin, one or more of: enhanced swelling in aqueous liquid; enhanced antibacterial activity; enhanced bacterial adsorption; enhanced fibroblast adhesion; enhanced fibroblast proliferation; and enhanced surface coating of silver nanoparticles.

Embodiment 22. The nanofiber of any prior embodiment, wherein the nanofiber is included as a filtration medium in a filter housing.

Embodiment 23. The nanofiber of any one of embodiments 1-21, wherein the nanofiber is included as a surface coating on a medical device.

Embodiment 24. The nanofiber of any one of embodiments 1-21, wherein the nanofiber is included as a surface coating on a biosensor.

Embodiment 25. A method of producing the nanofiber of any prior embodiment, comprising: providing a solvent mixture comprising nanofiber components and a solvent, wherein the nanofiber components comprise the synthetic polymer; and electrospinning the solvent mixture to thereby form a nanofiber.

Embodiment 26. The method of embodiment 25, wherein the nanofiber components further comprise a tannin, and the electrospinning generates a matrix comprising the synthetic polymer and the tannin.

Embodiment 27. The method of embodiment 26, wherein the synthetic polymer comprises polycaprolactone, the tannin comprises a condensed tannin, and: the nanofiber components are present in the solvent mixture in a concentration from about 4 to about 14 mg/mL; the solvent mixture has a viscosity from about 90 mPa s to about 130 mPa s; the solvent mixture has a conductivity from about 1 µS/cm to about 5 µS/cm; the electrospinning is performed at an applied voltage from about 10 kV to about 25 kV; the electrospinning is performed at a flow rate from about 0.5 mL/h to about 1.5 mL/h; and/or the electrospinning is performed with a needle-collector distance from about 8 cm to about 20 cm.

Embodiment 28. The method of embodiment 26, wherein the synthetic polymer comprises polycaprolactone, the tannin comprises a hydrolyzable tannin, and: the nanofiber components are present in the solvent mixture in a concentration from about 8 to about 14 mg/mL; the solvent mixture has a viscosity from about 115 mPa s to about 155 mPa s; the solvent mixture has a conductivity from about 0.5 µS/cm to about 3.0 µS/cm; the electrospinning is performed at an applied voltage from about 10 kV to about 20 kV; the electrospinning is performed at a flow rate from about 0.5 mL/h to about 2 mL/h; and/or the electrospinning is performed with a needle-collector distance from about 8 cm to about 20 cm.

Embodiment 29. The method of embodiment 25, wherein the nanofiber components comprise the synthetic polymer without the tannin, the electrospinning generates an matrix comprising the synthetic polymer without the tannin, and, after the electrospinning, the tannin is adhered to the matrix to thereby form the nanofiber comprising the synthetic polymer and the tannin.

Embodiment 30. A method of isolating cells, comprising contacting a cell-containing medium with the nanofiber of any one of embodiments 1-24, wherein cells in the cell-containing medium adhere to the nanofiber.

Embodiment 31. The method of embodiment 30, wherein the cells comprise bacteria.

Embodiment 32. The method of any one of embodiments 30-31, wherein the cells comprise fibroblasts.

Embodiment 33. The method of any one of embodiments 30-32, wherein the cell-containing medium is a fluid.

Embodiment 34. The method of embodiment 33, wherein the fluid is a liquid.

Embodiment 35. The method of embodiment 33, wherein the fluid is a gas.

Embodiment 36. The method of any one of embodiments 30-35, wherein the nanofiber is in the form of a nanofiber mat.

Embodiment 37. The method of any one of embodiments 30-36, wherein the cell-containing medium is a fluid, the nanofiber is in the form of a nanofiber mat, and the contacting comprises flowing the cell-containing medium through the nanofiber mat.

Embodiment 38. The method of any one of embodiments 30-35, wherein the nanofiber is included as a surface coating on a medical device.

Embodiment 39. The method of embodiment 38, wherein the cells comprise bacteria and the adherence of the cells to the nanofiber reduces bacterial growth.

Embodiment 40. The method of embodiment 38, wherein the cells comprise fibroblasts and the adherence of the cells to the cells to the nanofiber stimulates fibroblast proliferation.

Embodiment 41. A method of filtration, comprising flowing a fluid through a nanofiber mat, wherein the nanofiber mat comprises a nanofiber as recited in any one of embodiments 1-22.

Embodiment 42. The method of embodiment 41, wherein the fluid is a liquid.

Embodiment 43. The method of embodiment 41, wherein the fluid is a gas.

Embodiment 44. A method of detecting a cell, comprising contacting a medium suspected of containing the cell with a biosensor, wherein the biosensor is coated with the nanofiber of any one of embodiments 1-21.

Embodiment 45. The method of embodiment 44, wherein the cell comprises a bacterium.

We claim:

1. A nanofiber comprising a synthetic polymer and a tannin configured in the form of a composite nanofiber, wherein the tannin forms nodes on, or on and in, the nanofiber, wherein the nodes comprise spots of clustered tannin on a surface of the nanofiber.

2. The nanofiber of claim 1, wherein the synthetic polymer comprises a polyester, a semi-flexible rod polymer, a polyether, a polyurethane, a vinyl polymer, a poly(alkylene oxide), a polyanhydride, poly-glutamic acid, or a combination thereof.

3. The nanofiber of claim 1, wherein the synthetic polymer comprises a polyester, a semi-flexible rod polymer, or a combination thereof.

4. The nanofiber of claim 1, wherein the synthetic polymer comprises polycaprolactone, polyaniline, or a combination thereof.

5. The nanofiber of claim 1, wherein the synthetic polymer comprises a weight average molecular weight ($M_w$) from about 25 KDa to about 400 KDa.

6. The nanofiber of claim 1, wherein the tannin comprises a condensed tannin.

7. The nanofiber of claim 6, wherein the condensed tannin comprises a weight average molecular weight ($M_w$) from about 100 Da to about 100,000 Da.

8. The nanofiber of claim 1, wherein the tannin comprises a hydrolyzable tannin.

9. The nanofiber of claim 8, wherein the hydrolyzable tannin comprises a weight average molecular weight ($M_w$) from about 100 Da to about 30,000 Da.

10. The nanofiber of claim 1, wherein the nanofiber comprises the tannin and the synthetic polymer in a ratio by mass (mass tannin:mass synthetic polymer) from about 1:99 to about 60:40.

11. The nanofiber of claim 1, wherein the nanofiber has an average diameter in dry form from about 300 nm to about 450 nm.

12. The nanofiber of claim 1, wherein the nanofiber is in the form of a beadless fiber.

13. The nanofiber of claim 1, wherein the nanofiber is in the form of a nanofiber mat.

14. The nanofiber of claim 13, wherein the nanofiber mat in dry form has a mean pore area from about 300 $nm^2$ to about 750 $nm^2$.

15. The nanofiber of claim 1, wherein the nanofiber is in the form of a matrix comprising the synthetic polymer and the tannin.

16. The nanofiber of claim 1, wherein the nanofiber is in the form of a matrix comprising the synthetic polymer without the tannin, and the tannin is adsorbed only to the outer surface of the matrix.

17. The nanofiber of claim 1, wherein the tannin is non-covalently bound to the synthetic polymer.

18. The nanofiber of claim 1, wherein the tannin is covalently bound to the synthetic polymer.

19. The nanofiber of claim 1, further comprising silver nanoparticles coated on an outer surface of the nanofiber.

20. The nanofiber of claim 1, wherein the nanofiber exhibits, compared to a corresponding nanofiber lacking the tannin, one or more of: enhanced swelling in aqueous liquid; enhanced antibacterial activity; enhanced bacterial adsorption; enhanced fibroblast adhesion; enhanced fibroblast proliferation; and enhanced surface coating of silver nanoparticles.

21. The nanofiber of claim 1, wherein the nanofiber is included as a filtration medium in a filter housing.

22. The nanofiber of claim 1, wherein the nanofiber is included as a surface coating on a medical device.

23. The nanofiber of claim 1, wherein the nanofiber is included as a surface coating on a biosensor.

24. The nanofiber of claim 1, wherein:
the synthetic polymer comprises polycaprolactone, polyaniline, or a combination thereof;
the synthetic polymer comprises a weight average molecular weight ($M_w$) from about 25 KDa to about 400 KDa;
the tannin comprises a condensed tannin;
the condensed tannin comprises a weight average molecular weight ($M_w$) from about 100 Da to about 100,000 Da;
the nanofiber comprises the tannin and the synthetic polymer in a ratio by mass (mass tannin:mass synthetic polymer) from about 1:99 to about 60:40; and
the nanofiber is in the form of a matrix with the tannin and the synthetic polymer being mutually distributed with respect to each other throughout the nanofiber.

* * * * *